United States Patent
Nordsiek et al.

(10) Patent No.: US 9,072,876 B2
(45) Date of Patent: Jul. 7, 2015

(54) PUMP SYSTEMS AND METHODS FOR STORING AND DISPENSING A PLURALITY OF PRECISELY MEASURED UNIT-DOSES OF IMIQUIMOD CREAM

(75) Inventors: Michael T. Nordsiek, Wayne, PA (US); Kodumudi S. Balaji, Lansdale, PA (US)

(73) Assignee: MEDICIS PHARMACEUTICAL CORPORATION, Scottsdale, AZ (US)

( * ) Notice: Subject to any disclaimer, the term of this patent is extended or adjusted under 35 U.S.C. 154(b) by 446 days.

(21) Appl. No.: 12/875,787

(22) Filed: Sep. 3, 2010

(65) Prior Publication Data
US 2012/0035556 A1  Feb. 9, 2012

Related U.S. Application Data

(60) Provisional application No. 61/402,251, filed on Aug. 26, 2010, provisional application No. 61/377,336, filed on Aug. 26, 2010, provisional application No. 61/402,052, filed on Aug. 23, 2010, provisional (Continued)

(51) Int. Cl.
*G01F 11/00* (2006.01)
*A61M 35/00* (2006.01)
(Continued)

(52) U.S. Cl.
CPC ............ *A61M 35/003* (2013.01); *A61K 9/0014* (2013.01); *A61K 9/0031* (2013.01);
(Continued)

(58) Field of Classification Search
None
See application file for complete search history.

(56) References Cited

U.S. PATENT DOCUMENTS

| 4,689,338 | A * | 8/1987 | Gerster | 514/293 |
| 6,991,139 | B2 * | 1/2006 | Garcia et al. | 222/494 |

(Continued)

FOREIGN PATENT DOCUMENTS

| CA | 1271458 | 7/1990 |
| CA | 2649893 | 8/2010 |

(Continued)

OTHER PUBLICATIONS

Arany, I. et al., "Enhancement of the innate and cellular immune response in patients with genital warts treated with topical imiquimod cream 5%," *Antiviral Res*, 1999, vol. 43:55-63.

(Continued)

*Primary Examiner* — Jason Flick
*Assistant Examiner* — Diva K Chander
(74) *Attorney, Agent, or Firm* — Kilpatrick Townsend & Stockton, LLP; Kenneth R. Shurtz, Esq.

(57) ABSTRACT

The present invention is directed to airless storage and dispensing systems that include a pump or dispensing package pre-filled with a topical semi-solid imiquimod pharmaceutical formulation ("pump systems") and methods for storing and dispensing from the pump systems a plurality of precisely measured and uniform unit doses of a topical semi-solid imiquimod pharmaceutical formulation, and more particularly to pump systems, pre-filled with a topical imiquimod pharmaceutical cream and methods for delivering multiple precisely measured unit doses of a topical imiquimod pharmaceutical cream, and methods for using a controlled delivery pump system to store and dispense a plurality of consistent and precisely measured unit doses of a topical imiquimod pharmaceutical cream for use in topically treating a dermal and mucosal-associated condition, such as, external genital warts and/or perianal warts (EGWs), actinic keratosis or actinic keratoses (AK or AKs) and superficial basal cell carcinoma (sBCC).

76 Claims, 11 Drawing Sheets

Related U.S. Application Data application No. 61/376,154, filed on Aug. 23, 2010, provisional application No. 61/401,997, filed on Aug. 20, 2010, provisional application No. 61/375,580, filed on Aug. 20, 2010, provisional application No. 61/371,137, filed on Aug. 5, 2010.

(51) Int. Cl.
  *A61K 9/00* (2006.01)
  *A61K 9/06* (2006.01)
  *A61K 31/4745* (2006.01)
  *A61K 47/10* (2006.01)
  *B05B 11/00* (2006.01)

(52) U.S. Cl.
  CPC ............... *A61K9/0034* (2013.01); *A61K 9/06* (2013.01); *A61K 31/4745* (2013.01); *A61K 47/10* (2013.01); *B05B 11/0024* (2013.01); *B05B 11/0037* (2013.01); *B05B 11/0048* (2013.01); *B05B 11/3001* (2013.01); *B05B 11/3047* (2013.01)

(56) References Cited

U.S. PATENT DOCUMENTS

| | | | |
|---|---|---|---|
| 7,654,418 B2* | 2/2010 | Law et al. | 222/259 |
| 2002/0020715 A1* | 2/2002 | Gueret | 222/153.11 |
| 2005/0267144 A1* | 12/2005 | Mandrea | 514/292 |
| 2006/0043118 A1* | 3/2006 | Law et al. | 222/321.9 |
| 2006/0255071 A1* | 11/2006 | Behar et al. | 222/256 |
| 2007/0264317 A1* | 11/2007 | Yosha et al. | 424/448 |
| 2008/0119572 A1* | 5/2008 | Owens et al. | 514/789 |
| 2009/0232755 A1* | 9/2009 | Baumann | 424/47 |
| 2011/0021555 A1* | 1/2011 | Nordsiek et al. | 514/293 |
| 2011/0207766 A1* | 8/2011 | Nordsiek et al. | 514/293 |

FOREIGN PATENT DOCUMENTS

| | | |
|---|---|---|
| EP | 1629900 A2 | 3/2006 |
| WO | WO 2010/080345 | 7/2010 |
| WO | WO 2011/008324 | 1/2011 |
| WO | WO 2012/019158 | 9/2012 |

OTHER PUBLICATIONS

Berman, B. et al., "Actinic keratosis: sequelae and treatments," Recommendations from a consensus panel, *J Fam Pract*, May 2006, vol. 55(5)(suppl):1-8.

Bernstein, DI et al., Effects of the immunomodulating agent R-837 on acute and latent herpes simplex virus type 2 infections, *Antimicro Agents and Chemo*, 1989, 33(9):1511-1515.

Bernstein, DI et al., "Effects of therapy with an immunomodulator (Imiquimod, R-837) alone and with acyclovir on genital HSV-2 infection in guinea pigs when begun after lesion development," *Antiviral Res*, 1993, 20:45-55.

Dahl, MV, "Imiquimod: An immune response modifier," *J Am Acad Dermatol*, 2000, 43(1):S1-5.

Edwards, L., "Imiquimod in clinical practice," *J Am Acad Dermatol*, 2000, 43(1):512-17.

Edwards, L., "Self-administered topical 5% imiquimod cream for external anogenital warts," *Arch Dermatol*, 1998, 134:25-30.

Einspahr, JG et al., Reproducibility and expression of skin biomarkers in sun-damaged skin and actinic keratosis, *Cancer Epidemiol Biomarkers Pres*, Oct. 2006, 15(10):1841-1848.

Fact Sheet: "Human Papillomaviruses and Cancer: Questions and Answers," *National Cancer Institute*, pp. 1-11, www.cancer.gov/cancertopics/factsheet/RishkHPV (Reviewed Feb. 14, 2008).

Gaspari, AA et al., "Immunotherapy of basal cell carcinoma: evolving approached," *Derm Surg*, 2003, 29(10):1027-1034.

Gearhart, PA et al., "Human papillomavirus," *emedicine*, pp. 1-33, http://emedicine.medscape.com/article/219110 (Updated Mar. 8, 2010).

Gollnick H. et al., "Safety and efficacy of imiquimod 5% cream in the treatment of penile genital warts in uncircumcised men when applied three times weekly of once per day," *Int J STD and AIDS*, 2001, 12:22-28.

Harrison CJ et al., "Post therapy suppression of genital herpes simplex virus (HSV) recurrences and enhancement of HSV-specific T-cell memory by imiquimod in guinea pigs," *Antimicro Agents and Chemo*, 1994, 38(9):2059-2064.

Kende, M. et al., "Treatment of experimental viral infections with immunomodulators," *Adv Biosci*, 1988, 68:51-63.

Koutsky, L., "Epidemiology of genital human papillomavirus infection," *Am J Med*, 1997, 102(5A):3-8.

Koutsky, L., "Epidemiology of human papillomavirus infection," *Epidemiol Rev*, 1998, 10:122-163.

Kreuter, A., et al., "5% Imiquimod suppositories decrease the DNA load of intra-anal HPV types 6 and 11 in HIV-infected men after surgical ablation of condylomata acuminate [letter]," *Arch Dermatol*, Feb. 2006, 142(2):243-244.

Lebwohl, M et al., "Imiquimod 5% cream for the treatment of actinic keratosis: results from two phase III, randomized, double-blind, parallel group, vehicle-controlled trials," *J Am Acad Dermatol*, May 2004, 50(5):714-721.

Lyttle, PH, Surveillance report: disease trends at New Zealand sexually transmitted disease clinics 1977-1993, *Genitourin Med*, 1994, 70:329-335.

Mayeaux, EJ et al., Noncervical human papillomavirus genital infections, *Am Fam Physician*, 1995, 52:1137-1146.

Miller, RL et al., "Imiquimod cytokine induction and antiviral activity," *Intl Antiviral News*, 1995, 3(7):111-113.

Miller, RL et al., Imiquimod applied topically: a novel immune response modifier and new class of drug, *Int J Immunopharm*, 1999, 21:1-14.

Office Action issued in Canadian Patent Application No. 2713777, dated May 28, 2013, 5 pages.

Phelps, W. et al., "Antiviral therapy for human papillomaviruses: rationale and prospects," *Ann Intern Med*, 1995, 123:368-382.

Quatresooz, P. et al., "Crossroads between actinic keratosis and squamous cell carcinoma, and novel pharmacological issues," *Eur J Dermatol.*, Jan.-Feb. 2008, 18(1):6-10.

Sauder, DN., "Immunomodulatory and pharmacologic properties of imiquimods," *J Am Acad Dermatol*, 2000, 43(1):56-11.

Shah KV, Howley PM, "Papillomaviruses," In: Fields BN, Knipe DM, ed. *Fields Virology*, 1990, 2nd ed. New York, NY: Raven Press, (2)59:1651-1666.

Stockfleth E. et al., "Guidelines for the management of actinic keratosis," *Eur J Dermatol*, Nov.-Dec. 2006, 16(6):599-606.

Testerman, TL et al., "Cytokine induction by the immunomodulators imiquimod and S-27609," *J Leuk Biol*, 1995, 58:365-372.

Torres, A. et al., "Microarray analysis of aberrant gene expression in actinic keratosis: effect of the Toll-like receptor-7 agonist imiquimod," *Br J Dermatol*, Dec. 2007, 157(6):1132-47. Epub Oct. 28, 2007.

Tyring, SK et al., "A randomized, controlled, molecular study of condylomata acuminate clearance during treatment with imiquimod," *J Infect Dis*, 1998, 178(August):551-555.

Tyring, SK, "Immune-response modifiers: a new paradigm in the treatment of human papillomavirus," *Curr Ther Res*, 2000, 60(9):584-596.

Vatve, M. et al., "Management of field change in actinic keratosis," *Br J. Dermatol*, Dec. 2007, 157(52):21-24.

Weeks, CE et al., "Induction of interferon and other cytokines by imiquimod and its hydroxylated metabolite R-842 in human blood cells in vitro," *J Interferon Res*, 1994, 14:81-85.

Office Action dated Dec. 5, 2013 in corresponding Canadian Application No. 2,713,777; Owner: Medicis Pharmaceutical Corporation; 5 pages.

Extended European Search Report dated Jul. 8, 2014, from corresponding European Application No. 11815401.2; Owner: Medicis Pharmaceutical Corporation; 9 pages.

\* cited by examiner

Subject Accountability (External Genital Warts)

PUMP SYSTEMS AND METHODS FOR STORING AND DISPENSING A PLURALITY OF PRECISELY MEASURED UNIT-DOSES OF IMIQUIMOD CREAM

CROSS REFERENCE TO RELATED APPLICATIONS

This application claims priority benefit under 35 U.S.C. §119(e) to (1) U.S. Provisional Application No. 61/402,251, which was filed on Aug. 26, 2010 via U.S. Express Mail No. EG463456778US and is entitled "Pump Systems and Methods for Storing and Dispensing A Plurality of Precisely Measured Unit Doses of Imiquimod Cream", (2) U.S. Provisional Application No. 61/377,336, which was filed on Aug. 26, 2010 and is entitled "Pump Systems and Methods for Storing and Dispensing A Plurality of Precisely Measured Unit Doses of Imiquimod Cream, (3) U.S. Provisional Application No. 61/402,052, which was filed on Aug. 23, 2010 via U.S. Express Mail No. EG463456733US and is entitled "Pump Systems and Methods for Storing and Dispensing A Plurality of Precisely Measured Unit Doses of Imiquimod Cream", (4) U.S. Provisional Application No. 61/376,154, which was filed on Aug. 23, 2010 and is entitled "Pump Systems and Methods for Storing and Dispensing a Plurality of Precisely Measured Unit-Doses of Imiquimod Cream", (5) U.S. Provisional Application No. 61/401,997, which was filed on Aug. 20, 2010 via U.S. Express Mail No. EG463456781US and is entitled "Pump Systems and Methods for Storing and Reproducibly Dispensing Precisely Measured Unit Doses of Imiquimod Cream", (6) U.S. Provisional Application No. 61/375,580, which was filed on Aug. 20, 2010 and is entitled "Pump Systems and Methods for Storing and Reproducibly Dispensing Precisely Measured Unit Doses of Imiquimod Cream", and (7) U.S. Provisional Application No. 61/371,137, which was filed on Aug. 5, 2010 and is entitled "Systems and Methods for Storing and Dispensing Unit Doses of Imiquimod Cream", each of which, including its respective content, is incorporated herein by reference in its entirety.

FIELD OF THE INVENTION

The subject invention relates to unique storage and dispensing systems that include a pump or dispensing package pre-filled with a topical semi-solid imiquimod pharmaceutical formulation ("pump systems") and methods for storing and dispensing a plurality of precisely measured unit doses of a topical semi-solid imiquimod pharmaceutical formulation, and more particularly to pump systems pre-filled with an imiquimod pharmaceutical cream and methods for delivering multiple precisely measured unit doses of an imiquimod pharmaceutical cream, and methods for using a controlled delivery pump to store and dispense a plurality of precisely measured unit doses of a topical semi-solid imiquimod pharmaceutical formulation for use in treating a dermal and/or mucosal-associated condition, such as, external genital warts and/or perianal warts (EGWs), actinic keratosis or actinic keratoses (AK or AKs) and superficial basal cell carcinoma (sBCC).

BACKGROUND

External genital warts and perianal warts, i.e., condylomata acuminate, are caused by infection with human papilloma virus (HPV), the most common sexually transmitted virus in the Western world. See, e.g., Lyttle P H.: Surveillance report: disease trends at New Zealand sexually transmitted disease clinics 1977-1993. *Genitourin Med.,* 70:329-335 (1994); Mayeaux E J, Harper M B, Barksdale W, Pope J B.: Noncervical human papillomavirus genital infections. *Am Fam Physician.,* 52:1137-1146 (1995); and Shah K V, Howley P M.: Papillomaviruses. In: Fields, B N, Knipe D M, ed *Fields Virology.* 2nd ed. New York, N.Y.: Raven Press; (2)59: 1651-1666 (1990). Approximately 1% of the sexually active population between 15 and 49 years of age in the United States is estimated to have external genital warts. See, e.g., Koutsky L.: Epidemiology of human papillomavirus infection. *Epidemiol Rev.,* 10:122-163 (1998); and Koutsky L.: Epidemiology of genital human papillomavirus infection. *Am J Med.,* 102(5A):3-8 (1997). Most external genital warts are associated with HPV types 6 and 11. See, e.g., Phelps W, Alexander K A.: Antiviral therapy for human papillomaviruses: rationale and prospects. *Ann Intern Med.,* 123:368-382 (1995). HPV types 6 and 11 are typically labeled as low risk because infection with these types has low oncogenic potential and usually results in the formation of condylomata and low-grade precancerous lesions. See, e.g., Gearhart, P. A. and Randall, T. C.: Human Papillomavirus, emedicine, pages 1-33, http://emedicine.medscape.com/article/219110 (Updated: Mar. 8, 2010); and Fact Sheet: *Human Papillomaviruses and Cancer: Questions and Answers,* National Cancer Institute, pages. 1-11, www.cancer.gov/cancertopics/factsheet/RiskHPV (Reviewed Feb. 14, 2008).

Specific antiviral therapy for the treatment of external genital warts and perianal warts is lacking, but drug and other therapies have been used. Ablative treatment modalities include procedures such as surgical excision, laser therapy, and cryotherapy. Other approaches include topical treatments, such as acetic acid, podophylline, podophyllotoxin, and 5-fluorouracil, which are cytodestructive, and sinecatechins, whose mechanism of action is unknown. Each of these therapies have disadvantages such as inconvenient regimens, pain, burning associated with the therapy, scarring, itching and/or high recurrence rates.

On Feb. 27, 1997, imiquimod 5% cream was approved for the very first time by the U.S. Food and Drug Administration (FDA) for the treatment of external genital and perianal warts, i.e., condyloma acuminate (EGW or EGWs), in patients 12 years or older. See Aldara® Package Insert (Label) Revised: March 2007 (Attachment VIII). Imiquimod, an immune response modifier that stimulates the innate and adaptive immune response, has been demonstrated to be an effective and safe treatment for external genital warts and perianal warts. Stimulation of the immune response has been shown to decrease HPV viral load, Kreuter A, Brockmeyer N H, Weissenborn S J, et al.: 5% Imiquimod suppositories decrease the DNA load of intra-anal HPV types 6 and 11 in HIV-infected men after surgical ablation of condylomata acuminata [letter]. *Arch Dermatol.;* 142(2):243-4 (February, 2006), and thus may decrease the recurrence rate of visible warts, although observed rates after treatments do vary.

In the treatment of EGWs diagnosed in adults, the approved dosing regimen for Aldara® (imiquimod) 5% cream is 3 times per week, for up to 16 weeks of treatment. Aldara® (imiquimod) 5% cream should be applied 3 times per week to external genital/perianal warts. Aldara® (imiquimod) 5% cream treatment should continue until there is total clearance of the genital/perianal warts or for a maximum of 16 weeks. Examples of 3 times per week application schedules are: Monday, Wednesday, Friday or Tuesday, Thursday, Saturday. Aldara® (imiquimod) 5% cream should be applied prior to normal sleeping hours and left on the skin for 6-10 hours, after which time the cream should be removed by washing the area with mild soap and water. The prescriber should demonstrate the proper application technique to maximize the benefit of Aldara® (imiquimod) 5% cream therapy. It is recommended that patients wash their hands before and after applying Aldara® (imiquimod) 5% cream.

A study in 22 patients with genital/perianal warts comparing Aldara® (imiquimod) 5% cream and vehicle shows that Aldara® (imiquimod) 5% cream induces mRNA encoding cytokines including interferon-α at the treatment site. In addition, HPVL1 mRNA and HPV DNA are significantly decreased following treatment. However, the clinical relevance of these findings is unknown.

A thin layer of Aldara® (imiquimod) 5% cream should be applied to the wart area and rubbed in until the cream is no longer visible. The application site should not be occluded. Following the treatment period, the Aldara® (imiquimod) 5% cream should be removed by washing the treated area with mild soap and water. Local skin reactions at the treatment site are common. A rest period of several days may be taken if required by the patient's discomfort or severity caused by the treatment-related local skin reactions. Treatment may resume once the reactions subside. Non-occlusive dressings such as cotton gauze or cotton underwear may be used in the management of skin reactions. Aldara® (imiquimod) 5% cream is currently packaged in single-use packets or sachets which contain sufficient cream to cover a wart area of up to about 20 cm$^2$. Use of excessive amounts of cream and passive transfer of the cream should be avoided.

Actinic keratosis is a precancerous (premalignant) skin disorder caused by or associated with chronic exposure to radiant energy, such as sunlight. Actinic keratosis lesions (AKs) are small, red, rough spots or lesions occurring on sun exposed areas of the skin. Actinic keratosis lesions possess many of the same cellular changes observed in a skin cancer called squamous cell carcinoma (SCC). Research shows that a mutated version of the p53 gene is found in sun-damaged cells in the body and is present in more than about 90% of people who have AKs and SCC. Although most actinic keratosis lesions do not actually become cancerous, some AKs can become malignant.

It is believed that actinic keratosis develops in skin cells called "keratinocytes", which are the cells that constitute about 90% of the epidermis, the outermost layer of skin. Chronic sun exposure, over time, generates mutations in these cells and causes the cells to change in size, shape, the way they are organized, and the way they behave. In addition, the cellular damage can even extend to the dermis, the layer of skin beneath the epidermis.

Actinic keratosis lesions generally measure in size between about 2 to about 6 millimeters in diameter. AK lesions can range in color from skin-toned to reddish and often have a white scale on top. On occasion, AK lesions will form into the shape of animal horns. When this occurs, the AKs are known as "cutaneous horns."

People who are at higher risk for developing actinic keratosis tend to be fair-skinned and spend significant time outdoors, e.g., at work or at play, over the course of many years. AKs usually develop on those areas of the body that have been constantly exposed to the sun for years. Additionally, the skin often becomes wrinkled, mottled, and discolored from chronic sun exposure. Common locations for AKs include the face, ears, lips, balding scalp, back of the neck, upper chest, the tops of the hands and forearms. When AKs develop on the lips, the condition is known as actinic cheilitis. Actinic cheilitis can be characterized by a diffuse scaling on the lower lip that cracks and dries. In some cases, the lips will have a whitish discoloration on the thickened lip.

Actinic keratosis is generally more common after age 40, because actinic keratosis takes years to develop. However, even younger adults may develop actinic keratosis when living in geographic areas that are exposed to high-intensity sunlight year round, such as Florida and Southern California.

Actinic keratosis has become a significant health care issue in the United States of America. It is estimated that over 20 million Americans suffer from actinic keratoses, and that that number continues to grow. In fact, actinic keratosis is so common today that treatment for actinic keratosis ranks as one of the most frequent reasons people consult dermatologists.

Once an immunocompetent adult is diagnosed with clinically visible AKs, a variety of treatment options are currently available. These options include physically removing the AKs by (1) freezing them with liquid nitrogen, (2) using a laser to burn the AKs, (3) scraping the AKs off, or (4) using topical creams to treat the AKs. One such cream that can be applied to the skin for the treatment of AKs is Aldara® (imiquimod) 5% cream.

On Mar. 2, 2004, Aldara® (imiquimod) 5% cream was approved by the FDA, under section 505(b) of the Federal Food, Drug and Cosmetic Act, for the treatment of clinically typical, nonhyperkeratotic, nonhypertrophic actinic keratoses on the face and scalp in immunocompetent adults Imiquimod, an immune response modifier that stimulates the innate and adaptive immune response, has been demonstrated to be an effective and safe treatment for AKs. Aldara® (imiquimod) 5% cream works from within by activating the adult's own immune system to treat disease.

In the treatment of adults diagnosed with actinic keratosis, the approved dosing regimen for Aldara® (imiquimod) 5% cream is 2 times per week, for a full 16 weeks to a defined treatment area on the face or scalp (but not both concurrently). See Aldara® Package Insert (Label) Revised: March 2007 (Attachment VIII).

According to the approved Aldara® Package Insert (Label) Revised: March 2007 (Attachment VIII), the treatment area is defined as one contiguous area of up to approximately 25 cm$^2$ (e.g., 5 cm×5 cm) on the face (e.g. forehead or one cheek) or on the scalp, and examples of 2 times per week application schedules are Monday and Thursday, or Tuesday and Friday. The Aldara® Package Insert (Label) Revised: March 2007 (Attachment VIII) further instructs that the Aldara® (imiquimod) 5% cream should be applied to the entire treatment area and rubbed in until the cream is no longer visible. The Aldara® Package Insert (Label) Revised: March 2007 (Attachment VIII) cautions that no more than one packet of Aldara® (imiquimod) 5% cream should be applied to the contiguous treatment area at each application, and the Aldara® (imiquimod) 5% cream should be applied prior to normal sleeping hours and left on the skin for approximately 8 hours, after which time the cream should be removed by washing the area with mild soap and water.

The Aldara® Package Insert (Label) Revised: March 2007 (Attachment VIII) further advises that prescribers should demonstrate the proper application technique to maximize the benefit of Aldara® (imiquimod) 5% cream therapy.

The Aldara® Package Insert (Label) Revised: March 2007 (Attachment VIII) also recommends that patients should wash their hands before and after applying the Aldara® (imiquimod) 5% cream as well as the treatment area with mild soap and water and allow the area to dry thoroughly (at least 10 minutes) before applying Aldara® (imiquimod) 5% cream.

The Aldara® Package Insert (Label) Revised: March 2007 (Attachment VIII) further cautions that contact with the eyes, lips and nostrils should be avoided and warns that Aldara® (imiquimod) 5% cream is not for oral, ophthalmic, or intravaginal use.

Because the Aldara® (imiquimod) 5% cream is currently packaged in single-use packets, with 12 packets supplied per box, the Aldara® Package Insert (Label) Revised: March 2007 (Attachment VIII) instructs that patients should be prescribed no more than 3 boxes (36 packets) for the 16-week treatment period, and that unused packets should be discarded. The Aldara® Package Insert (Label) Revised: March 2007 (Attachment VIII) clearly warns that partially-used packets should be discarded and not reused.

Aldara® (imiquimod) 5% cream is also FDA approved to treat superficial basal cell carcinoma (sBCC), a form of skin cancer. See, e.g., Aldara® Package Insert (Label) Revised: March 2007 (Attachment VIII).

Skin cancer can occur anywhere on the body. Skin cancer, however, is most commonly diagnosed on skin that, like with AKs, has been in constant exposure to intense sunlight, especially during childhood or young adulthood. According to the American Cancer Society, the most common type of skin cancer is basal cell carcinoma (BCC), affecting about 800,000-900,000 Americans each year.

BCC develops within the basal cells, which are found within the basal layer of the epidermis or the top layer of the skin. Basal cells are typically small and round and continually divide to produce new skin cells and replace old ones.

BCC is typically a slow growing disease which can metastasize to other areas of the body including the lymph nodes, bone or other tissues beneath the skin if left untreated. Basal cell carcinoma occurs most often on sun exposed areas of the skin such as the head or neck. Although basal cell carcinoma rarely spreads to other parts of the body, it may cause local tissue destruction and it can be very destructive and disfiguring.

There are several types of BCC, including nodular basal cell carcinoma, superficial basal cell carcinoma (sBCC), small basal cell carcinoma, morpheaform basal cell carcinoma, infiltrating basal cell carcinoma, pigmented basal cell carcinoma, micronodular basal cell carcinoma and cystic basal cell carcinoma, each of which manifests a different pattern of behavior.

If allowed to progress without treatment, BCC can cause clinically significant morbidity. Because BCC most commonly affects the head and neck, cosmetic disfigurement is common. In addition, if there is orbital involvement, loss of vision or even loss of an eye may occur. BCC lesions are prone to ulceration and infection and, if there is perineural spread or deep and extensive skin invasion, nerve function can be lost. Death from BCC, however, is uncommon.

A history of chronic recreational or occupational sun exposure is typically observed in patients diagnosed with basal cell carcinoma. Common symptoms presented at diagnosis include lesions or sores that (a) won't heal, (b) vary in duration, and (c) often bleed when exposed to mild trauma, such as towel washing or drying.

Because there are several subtypes of BCC, it is critical for the health care provider to recognize and distinguish between the various subtypes in order to prescribe appropriate therapy. For example, aggressive therapy is often necessary for variants such as micronodular, infiltrating, morpheaform and superficial basal cell carcinoma.

Superficial basal cell carcinoma (sBCC) is one subtype of basal cell carcinoma. sBCC is the most common form of skin cancer, but it is readily treatable if identified and treated early. sBCC is generally diagnosed by a healthcare provider after biopsy. Typically, sBCC slowly progresses and clinically appears as erythematosus eruptions or lesions. sBCC lesions may appear as new growths on the skin, as open sores that fail to heal, or as changes in appearance of an old growth on the skin. Generally, however, the sBCC lesions are usually not painful and may have different shapes and colors. sBCC lesions often present as pink to red-brown scaly patches or papules with a whitish scale. The sBCC lesions appear multicentric wherein clinically normal skin and clinically involved skin often intervene or commingle. The sBCC patches or papules may mimic eczema or psoriasis. sBCC skin changes to look for include the following:

A small, smooth, shiny lump that may be pale or waxy;
A firm, red lump;
A sore or lump that bleeds or is covered by a scab; and/or
A red or brown patch that is rough or scaly and may itch or become tender.

sBCC is usually treated by surgical removal.

On Jul. 14, 2004, the FDA approved the use of Aldara® (imiquimod) 5% cream under biopsy-confirmed, primary superficial basal cell carcinoma (sBCC) in immunocompetent adults, with a maximum tumor diameter of 2.0 cm, located on the trunk (excluding anogenital skin), neck, or extremities (excluding hands and feet), only when surgical methods are medically less appropriate and patient follow-up can be reasonably assured. According to the Aldara® Package Insert (Label) Revised: March 2007 (Attachment VIII), the histological diagnosis of sBCC should be established prior to treatment with Aldara® (imiquimod) 5% cream, because Aldara® (imiquimod) 5% cream at that time was not approved for the treatment of other types of basal cell carcinomas, such as nodular and morpheaform (fibrosing or sclerosing) types.

In the treatment of sBCC diagnosed in adults, the approved dosing regimen for Aldara® (imiquimod) 5% cream is 5 times per week for a full 6 weeks to a biopsy-confirmed superficial basal cell carcinoma. See Aldara® Package Insert (Label) Revised: March 2007. An example of a 5 times per week application schedule is to apply Aldara® (imiquimod) 5% cream, once per day, Monday through Friday, for six full weeks. Aldara® (imiquimod) 5% cream should be applied prior to normal sleeping hours and left on the skin for approximately 8 hours, after which time the cream should be removed by washing the area with mild soap and water.

According to the Aldara® Package Insert (Label) Revised: March 2007, the prescriber should demonstrate the proper application technique to maximize the benefit of Aldara® (imiquimod) 5% cream therapy.

It is also recommended in the Aldara® Package Insert (Label) Revised: March 2007 that patients should wash their hands before and after applying Aldara® (imiquimod) 5% cream and that the patient should wash the treatment area with mild soap and water and allow the area to dry thoroughly before applying the cream.

According to the Aldara® Package Insert (Label) Revised: March 2007, the target sBCC tumor should have a maximum diameter of 2 cm and be located on the trunk (excluding anogenital skin), neck, or extremities (excluding hands and feet). Also according to the Aldara® Package Insert (Label) Revised: March 2007, the treatment area should include a 1 cm margin of skin around the tumor, and that sufficient cream should be applied to cover the treatment area, including 1 centimeter of skin surrounding the tumor. The Aldara® Package Insert (Label) Revised: March 2007 further instructs that the Aldara® (imiquimod) 5% cream should be rubbed into the treatment area until the cream is no longer visible.

As reported in the Aldara® Package Insert (Label) Revised: March 2007, the amount of Aldara® (imiquimod) 5% cream that should be used to treat sBCC is reproduced in Table 1 as follows.

TABLE 1

Amount of Aldara ® Cream to Use for sBCC

| Target Tumor Diameter | Size of Cream Droplet to be Used (diameter) | Approximate Amount of Aldara ® to be Used |
|---|---|---|
| 0.5 to <1.0 cm | 4 mm | 10 mg |
| 1.0 to <1.5 cm | 5 mm | 25 mg |
| 1.5 to 2.0 cm | 7 mm | 40 mg |

According to the Aldara® Package Insert (Label) Revised: March 2007, contact with the eyes, lips and nostrils should be avoided and warns that Aldara® (imiquimod) 5% cream is not for oral, ophthalmic or intravaginal use.

Aldara® (imiquimod) 5% cream is packaged in single-use packets or sachets, with 12 packets supplied per box. Patients should be prescribed no more than 3 boxes (36 packets) for the 6-week treatment period. Unused packets and partially-used packets should be discarded and not reused. See Aldara® Package Insert (Label) Revised: March 2007 (Attachment VIII).

Thus, to date, the FDA has approved imiquimod 5% cream, commercially available under the brand name Aldara®, to treat dermal and/or mucosal-associated conditions, namely, the topical treatment of: (1) external genital and perianal warts, i.e., condyloma acuminate, in patients 12 years or older; (2) clinically typical, nonhyperkeratotic, nonhypertrophic AKs on the face or scalp in immunocompetent adults; and (3) biopsy-confirmed, primary sBCC in immunocompetent adults.

More recently, lower dosage strength formulations of imiquimod cream have been developed for use in effectively treating AKs and EGWs, which contain imiquimod in an amount by weight of between about 1% to about 4.25%, and preferably about 2.5% or about 3.75%. In conjunction with these lower dosage strength formulations, the treatment regimens for AKs and EGW have been uniquely shortened and simplified. These reduced dosage strength formulations and modified treatment regimens are disclosed in (1) U.S. patent application Ser. No. 12/636,613, (2) U.S. patent application Ser. No. 12/771,076, (3) PCT Publication No. WO/2010/080345, (4) PCT International Application No. PCT/US2009/067759, (5) PCT International Application No. PCT/US2010/33245, (6) Canadian Patent No. 2,649,893, issued on Aug. 3, 2010 and entitled "Lower Dosage Strength Imiquimod Formulations and Short Dosing Regimens for treating Actinic Keratosis", (7) the Zyclara® Package Insert (Label) (Attachment IX) for AK treatment with Zyclara® (imiquimod) 3.75% cream, (8) the proposed Zyclara® Package Insert (Label) (Attachment X) submitted to the FDA for EGW treatment with Zyclara® (imiquimod) 3.75% cream, (9) the Zyclara® Canada Product Monograph (Attachment XI) for AK treatment with Zyclara® (imiquimod) 3.75% cream, (10) the proposed Zyclara® Canada Product Monograph (Attachment XII) submitted to Health Canada for EGW treatment with Zyclara® (imiquimod) 3.75% cream, (11) the proposed Zyclara® Package Insert (Label) (Attachment XIII) for submission to the FDA for AK treatment with a pump pre-filled with Zyclara® (imiquimod) 3.75%, (12) the proposed Zyclara® Canada Product Monograph (Attachment XIV) for submission to Health Canada for AK treatment with a pump pre-filled with Zyclara® (imiquimod) 3.75%, and (13) the draft Zyclara® Package Insert (Label) (Attachment XV) for submission to the FDA for AK treatment with a pump pre-filled with Zyclara® (imiquimod) 2.5% cream, each of which is incorporated herein by reference in its entirety.

As discussed in U.S. patent application Ser. No. 12/771,076, and PCT International Application No. PCT/US2010/33245, a patient diagnosed with EGW can apply an effective amount of a lower strength formulation of imiquimod cream, such as a 2.5% or a 3.75% w/w formulation, to the wart area once a day for up to 8 weeks to achieve at least partial, if not complete, clearance of the wart.

Results from a Phase III program evaluating imiquimod 3.75% and 2.5% creams for the treatment of EGW, applied once daily for up to 8 weeks, demonstrated that both dosage strengths were well-tolerated and more efficacious than placebo. According to investigators conducting the study, strong efficacy results with the 3.75% unique formulation along with an enhanced safety profile were observed. More specifically, of those who achieved initial complete clearance and entered the 12-week follow-up, complete clearance was sustained in about 69.6% of the subjects on Zyclara® (imiquimod) 3.75% cream. As to the safety profile, a low incidence of treatment-related adverse events such as itching (2.5%), burning (5.8%) or pain (6.8%) at the application sites were observed, and no treatment-related reported systemic adverse events of headache or flu-like symptoms were observed. These surprising data were included in a New Drug Application (NDA) accepted for review by the FDA for the use of Zyclara® (imiquimod) 3.75% cream in an eight-week treatment regimen for the treatment of EGW.

With respect to AK treatment, the FDA, on Mar. 30, 2010, approved a topical 3.75% imiquimod pharmaceutical cream, commercially available under the brand name Zyclara®, to treat clinically visible or palpable actinic keratosis lesions (AKs), of the full face or balding scalp in immunocompetent adults. This newly approved dosing regimen with Zyclara® (imiquimod) 3.75% cream to treat AKs is a novel 6-week treatment regimen involving three cycles, that are equal in duration. In the first cycle of the 6-week treatment regimen, the Zyclara® (imiquimod) 3.75% cream is applied daily for two weeks to the targeted area, i.e., the full face or balding scalp diagnosed with AKs. In the second cycle of the 6-week treatment regimen designated as a rest period cycle, the Zyclara® (imiquimod) 3.75% cream is not applied to the targeted area. In the third or final cycle of the 6-week treatment regimen, the Zyclara® (imiquimod) 3.75% cream is again applied daily for two weeks to the targeted area. This unique 6-week treatment regimen to treat AKs with Zyclara® (imiquimod) 3.75% cream is referred to as a "2-week×~2-week×2-week" or simply a "2×2×2" treatment regimen. See Zyclara®Package Insert (Label) (Attachment IX) attached hereto. See also the proposed Zyclara® Package Insert (Label) for Zyclara® (imiquimod) 2.5% cream to treat AKs in accordance with the 2×2×2" treatment cycle (Attachment XV).

Alternatively, a unique 9-week treatment regimen may be employed to treat AKs with Zyclara® (imiquimod) 3.75% cream or Zyclara® (imiquimod) 2.5% cream, wherein the 9 week treatment regimen involves three cycles as follows: "3-week×3-week×3-week" or simply a "3×3×3" treatment regimen. Like with the 2×2×2 treatment regimen, the Zyclara® cream is applied daily to the targeted or treatment area in the first and third cycles, i.e., applied daily during the first and last 3-week cycles. However, during the second or middle 3-week cycle, it too is a rest period wherein no Zyclara® cream is applied during the second cycle.

One of the unique benefits associated with this new and improved treatment regimen, the Zyclara® (imiquimod) 3.75% cream serendipitously treats sub-clinical AKs (not clinically visible—not initially detected) located in the targeted treatment area at the same time of treatment of clinically visible AKs. Because the Zyclara® (imiquimod) 3.75% cream is applied to the "entire" face or "entire" balding scalp diagnosed with clinically visible AKs, unlike with current Aldara® treatment, the sub-clinical AKs within such treatment area are simultaneously treated with the Zyclara® (imiquimod) 3.75% cream during this "2×2×2" treatment regimen of the clinically visible AKs. These previously unseen AKs, that could appear during treatment, may therefore clear before they have a chance to develop further as a result of this unique "2×2×2" treatment regimen with Zyclara® (imiquimod) 3.75% cream.

The drug imiquimod, contained in both Aldara® and Zyclara®, is an immune response modifier. Chemically, imiquimod is known as 1-(2-methylpropyl)-1H-imidazo[4,5-c]quinolin-4-amine or 1-isobutyl-1H-imidazo[4,5-c]-quinolin-4-amine. Imiquimod has a molecular formula of $C_{14}H_{16}N_4$ and a molecular weight of 240.3. The chemical structural formula for imiquimod is as follows:

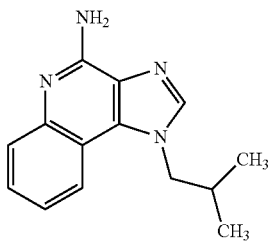 [SMILES: CC(C)Cn1cnc2c(N)nc3ccccc3c21]

Common to each of the FDA-approved treatments with imiquimod for treating EGWs, AKs and sBCC, the correct amount of cream or a specific unit dose to be applied each time by the patient is required for effective therapy. Also common to each of such FDA-approved treatments with imiquimod, is the inconvenient and imprecise use of single-use packets or sachets to apply the topical imiquimod pharmaceutical creams to the treatment areas.

For example, if the Aldara® (imiquimod) 5% cream or Zyclara® (imiquimod) 3.75% cream is applied too thickly or generously, the over dosage can exacerbate unwanted site reactions or local skin reactions, such as erosions or ulcerations, causing pain or dysfunction (e.g., of the foreskin or urethra), and cause undesirable systemic absorption of the imiquimod leading to flu-like symptoms and headaches. Moreover, if the patient is not careful, the patient will inadvertently apply residual Aldara® (imiquimod) 5% cream or Zyclara® (imiquimod) 3.75% cream to other areas of the body compounding over dosage issues that can further exacerbate the unwanted side effects.

If, however, too little imiquimod cream is applied to the targeted areas, the patient may not achieve the maximum level or even an effective level of therapeutic benefit.

Also common to each of the FDA-approved treatments with imiquimod for treating EGW, AK and sBCC, the pharmaceutical concentration and stability of the imiquimod formulation provided to the patient must be maintained throughout the duration of the treatment, which could be for as long as 16 weeks when treating EGWs and AKs with Aldara® (imiquimod) 5% cream or for up to 8 weeks when treating EGWs with Zyclara® 3.75% (imiquimod) cream or for up to 6 weeks when treating sBCC with Aldara® (imiquimod) 5% cream. Thus, the storage devices should not adversely impact the stability, uniformity, dosing concentration or dosing technique of the pre-filled topical semi-solid imiquimod pharmaceutical formulation.

Each gram of Aldara® (imiquimod) 5% cream contains 50 mg of imiquimod and each gram of the Zyclara® (imiquimod) 3.75% cream contains 37.5 mg of imiquimod. The Aldara® (imiquimod) 5% cream and the Zyclara® (imiquimod) 3.75% cream are each formulated in an off-white oil-in-water vanishing cream base consisting of isostearic acid, cetyl alcohol, stearyl alcohol, white petrolatum, polysorbate 60, sorbitan monostearate, glycerin, xanthan gum, purified water, benzyl alcohol, methylparaben, and propylparaben. The Aldara® (imiquimod) 5% cream is packaged in single-use packets or sachets, each containing 250 mg of cream, equivalent to 12.5 mg of imiquimod. The Zyclara® (imiquimod) 3.75% cream is packaged in single-use packets or sachets, each containing 250 mg of cream, equivalent to 9.375 mg of imiquimod.

Unfortunately, single-use packets or sachets pre-filled with an imiquimod pharmaceutical cream are not without drawback. There are several disadvantages associated with providing an imiquimod pharmaceutical cream to a patient in a single-use packet or sachet. Single-use packets or sachets pre-filled with a topical imiquimod pharmaceutical cream are, for example, notoriously messy, difficult and clumsy to use, and more importantly notably imprecise. These known drawbacks can lead to needless product waste, overdosing, inadequate dosing, failed compliance, contamination and/or passive (unintended) transfer to other areas of the patients' bodies, such as the eyes, ears, nose, mouth and vagina.

To underscore these drawbacks, patients often fail to apply the appropriate dosage amount or to ensure that all of the imiquimod cream is squeezed out of the single-use packet or sachet during application to the treatment area. Consequently, patients are frequently under-dosed or over-dosed, which can lead to poor patient compliance.

This problem is recognized in the FDA-approved Labels and Health Canada-approved Labels for both the Aldara® (imiquimod) 5% cream and the Zyclara® (imiquimod) 3.75% cream, as well as in the proposed FDA Labels and Health Canada Labels for the Zyclara® (imiquimod) 3.75% cream and in the draft FDA-Label for Zyclara® (imiquimod) 2.5% cream, each of which are incorporated herein by reference in their entireties. See, for example, Attachments VIII and XV, respectively. In each of the FDA-approved and FDA-proposed Labels and in each of the Health Canada-approved and Health Canada-proposed Labels, the prescriber is clearly instructed to demonstrate the proper application technique for the Aldara® (imiquimod) 5% cream, the Zyclara® (imiquimod) 3.75% cream and the Zyclara® (imiquimod) 2.5% cream, respectively, to the patients to minimize or avoid these drawbacks. Thus, dosing inconsistencies and product waste associated with single-use packets or sachets pre-filled with a topical imiquimod pharmaceutical cream are problematic, common and cause for concern.

Another drawback associated with single-use packets or sachets pre-filled with a topical imiquimod pharmaceutical cream concerns excessive contact with and improper application technique of the dispensed imiquimod pharmaceutical creams from the single-use packets or sachets by the patients. Because imiquimod is an immune response modifier, minimal patient contact and proper application technique is important to avoid imiquimod cream contamination, imprecise dosing, product waste, passive transfer to other parts of the patient's body that are outside of the treatment area, such as the eyes, ears, nose, mouth and vagina. These problems are also recognized in each of the FDA-approved, Health Canada-approved and proposed Labels wherein each Label (a) instructs the patients to thoroughly wash their hands "before" and "after" imiquimod cream application, (b) cautions that topical imiquimod creams contact with eyes, lips and nostrils should be avoided, and (c) warns that topical imiquimod creams are not for oral, ophthalmic, or intravaginal use. See Attachments VIII-XV, each of which is incorporated herein by reference in its entirety.

In yet another drawback, single-use packets or sachets pre-filled with a topical imiquimod pharmaceutical cream can be very difficult and cumbersome to use, especially when elderly patients are involved. Opening a single-use packet or sachet pre-filled with a topical imiquimod cream to dispense the imiquimod cream to "only" the targeted area without excessive handling or passive transfer can in some instances present real application technique challenge to those patients inflicted with, for example, limited dexterity, crippling arthritis, vision loss and/or visual acuity loss, which are commonly observed in elderly patients.

In still another drawback, needless product waste often occurs with single-use packets or sachets pre-filled with a topical imiquimod cream. Clear instruction to patients provides that undispensed imiquimod cream and unopened individual packets or sachets pre-filled with a topical imiquimod cream must be discarded. This particular drawback is highlighted in all Labels, the FDA-approved and proposed Labels and the Health Canada approved and proposed Labels for Aldara® (imiquimod) 5% cream and Zyclara® (imiquimod) 3.75% cream, respectively. As stated above, and according to such Labels, unopened and partially used single-use packets or sachets pre-filled with a topical imiquimod cream must be discarded and not reused. See Attachments VIII-XII. See also Attachments XIII-XV.

In yet another drawback associated with single-use packets or sachets pre-filled with a topical imiquimod cream, the single use packets or sachets can be easily lost or misplaced due to the fact that several single-use packets or sachets must be purchased to complete a full course of therapy. This drawback and inconvenience can cause further product waste and needless elevated treatment costs due to necessary product replacement. More seriously, this drawback and inconvenience can lead to failed patient compliance and ineffective imiquimod therapy.

In still another drawback associated with such single-use packets or sachets, imiquimod cream degradants may develop over time as a result of storage in the single-use packets or sachets. This drawback can cause an adverse effect on overall efficacy and/or stability of the imiquimod cream formulations packaged within the single-use packets or sachets.

Thus, given the numerous drawbacks associated with single-use imiquimod cream packets or sachets, there is a real need for a simple, safe, clean, easy-to-use, compact, reliable and all-in-one storage system for dispensing topical semi-solid imiquimod pharmaceutical formulations that: (i) can dispense a controlled and precise amount of imiquimod cream each and every time the topical imiquimod formulation is applied to a treatment area, (ii) is easy and convenient for any patient, young or old, to use; (iii) improves imiquimod therapy compliance and effectiveness, (iv) provides the same unit dose, such as approximately 250 mg of imiquimod formulation, per each actuation, i.e., a reproducible dose amount, so that an effective dose is administered each and every time; (v) does not interfere with or hinder imiquimod application technique, (vi) minimizes if not eliminates product waste and product loss, (vii) minimizes if not eliminates excessive patient contact to avoid passive transfer; (viii) minimizes and/or prevents degradant formation during imiquimod formulation storage; and (ix) is compatible for use with topical semi-solid imiquimod formulations, for example, topical 2.5%, 3.75% and 5% weight to weight imiquimod creams, for treating dermal and/or mucosal-associated conditions, such as external genital warts, perianal warts, actinic keratoses and superficial basal cell carcinoma.

SUMMARY OF THE INVENTION

The present invention overcomes certain of the above-mentioned problems and drawbacks of the present state of the art of topical imiquimod therapy using single-use packets or sachets pre-filled with an imiquimod pharmaceutical cream through the development of a novel and unique storage and dispensing system that includes a pump or dispensing package pre-filled with a topical semi-solid imiquimod pharmaceutical formulation (hereinafter, a "pump system"), preferably a topical imiquimod pharmaceutical cream, in a selected dosage strength for dispensing a plurality of precisely measured unit-doses of the imiquimod formulation over pump life, in which each precisely measured unit dose dispensed is consistent in uniformity and amount, for effectively treating dermal and/or mucosal-associated conditions, such as external genital warts or perianal warts (EGWs), actinic keratosis or actinic keratoses (AK or AKs) or superficial basal cell carcinoma (sBCC).

Uniquely, the novel pump systems of the present invention are clean and sanitary, safe and simple and easy to use. In addition, the novel and unique pump systems of the present invention are compact (hand held) and easy to store, they are reliable, they minimize product waste, and they improve application technique of the dispensed topical semi-solid imiquimod pharmaceutical formulations when treating dermal and/or mucosal-associated conditions, such as EGWs, AKs or sBCC.

In view of these and other novel and unique features of the pump systems of the present invention, it is believed that the effectiveness and benefits of topical imiquimod therapy can now be maximized and that certain if not all drawbacks associated with the use of single-use packets or sachets to deliver topical imiquimod pharmaceutical cream can now be minimized if not eliminated.

The unique pump systems of the present invention include, inter alia, a dispensing package that has a tubular main body portion and a manually-operated airless pumping device mounted on the main body portion. The main body portion of the dispensing package defines a fluid storage chamber. The airless pumping device defines a dispensing duct which terminates in a self-closing discharge orifice. In alternative embodiments, the airless pumping device can include a cap or cover for sealing or covering the discharge orifice. The cap or cover can be operated automatically or manually.

The pump system of the present invention further includes a topical semi-solid imiquimod pharmaceutical formulation, such as a topical imiquimod pharmaceutical cream formulation, which is disposed at least partially within the fluid storage chamber defined in the main body portion of the dispensing package. The system is constructed such that manual operation of the airless pumping device causes a portion of the imiquimod cream to be withdrawn from within the fluid storage chamber into the dispensing duct thereby causing the self-closing discharge orifice to open and to dispense, per actuation, a predefined, uniform and precisely measured unit-dose amount of a topical imiquimod pharmaceutical cream formulation from the dispensing package.

Thus, the novel pump systems of the present invention now afford patients with the unique advantage of applying a consistent, precisely measured and uniform unit-dose of a topical semi-solid imiquimod pharmaceutical formulation from a clean, safe, easy and simple to use, compact and reliable pump system to a treatment area per each application, so that application technique and patient compliance are improved and the effectiveness and benefits of topical imiquimod therapy are maximized, while minimizing (a) imprecise or inconsistent dosing amounts, i.e., under-dosing or over-dosing, (b) unwanted passive transfer of the dispensed topical imiquimod cream due to improper handling of the imiquimod cream and poor application technique, (c) imiquimod cream waste, and (d) unused product and/or product loss, each of which can contribute to poor patient compliance and less effective, if not ineffective, topical imiquimod therapy.

Preferably, a topical semi-solid imiquimod pharmaceutical formulation contains imiquimod in an amount by weight of between about 1% and about 10% w/w and more preferably a topical semi-solid imiquimod pharmaceutical formulation contains imiquimod in an amount by weight of between about 1% and about 5%. Even more preferably, the topical semi-solid imiquimod pharmaceutical formulations can contain imiquimod in an amount by weight of between about 1% and 4.25% w/w, and most preferably, the topical semi-solid imiquimod pharmaceutical formulations can contain imiquimod in an amount by weight of about 2.5%, about 3.75% or about 5%.

In a preferred embodiment, the fluid storage chamber formed in the main body portion of the dispensing device is adapted and configured for storing about 15 grams of a topical semi-solid imiquimod pharmaceutical formulation, namely, a topical imiquimod pharmaceutical cream formulation, e.g., Aldara® (imiquimod) 5% cream, Zyclara® (imiquimod) 3.75% cream or a 2.5% imiquimod pharmaceutical cream described herein. In alternative constructions, the fluid storage chamber can be adapted and configured for storing about 7.5 grams of a topical semisolid imiquimod pharmaceutical formulation, such as a topical imiquimod pharmaceutical cream formulation, namely, Aldara® (imiquimod) 5% cream, Zyclara® (imiquimod) 3.75% cream or a 2.5% imiquimod pharmaceutical cream described herein.

It should be understood by those versed in this art that the pump systems of the present invention can be pre-filled with any suitable topical semi-solid imiquimod pharmaceutical formulation, such as a cream, an ointment, a lotion, a balm, a salve or the like, that can be effectively dispensed there from in accordance with the teachings of the present invention without departing from the purpose or scope of the present invention. Thus, when the pump systems of the present invention are described as being pre-filled with a topical imiquimod pharmaceutical cream, such description is done so for exemplary purposes without intent to be bound to any particular topical semi-solid imiquimod dosage form or formulation.

It is envisioned that certain constructions of the present invention further include a take-up piston which is slidably disposed within the tubular main body portion so as to partially define the fluid storage chamber. The take-up position moves axially towards the pumping device when the pumping device is manually operated, so as to reduce the volume of the fluid storage chamber by an amount which is equivalent to the volume of imiquimod cream formulation dispensed from the dispensing package, i.e., the unit-dose amount. In constructions wherein the take-up piston defines a portion of the fluid storage chamber, it can be positioned during assembly to established the desired volume of the fluid storage chamber. For example, if it is desired to pre-fill the dispensing device with 15 g of an imiquimod cream, the piston can be initially positioned during the filling operation at a distance from the top of the main body portion of the dispensing package such that the volume of the fluid storage chamber corresponds to the volume required to hold 15 g of imiquimod cream. Alternatively, if 7.5 grams of cream is to be stored, the piston can be moved the appropriate distance towards the top of the main body portion of the dispensing package to accommodate 7.5 g of imiquimod cream. Of course, it should be appreciated by those versed in this art that the imiquimod pump systems of the present invention contemplate functional fluid storage chambers that can accommodate any desired volume of imiquimod cream, including fluid storage chambers that can hold and store volumes greater or lesser than 7.5 g or 15 g of imiquimod cream, so long as the objectives of the present invention are not defeated.

Preferably, with each operation of the pumping device, an amount of the imiquimod cream formulation which is within about 15% of the predefined unit dose is discharged from the dispensing device per actuation. Still further, after multiple operations of the pumping device, the overall average of the dose value is within about 10% of the predefined unit dose per actuation. In certain constructions, it is envisioned that the predefined unit dose amount dispensed per actuation is about 250 mg, and more preferably about 240 mg.

It is preferred that no more than about 5 manual actuations of the pumping device are required to effectively prime the pumping device and start observing the discharging of imiquimod cream formulation from the self-closing discharge orifice.

Following the initial operation or priming of the pumping device, imiquimod cream uniquely remains within the dispensing duct, i.e., the pump is now primed. Preferably, about 85% or more of the imiquimod cream contained within the dispensing duct of the pumping device following each actuation remains in the dispensing duct during storage and prior to the next actuation by the patient, so that the same uniform and consistent unit dose amount is dispensed per each actuation, even when a pump system of the present invention has been stored (static—not actuated) for a few days or a few weeks between actuations, consistent with the prescribed treatment regimens and/or rest periods taken when treating a diagnosed dermal and/or mucosal-associated condition, such as, external genital warts, perianal warts, actinic keratosis or superficial basal cell carcinoma, with a topical semi-solid imiquimod pharmaceutical formulation as described herein.

The present invention is further directed to a pump system for treating a subject diagnosed with a dermal and/or mucosal-associated conditions, such as genital warts or perianal warts, actinic keratosis or superficial basal cell carcinoma, which includes, inter alia, a dispensing package that is pre-filled with a topical semi-solid imiquimod pharmaceutical formulation, such as an imiquimod cream formulation. The dispensing package includes a lower subassembly and an upper subassembly. The lower subassembly has a tubular body portion that defines an elongated interior fluid storage chamber into which a take-up piston element is slidably disposed. The upper subassembly is mounted upon the lower subassembly and includes a dispensing head and an airless pumping mechanism. The dispensing head has an internal fluid passage or discharge duct formed therein which terminates in a self-closing outlet. The dispensing head also includes a finger-operated actuator which is operatively associated with the airless pumping mechanism. The dispensing package may further include a cap to seal or cover the dispensing head or nozzle.

The topical semi-solid imiquimod pharmaceutical formulation, e.g., an imiquimod cream formulation, is disposed at least partially within the fluid storage chamber defined in the tubular body portion of the lower subassembly of the dispensing package. Operation of the finger-operated actuator causes the airless pumping mechanism to withdraw a portion of the imiquimod cream from within the interior chamber and to dispense the imiquimod cream into the internal fluid passage formed in the dispensing head wherein the pressure of the dispensed cream causes the self-closing outlet to open thereby discharging a predetermined final unit dose of imiquimod cream from the dispensing head.

In certain preferred embodiments, the take-up piston is disposed within the tubular body portion so as to partially define the fluid storage chamber. The take-up position is arranged such that it moves axially towards the pumping device when the pumping device is manually operated, so as to reduce the volume of the fluid storage chamber by an amount which is equivalent to the volume of imiquimod cream dispensed from the dispensing package, i.e., the unit dose amount, as discussed above.

In a pump system for treating a subject diagnosed with a dermal and/or mucosal-associated conditions, such as EGWs, AKs or sBCC, the pump system includes a dispensing package that has a tubular main body portion and a manually-operated airless pumping device mounted on the main body portion. The main body portion of the dispensing package defines a fluid storage chamber which is in fluid communication with a dispensing duct which is defined in the pumping device and that terminates in a discharge orifice.

The pump system of the present invention further includes a mechanism for closing the discharge orifice when the dispensing package is not in use and a topical semi-solid imiquimod pharmaceutical formulation, e.g., an imiquimod cream formulation, that is disposed at least partially within the fluid storage chamber defined in main body portion of the dispensing package. Wherein, manual operation of the airless pumping device causes a portion of the imiquimod cream to be withdrawn from within the fluid storage chamber and a predefined unit dose of imiquimod cream to be dispensed from the discharge orifice of the dispensing package. Preferably, the mechanism for closing the discharge orifice when the dispensing package is not in use includes a shutter element that has a self-closing orifice. Alternatively or additionally, the mechanism for closing the discharge orifice when the dispensing package is not in use can include a cap, a cover or a plug.

The present invention is also directed to methods for treating dermal and/or mucosal-associated conditions with the novel and unique pump systems pre-filled with topical semi-solid imiquimod pharmaceutical formulations. Generally speaking, the methods of the present invention comprise treating a dermal and/or mucosal-associated condition with a topical semi-solid imiquimod pharmaceutical formulation dispensed from a novel and unique imiquimod pump system of the present invention in accordance with effective treatment regimens, such as those treatment regimens described herein. For example, the methods of the present invention comprise (1) actuating a primed dispensing pump system pre-filled with a topical semi-solid imiquimod pharmaceutical formulation to dispense there from an effective precisely measured unit-dose amount of the pre-filled topical semi-solid imiquimod pharmaceutical formulation for treating a dermal and/or mucosal-associated condition, wherein the unit-dose amount dispensed per each actuation is the same effective precisely measured unit-dose amount for consistent dose application over the course of the treatment regime, and (2) applying the dispensed unit-dose amount to a treatment area diagnosed with a dermal and/or mucosal-associated condition in accordance with the treatment regimen to treat the diagnosed dermal and/or mucosal-associated condition.

It of course should be understood that the methods of the present invention contemplate the use of any suitable topical semi-solid imiquimod pharmaceutical formulation, preferably imiquimod pharmaceutical creams, wherein the imiquimod is present in an amount by weight of about 1% to about 10% w/w, and more preferably in an amount by weight of about 1% to about 5% w/w, and even more preferably in an amount by weight of about 2.5% w/w, about 3.75% w/w and about 5% w/w.

It should also be understood, as discussed above, that the methods of the present invention envision treatment of dermal and/or mucosal-associated conditions such as external genital warts and/or perianal warts (EGWs), actinic keratosis (AKs) and superficial basal cell carcinoma (sBCC) in accordance with effective treatment regimens such as those described here in throughout.

Thus, when practicing the pump systems of the present invention, each unit-dose amount dispensed from an imiquimod pump system per each actuation is the same precisely measured unit-dose amount, preferably pre-selected at the time of pump fill, so that the same precisely measured unit-dose amount of the pre-filled topical semi-solid imiquimod pharmaceutical formulation is delivered to the targeted treatment area per each application in accordance with an effective treatment regimen, so that the effectiveness and benefits of topical imiquimod treatment of a treated dermal and/or mucosal-associated condition, such as EGWs, AKs or sBCC, are maximized and the drawbacks associated with single-use imiquimod packets or sachets are minimized, if not eliminated.

To further illustrate certain unique advantages of the pump systems of the present invention, once such a pump system pre-filled with a topical semi-solid imiquimod pharmaceutical formulation, such as a 3.75% w/w imiquimod cream as described herein, is primed, each pre-selected unit-dose amount of the 3.75% w/w imiquimod cream dispensed there after will be repeatedly and consistently dispensed over pump life. Thus, if the pre-selected unit-dose amount to be delivered per actuation is about 240 mg, each single actuation of a primed pump system will consistently deliver about 240 mg of the 3.75% imiquimod cream.

Of course, it should be appreciated that the number of single unit-doses that will be dispensed over pump life will be a function of the total pre-fill volume and the pre-selected unit-dose amount. Thus, if the pre-fill volume is, e.g., 15 g, and the pre-selected unit-dose amount per actuation or pump is about 240 mg, such a pre-filled pump will have the ability to deliver about 62 unit-doses of imiquimod cream at about 240 mg/pump over pump life. If, however, the pre-fill pump volume is, e.g., 7.5 g, such a pre-filled pump will have the ability to deliver about 31 unit-doses of imiquimod cream at about 240 mg/pump over pump life.

Thus, a pump system of the present invention pre-filled with about 15 g of, for example, a 3.75% w/w imiquimod cream or a 5% w/w imiquimod cream, can accommodate, for example, the following two treatment regimens for treating EGWs when each unit-dose dispensed is: (1) single unit doses of about 240 mg of a 3.75% imiquimod cream/pump that is to be applied daily for up to 8 weeks or for up to a total of about 56 single unit-doses of 3.75% imiquimod cream (56 individual pumps) over the course of the treatment regimen; or (2) single unit-doses of about 240 mg of a 5% imiquimod cream/pump to be applied three times a week for up to 16 weeks or for up to a total of about 48 single unit-doses of 5% imiquimod cream (48 individual pumps) over the course of the treatment regimen. On the other hand, if a pump system of the present invention is prefilled with about 7.5 g of, for example, a 3.75% w/w imiquimod cream or a 5% w/w imiquimod cream, such a pre-filled pump can accommodate the following two treatment regimens for treating AKs or sBCC when each unit-dose dispensed is: (1) single unit doses of about 240 mg of a 3.75% imiquimod cream/pump applied daily in accordance with a 2×2×2 treatment regimen to treat AKs or for up to a total of about 28 single unit-doses of 3.75% imiquimod cream (28 individual pumps) over the course of the 2×2×2 treatment regimen for AK treatment; or (2) single unit-doses of about 240 mg of a 5% imiquimod cream/pump applied five times a week for up to 6 weeks to treat sBCC or for up to a total of about 30 single unit-doses of 5% imiquimod cream (30 individual pumps) over the course of the treatment regimen for sBCC treatment.

It should be appreciated that the above is described when only a single pump for dispensing an unit-dose amount of about 240 mg/unit-dose is to be applied during the appropriate treatment regimen. However, when a unit-dose of about 480 mg/unit-dose is required per application in accordance with an appropriate treatment regimen, two pumps or actuation will be required (if the pre-set unit dose per pump is about 240 mg/pump) to deliver the necessary 480 mg unit-dose per application and that at least two 7.5 g or at least two 15 g pumps should be prescribed and dispensed to complete the prescribed treatment regimen when appropriate. Thus, it should be realized by those of skill in the art that the number of pump systems pre-filled with a topical semi-solid imiquimod pharmaceutical formulation that are to be prescribed and dispensed will, of course, depend upon (1) the pre-fill volume of the pump system, (2) the precisely measured amount of the unit-dose dispensed per pump or actuation, and (3) the appropriate treatment regimen selected to treat a treatment area diagnosed with a dermal and/or mucosal-associated condition, such as EGWs, AKs or sBCC.

To illustrate further, a method of the present invention contemplates treating a patient diagnosed with a dermal and/or mucosal-associated condition, such as EGWs, AKs or sBCC, with a topical semi-solid imiquimod pharmaceutical formulation, wherein such method includes: (1) priming a pump system pre-filled with a topical semi-solid imiquimod pharmaceutical formulation, e.g., an imiquimod cream, to prepare the pump system to dispense a plurality of predefined, precisely measured and consistent unit-doses of the topical imiquimod formulation to treat the diagnosed dermal and/or mucosal condition in accordance with an appropriate treatment regimen; (2) pumping the primed pump system no more than twice to dispense one of the predefined and precisely measured unit-doses onto a treatment area diagnosed with the dermal and/or mucosal-associated condition in accordance with an appropriate treatment regimen, (3) rubbing the dispensed unit dose amount of topical imiquimod cream into the treatment area until the dispensed unit-dose is no longer visible, (4) leaving the rubbed-in unit dose on the treatment area for a sufficient treatment period in accordance with the appropriate treatment regimen, for effectively treating the diagnosed dermal and/or mucosal condition; and (5) repeating the above-recited pumping or actuating step (2), the above-recited rubbing step (3) and the above-recited leaving step (4) a number of times as specified by the appropriate treatment regimen to effectively treat the diagnosed dermal and/or mucosal-associated condition and to maximize the benefit of topical imiquimod treatment.

When practicing the methods of the present invention, it is preferable for the patient to wash his/her hands with mild soap and water before and after dispensing each prescribed unit-dose from an imiquimod pump system of the present invention. It is also preferable to wash the treatment area diagnosed with a dermal and/or mucosal-associated condition with soap and water and to allow the washed treatment area to dry before dispensing the prescribed unit-dose from the pump system and applying such dispensed unit-dose to the targeted treatment area. Also, when carrying out the methods of the present, it is preferable to avoid contacting the dispensed unit-dose with the eyes, lips, nostrils, mouth and/or vagina of the patient.

More specifically, a method of the present invention comprises applying a topical semi-solid imiquimod pharmaceutical formulation, and preferably applying a topical imiquimod pharmaceutical cream, dispensed from an airless pump system of the present invention, equipped with a cap for protecting the dispensing head, to a treatment area of a patient diagnosed with a dermal and/or mucosal-associated condition to treat the dermal and/or mucosal-associated condition. More particularly, this one such method comprises (a) washing a treatment area diagnosed with a dermal and/or mucosal-associated condition to treat the dermal and/or mucosal-associated condition where the imiquimod cream will be applied with mild soap and water, (b) allowing the washed treatment area to dry, (c) washing the hands of the patient and allowing the washed hands to dry, (d) removing the cap from the pump system prefilled with a topical imiquimod pharmaceutical cream, (e) tilting the pump system for dispensing the imiquimod cream there from, (f) priming the pump system by firmly pressing the top of the pump or dispensing head all the way down up to about five times as needed until the imiquimod cream appears at the dispensing head outlet, (g) dispensing the primed imiquimod cream from the dispensing head into a paper tissue and then discarding such dispensed cream, (h) pressing the top of the pump system or dispensing head all of the way down up to two times as needed to dispense a precisely measured unit-dose of the topical imiquimod pharmaceutical cream into the hand of the patient, (i) applying the precisely measured unit-dose of the topical imiquimod pharmaceutical cream to the washed and dried treatment area in accordance with a prescribed treatment regimen for treating the treatment area diagnosed with the dermal and/or mucosal-associated condition, (j) rubbing the applied unit-dose all the way into the washed and dried treatment area, (k) re-washing the hands of the patient after the unit-dose has been rubbed into the washed and dried treatment area, (l) leaving the rubbed-in imiquimod cream on the treatment area, without wetting or washing the treated treatment area, for up to about 8 hours to treat the dermal and/or mucosal-associated condition, (m) re-washing the treated treatment area with soap and water after the 8 hours has passed, and (n) repeating the said steps (h) through (m) herein in accordance with a prescribed treatment regimen to dispense and apply precisely measured and reproducible unit-doses of the topical imiquimod pharmaceutical cream to effectively treat the diagnosed dermal and/or mucosal-associated condition, wherein each said unit-dose dispensed from the pump system of the present invention during step (h) is a precisely measured, consistent, reproducible and uniform amount, so that they same dosage amount of the topical imiquimod pharmaceutical cream is applied each and every time over the course of the prescribed treatment regimen, thereby avoiding dosing inconsistencies and other drawbacks observed or associated with single-use packets or sachets.

It is also a feature of the present invention to instruct prescribers and patients as to: (1) the correct use of the pre-filled imiquimod pump systems and treatment regimens in order to optimally practice the pre-filled imiquimod pump systems of the present invention to effectively treat dermal and/or mucosal associated conditions, such as EGWs, AKs or sBCC, with topical imiquimod therapy; (2) the correct way for prescribers to prescribe the pre-filled imiquimod pump systems, including the treatment regimens, of the present invention to effectively treat dermal and/or mucosal associated conditions, such as EGWs, AKs or sBCC; and (3) the correct way for patients in need of therapy to practice the pre-filled imiquimod pump systems in accordance with the present invention to effectively treat dermal and/or mucosal associated conditions, such as EGWs, AKs or sBCC, and to maximize the benefits of topical imiquimod therapy.

The present invention also contemplates the use of instructions provided on, for example, a label, package insert or other communicative materials to teach prescribers and/or patients how to correctly and most effectively prescribe and use, respectively, the pre-filled imiquimod pump systems of the present invention to effectively treat dermal and/or mucosal associated conditions, such as EGWs, AKs or sBCC, and to maximize the benefits of topical imiquimod therapy.

Thus, it should now be clear that the present invention uniquely affords a proper, safe, convenient, easy and advantageous way to use the novel pre-filled imiquimod pumps to practice treatment regimens of the present invention to improve patient compliance and to more effectively treat dermal and/or mucosal-conditions, such as EGWs, AKs or sBCC, with topical semi-solid imiquimod pharmaceutical formulations, such as with topical semi-solid imiquimod pharmaceutical creams, while mitigating, if not eliminating, the drawbacks associated with the use of single-use packets or sachets pre-filled with topical imiquimod formulations to treat the same skin disorders.

The above summary of the present invention is not intended to describe each disclosed embodiment or every implementation of the present invention. The description and examples that follow more particularly exemplify illustrative embodiments. In several places throughout the specification, guidance is provided through lists of examples, which examples can be used in various combinations. In each instance, the recited list serves only as a representative group and should not be interpreted as an exclusive list.

BRIEF DESCRIPTION OF THE DRAWINGS

So that those having ordinary skill in the art to which the present invention pertains will more readily understand how to employ the pump systems and methods of the present invention, embodiments thereof will be described in more detail herein below with reference to the drawings, wherein.

Figure 1:
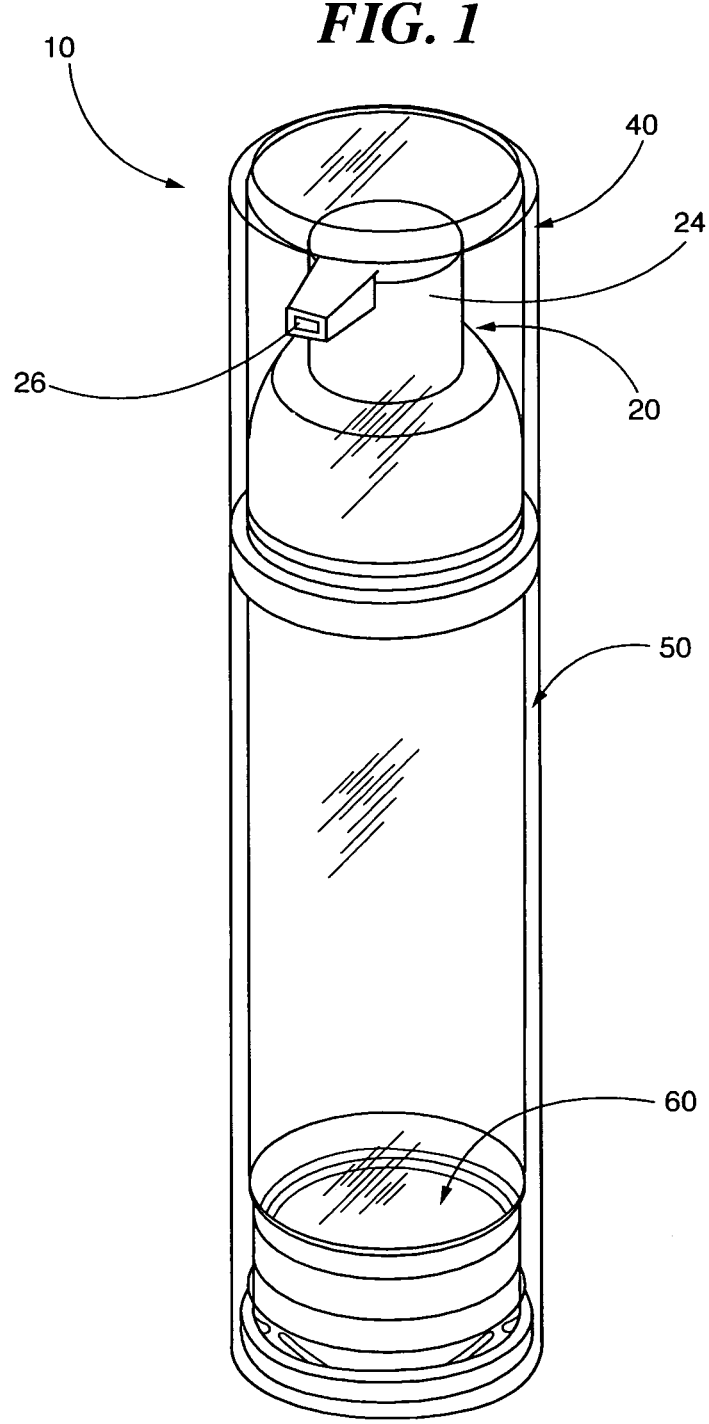
FIG. 1 is a perspective view of a dispensing package which has been constructed in accordance with a preferred embodiment of the present invention.

These and other aspects of the subject invention will become more readily apparent to those having ordinary skill in the art from the following detailed description of the invention taken in conjunction with the drawings and examples.

DETAILED DESCRIPTION

Disclosed herein are detailed descriptions of specific embodiments of the devices, systems and methods for storing and dispensing unit doses of a topical semi-sold imiquimod pharmaceutical formulation, such as an imiquimod cream. It will be understood that the disclosed embodiments are merely examples of the way in which certain aspects of the invention can be implemented and do not represent an exhaustive list of all of the ways the invention may be embodied. Indeed, it will be understood that the pump systems, devices, methods and package assemblies described herein may be embodied in various and alternative forms. The figures are not necessarily to scale and some features may be exaggerated or minimized to show details of particular components. Well-known components, materials or methods are not necessarily described in great detail in order to avoid obscuring the present disclosure. Any specific structural and functional details disclosed herein are not to be interpreted as limiting, but merely as a basis for the claims and as a representative basis for teaching one skilled in the art to variously employ the invention.

Thus, by way of illustrating and providing a more complete appreciation of the present invention and many of the attendant advantages thereof, the following detailed description and examples are given concerning the novel methods and compositions.

Unless otherwise indicated, all numbers expressing quantities, ratios, and numerical properties of ingredients, reaction conditions, and so forth used in the specification and claims are to be understood as being modified in all instances by the term "about".

All parts, percentages, ratios, etc. herein are by weight unless indicated otherwise.

As used herein, the singular forms "a" or "an" or "the" are used interchangeably and intended to include the plural forms as well and fall within each meaning, unless expressly stated otherwise. Also as used herein, "at least one" is intended to mean "one or more" of the listed elements. Singular word forms are intended to include plural word fauns and are likewise used herein interchangeably where appropriate and fall within each meaning, unless expressly stated otherwise. Except where noted otherwise, capitalized and non-capitalized forms of all terms fall within each meaning.

The compound imiquimod is a known antiviral agent that is also known to induce interferon biosynthesis. It can be prepared using the method disclosed in U.S. Pat. No. 4,689,338, the disclosure of which is incorporated herein by reference in its entirety. The compound can be used to treat dermal and/or mucosal-associated conditions, such as external genital and perianal warts (EGWs), actinic keratoses (AKs) or superficial basal cell carcinoma (sBCC). The amount of imiquimod present in a topical semi-solid imiquimod pharmaceutical formulation of the present invention will be an effective amount to treat a dermal and/or mucosal-associated condition, for example, (a) EGWs, (b) AKs or (c) sBCC, as described herein. An example of an effective amount of imiquimod in a formulation of the present invention is between about 1. percent and about 10 percent by weight based on the total weight of a formulation, more preferably between about 2.5% and 5%, and more preferably about 1.25%, 1.5%, 1.75%, 2.0%, 2.25%, 2.5%, 2.75%, 3.0%, 3.25%, 3.5%, 3.75%, 4.0%, 4.25%, 4.5%, 4.75% and 5%, even more preferably between about 2.0%, 2.25%, 2.5%, 2.75%, 3.0%, 3.25%, 3.5%, 3.75% and 4.0%, and still even more preferably between about 2.5%, 2.75%, 3.0%, 3.25%, 3.5% and 3.75%. Imiquimod formulations of the present invention that contain about 2.5% imiquimod, about 3.75% imiquimod or about 5% imiquimod by weight based on the total weight of the formulations are most preferred.

By the term "bioequivalence or bioequivalent", as used herein, it refers to topical semi-solid imiquimod pharmaceutical formulations in which they are pharmaceutically equivalent and their bioavailabilities (rate and extent of absorption) after administration in the same molar dosage or amount are similar to such a degree that their therapeutic effects, as to safety and efficacy, are essentially the same. In other words, bioequivalence or bioequivalent means the absence of a significant difference in the rate and extent to which imiquimod becomes available from such formulations at the site of imiquimod action when administered at the same molar dose under similar conditions, e.g., the rate at which imiquimod can leave such a formulation and the rate at which imiquimod can either cross the stratum corneum and/or become available at the site of action to treat a dermal and/or mucosal-associated condition, e.g., EGWs, AKs or sBCC. In other words, there is a high degree of similarity in the bioavailabilities of two topical semi-solid imiquimod pharmaceutical formulations (of the same galenic form) from the same molar dose, that are unlikely to produce clinically relevant differences in therapeutic effects, or adverse reactions, or both. The terms "bioequivalence", as well as "pharmaceutical equivalence" and "therapeutic equivalence" are also used herein as defined and/or used by (a) the FDA, (b) the Code of Federal Regulations ("C.F.R."), Title 21, and/or (c) Health Canada.

By the term "bioavailability or bioavailable", as used herein, it means generally the rate and extent of absorption of imiquimod into the systemic circulation and, more specifically, the rate or measurements intended to reflect the rate and extent to which imiquimod becomes available at the site of action or is absorbed from a topical semi-solid imiquimod pharmaceutical formulation and becomes available at the site of action. In other words, and by way of example, the extent and rate of imiquimod absorption from a topical semi-solid imiquimod pharmaceutical formulation of the present invention as reflected by a time-concentration curve of imiquimod in systemic circulation.

By "pharmaceutical equivalence" or "pharmaceutically equivalent", as used herein, it refers to topical semi-solid imiquimod pharmaceutical formulations of the present invention that contain the same amount of imiquimod, in the same dosage forms, but not necessarily containing the same inactive ingredients, for the same route of administration and meeting the same or comparable compendia or other applicable standards of identity, strength, quality, and purity, including potency and, where applicable, content uniformity and/or stability.

By "therapeutic equivalence" or "therapeutically equivalent", it is meant herein to mean those topical semi-solid imiquimod pharmaceutical formulations which (a) will produce the same clinical effect and safety profile when practicing treatment regimens to treat a dermal and/or mucosal-associated condition, namely, EGWs, AKs or sBCC, in accordance with the present invention and (b) are pharmaceutical equivalents, e.g., they contain imiquimod in the same dosage form, they have the same route of administration; and they have the same imiquimod strength. In other words, therapeutic equivalence means that a chemical equivalent of a topical semi-solid imiquimod pharmaceutical formulation of the present invention (i.e., containing the same amount of imiquimod in the same dosage form) when administered to the same individuals in the same dosage regimen will provide essentially the same efficacy and toxicity.

The topical semi-solid imiquimod pharmaceutical formulations, such as the topical imiquimod pharmaceutical creams, according to the present invention can be applied to any suitable location, for example, applied topically to dermal and/or mucosal surfaces. In the case of dermal application, for example, depending on the imiquimod concentration, formulation composition, and dermal surface, the therapeutic effect of imiquimod may extend only to the superficial layers of the dermal surface or to tissues below the dermal surface. Thus, another aspect of the present invention is directed to a method for the treatment of a dermal and/or mucosal-associated condition comprising applying to skin one of the imiquimod creams via a pump system of the present invention. As used herein, a "dermal and/or mucosal-associated condition" means an inflammatory, infectious, neoplastic or other condition that involves a dermal and/or mucosal surface or that is in sufficient proximity to a dermal and/or mucosal surface to be affected by a therapeutic agent topically applied to the surface. Examples of a dermal and/or mucosal-associated condition include warts, atopic dermatitis, postsurgical scars, lesions caused by a herpes virus, and epidermal neoplasias, such as for example actinic keratosis, pre-actinic keratosis lesions, malignant melanomas, basal cell carcinoma, and squamous cell carcinoma.

In some embodiments, the topical semi-solid imiquimod pharmaceutical formulations, e.g., topical imiquimod pharmaceutical creams, are particularly advantageous for use with the pump systems of the present invention for dermal and/or mucosal application for a period of time sufficient to obtain a desired therapeutic effect without undesired systemic absorption of the imiquimod.

In view of the above, it should be understood by those versed in this art that the present invention contemplates pump systems and methods for storing and dispensing consistent and uniform unit dose amounts of an effective topical semi-solid imiquimod pharmaceutical formulation, and more particularly to pump systems, pre-filled with any effective topical semi-solid imiquimod pharmaceutical formulation, and methods for delivering a precisely measured unit dose amount of any effective topical semi-solid imiquimod pharmaceutical formulation, and still more particularly to pump systems pre-filled with an effective topical semi-solid imiquimod pharmaceutical formulation, and methods for using a controlled delivery pump to store and dispense multiple unit doses of an effective topical semi-solid imiquimod pharmaceutical formulation for use in treating dermal and mucosal-associated conditions, such as, EGWs, AKs and sBCC. It should therefore be understood by those versed in this art that the present invention also contemplates pump systems pre-filled with an effective topical semi-solid imiquimod pharmaceutical formulation that is bioequivalent, pharmaceutically equivalent and/or therapeutically equivalent to, for example, Aldara® (imiquimod) 5% cream, Zyclara®(imiquimod) 3.75% cream or a 2.5% imiquimod cream or any imiquimod formulation set forth herein, or which meets or has the same imiquimod bioavailability as, for example, Aldara® (imiquimod) 5% cream, Zyclara® (imiquimod) 3.75% cream, or a 2.5% imiquimod cream or any other imiquimod formulation set forth herein, as defined by the FDA, the C.F.R. and/or Health Canada.

For ease of description, the components of this invention are described in an upright operating position, and terms such as upper, lower, front, rear, horizontal, etc., are used with reference to this position. It will be understood, however, that the components of this invention may be manufactured, stored, transported, used and sold in an orientation other than the positions described herein.

FIGs. illustrating the components show some mechanical elements that are known and will be recognized by one skilled in the art. The detailed descriptions of such elements are not necessary to an understanding of the invention, and accordingly, are herein presented only to the degree necessary to facilitate an understanding of the novel and unique features of the present invention.

Referring now to FIG. 1, which illustrates a dispensing package which has been constructed in accordance with a preferred embodiment of the present invention and is designated generally by the reference numeral 10. As will be discussed herein below, package 10 is specially adapted for storing and dispensing unit doses of a topical semi-solid imiquimod pharmaceutical formulation, such as an imiquimod cream formulation.

The dispensing package 10 includes a dispensing head 20 having a projecting, finger-operable pump 22 (see FIGS. 3 and 4) and an external actuator button or plunger 24. The pump 22 is a non-venting type that has a pump chamber in which is disposed a pressurizing piston that can be actuated by pressing down on plunger 24, so as to dispense a quantity of the fluid product from a dispensing orifice or self-closing slit 26, which will be described in greater detail herein below.

An optional cover or cap 40 may be releasably mounted over dispensing head 20. The cap 40 is shown as molded from a substantially transparent material. However, in many applications, the cap 40 is preferably made from any suitable opaque material.

The dispensing package 10 includes a tubular structure or hollow body 50 for containing the imiquimod cream. The hollow body 50 is illustrated in the figures as being made from a substantially transparent material, such as a transparent thermoplastic material. However, in many applications, the body is preferably made from any suitable opaque material.

The body 50 most typically would have a circular, transverse cross section. However, the hollow body 50 may have an oval shape, or some other shape, wherein the internal, transverse cross section is substantially uniform along most of its length.

Figure 2:
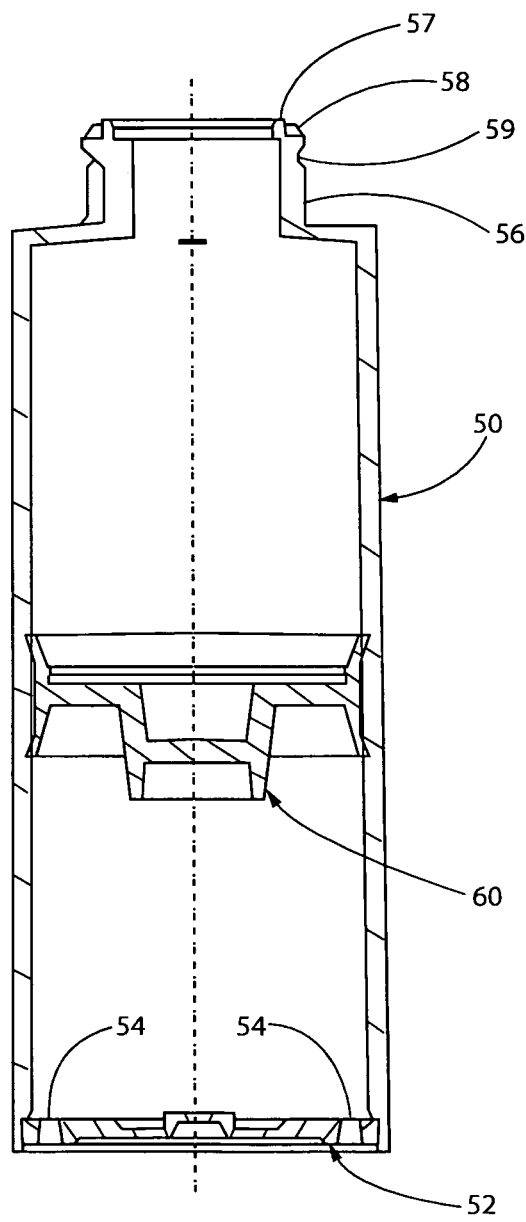
FIG. 2 is a cross-sectional view of a lower or first subassembly of the dispensing package of FIG. 1, which includes a hollow body along with the take-up piston and base closure member.

As shown in FIG. 2, the bottom of the hollow body 50 has an open end which is normally closed by a base closure member 52, which defines one or more apertures 54. The closure member 52 has a transverse cross-section corresponding generally to the transverse cross section of the hollow body 50. The closure member 52 is typically secured to the bottom of the hollow member 50 by means of a snap-fit engagement, by adhesive, or by other suitable means. However, prior to securing the closure member 52 to the hollow body 50, a follower or take-up piston 60 is inserted into the lower, open end of the hollow body 50. The piston sealingly engages the interior surface of the hollow body 50 and is adapted to slidingly move axially upwardly in the hollow body 50. The piston 60 can thus function as a take-up piston for moving toward the pump 22 at the upper, discharge end of the hollow body 50.

The take-up piston 60 moves toward the pump 22 at the discharge end of the body 50 in response to the discharge of any amount of fluid, such as imiquimod cream, from the body 50 so as to decrease the internal volume of the body 50 by an amount equal to the volume of the amount of fluid product which is discharged, i.e., the unit-dose amount. The movement of the piston 60 is effected by the atmospheric pressure of the ambient air which acts against the exterior, bottom surfaces of the piston 60. It will be appreciated that the vent passages 54 in the bottom end closure-member 52 insure that the ambient atmosphere will be in continuous contact with the exterior of the piston 60 regardless of how far the piston 60 travels up in the hollow body 50.

The particular design and configuration of the take-up piston 60 are matters of design choice consistent with the configuration used for the hollow body 50. Any suitable conventional or special piston design may be employed. The details of the design per se of such a piston 60 form no part of the present invention. It should be noted that the initial position of the piston within the hollow body 50 is dictated by the total amount of imiquimod cream to be supplied to the patient based on the anticipated dosing regimen. For example, if it is desired to dispense to the patient 15 g of imiquimod cream, the piston would be initially located lower than the setting for 7.5 g of cream.

The upper, discharge end of the body 50 defines a reduced-diameter neck 56. The upper end of the neck defines an external, peripheral shoulder 58. The side of the neck defines an annular, outwardly open groove 59. The distal end of the neck 56 defines an upwardly projecting, annular rim 57 at the inside diameter of the shoulder 58. In a preferred embodiment, the hollow body 50 is injection molded from a suitable thermoplastic material.

The hollow body 50, along with the take-up piston 60 and base closure member 52, may be characterized as the lower subassembly or first subassembly. However, in some applications, the base closure member 52 may be omitted altogether from the first, or lower, subassembly. In any event, after the lower subassembly has been assembled, it can be filled with the imiquimod cream, and then the additional package components, comprising an upper subassembly or second subassembly as described below, are installed on the filled, first subassembly.

Figure 3:
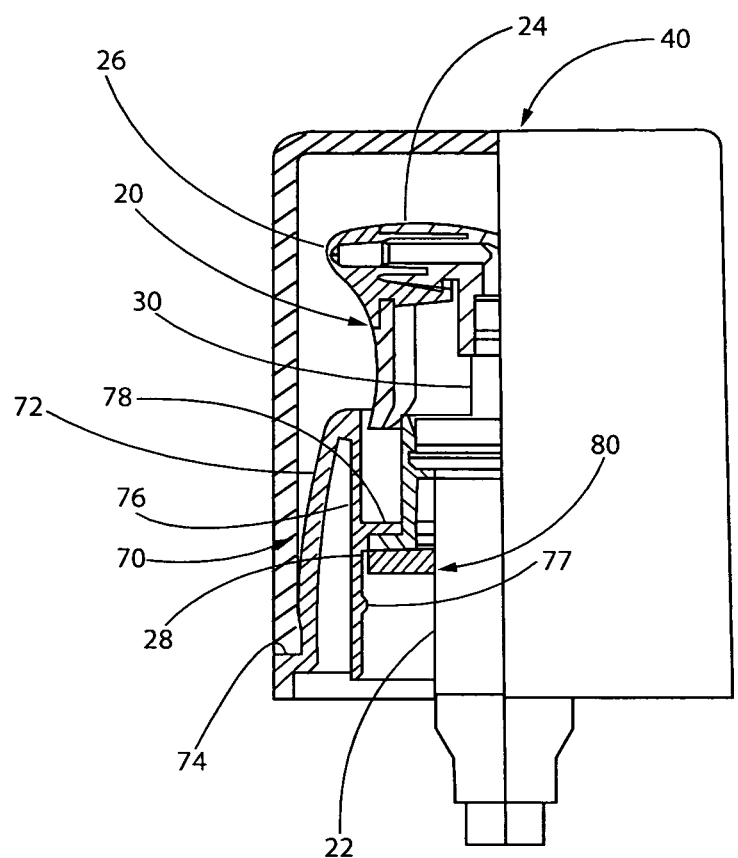
FIG. 3 is a partial cross-sectional view of an upper or second subassembly of the dispensing package of FIG. 1, which includes a dispensing head, a finger-operable pump, a holding member and a cap.

Referring now to FIG. 3, there is illustrated the second subassembly or upper subassembly, which is designed for being mounted to the lower subassembly and comprises at least three components; a finger operable pump 22, a dispensing head 20; and a holding member 70. The dispensing head 20 may be regarded as part of the pump 22. Additional components are also preferably included in the upper subassembly, and such additional components may include a gasket 80 (FIG. 4) and the cap or cover 40 (FIG. 3).

Figure 4:
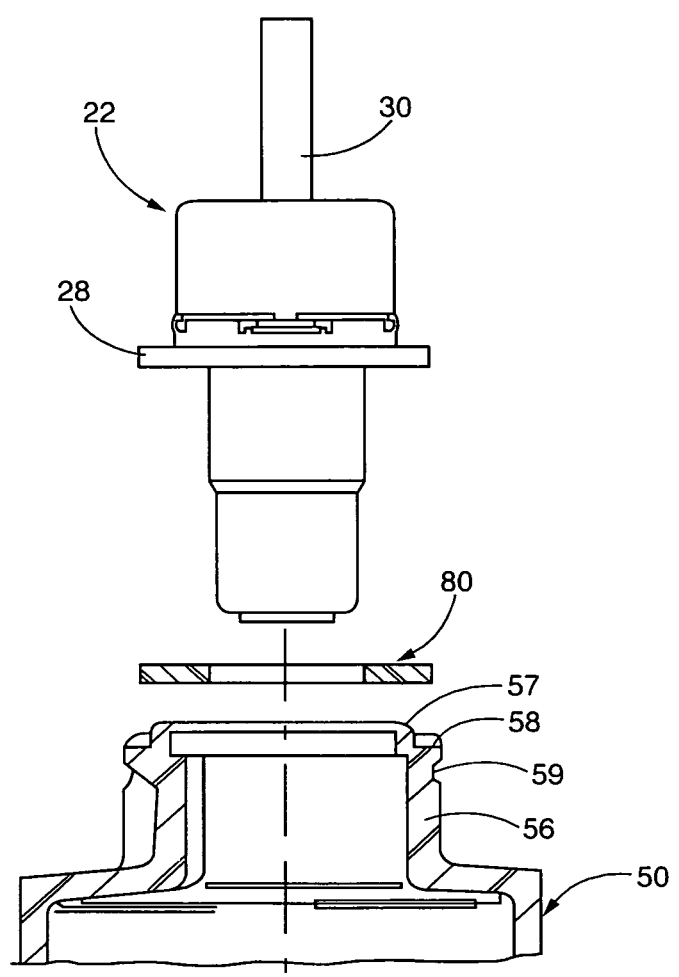
FIG. 4 provides a side elevational view of the finger-operable pump of the upper subassembly, and a cross-sectional view of an o-ring gasket and the hollow body associated with the lower subassembly.

The exterior of the pump 22 is designed to be mounted within the holding member 70, along with the gasket 80 if the gasket is employed. Specifically, the pump 22 has a radially extending mounting flange 28 (FIGS. 3 and 4). The pump 22 may also include one or more bosses or ribs (not shown) which are spaced above the pump flange 28 to define an annular recess between the flange 28 and the ribs and can be used to secure the pump 22 to the holding member 70.

The internal pumping mechanism of the pump 22 may be of any appropriate conventional or special non-venting design. Typically, a conventional, non-venting pump (airless), such as the pump 22 illustrated in the figures, has an interior chamber (not visible) which has a check valve at the lower end and in which is disposed a pressurizing piston (not visible). The pressurizing piston is arranged to cooperate with a hollow stem 30 which extends out through the top of the body of the pump 22 and which is received within the pump actuator button 24.

The stem 30 and the piston within the pump body can move downwardly together in the pump chamber, but the hollow stem 30 can also move for some distance separately relative to the piston, so as to establish communication through the hollow stem 30 between the pump chamber and the actuator button 24. One or more springs (not visible in the figures) act against the piston and/or stem 30 inside the pump body to bias the piston, stem 30, and actuator button 24 upwardly to an elevated rest position when finger pressure is released. As will be discussed in more detail herein below, when the actuator button 24 is pressed, an unit-dose amount of product is dispensed from the pump 22.

One conventional non-venting pump that may be employed in accordance with the present invention is the pump designated EV09/240 and sold by Valois S. A., 50 Avenue de L'Europe, 78160 Marly le roi, France. It will be appreciated, however, that the detailed design and operation of the internal components of such a pump, which may be employed for the pump 22 described herein, form no part of the present invention.

The holding member 70 includes a peripheral, convex shroud 72 providing a pleasing, external configuration. The bottom of the shroud 72 has a laterally projecting flange or shoulder 74. At four locations around the shroud 72 above the flange 74, there are small, outwardly projecting protuberances (not shown) which are adapted to establish a snap-fit engagement in an annular groove formed in the interior bottom of the cap or cover 40. The cap or cover 40 and/or the lower portion of the holding member shroud 72 are resiliently deflectable, so as to accommodate relative movement between the cap 40 and shroud 72 as the cap 40 is installed on the package. The cap 40 and/or shroud 72 deflect sufficiently so that the cap bead can be located below, and adjacent, the protuberances of the holding member shroud 72. This confronting relationship establishes the snap-fit engagement.

Projecting downwardly from the shroud 72 of the holding member 70 is an annular sleeve 76. See FIG. 3. The sleeve 76 defines an opening, bore, or passage for accommodating the annular neck 56 of the hollow body 50 and for accommodating the upwardly projecting portion of the pump 22.

An annular flange 78 extends radially inwardly from the holding member annular sleeve 76 for engaging the upper surface of the pump flange 28. See FIG. 3. The sleeve 76 also includes an inwardly extending bead 77 for being received in the annular groove 59 defined in the hollow body neck 50.

Typically, the pump 22 is initially disposed in the holding member 70, along with the gasket 80, if employed. To this end, the installation is accomplished with the pump actuator 24 initially removed from the pump. Relative movement between the pump 22 and the holding member 77 is effected so as to introduce the pump into the holding member 70 from the bottom end of the holding member.

As noted above, prior to mounting the two subassemblies together, the lower subassembly is filled with the topical semi-solid imiquimod pharmaceutical formulation, such as an imiquimod cream formulation. This can be conveniently done pursuant to a conventional or special filling process which is typically performed under vacuum. Preferably, vacuum (i.e., a reduced pressure) is created by a suitable vacuum system around the body 50. The air below the piston 60 within the body 50 is evacuated through the vent holes/apertures 54 in the base closure member 52 of the body 50. Then the fluid product is discharged from a filling machine into the hollow body 50 through the opening in the body neck 56. Next, with vacuum still enveloping the components, the upper subassembly (comprising the pump 22, holding member 70, gasket 80 if employed, and cap 40 if employed) is moved into position on the lower subassembly hollow body 50 so as to establish the snap-fit engagement between the hollow body 50 and holding member 70.

The particular process and detailed operation of filling the body 50 and mounting the upper subassembly on the lower subassembly form no part of the present invention.

When the two subassemblies are properly mounted together as shown in FIG. 1, the pump flange 28 urges the gasket 80 into sealing engagement with the upper end of the body neck rim 57. However, depending upon the materials employed in the construction of the pump 22 and/or body rim 57 or neck 56, the gasket 80 may either be omitted altogether or be included as a unitary part of either the pump flange 28 or the upper end of the body neck 56.

The set of components provided according to the present invention can be readily manufactured from material which is compatible with the imiquimod cream. Provided below are the results of a stability studies which have been conducted to ensure certain polymeric materials are compatible with an imiquimod cream.

The set of components can be readily assembled to provide a compact package which is clean, safe, reliable, simple and easy-to-use to dispense consistent and uniform unit-dose amounts of a topical semi-solid imiquimod pharmaceutical formulation, such as an imiquimod cream, to treat a dermal and/or mucosal-associated condition. Except for the removable cap 40, the components are not readily disassembled, and the completed package protects a topical semi-solid imiquimod pharmaceutical formulation from degradation, oxidation, and/or external contaminants.

Figure 5:
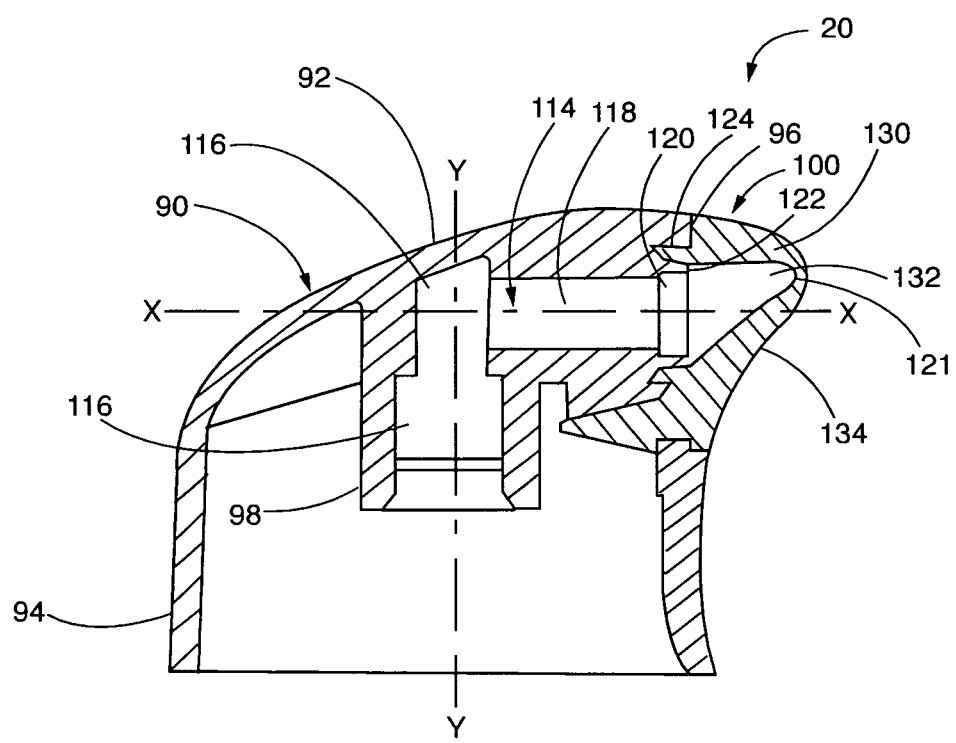
FIG. 5 is a cross-sectional view of the dispensing head used in the dispensing package of FIG. 1, the dispensing head including a body portion and a shutter member.
Figure 6:
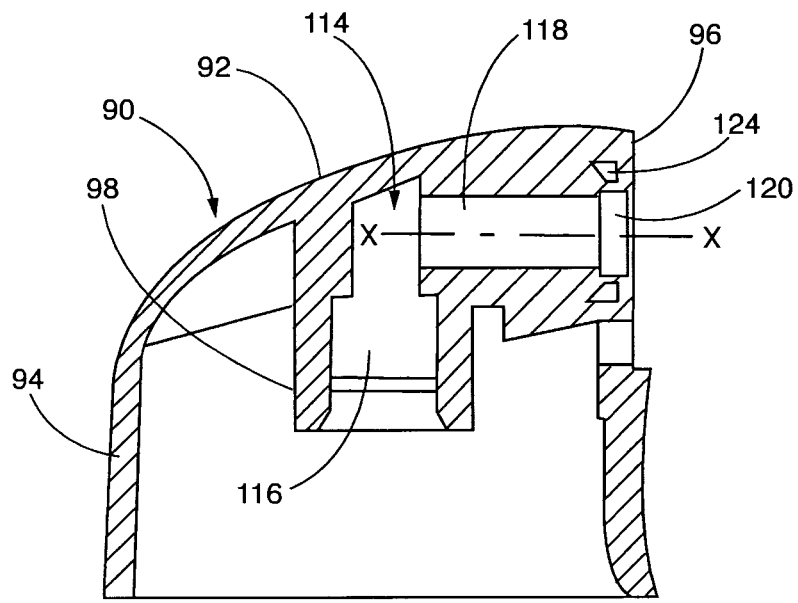
FIG. 6 is a cross-sectional view of the body portion of the dispensing head of FIG. 5.
Figure 7:
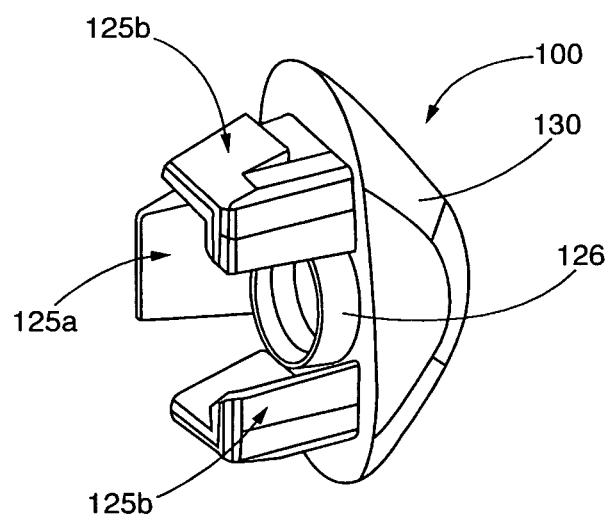
FIG. 7 is a perspective view taken from the rear side of the shutter member of the dispensing head of FIG. 5.

Referring now to FIG. 5, it provides a cross-sectional view of dispenser head 20. In the embodiment shown in the FIGs., the dispenser head 20 is made up of two component elements, namely a body 90, FIG. 6, and a shutter 100, FIG. 7. The two elements may be made by injecting suitable plastics materials into appropriate molds. The body 90 is preferably made of a plastics material that is harder or stiffer than the shutter 100.

The body 90, which is preferably integrally molded in one piece, comprises a push top wall 92 which serves a pusher surface against which one or more fingers of one hand can be applied and can exert a pressing force. In this example, the top wall 92 has a complex shape that is both rounded and inclined. This is an ergonomic shape for the position of a finger with the tip phalanx of the finger placed on the highest portion of the top wall 92. In addition, the body 90 forms a peripheral side skirt 94 which extends from the top wall 92 downwards. The skirt 94 has a configuration that is also complex, but that is substantially cylindrical.

Where the top wall 92 is at its highest, the skirt 94 forms a join surface 96 that is exactly plane in this example. The join surface 96 is provided with plurality of openings or slots, as is described below. Shutter 100, described below, is designed to be mounted on the body 90 at the join surface 96.

The body 90 of dispensing head 20 internally defines a connection sleeve 98 serving to receive the top end of the hollow stem 30 of pump 22. The socket formed by the connection sleeve 98 may be of the force-fitting type or of the snap-fastening type. The rod-receiving socket is extended by a dispensing duct 114 which defines an axial inlet 116. This inlet is disposed on a vertical longitudinal axis Y which coincides with the axis of the dispenser member and of its actuating rod. Naturally, the inlet 116 is open facing downwards so as to communicate with the socket formed by the connection sleeve 98 in which the top end of the hollow stem 30 of pump 22 is to be engaged.

In many cases, the body 90, and more generally the dispenser head 20, is mounted to rotate about said vertical axis Y. The dispensing duct 114 also forms a radial passageway 118 which opens out at the join surface 96 via an outlet 120. The outlet 120 and the passageway 118 that connects the inlet 116 to the outlet 120 extend along a dispensing or outlet axis X. The outlet axis X extends substantially perpendicularly to the vertical longitudinal axis Y. However, the axis X may extend slightly or significantly upwards or downwards relative to the axis Y.

Join surface 96 includes a circular groove 124 which extends from the join surface 96 into the body 90 in substantially the same direction as the outlet axis X. The groove 124 thus forms a sort of annular trench whose depth extends horizontally.

As explained below, the function of said groove 124 is to provide sealing with the shutter 100. The shutter 100 forms a dispensing spout 130 internally forming an outlet or dispensing chamber 132. The chamber 132 terminates at self-closing slit 26 that forms a dispensing orifice. The self-closing slit 28 has edges that are in touching leak-tight contact in the rest position, i.e., whenever the chamber 132 does not contain any fluid subjected to a pressure higher than a threshold pressure making it possible to separate the edges of the slit and thus to open the self-closing slit 28. In the embodiment shown in the FIGS., the bottom surface 134 of the dispensing chamber 132 is inclined upwards and thus constitutes a convergence wall suitable for directing the fluid under pressure towards the dispensing orifice.

Fixing catches 125a and 125b extend from the rear of the shutter 100 and secure the shutter to the body 90 in snap-fit engagement. In the non-limiting embodiment, there are a bottom catch 125a and two side catches 125b. The three catches extend from the rear of the shutter 100 around the sealing lip 126.

The shutter 100 is fitted to the body 90 by causing the catches 125A and 125b to penetrate into respective holding recesses formed in the body 90. When the shutter 100 is fitted to the body 90, the sealing lip 126 is caused to be pressed into the groove 124 so as to come into leak-tight contact with the two side walls of said groove, and advantageously also with the end-wall thereof. Leak-tight contact is thus obtained at three points that have very good sealing quality, since the lip is in tight-fitting engagement between the two facing side walls.

Once the package is filled, the priming of the actuator allows the imiquimod product to fill into the pump 22 and the dispensing duct 114. Once the pump 22 is fully primed with imiquimod product, each additional actuation will cause a precise dosage amount of the imiquimod product to be dispensed. Moreover, each actuation causes the take-up piston 60 to rise until ultimately, the piston reaches the top of the package and empties and remaining product.

A series of trials were conducted to determine the suitability of the dispensing device for use with topical imiquimod pharmaceutical cream. A series of pump systems were evaluated for 2.5%, 3.75% and 5% w/w imiquimod creams targeting a pump system that could deliver approximately 250 mg of the product per actuation mimicking the dosage/delivery of the commercially available single use 250 mg packets or sachets.

Two pump system constructions were evaluated: Albion EV09/1500-30 mL (hereinafter "Albion") and VP39/70 p1-15 mL Digital Actuator Nova Pump EV09/150 ("Nova"). Like the previously described dispensing package, the Albion pump system includes a tubular base member in which a topical imiquimod pharmaceutical cream is retained. The Nova pump system stores a topical imiquimod pharmaceutical cream in an aluminum pouch.

One difference between these two pumps are how they are designed to operate and the product contact materials used to manufacture the respective pump components. In order to determine which, if either, pump design and product contact components are best suited for consistently and uniformly dispensing precise unit-dose amounts of the 2.5%, 3.75% and 5% w/w imiquimod pharmaceutical creams, even after use interruption and storage for a period of time, a series of performance tests, filling trials and stability studies are conducted.

While the topical semi-solid imiquimod pharmaceutical formulations of the present invention can be formulated into any form known to the art, such as a cream, an ointment, a gel or a lotion, it should be understood that such semi-solids may be packaged into the multi-dose, pump systems of the present invention for treatment of a dermal and/or mucosal-associated condition, such as EGWs, AKs or sBCC. A packaged amount of a topical semi-solid imiquimod pharmaceutical formulation contemplated by the present invention includes any suitable packaged amount, for completing one or more treatment regimens for treating a dermal and/or mucosal-associated condition, such as EGWs, AKs or sBCC, such as an amount between about 5 grams and 30 about grams, more preferably about 5 grams, about 7.5 grams, about 10 grams, about 12.5 grams, about 15 grams, about 17.5 grams, about 20 grams, about 22.5 grams, about 25 grams, about 27.5 grams, about 30 grams or more, and more preferably about 7.5 grams and about 15 grams. An actuated unit-dose amount of a topical semi-solid imiquimod formulation that may be dispensed from a pump system of the present invention includes any effective unit-dose amount for treating a prescribed dermal and/or mucosal condition discussed herein above, such as an actuated unit dose amount of about 125 mg to about 500 mg or more, and preferably about 150 mg, about 175 mg, about 200 mg, about 225 mg, about 240 mg., about 250 mg, about 275 mg, about 300 mg, about 325 mg, about 350 mg, about 375 mg, about 400 mg, about 425 mg, about 450 mg, about 500 mg or more, and more preferably about 240 mg or about 250 mg per actuation.

As indicated herein above, the present invention also contemplates bioequivalent or interchangeable topical semi-solid imiquimod pharmaceutical formulations. By way of an example, bioequivalent or interchangeable dosage strength topical semi-solid imiquimod pharmaceutical formulations, as contemplated by the present invention, include topical semi-solid imiquimod pharmaceutical formulations that have respective comparable in-vivo serum profiles, i.e., wherein the in-vivo parameters are either the same or may vary up to about ±25% or more, when such a 2.5%, 3.75% or 5% topical semi-solid imiquimod pharmaceutical formulation is topically administered daily to the same individual in the same dosage regimen in accordance with dosage regimens described herein to treat a dermal and/or mucosal-associated condition, such as external or perianal warts, actinic keratosis or superficial basal cell carcinoma. In other words, two or more topical semi-solid imiquimod pharmaceutical formulations having the same imiquimod concentration but different formulations will be considered bioequivalent or interchangeable if their respective in-vivo parameters are either the same or vary up to about ±25% or more, when such topical semi-solid imiquimod pharmaceutical formulations are topically administered daily to an individual in the same dosage regimen in accordance with dosage regimens described herein to treat a dermal and/or mucosal-associated condition, such as EGWs, AK s or sBCC carcinoma.

By way of an example, bioequivalent or interchangeable 3.75% dosage strength topical semi-solid imiquimod pharmaceutical formulations, as contemplated by the present invention, include topical semi-solid 3.75% imiquimod pharmaceutical formulations that have comparable in-vivo serum profiles, i.e., wherein the following in-vivo parameters are either the same or may vary up to about ±25% or more, when approximately 500 mg of each such formulation (about 18.75 mg imiquimod) or less is applied daily for 21 days to an AK treatment area of about 200 cm2 on the face or balding scalp between about day 8 and day 14 and, selected from one or more of the following in-vivo serum profiles:

(a) a Day 21 $T_{max}$ of from about 4 hours to about 16 hours and preferably a mean $T_{max}$ of about 7.4 hours with a standard deviation ("SD") of about 3.5, a median $T_{max}$ of about 9 hours and a geometric mean $T_{max}$ of about 6.6 hours and a coefficient of variation ("CV") of about 48%;

(b) a Day 21 $C_{max}$ of from about 0.07 to about 0.6 ng/ml and preferably a mean $C_{max}$ of about 0.3 ng/ml with a standard deviation of about 0.16, a median $C_{max}$ of about 0.35 and a geometric mean $C_{max}$ of about 0.27 ng/ml and a coefficient of variation of about 49%;

(c) a Day 21 $T_{1/2}$ of from about 9.7 to about 84 hours and preferably a mean $T_{1/2}$ of about 29.3 hours with a standard deviation of about 17, a median $T_{1/2}$ of about 25.6 hours and a geometric mean $T_{1/2}$ of about 26 hours and a coefficient of variation of about 58%;

(d) a Day 21 $AUC_{0-24}$ of from about 1.1 to about 12 ng hr/ml and preferably a mean $AUC_{0-24}$ of about 6 ng hr/ml with a standard deviation of about 3, a median $AUC_{0-24}$ of about 7 ng hr/ml and a geometric mean $AUC_{0-24}$ of about 5 ng hr/ml and a coefficient of variation of about 52%;

(e) a Day 21 $\lambda z$ of from about 0.008 $hr^{-1}$ to about 0.07 $hr^{-1}$ and preferably a mean $\lambda z$ of about 0.03 $hr^{-1}$ with a standard deviation of about 0.01, a median $\lambda z$ of about 25.6 $hr^{-1}$ and a geometric mean $\lambda z$ of about 0.03 $hr^{-1}$ and a coefficient of variation of about 49%;

(f) a Day 21 $C_{min}$ of from about 0.06 to about 0.4 and preferably a mean $C_{min}$ of about 0.20 with an SD of about 0.11, a median $C_{min}$ of about 0.19 and a geometric mean $C_{min}$ of about 0.17 and a coefficient of variation of about 55%;

(g) at Day 14/7 (a ratio of the trough concentration at Day 14 over the trough concentration at Day 7), a trough concentration geometric mean ratio of about 1.09 with a 90% confidence interval ("CI") within a range of between about 0.8 and about 1.5;

(h) at Day 21/14 (a ratio of the trough concentration at Day 21 over the trough concentration at Day 14), a trough concentration geometric mean ratio of about 1.33 with a 90% confidence interval ("CI") within a range of between about 0.9 and about 1.9;

(i) at Day 22/21 (a ratio of the trough concentration at Day 22 over the trough concentration at Day 21) a trough concentration geometric mean ratio of about 0.93 with a 90% confidence interval ("CI") within a range of between about 0.6 and about 1.3;

(j) a mean peak imiquimod serum concentration of about 0.323 ng/ml at Day 21;

(k) a Day 21 RAUC of from about 1 to about 7 and preferably a mean RAUC of about 4 with a standard deviation of about 2, a median RAUC of about 3.5 and a geometric mean RAUC of about 3.3 and a coefficient of variation of about 56%;

(l) a Day 21 $RC_{max}$ of from about 0.5 to about 5 and preferably a mean $RC_{max}$ of about 3 with a standard deviation of about 1.5, a median $RC_{max}$ of about 2.7 and a geometric mean $RC_{max}$ of about 2.4 and a coefficient of variation of about 54%;

(m) a Day 21 $L\lambda z_{eff}$ of from about 0.006 $hr^{-1}$ to about 0.08 $hr^{-1}$ and preferably a mean $L\lambda z_{eff}$ of about 0.02 $hr^{-1}$ with a standard deviation of about 0.02, a median $L\lambda z_{eff}$ of about 0.01 $hr^{-1}$ and a geometric mean $L\lambda z_{eff}$ of about 0.16 $hr^{-1}$ and a coefficient of variation of about 97%; and (n) a Day 21 $T^{1/2}_{eff}$ of from about 8 hr to about 110 hr and preferably a mean $T^{1/2}_{eff}$ of about 55 hr with a standard deviation of about 36, a median $T^{1/2}_{eff}$ of about 50 hr and a geometric mean $T^{1/2}_{eff}$ of about 42 $hr^{-1}$ and a coefficient of variation of about 66%.

By way of another example, bioequivalent or interchangeable topical semi-solid 3.75% imiquimod pharmaceutical formulations contemplated by the present invention include topical semi-solid 3.75% imiquimod pharmaceutical formulations that, when approximately 250 mg of each such topical semi-solid imiquimod pharmaceutical formulation' (about 9.375 mg imiquimod) or less is applied daily for 21 days to EGWs in the genital/perianal area with a total wart area of greater than or equal to 100 mm², provide a comparable in-vivo serum profile selected from one or more of the following:

(a) a Day 21 mean $T_{max}$ of about 9.7 hours with a standard deviation ("SD") of about 4.0, a median $T_{max}$ of about 12 hours and a geometric mean $T_{max}$ of about 8.3 hours and a coefficient of variation ("CV") of about 41%;

(b) a Day 21 mean $C_{max}$ of about 0.488 ng/ml with a standard deviation of about 0.368, a median $C_{max}$ of about 0.45 and a geometric mean $C_{max}$ of about 0.39 ng/mL and a coefficient of variation of about 75%;

(c) a Day 21 $T_{1/2}$ of from about 6.8 to about 54 hours and preferably a mean $T_{1/2}$ of about 24.1 hours with a standard deviation of about 12, a median $T_{1/2}$ of about 22.8 hours and a geometric mean $T_{1/2}$ of about 21 hours and a coefficient of variation of about 51%;

(d) a Day 21 $AUC_{0-24}$ of from about 1.9 to about 14 ng-hr/mL and preferably a mean $AUC_{0-24}$ of about 6.8 ng.hr/mL with a standard deviation of about 3.6, a median $AUC_{0-24}$ of about 6.6 ng.hr/mL, and a geometric mean $AUC_{0-24}$ of about 5.8 ng-hr/mL and a coefficient of variation of about 53%;

(e) a Day 21 $\lambda z$ of from about 0.013 $hr^{-1}$ to about 0.102 $h^-$ and preferably a mean $\lambda z$ of about 0.037 $hr^{-1}$ with a standard deviation of about 0.02, a median $\lambda z$ of about 0.03 $hr^{-1}$ and a geometric mean $\lambda z$ of about 0.03 $hr^{-1}$ and a coefficient of variation of about 60%;

(f) a Day 21 $C_{min}$ of from about 0.025 to about 0.47 and preferably a mean $C_{min}$ of about 0.158 with an SD of about 0.121, a median $C_{min}$ of about 0.14 and a geometric mean $C_{min}$ of about 0.11 and a coefficient of variation of about 77%;

(g) at Day 14/7 (a ratio of the trough concentration at Day 14 over the trough concentration at Day 7), a trough concentration geometric mean ratio of about 1.13 with a 90% confidence interval ("CI") within a range of between about 0.7 and about 1.7;

(h) at Day 21/14 (a ratio of the trough concentration at Day 21 over the trough concentration at Day 14), a trough concentration geometric mean ratio of about 0.84 with a 90% confidence interval ("CI") within a range of between about 0.5 and about 1.3;

(i) at Day 22/21 (a ratio of the trough concentration at Day 22 over the trough concentration at Day 21) a trough concentration geometric mean ratio of about 1.12 with a 90% confidence interval ("CI") within a range of between about 0.7 and about 1.6;

(j) a mean peak imiquimod serum concentration of about 0.488 ng/mL at Day 21;

(k) a Day 21 RAUC of from about 0.6 to about 7 and preferably a mean RAUC of about 2.2 with a standard deviation of about 1.8, a median RAUC of about 1.8 and a geometric mean RAUC of about 1.7 and a coefficient of variation of about 81%;

(l) a Day 21 $RC_{max}$ of from about 0.5 to about 5 and preferably a mean $RC_{max}$ of about 2.3 with a standard deviation of about 1.6, a median $RC_{max}$ of about 1.7 and a geometric mean $RC_{max}$ of about 1.8 and a coefficient of variation of about 70%;

(m) a Day 21 $L\lambda z_{eff}$ of from about 0.006 $hr^{-1}$ to about 0.09 $hr^{-1}$ and preferably a mean $L\lambda z_{eff}$ of about 0.04 $hr^{-1}$ with a standard deviation of about 0.03, a median $L\lambda z_{eff}$ of about 0.03 $hr^{-1}$ and a geometric mean $L\lambda z_{eff}$ of about 0.03 $hr^{-1}$ and a coefficient of variation of about 69%;

(n) a Day 21 $T^{1/2}_{eff}$ of from about 8 hr to about 111 hr and preferably a mean $T^{1/2}_{eff}$ of about 31 hr with a standard deviation of about 30, a median $T^{1/2}_{eff}$ of about 22 hr and a geometric mean $T^{1/2}_{eff}$ of about 23 $h^{-1}$ and a coefficient of variation of about 97%;

(o) a Day 21 $C_{max}$ in female patients about 61% higher in female subjects than in male subjects (0.676 versus 0.420 ng/mL) and total systemic exposure AUC 0-24 8% higher in female subjects than in male subjects (7.192 versus 6.651 ng-hr/mL) when data is not dose normalized;

(p) a Day 21 $C_{max}$ in female patients about 35% higher than in male subjects (0.583 versus 0.431 ng/mL) and AUC 0-24 about 6% lower in female subjects than in male subjects (6.428 versus 6.858 ng-hr/mL) when using dose normalization to adjust for differences in dosage and reported without subjects who missed an application of study drug during the last week of dosing; and/or (q) a median $T_{max}$ occurring approximately twice as quickly in female subjects (about 6.50 hours) as in male subjects (about 12.0 hours).

In accordance with the present invention, mean peak serum concentrations are achieved with the topical semi-solid imiquimod pharmaceutical formulations of the Examples (see also Attachments I-XV) when topically applied as discussed herein throughout. For example, a mean peak serum concentration of about 0.488 ng/mL is achieved with a 3.75% dosage strength imiquimod pharmaceutical formulation 202 of Example 21 after about 9.4 mg of imiquimod is applied to the affected treatment area each day for up to 8 weeks.

Examples of various embodiments of the present invention will now be further illustrated with reference to the following examples. Thus, the following examples are provided to illustrate the present invention, but are not intended to be limiting thereof. Parts and percentages are by weight unless otherwise specified. Examples of topical imiquimod cream and ointment compositions contemplated by the present invention are described in U.S. Pat. Nos. 4,689,338 and 5,238,944, which are incorporated herein by reference in their entireties. Percent modifications for, e.g., imiquimod and vehicle, to generate imiquimod formulations as described herein are likewise contemplated by the present invention. In addition, the formulations described and disclosed in U.S. Pat. No. 7,655,672, U.S. Patent Publication No. 2007/0123558, Ser. No. 11/276,324, U.S. Patent Publication No. 2007/0264317, U.S. Ser. No. 11/433,471, U.S. Patent Publication No. 2007/0900550 and PCT Publication No. WO2008098232 (A1), are also contemplated by the present invention and are incorporated herein by reference in their entireties.

EXAMPLE 1

Pump Performance Attribute Tests

A series of pump performance attribute testing is conducted to assess the best pump design for, for example, by weight 2.5%, 3.75% and 5% w/w imiquimod creams, such as described in Examples 16 and 20. The performance attributes tests and respective acceptance criteria are described below.

A. Priming:

The purpose of this test is to determine the number of actuations necessary to start observing delivery of the product dispensed from the actuator. Additionally, the number of pump depressions, i.e., the number of depressions/actuations required until the first full dose is delivered is also monitored.

Acceptance Criteria: The number of actuations to start observing delivery of the product dispensed from the actuator must be less than or equal to 5 actuations.

B. Dosage Reproducibility:

The purpose of this test is to measure the doses restituted by the pump and verify the consistency of the dose value with time. Pumps are actuated manually.

Acceptance Criteria: For each pump, the average of 10 individual dose values must be within about 10% of the pumps nominal value of about 240 mg and each individual dose value must be within about 15% of the pump's nominal value of about 240 mg.

C. Sealing Integrity Under Vacuum:

The purpose of this test is to evaluate the sealing integrity of a specific pump and container configuration when placed under vacuum. The sealing integrity of a pump corresponds to its ability to retain the product in the container and play its role in the closure of the system. Unprimed pump samples are filled with the product to be tested, are positioned horizontally for about 20 minutes at room temperature in a vacuum chamber at about 24" Hg depression.

Acceptance Criteria: There must be no visual sign of leakage.

D. Weight Loss at Atmospheric Pressure:

The purpose of this test is to evaluate the sealing integrity of each pump and container configuration stored under specific conditions. For this test, filled samples are weighed, stored at specific conditions and then weighed again to measure for any weight loss.

Acceptance Criteria: Weight loss values must typically not exceed about 0.3% after 4 weeks at room temperature and about 1.0% after about 4 weeks at about 45° C. (based on the total weight of the package).

E. Restitution Rate:

The purpose of this test is to determine the portion of product delivered by a package after the pump can no longer dispense any product and compare it to the quantity of product used to fill the package.

Acceptance Criteria: The restitution rates depend on the type of package and the type of filling (airless or atmospheric).

F. Dose Through Life:

This test measures the dose restituted by the pump/device mechanism during each actuation until the container is empty. Devices are manually actuated.

Acceptance Criteria: The overall average of the dose value must be within about 10% of the pump's nominal dose value of about 240 mg of product. Each individual dose value must be within about 15% of the pump's nominal dose value. The pump is considered to have met the Dose through life criteria if it provides about 240 mg of product and if it meets restitution rate criteria.

G. Loss of Prime:

The purpose of this test is to evaluate the ability of a pump to retain its prime over a specific storage time. The loss of prime is defined as the amount of product that returns from the dose chamber back into the container after storage in an upright position. "Shot" weights are measured before and after storage to determine the loss of prime and the percentage of dose retained.

Acceptance. Criteria: The pump must retain its prime during storage. The percentage of dose retained (ratio of dose after storage to dose before storage) must be more than about 85% in order to deliver a consistent, uniform and effective dosage amount.

H. Gasket Swelling:

This test measures the change in thickness of the gasket following storage in contact with the product. Relevant sets of gaskets (two gaskets per set) with the same chemical composition and similar thickness are stored at about 45° C. for about 8 weeks containers filled with product to be tested. The samples are stored at about 45° C. at about 1, about 4 and about 8 weeks interval are tested for the thickness of the gaskets at about room temperature. Additionally, the following conditions are observed: gaskets' deformation and color change in product or gaskets; samples will be compared with a control sample.

Acceptance Criteria: The swelling of the gasket should be not more than about 15%. Also there should be no shrinking and no discoloration of the gasket and the product.

I. Migration:

The purpose of this test is to check that the pigments in a colored plastic material do not migrate into the customer's formulation. After priming, samples will be stored at about 45° C. for about 1 week. On each day, two samples will be actuated and the dispensed bulk will be compared to the control sample. Additionally after about 4 weeks at about 45° C. all samples will be emptied and bulk will be compared to the control sample. The dispensed product will be examined and inspected for the presence of pigments that might have migrated from the actuator or for any color modification of the bulk when compared to the bulk dispensed by the control sample.

Acceptance Criteria: It is considered that migration has occurred if the presence of colored pigments is observed in the tested product when compared to the product dispensed by the controlled samples.

J. Corrosion of the Metal Components:

The purpose of this test is to assess the compatibility between the active formulation and the pump metal components after being in contact for a specific period of time.

Corrosion of the Pump Metal Components is defined as the oxidation of pump metal components when exposed to the active formulation. Relevant components (spring(s) and stainless steel ball) will be stored in containers in intimate contact with product, at ambient temperature and elevated temperature (about 45° C./75% RH). Components will be inspected at 3 days, 1 week, 2 weeks, 4 weeks, 8 weeks, 12 weeks and 24 weeks. Components are inspected for oxidation on the pump metal components at each time point.

Acceptance Criteria: The results are verified against the reference sample.

K. Discoloration of Formulation:

The purpose of this test is to assess the compatibility between the product and the pump components after being in contact with the product for a specific period of time. Discoloration of Formulation is defined as the change of color of active formulation when in contact with pump components for a specific amount of time. The components will be stored in containers at ambient temperature and elevated temperature (about 45° C./75% RH). Change of color in the active product will be examined at 3 days, 1 week, 2 weeks, 4 weeks, 8 weeks, 12 weeks and about 24 weeks at Room Temperature and about 45° C./75% RH.

Acceptance Criteria: The results are verified against the reference sample.

L. Pouch Compatibility (Nova System Only):

The purpose of this test is to verify the compatibility of a pouch foil material with the formulation after 4 weeks of aging at about 45° C. in terms of welding resistance and physical appearance. After aging, each sample will be cut into two 15 mm strip film and a total of 10 test strips is obtained. Strips will be measured for the split force using the dynamometer. Samples will be visually inspected to verify the absence of physical defects such as de-lamination, blistering or spotting.

Acceptance Criteria: Pull force that is required to split the welded parts of the foil must be about 1.5 Kg minimum and no physical defects are observed after storage for about 4 weeks at 45° C.

EXAMPLE 2

Pump Filling Trials

A series of pump filling trials were conducted at two different facilities. In both facilities the filling process and equipment were identical. In each process, the cream formulation is filled under vacuum into the container barrel using volumetric dose pumps. The barrel and the pump head or upper assembly with the actuator is joined ("snapped on") to the pump body under vacuum. This packaging process enables delivery of a precise quantity of product by depression of the pump mechanism, avoiding any contact with air.

The filling trials as well as any salient observations and conclusions for each trial are described below.

A. Filling Trial #s F008-08 and F009-08 at Facility I

Initial fill trials are conducted on the Albion pump system to determine the capability of the filling equipment to fill the creams and also the flowability of the cream during the filling process. The pump body and the stem are made of polybutylene terephthalate, the actuator is made of polypropylene homopolymer/low density polyethylene and the piston is made of high density polyethylene material.

A fill weight of about 7.5 g and about 15 g are selected for these trial runs. These fill weights correspond to the quantity of cream necessary to provide a full course of therapy to the patient depending on which indication is being treated. The filling trial runs prove that Imiquimod cream about 2.5% w/w (Lot #GJB070) manufactured by 3M, Loughborough, UK, can successfully be packaged using the airless filling process per Valois filling parameters.

The filling trials prove that the about 2.5% w/w cream can be successfully filled into the pumps. However, it is also noted that filling issues causing lower pump delivery values, i.e., shot weight, are caused by air bubbles entrapped in the bulk cream. This problem is corrected by avoiding introduction of air during the transfer of the product from the storage drum to the filling hopper.

All performance tests and physical stability screening data support that the Albion Pump Model Albion 30 ml EV09/150 pl and VP39/70-15 ml Digital actuator can be successfully filled and warrant further development.

B. Filling Trials #s 2027 through 2324 at Facility II

These series of trials focuses on selecting which Albion and/or Nova Pump Model to commercialize, pump fill overages that are required to ensure a about 7.5 gm and about 15 gm pump delivery, pump actuator size, use of a cocoon tip, and contact materials to be used in each respective pumps. In addition, several of the package presentations are placed on RT and accelerated conditions to help select the most compatible pump design for Imiquimod about 2.5%, about 3.75% and about 5% w/w cream.

The trials and corresponding observations are discussed below:

1.) Filling #s 2022 (about 2.5%) and 2026 (about 3.75%)—about 7.5 g Fill Weight.

Albion 15 ml pump with standard actuator, standard piston and about 150 μl dosing is filled with imiquimod cream about 2.5% w/w (lot #GJJ067) and imiquimod cream about 3.75% w/w (Lot #GJJ068). The piston is made of high density polyethylene and the position of the piston inside the pump is set to deliver about 7.5 g.

The product-components compatibility are satisfactory but the weight loss for about 4 weeks at about RT and loss of prime at about 1 week are not acceptable in both trials.

2.) Filling #s 2023 about (2.5%) and 2027 (about 3.75%)—about 15 g Fill Weight.

Albion 15 ml pump with standard actuator, standard piston and about 150 dosing is filled with imiquimod cream about 2.5% w/w (lot #GJJ067) and imiquimod cream about 3.75% w/w (Lot #GJJ068). The piston is made of high density polyethylene and the position of the piston inside the pump was set to deliver about 15 g.

The product-components compatibility is satisfactory but loss of prime at about 2 weeks is not acceptable in both trials.

3.) Filling #s 2024 (about 2.5%)—about 7.5 g Fill Weight.

Nova 15 ml with aluminum pouch pack standard actuator about 150 μl is filled with about 7.5 g of Imiquimod cream about 2.5% w/w (Lot #GJJ067).

During the testing it is observed that the pouch material is delaminating and not suitable for this cream product. It is theorized that the high concentration (about 20%) of isostearic acid in the cream formulation causes the delamination of these pouches.

4.) Filling #s 2025 (about 2.5%)—about 15 g Fill Weight.

Nova 30 ml with aluminum pouch pack standard actuator about 150 μl with pouch is filled with about 15 g of about 2.5% w/w of the cream (Lot #GJJ067).

On testing, it is observed that the pouch material is delaminating and not suitable for this cream product.

5.) Filling #s 2028 (about 3.75%)—about 7.5 g Fill Weight.

Nova 15 ml with aluminum pouch pack standard actuator about 150 μl with pouch is filled with about 7.5 g of about 3.75% of the cream (Lot #GJJ068).

On testing it is observed that the pouch material is delaminating and not suitable for this cream product.

6.) Filling #2029 (about 3.75%)—about 15 g Fill Weight.

Nova 30 ml with aluminum pouch pack standard actuator about 150 μl with pouch is filled with about 15 g of the cream (Lot #GJJ068).

On testing, it is observed that the pouch material is delaminating and not suitable for this cream product.

7.) Filling #2060 (about 5.0%)—about 7.5 g Fill Weight.

Albion 15 ml piston pump with standard actuator dosage about 150 μl with the position of the piston inside the pack set to deliver about 7.5 g is filled with Aldara® Cream 5% w/w (lot #GJF033).

The product-components compatibility is satisfactory but loss of prime at 2 week is not acceptable.

8.) Filling #2061 (about 5.0%)—about 15 g Fill Weight.

Albion 15 ml piston pump with standard actuator dosage about 150 μl with the position of the piston inside the pack set to deliver about 15 g is filled with Aldara® Cream about 5% w/w (lot #GJF033).

The product-components compatibility is satisfactory but loss of prime at about 1 week is not acceptable.

9.) Filling #2062 (about 5%)—about 7.5 g Fill Weight.

Nova 15 ml with aluminum pouch pack standard actuator about 150 μl with pouch is filled with about 7.5 g of Aldara® Cream about 5% w/w (Lot #GJF033).

Delamination of pouch material and loss of prime at about 2 weeks are not acceptable.

10.) Filling #2063 (about 5%)—about 15 g Fill Weight.

Nova 30 ml with aluminum pouch pack standard actuator about 150 μl with pouch is filled with about 15 g of Aldara® Cream about 5% w/w (Lot #GJF033).

Delamination of pouch material and loss of prime at about 2 days are not acceptable.

11.) Filling #2084 (about 2.5%)—about 15 g Fill Weight.

Albion 15 ml EV09/240 µl pump with standard actuator dosage about 240 µl to deliver about 240 mg shot weight is filled with low strength Imiquimod cream about 2.5% w/w (Lot GJJ067).

All physical test results are acceptable but there is a trend for loss of prime to decrease. However at about 4 weeks, the loss of prime is about 85.2% which is at the lower limit (about 85.0%) of the specification for loss of prime.

12.) Filling #s 2085 (3.75%)—about 15 g Fill Weight.

Albion 15 ml EV09/about 240 µl pump with standard actuator dosage about 240 µl to deliver about 40 mg shot weight is filled with low strength Imiquimod cream about 3.75% w/w (lot #GJJ068).

All the physical test results are acceptable; however loss of prime at 4 weeks testing is at about 78.2% which fails the acceptance criteria limit of about 85.0%.

13.) Filling #2103 (5%)—about 15 g Fill Weight.

Albion 15 ml EV09/about 240 µl pump with standard actuator dosage about 240 µl with the position of the piston inside the pack set to deliver about 15 g is filled with imiquimod cream about 5% w/w (lot #GJF033).

All the physical test results are acceptable but loss of prime at about 4 weeks testing is at about 79.5% and fails the acceptance criteria limit of about 85.0%.

Summary of Trials #s 2022-2103.

Based on the results from trials #2022, 2023, 2024, 2025, 2026, 2027, 2028, 2029, 2060, 2061, 2062, 2063, 2084, 2085 and 2103, there is a potential for failure for loss of prime using the standard actuator. It is theorized that these failures are attributable to the possibility of drying of the cream at the exposed tip of actuator nozzle.

To prevent the potential of drying of the cream and also protect the cream from the atmospheric environment, a pump with shutter or cocoon actuator is investigated. However, in order to utilize the cocoon actuator, the pump size is adjusted to from about 15 mL to about 30 mL.

Pumps with a cocoon actuator in about 30 mL volume pump are subsequently tested. These pumps also utilize a piston made of low density polyethylene material (standard), while the pumps that are tested previously used high density polyethylene pistons. Initial tests are carried out with pumps with low density polyethylene pistons to check for performance of the pump with the cream.

14.) Filling #2274 (about 3.75%)—about 7.5 g Fill Weight. Filling #2275 (about 3.75%)—about 15 g fill weight.

Albion 30 mL pump EV9/about 240 µl equipped with a cocoon actuator dosage about 240 µl with the piston made up of low density polyethylene are filled at about 7.5 g and about 15 g fill weights using Imiquimod cream about 3.75% w/w (Lot #GJJ068). The fill weights are determined to be about 10.5 grams with the restitution rate of about 7.5 g and about 18 g with the restitution rate of about 15 g as almost about 3 g of the cream is held back in the dosing chamber. All pumps have their piston moved to the position during the snapping of the actuator unit to avoid empty space on the top of the pump barrel.

Once again, Study #s 2274 and 2275 utilizing pumps with standard piston made of low density polyethylene material, where as all previous studies are conducted using pistons made up of high density polyethylene material.

All the physical test results are acceptable and loss prime at about 4 weeks testing is at about 95.8% and about 96.6% respectively thus possibly confirming the earlier theory that the failure for loss prime may be attributed to drying of the cream at nozzle tip once actuated. The use of the cocoon actuator or shutter surprisingly and unexpectedly, but successfully, corrected the loss of prime issue.

15.) Filling #2324 (about 3.75%)—about 7.5 g Fill Weight.

This study is initiated with Albion 30 mL Pump EV9/about 240 µl and cocoon actuator with piston made of high density polyethylene material (the pump body and the stem are made of polybutylene terephthalate, the actuator is made of polypropylene homopolymer/low density polyethylene and the piston is made of high density polyethylene material). The pump is filled with Imiquimod cream about 3.75% w/w (lot #GJJ068). Based on evaluating the restitution rate, it is estimated that approximately 3 g of the cream is left in the pump chamber. As a result, a fill weight of about 10.5 g is required to meet about 7.5 g Label claim.

The main goal of this study is to prove that the change of piston material from low density to high density polyethylene material does not affect the performance of the pump systems of the present invention.

EXAMPLE 3

Stress and Stability Testing Results

A. Stress Testing/Stability Results

Several observations are made during the stress testing of the about 2.5%, about 3.75% and about 5% w/w imiquimod creams filled in the above filling trials (#2022 to #2029).

The observations are as follows:

1. Delamination is observed of the Nova laminated pouch material when it is stored at accelerated conditions (i.e. ≥about 40° C.). This leads to discontinuing any further development work with this pump model.

2. Loss of prime in both Nova and Albion pump models is observed after one week of storage. This is surprisingly corrected by using the Albion pump with cocoon actuator.

B. Stability Testing Results

Several stability programs per ICH guidelines involving a series of pump options, components, fill weights and imiquimod creams are initiated.

Table 2 illustrates the stability studies and the corresponding creams that are used, fill run number, lot number of bulk cream that is used, fill weight, pump model and packaging description.

Described below is a summary of each of the stability studies that are conducted. The data collected for each stability study can be found in Attachments I-IV.

TABLE 2

| Table 2. Imiquimod Cream Stability Studies | | | | | | |
|---|---|---|---|---|---|---|
| Stability Study | Imiquimod (IMQ) Cream w/w | Fill Run # | Bulk Cream Lot # | Fill Weight | Pump Model | Package Information |
| GW 805-01 | 2.5% IMQ | 2022 | GJJ067 - 2.5% | 7.5 g | Albion EV09/150 - 15 mL | 7.5 g fill in 15 mL Albion pump with 150 µl actuator |

TABLE 2-continued

Table 2. Imiquimod Cream Stability Studies

| Stability Study | Imiquimod (IMQ) Cream w/w | Fill Run # | Bulk Cream Lot # | Fill Weight | Pump Model | Package Information |
|---|---|---|---|---|---|---|
| GW 805-01 | 2.5% IMQ | 2023 | GJJ067 - 2.5% | 15 g | Albion EV09/150 - 15 mL | 15 g fill in 15 mL Albion pump with 150 µl actuator |
| GW 805-01 | 2.5% IMQ | 2024 | GJJ067 - 2.5% | 7.5 g | Nova Pump EV09/150 - 15 mL pouch | 7.5 g fill in 15 mL Nova pump with 150 mL Aluminum pouch |
| GW 805-01 | 2.5% IMQ | 2025 | GJJ067 - 2.5% | 15 G | Nova Pump EV09/150 - 30 mL | 15 g fill in 15 mL Nova pump with 30 mL Aluminum pouch |
| GW 805-01 | 3.75% IMQ | 2026 | GJJ068 - 3.75% | 7.5 g | Albion EV09/150 - 15 mL | 7.5 g fill in 15 mL Albion pump with 150 µl actuator |
| GW 805-01 | 3.75% IMQ | 2027 | GJJ068 - 3.75% | 15 g | Albion EV09/150 - 15 mL | 15 g fill in 15 mL Albion pump with 150 µl actuator |
| GW 805-01 | 3.75% IMQ | 2028 | GJJ068 - 3.75% | 7.5 g | Nova Pump EV09/150 - 15 mL pouch | 7.5 g fill in 15 mL Nova pump with 15 ml Aluminum pouch |
| GW 805-01 | 3.75% IMQ | 2029 | GJJ068 - 3.75% | 15 g | Nova Pump EV09/150 - 30 mL pouch | 15 g fill in 15 mL Nova pump with 30 mL Aluminum pouch |
| GW 906-01 | 5% Aldara | 2080 | GJF033 - 5% | 7.5 g | Albion EV09/150 - 15 mL | 7.5 g fill in 15 mL Albion pump with 150 µl actuator |
| GW 906-01 | 5% Aldara | 2081 | GJF033 - 5% | 15 g | Albion EV09/150 - 15 mL | 15 g fill in 15 mL Albion pump with 150 µl actuator |
| GW 906-01 | 5% Aldara | 2082 | GJF033 - 5% | 7.5 g | Nova Pump EV09/150 - 15 mL pouch | 7.5 g fill in 15 mL Nova pump with 15 mL Aluminum pouch |
| GW 906-01 | 5% Aldara | 2083 | GJF033 - 5% | 15 g | Nova Pump EV09/150 - 30 mL pouch | 15 g fill in 15 mL Albion pump with 30 mL Aluminum pouch |
| GW 805-01 | 2.5% IMQ | 2084 | GJJ067 - 2.5% | 15 g | Albion EV09/240 - 15 mL | 15 g fill in 15 mL Albion pump with 240 µl actuator |
| GW 907-01 | 3.75% IMQ | 2085 | GJJ068 - 3.75% | 15 g | Albion EV09/240 - 15 mL | 15 g fill in 15 mL Albion pump with 240 µl actuator |
| GW 907-01 | 5% Aldara | 2103 | GJF033 - 5% | 15 g | Albion EV09/240 - 15 mL | 15 g fill in 15 mL Albion pump with 240 µl actuator |
| GW 907-01 | 3.75% IMQ | 2274 | GJJ068 - 3.75% | 7.5 g | Albion EV09/240 - 30 mL with cocoon | 15 g fill in 15 mL Albion pump with 240 µl cocoon actuator/PEBD piston |
| GW 921-01 | 3.75% IMQ | 2275 | GJJ068 - 3.75% | 15 g | Albion EV09/240 - 30 mL with cocoon | Albion EV09/240 - 30 mL with cocoon actuator/PEBD piston 15 g fill |
| GW 921-01 | 3.75% IMQ | 2324 | GJJ068 - 3.75% | 7.5 g | Albion EV09/240 - 30 mL with cocoon | Albion EV09/240 - 30 mL with cocoon actuator/PEHD piston 15 |

Figure 8:
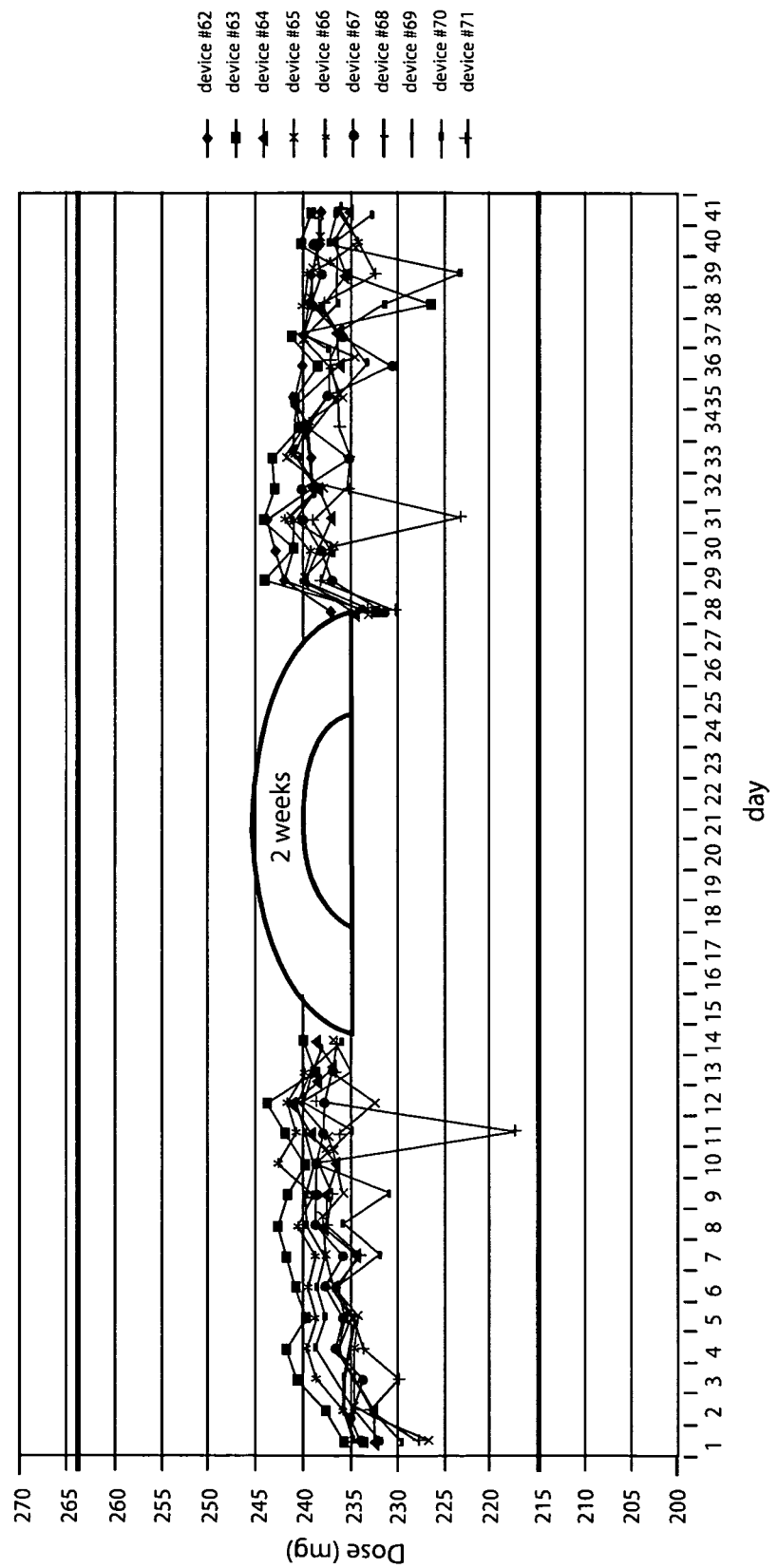
FIG. 8 shows a study regarding the evolution of daily dispensed doses from 10 packagings over a six week cycle using an Albion 30 piston LDPE restitution 7.5 ml±EV09/240±Cocoon pre-filled with an imiquimod 3.75% cream (conditions are under vacuum) to simulate a patient's clinical treatment period of 2×2×2. In this study, a pump is first primed and then actuated once every day for 2 weeks, then left static for 2 weeks, and then again actuated once daily for 2 more weeks to examine dose amount dispensed following each actuation. This study involves three two cycles (2×2×2) and shows that each dose dispensed per single daily actuation during the first two week cycle and again during the third two week cycle was about 240 mg of imiquimod 3.75% cream. See also Attachment VI below.
Figure 9:
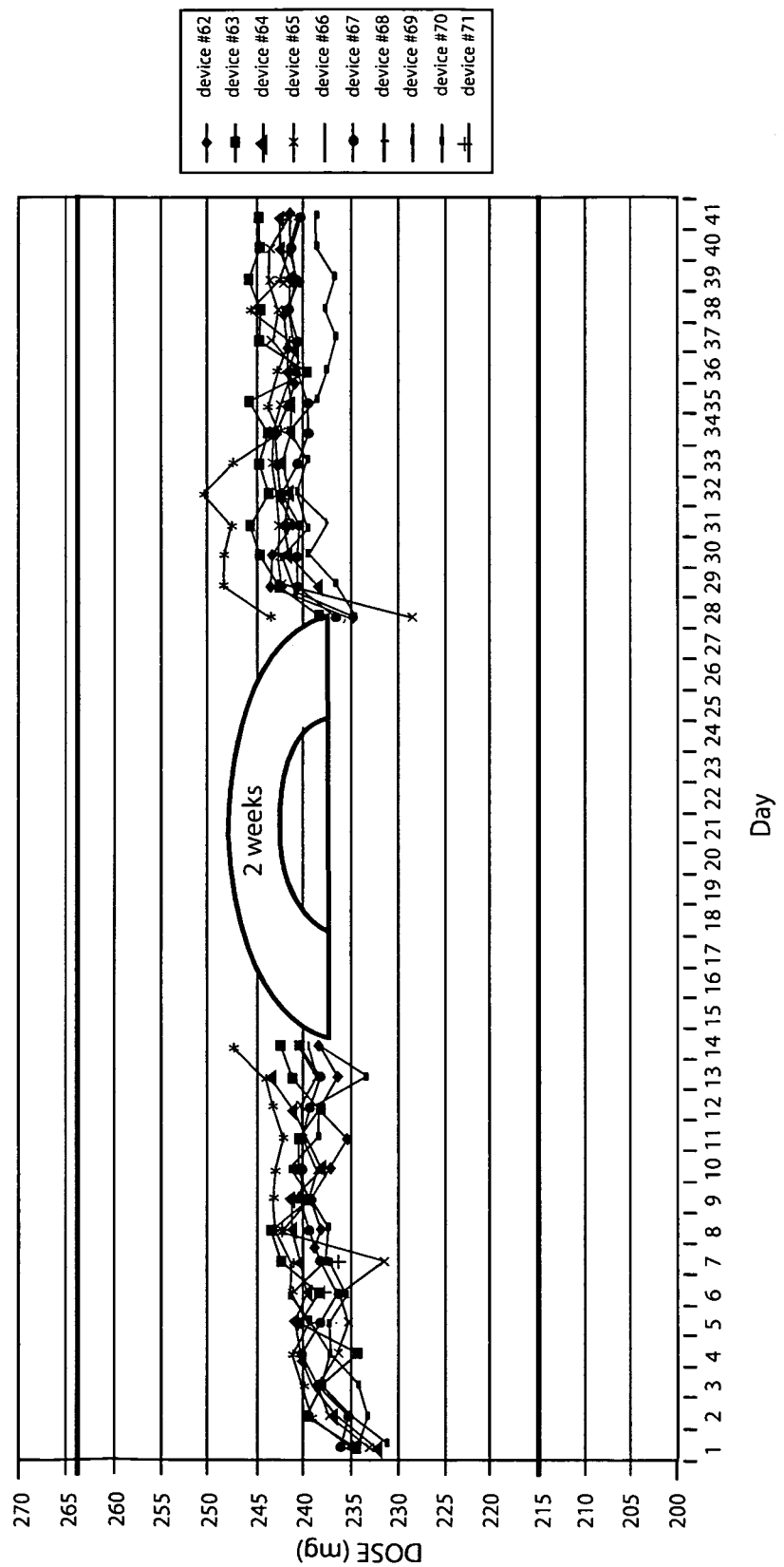
FIG. 9 shows a study regarding the evolution of daily dispensed doses from 10 packagings over a six week cycle using an Albion 30 piston LDPE restitution 15 ml±EV09/240±Cocoon pre-filled with an imiquimod 3.75% cream (conditions are under vacuum) to simulate a patient's clinical treatment period of 2×2×2. In this study, a pump is first primed and then actuated once every day for 2 weeks, then left static for 2 weeks, and then again actuated once daily for 2 more weeks to examine dose amount dispensed following each actuation. This study involves three two cycles (2×2×2) and shows that each dose dispensed per single daily actuation during the first two week cycle and again during the third two week cycle was about 240 mg of imiquimod 3.75% cream (see also Attachment VI below).

*The 2.5%, 3.75% and 5.0% imiquimod creams are isa cream formulation numbers 146, 202 and 16, respectively, and are the creams used in Examples 1-4, FIGS. 8 and 9 and Attachments I-XV, respectively.

1.) Stability Study GW 805-01—Summary.

Several observation/conclusions can be drawn from this study.

First, the delamination of the Nova pump pouch can be clearly viewed as early as about 2 months under accelerated conditions (about 40° C./75% RH).

All other testing (imiquimod assay, viscosity, benzyl alcohol, methyl and propyl parabens, pH, and 4 hydroxy imiquimod) remain well within specification and within the trend that is observed in the stability data for each cream in the commercial sachets presentation. The n-oxide testing is not performed initially as the method is not developed, however the method is available for testing the samples that are stored for about 9 month period at about 25 C160 RH and no detectable levels of n-oxide are observed.

This data can be seen in Attachment I.

2.) Stability Study GW 906-01—Summary.

This study is conducted to determine the compatibility/stability of the Aldara® about 5% w/w (imiquimod) cream formulation in both about 7.5 g and about 15 g fill weight in Albion and Nova pump systems. The stability of the formulations in both the Albion over about nine months and Nova pumps over about a three month period are consistent and passes all specifications. However, a notable difference in lower viscosities of the formulations at about T=0 and at subsequent time points can be observed which is due to the age (≈6 months) of the bulk cream that is used for filling trials. Furthermore, the internal surfaces of the pouch for the Nova pumps that is stored at about 40° C./75% RH are observed to delaminate after about 2 months at both fill volumes (about 7.5 and about 15 g), and are subsequently discontinued from testing after the about 3 month time point.

The stability data up to and including about 9 months, indicates that the Albion pump at the fill volumes of about 7.5 and about 15 g with the Aldara® about 5% w/w formulation is suitable for commercial use.

Both fill volumes (about 7.5 and about 15 g) is stored in the Albion pumps at about 40° C. 175% RH for about 3 months passes the PET test for all organisms according to the European Pharmacopeia and for the organism *E. coli*, which is an additional requirement for the United States Pharmacopeia.

All other testing (imiquimod assay, viscosity, benzyl alcohol, methyl and propyl parabens, pH, and 4 hydroxy imiquimod) remain well within specification and within the trend that is observed in the stability data for Aldara® 5% w/w cream in the commercial sachets presentation.

The samples are also analyzed using the n-oxide method following about 9 months storage at about 25° C./60% RH and no detectable levels of n-oxide are observed.

This data is in Attachment II.

3.) Stability Study GW 907-01—Summary.

The stability of the formulations in the Albion pump over about six months for all three concentrations of imiquimod (about 2.5%, about 3.75% and about 5% w/w) meet all specifications (imiquimod assay, viscosity, benzyl alcohol, methyl and propyl parabens, pH, and 4 hydroxy imiquimod) and compare well with the equivalent formulations that are stored in borosilicate glass vials over the same period of time. The results also demonstrate the same trends that are observed in the stability data for each cream in the commercial sachet presentation. However, a notable difference between the results in this study and those that are observed in other 2.5%, 3.75% and 5% w/w imiquimod creams. In the commercial sachet presentation are the lower viscosities of the formulations at about T=0 and the subsequent time points. This is the direct result of the age of the bulk cream (≈2 months) prior to filling.

The samples are also analyzed using the n-oxide method following 9 months storage at about 25° C./60% RH and no detectable levels of n-oxide are observed.

In addition, all the formulations that are stored in the Albion pumps at about 40° C.175 RH for about 3 months passes Preservative Efficacy Test (PET) for all organisms according to the European Pharmacopeia and for the organism *E. coli* which is an additional requirement for the United States Pharmacopeia. This data is in Attachment III.

4.) Stability Study GW 921-01—Summary.

The stability of Imiquimod cream about 3.75% in Albion 30 mL EV09/about 240 µl (the pump body and the stem are made of polybutylene terephthalate, the actuator is made of polypropylene homopolymer/low density polyethylene and the piston is made of high density polyethylene material). The pump is equipped with a cocoon actuator. The test results for samples that are stored for about 6 months at about 25° C./60% RH and about 40° C./75 RH meet all specifications (imiquimod assay, viscosity, benzyl alcohol, methyl and propyl parabens, pH, and 4 hydroxy imiquimod). In addition, the data compares well with the equivalent formulation that is stored in borosilicate glass vials over the same period of time and also within the trends that are observed in the stability data for each cream in the commercial sachet presentation. The data for top, middle and bottom samples that are taken for imiquimod, parabens indicate that the product is homogenous in the pump.

All samples are also analyzed using the n-oxide method following 6 months storage at about 25° C./60% RH and about 40° C./75 RH. There are no detectable levels of n-oxide observed. This data is in Attachment IV.

EXAMPLE 4

Additional Studies Conducted

A. USP Extractable Testing

The pump delivery system, Albion 30 mL EV09/about 240 µl is equipped with a cocoon actuator (pump body and the stem are made of polybutylene terephthalate, the actuator is made of polypropylene homopolymer/low density polyethylene and the piston is made of high density polyethylene material) that is selected for commercial use meets USP 32/NF 27 <661> Physicochemical Tests-Plastics, and USP <281> for Residue on Ignition.

This report is provided in Attachment V.

B. Patient in Use Test

In addition to the tests discussed in this report, Albion 30 mL EV09/about 240 µl with cocoon actuator (the pump body and the stem are made of polybutylene terephthalate, the actuator is made of polypropylene homopolymer/low density polyethylene and the piston is made of high density polyethylene material) is tested to simulate the patient's clinical treatment period for 2 weeks on 2 weeks off and 2 weeks on. See FIGS. 8 and 9 and Attachment VI.

In this study, the pump is primed and actuated once every day for 2 weeks and then left static for 2 weeks. At the end of 2 weeks of no pump actuation, the pump is again actuated for 2 more weeks to check if a consistent and uniform dosage amount of cream is available to patient for the treatment period. The results are acceptable as the pump provides approximately 240 mg cream for each daily application during all 4 weeks of the treatment. See FIGS. 8 and 9. The data is provided in the Attachment VI.

C. Leak Test During Stability Study

During the course of the stability studies (about 12 month time point for GW 805, 906, 907 and 9 months for GW 921), it is decided to place all pumps on their sides to monitor leaking and delivery performance.

There is no leaking of the product from the pumps and all pumps delivery performance is acceptable.

Based on the satisfactory physical, chemical and performance testing data, Albion 30 mL EV09/about 240 µA cocoon actuator (the pump body and the stem are made of polybutylene terephthalate, the actuator is made of polypropylene homopolymer/low density polyethylene and the piston is made of high density polyethylene material) is remarkable and surprisingly acceptable and, therefore, selected for commercialization. In addition, the NDA registration stability batches using this pump filled at both about 7.5 g and about 15 g fill using 3.75% and 5% w/w imiquimod cream are manufactured and are placed on stability at 3M, Loughborough, UK. This pump system is covered under Valois's DMF number 18156 "Albion 30 nil Piston Assembled Barrel+

EV09/240 Pump+PR820 Cocoon Actuator+Cap". The pump parts, assembly and specifications are provided in Attachment VII. See also FIGS. 10 and 11.

EXAMPLE 5

Imiquimod Cream Formulation 5

A cream according to the present invention is prepared from the following ingredients in Table 3.

TABLE 3

Imiquimod Cream Formulation 5

| Oil Phase | Example 5 % by Weight | Example 5 Amount |
|---|---|---|
| 1-isobutyl-1H-imidazo[4.5-c]-quinolin-4-amine | 1.0 | 40.0 g |
| Isostearic acid | 10.0 | 400.0 g |
| Benzyl alcohol | 2.0 | 80.0 g |
| Cetyl alcohol | 2.2 | 88.0 g |
| Stearyl alcohol | 3.1 | 124.0 g |
| Polysorbate 60 | 2.55 | 102.0 g |
| Sorbitan monostearate | 0.45 | 18.0 g |
| Aqueous Phase Glycerin | 2.0 | 80.0 g |
| Methylparaben | 0.2 | 8.0 g |
| Propylparaben | 0.02 | 0.8 g |
| Purified water | 76.48 | 3059.2 g |

The materials listed above were combined according to the following procedure.

The glycerin, methylparaben, propylparaben and water were weighed into a 4 liter glass beaker then heated on a hot plate with stirring until the parabens isostearic acid and 1-isobutyl-1H-imidazo[4,5-c]quinolin-4-amine were weighed into an 8 liter stainless steel beaker and heated on a hot plate until the amine was in solution (the temperature reached 69° C.). The benzyl alcohol, cetyl alcohol, stearyl alcohol, polysorbate 60 and sorbitan monostearate were added to the isostearic acid solution and heated on a hot plate until all material was dissolved (the temperature reached 75° C.). With both phases at approximately the same temperature (65°-75° C.), the water phase was added to the oil phase. The mixture was mixed with a homogenizer for 13 minutes then put into a cool water bath and mixed with a 3 inch propeller for 40 minutes (the temperature was 29° C.). The resulting cream was placed in glass jars.

EXAMPLES 6-13

Imiquimod Cream Formulations 6-13

Using the general method of Example 5, the imiquimod cream formulations shown in Tables 4 and 5 are prepared.

TABLE 4

Imiquimod Cream Formulations 6-9

| | % by Weight | | | |
|---|---|---|---|---|
| Oil Phase | Example 6 | Example 7 | Example 8 | Example 9 |
| 1-isobutyl-1H-imidazo[4,5-c]quinolin-4-amine | 1.0 | 1.0 | 1.0 | 1.0 |
| Isostearic acid | 10.0 | 10.0 | 5.0 | 5.0 |
| Benzyl alcohol | | 2.0 | | |
| Cetyl alcohol | | 1.7 | | |
| Stearyl alcohol | | 2.3 | | |
| Cetearyl alcohol | 6.0 | | 6.0 | 6.0 |
| Polysorbate 60 | 2.55 | 2.55 | 2.55 | 2.55 |
| Sorbitan monostearate | 0.45 | 0.45 | 0.45 | 0.45 |
| Brij ™ 30[a] | | | | 10.0 |
| Aqueous Phase | | | | |
| Glycerin | 2.0 | 2.0 | 2.0 | 2.0 |
| Methylparaben | 0.2 | 0.2 | 0.2 | 0.2 |
| Propylparaben | 0.02 | 0.02 | 0.02 | 0.02 |
| Purified water | 77.78 | 77.78 | 82.78 | 72.78 |

[a]Brij ™ 30 (polyoxyethylene(4) lauryl ether) is available from ICI Americas, Inc.

TABLE 5

Imiquimod Cream Formulations 10-13

| | % by Weight | | | |
|---|---|---|---|---|
| | Example 10 | Example 11 | Example 12 | Example 13 |
| Oil Phase | | | | |
| 1-isobutyl-1H-imidazo[4,5-c]quinolin-4-amine | 1.0 | 1.0 | 1.0 | 1.0 |
| Isostearic acid | 10.0 | 25.0 | 10.0 | 6.0 |
| Benzyl alcohol | | 2.0 | | 2.0 |
| Cetyl alcohol | | 2.2 | 1.7 | |
| Stearyl alcohol | | 3.1 | 2.3 | |
| Cetearyl alcohol | 6.0 | | | 6.0 |
| Polysorbate 60 | 2.55 | 3.4 | 2.55 | 2.55 |
| Sorbitan monostearate | 0.45 | 0.6 | 0.45 | 0.45 |
| Brij ™ 30[a] | 10.0 | | | |
| Aqueous Phase | | | | |
| Glycerin | 2.0 | 2.0 | 2.0 | 2.0 |
| Methylparaben | 0.2 | 0.2 | 0.2 | 0.2 |
| Propylparaben | 0.02 | 0.02 | 0.02 | 0.02 |
| Purified water | 67.78 | 60.48 | 79.78 | 79.78 |

[a]Brij ™ 30 (polyoxyethylene(4) lauryl ether) is available from ICI Americas, Inc.

EXAMPLE 14

Imiquimod Cream Formulation 14

A cream according to the present invention is prepared from the following ingredients in the following Table 6.

TABLE 6

Imiquimod Cream Formulation 14

| | % by Weight | Amount |
|---|---|---|
| Oil Phase | | |
| 1-isobutyl-1H-imidazo[4,5-c]quinolin-4-amine | 1.0 | 3.00 g |
| Isostearic acid | 5.0 | 15.0 g |
| White petrolatum | 15.0 | 45.0 g |
| Light mineral oil | 12.8 | 38.4 g |
| Aluminum stearate | 8.0 | 24.0 g |
| Cetyl alcohol | 4.0 | 12.0 g |
| Witconol ™ 14[a] | 3.0 | 9.00 g |
| Acetylated lanolin | 1.0 | 3.0 g |
| Propylparaben | 0.063 | 0.19 g |

TABLE 6-continued

Imiquimod Cream Formulation 14

|  | % by Weight | Amount |
|---|---|---|
| Aqueous Phase |  |  |
| Veegum ™ K[b] | 1.0 | 3.0 g |
| Methylparaben | 0.12 | 0.36 g |
| Purified water | 49.017 | 147.05 g |

[a]Witconol ™ 14 (polyglyceryl4 oleate) is available from Witco Chemical Corp. Organics Division
[b]Veegum ™ K (colloidal magnesium aluminum silicate) is available from R. T. Vanderbilt Company Inc.

The materials listed above were combined according to the following procedure: The 1-isobutyl-1H-imidazo[4,5-c]quinolin-4-amine and the isostearic acid were weighed into a glass jar and heated with occasional stirring until the amine was dissolved (the temperature reached 68° C.). To this solution was added, the petrolatum, mineral oil, aluminum stearate, cetyl alcohol, Witconol™ 14, acetylated lanoline and propylparaben. The mixture was heated to 75° C. In a separate beaker, the methylparaben and water were combined and heated until the paraben dissolved (the temperature reached 61° C.). The Veegum™ K was added to the aqueous solution and heated at 75° C. for 30 minutes while mixing with a homogenizer. With both phases at 75° C., the aqueous phase was slowly added to the oil phase while mixing with a homogenizer. Mixing was continued for 30 minutes while maintaining a temperature to about 80° C. The jar was then capped and the formulation was allowed to cool.

EXAMPLE 15

Imiquimod Ointment Formulation 15(a) and 15(b)

An ointment according to the present invention is prepared from the ingredients in the following Table 7.

TABLE 7

Imiquimod Cream Formulation 15(a)

|  | Example 15(a) % by Weight | Example 15(a) Amount |
|---|---|---|
| 1-isobutyl-1H-imidazo[4,5-c]quinolin-4-Amine | 1.0 | 0.20 g |
| Isostearic acid | 5.0 | 1.00 g |
| Mineral oil | 12.8 | 2.56 g |
| White petrolatum | 65.2 | 13.04 g |
| Cetyl alcohol | 4.0 | 0.80 g |
| Acetylated lanolin | 1.0 | 0.20 g |
| Witconol ™ 143.0 | 3.0 | 0.60 g |
| Aluminum stearate | 8.0 | 1.60 g |

The materials listed above are combined according to the following procedure.

The 1-isobutyl-1H-imidazo[4,5-c]quinolin-4-amine and the isostearic acid were placed in a glass jar and heated with stirring until the amine was dissolved. The remaining ingredients were added and the resulting mixture was heated to 65° C. and then mixed while being allowed to cool to room temperature.

Using the general procedure of Example 15, an ointment containing the ingredients in the following Table 8 is prepared.

TABLE 8

Imiquimod Ointment Formulation 15(b)

|  | Example 15(b) % by Weight | Example 15(b) Amount |
|---|---|---|
| 1-isobutyl-1H-imidazo[4,5-c]quinolin-4-Amine | 1.0 | 0.20 g |
| Isostearic acid | 6.0 | 1.20 g |
| Polyethylene Glycol 400 | 55.8 | 11.16 g |
| Polyethylene Glycol 3350 | 32.6 | 6.52 g |
| Stearyl alcohol | 4.6 | 0.92 g |

EXAMPLES 16-18

Imiquimod Cream Formulations 16-18

Creams of the present invention are prepared using the ingredients shown in Table 9. The Example 1 except that benzyl alcohol was used with the isostearic acid to dissolve the 1-sobutyl-1H-imidazo[4,5-c]quinolin-4-amine.

TABLE 9

Imiquimod Cream Formulations 16-18

|  | Example 16 Amount % by Weight | Example 17 Amount % by Weight | Example 18 Amount % by Weight |
|---|---|---|---|
| Oil Phase |  |  |  |
| 1-isobutyl-1H-imidazo[4,5-c]quinolin-4-amine | 5.0 | 5.0 | 4.85 |
| Isostearic acid | 25.0 | 25.0 | 24.3 |
| Benzyl alcohol | 2.0 | 2.0 | 1.94 |
| Cetyl alcohol | 2.2 | 2.2 | 1.16 |
| Stearyl alcohol | 3.1 | 3.1 | 1.75 |
| Petrolatum | 3.0 |  | 2.91 |
| Polysorbate 60 | 3.4 | 3.4 | 4.13 |
| Sorbitan monostearate | 0.6 | 0.6 | 0.73 |
| Stearic acid |  |  | 9.71 |
| Aqueous Phase |  |  |  |
| Glycerin | 2.0 | 2.0 | 1.94 |
| Methylparaben | 0.2 | 0.2 | 0.19 |
| Propylparaben | 0.02 | 0.02 | 0.02 |

EXAMPLES 19 and 20

Imiquimod Cream Formulations 19 and 20

A cream according to the present invention is prepared from the ingredients in the following Table 10.

TABLE 10

Imiquimod Cream Formulations 19 and 20

|  | Example 19 % by Weight Amount | Example 20 % by Weight Amount |
|---|---|---|
| Oil Phase |  |  |
| 1-isobutyl-1H-imidazo[4,5-c]quinolin-4-amine | 4.0 | 0.80 g |
| Isostearic acid | 20.0 | 4.00 g |
| Benzyl alcohol | 2.0 | 0.40 g |
| Cetyl alcohol | 2.2 | 0.49 g |
| Stearyl alcohol | 3.1 | 0.62 g |
| Polysorbate 60 | 3.4 | 0.68 g |
| Sorbitan monostearate | 0.6 | 0.12 g |

TABLE 10-continued

Imiquimod Cream Formulations 19 and 20

| | Example 19 % by Weight Amount | Example 20 % by Weight Amount |
|---|---|---|
| Aqueous Phase | | |
| 1-isobutyl-1H-imidazo[4,5-c]quinolin-4-amine | 1.0 | 0.2 g |
| Glycerin | 2.0 | 0.4 g |
| 85% Lactic acid | 1.0 | 0.22 g |
| Methylparaben | 0.2 | 0.04 g |
| Propylparaben | 0.02 | 0.004 g |
| Purified water | 60.48 | 12.0 g |

The materials listed above are combined according to the following procedure: The isostearic acid and 0.8 g of 1-isobutyl-1H-imidazo[4,5-c]quinolin-4-amine or 1-(2-methylpropyl-1H-imidazo[4,5-c]quinolin-4-amine were combined in a glass jar and heated with stirring until the amine had dissolved. The remaining oil phase ingredients were added to this solution and the mixture was heated to about 70° C. The aqueous phase ingredients were weighed into a separate beaker and heated with stirring until the amine and the parabens had dissolved. With both phases at about 70° C., the water phase was added to the oil phase and mixed with a propeller until the mixture cooled to room temperature.

EXAMPLE 21

Imiquimod Cream Formulations 21-254
Topical Imiquimod Pharmaceutical Cream Formulations

TABLE 11

Lower Dosage Strength Imiquimod Cream Formulations 21-254

| Excipients Formulation | % w/w 21 | % w/w 22 | % w/w 23 | % w/w 24 | % w/w 25 | % w/w 26 |
|---|---|---|---|---|---|---|
| Fatty acid* | 15.00 | 15.00 | 15.00 | 20.00 | 15.00 | 20.00 |
| Cetyl alcohol | 2.20 | 2.20 | 2.20 | 2.20 | 2.20 | 2.20 |
| Stearyl alcohol | 3.10 | 3.10 | 3.10 | 3.10 | 3.10 | 3.10 |
| White petrolatum | 1.00 | 3.00 | 2.00 | 3.00 | 6.00 | 3.00 |
| Polysorbate 60 | 3.40 | 3.40 | 3.40 | 3.40 | 3.00 | 3.00 |
| Sorbitan Monostearate | 0.60 | 0.60 | 0.60 | 0.60 | 1.00 | 1.00 |
| Glycerin | 2.00 | 2.00 | 5.00 | 2.00 | 5.00 | 3.00 |
| Xanthan gum | 0.50 | 0.50 | 0.50 | 0.50 | 0.75 | 0.75 |
| Purified water | 68.98 | 66.98 | 64.98 | 61.98 | 60.73 | 60.73 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 1.00 | 1.00 | 1.00 | 1.00 | 1.00 | 1.00 |
| Total | 100.00 | 100.00 | 100.00 | 100.00 | 100.00 | 100.00 |

| Excipients Formulation | % w/w 27 | % w/w 28 | % w/w 29 | % w/w 30 | % w/w 31 | % w/w 32 |
|---|---|---|---|---|---|---|
| Fatty acid* | 15.00 | 15.00 | 15.00 | 25.00 | 18.0 | 25.00 |
| Cetyl alcohol | 2.20 | 2.20 | 2.20 | 2.20 | 2.20 | 2.70 |
| Stearyl alcohol | 3.10 | 3.10 | 3.10 | 3.10 | 3.10 | 3.80 |
| White petrolatum | 3.00 | 6.00 | 6.00 | 3.00 | 5.00 | 3.00 |
| Polysorbate 60 | 3.40 | 3.40 | 3.00 | 3.40 | 3.00 | 3.40 |
| Sorbitan Monostearate | 0.60 | 0.60 | 1.00 | 0.50 | 1.00 | 0.60 |
| Glycerin | 2.00 | 5.00 | 5.00 | 2.00 | 5.00 | 2.00 |
| Xanthan gum | 0.50 | 0.50 | 0.50 | 0.50 | 0.50 | 0.50 |
| Purified water | 66.98 | 60.98 | 60.98 | 57.08 | 58.98 | 55.78 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 1.00 | 1.00 | 1.00 | 1.00 | 1.00 | 1.00 |
| Total | 100.00 | 100.00 | 100.00 | 100.00 | 100.00 | 100.00 |

| Excipients Formulation | % w/w 33 | % w/w 34 | % w/w 35 | % w/w 36 | % w/w 37 | % w/w 38 |
|---|---|---|---|---|---|---|
| Fatty acid* | 25.00 | 15.00 | 20.00 | 20.00 | 20.00 | 20.00 |
| Cetyl alcohol | 2.20 | 2.00 | 2.20 | 2.20 | 2.20 | 2.20 |
| Stearyl alcohol | 3.10 | 2.00 | 3.10 | 3.10 | 3.10 | 3.10 |
| White petrolatum | 3.00 | 3.40 | 5.00 | 3.00 | 5.00 | 3.00 |
| Polysorbate 60 | 3.40 | 3.80 | 3.40 | 3.40 | 3.40 | 3.40 |
| Sorbitan Monostearate | 0.60 | 0.2 | 0.60 | 0.60 | 0.60 | 0.60 |
| Glycerin | 2.00 | 3.00 | 2.00 | 5.00 | 5.00 | 2.00 |
| Xanthan gum | 1.00 | 0.30 | 0.50 | 0.50 | 0.50 | 0.50 |
| Purified water | 56.48 | 67.08 | 59.98 | 58.98 | 56.98 | 61.98 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 1.00 | 1.00 | 1.00 | 1.00 | 1.00 | 1.00 |
| Total | 100.00 | 100.00 | 100.00 | 100.00 | 100.00 | 100.00 |

| Excipients Formulation | % w/w 39 | % w/w 40 | % w/w 41 | % w/w 42 | % w/w 43 | % w/w 44 |
|---|---|---|---|---|---|---|
| Fatty acid* | 15.00 | 15.00 | 15.00 | 20.00 | 15.00 | 20.00 |
| Cetyl alcohol | 2.20 | 2.20 | 2.20 | 2.20 | 2.20 | 2.20 |
| Stearyl alcohol | 3.10 | 3.10 | 3.10 | 3.10 | 3.10 | 3.10 |
| White petrolatum | 1.00 | 3.00 | 2.00 | 3.00 | 6.00 | 3.00 |
| Polysorbate 60 | 3.40 | 3.40 | 3.40 | 3.40 | 3.00 | 3.00 |
| Sorbitan Monostearate | 0.60 | 0.60 | 0.60 | 0.60 | 1.00 | 1.00 |
| Glycerin | 2.00 | 2.00 | 5.00 | 2.00 | 5.00 | 3.00 |
| Xanthan gum | 0.50 | 0.50 | 0.50 | 0.50 | 0.75 | 0.75 |
| Purified water | 68.73 | 66.73 | 64.73 | 61.73 | 60.48 | 60.48 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 1.25 | 1.25 | 1.25 | 1.25 | 1.25 | 1.25 |
| Total | 100.00 | 100.00 | 100.00 | 100.00 | 100.00 | 100.00 |

| Excipients Formulation | % w/w 45 | % w/w 46 | % w/w 47 | % w/w 48 | % w/w 49 | % w/w 50 |
|---|---|---|---|---|---|---|
| Fatty acid* | 15.00 | 15.00 | 15.00 | 25.00 | 18.0 | 25.00 |
| Cetyl alcohol | 2.20 | 2.20 | 2.20 | 2.20 | 2.20 | 2.70 |
| Stearyl alcohol | 3.10 | 3.10 | 3.10 | 3.10 | 3.10 | 3.80 |
| White petrolatum | 3.00 | 6.00 | 6.00 | 3.00 | 5.00 | 3.00 |
| Polysorbate 60 | 3.40 | 3.40 | 3.00 | 3.40 | 3.00 | 3.40 |
| Sorbitan Monostearate | 0.60 | 0.60 | 1.00 | 0.50 | 1.00 | 0.60 |
| Glycerin | 2.00 | 5.00 | 5.00 | 2.00 | 5.00 | 2.00 |
| Xanthan gum | 0.50 | 0.50 | 0.50 | 0.50 | 0.50 | 0.50 |
| Purified water | 66.73 | 60.73 | 60.73 | 56.83 | 58.73 | 55.53 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 1.25 | 1.25 | 1.25 | 1.25 | 1.25 | 1.25 |
| Total | 100.00 | 100.00 | 100.00 | 100.00 | 100.00 | 100.00 |

| Excipients Formulation | % w/w 51 | % w/w 52 | % w/w 53 | % w/w 54 | % w/w 55 | % w/w 56 |
|---|---|---|---|---|---|---|
| Fatty acid* | 25.00 | 15.00 | 20.00 | 20.00 | 20.00 | 20.00 |
| Cetyl alcohol | 2.20 | 2.00 | 2.20 | 2.20 | 2.20 | 2.20 |
| Stearyl alcohol | 3.10 | 2.00 | 3.10 | 3.10 | 3.10 | 3.10 |
| White petrolatum | 3.00 | 3.40 | 5.00 | 3.00 | 5.00 | 3.00 |
| Polysorbate 60 | 3.40 | 3.80 | 3.40 | 3.40 | 3.40 | 3.40 |

TABLE 11-continued

Lower Dosage Strength Imiquimod Cream Formulations 21-254

| Excipients | | | | | | |
|---|---|---|---|---|---|---|
| Sorbitan Monostearate | 0.60 | 0.2 | 0.60 | 0.60 | 0.60 | 0.60 |
| Glycerin | 2.00 | 3.00 | 2.00 | 5.00 | 5.00 | 2.00 |
| Xanthan gum | 1.00 | 0.30 | 0.50 | 0.50 | 0.50 | 0.50 |
| Purified water | 56.23 | 66.83 | 59.73 | 58.73 | 56.73 | 61.73 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 1.25 | 1.25 | 1.25 | 1.25 | 1.25 | 1.25 |
| Total | 100.00 | 100.00 | 100.00 | 100.00 | 100.00 | 100.00 |

| Excipients Formulation | % w/w 57 | % w/w 58 | % w/w 59 | % w/w 60 | % w/w 61 | % w/w 62 |
|---|---|---|---|---|---|---|
| Fatty acid* | 15.00 | 15.00 | 15.00 | 20.00 | 15.00 | 20.00 |
| Cetyl alcohol | 2.20 | 2.20 | 2.20 | 2.20 | 2.20 | 2.20 |
| Stearyl alcohol | 3.10 | 3.10 | 3.10 | 3.10 | 3.10 | 3.10 |
| White petrolatum | 1.00 | 3.00 | 2.00 | 3.00 | 6.00 | 3.00 |
| Polysorbate 60 | 3.40 | 3.40 | 3.40 | 3.40 | 3.00 | 3.00 |
| Sorbitan Monostearate | 0.60 | 0.60 | 0.60 | 0.60 | 1.00 | 1.00 |
| Glycerin | 2.00 | 2.00 | 5.00 | 2.00 | 5.00 | 3.00 |
| Xanthan gum | 0.50 | 0.50 | 0.50 | 0.50 | 0.75 | 0.75 |
| Purified water | 68.48 | 66.48 | 64.48 | 61.48 | 60.23 | 60.23 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 1.50 | 1.50 | 1.50 | 1.50 | 1.50 | 1.50 |
| Total | 100.00 | 100.00 | 100.00 | 100.00 | 100.00 | 100.00 |

| Excipients Formulation | % w/w 63 | % w/w 64 | % w/w 65 | % w/w 66 | % w/w 67 | % w/w 68 |
|---|---|---|---|---|---|---|
| Fatty acid | 15.00 | 15.00 | 15.00 | 25.00 | 18.0 | 25.00 |
| Cetyl alcohol | 2.20 | 2.20 | 2.20 | 2.20 | 2.20 | 2.70 |
| Stearyl alcohol | 3.10 | 3.10 | 3.10 | 3.10 | 3.10 | 3.80 |
| White petrolatum | 3.00 | 6.00 | 6.00 | 3.00 | 5.00 | 3.00 |
| Polysorbate 60 | 3.40 | 3.40 | 3.00 | 3.40 | 3.00 | 3.40 |
| Sorbitan Monostearate | 0.60 | 0.60 | 1.00 | 0.50 | 1.00 | 0.60 |
| Glycerin | 2.00 | 5.00 | 5.00 | 2.00 | 5.00 | 2.00 |
| Xanthan gum | 0.50 | 0.50 | 0.50 | 0.50 | 0.50 | 0.50 |
| Purified water | 66.48 | 60.48 | 60.48 | 56.58 | 58.48 | 55.28 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 1.50 | 1.50 | 1.50 | 1.50 | 1.50 | 1.50 |
| Total | 100.00 | 100.00 | 100.00 | 100.00 | 100.00 | 100.00 |

| Excipients Formulation | % w/w 69 | % w/w 70 | % w/w 71 | % w/w 72 | % w/w 73 | % w/w 74 |
|---|---|---|---|---|---|---|
| Fatty acid* | 25.00 | 15.00 | 20.00 | 20.00 | 20.00 | 20.00 |
| Cetyl alcohol | 2.20 | 2.00 | 2.20 | 2.20 | 2.20 | 2.20 |
| Stearyl alcohol | 3.10 | 2.00 | 3.10 | 3.10 | 3.10 | 3.10 |
| White petrolatum | 3.00 | 3.40 | 5.00 | 3.00 | 5.00 | 3.00 |
| Polysorbate 60 | 3.40 | 3.80 | 3.40 | 3.40 | 3.40 | 3.40 |
| Sorbitan Monostearate | 0.60 | 0.2 | 0.60 | 0.60 | 0.60 | 0.60 |
| Glycerin | 2.00 | 3.00 | 2.00 | 5.00 | 5.00 | 2.00 |
| Xanthan gum | 1.00 | 0.30 | 0.50 | 0.50 | 0.50 | 0.50 |
| Purified water | 55.98 | 66.58 | 59.48 | 58.48 | 56.48 | 61.48 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 1.50 | 1.50 | 1.50 | 1.50 | 1.50 | 1.50 |
| Total | 100.00 | 100.00 | 100.00 | 100.00 | 100.00 | 100.00 |

| Excipients Formulation | % w/w 75 | % w/w 76 | % w/w 77 | % w/w 78 | % w/w 79 | % w/w 80 |
|---|---|---|---|---|---|---|
| Fatty acid* | 15.00 | 15.00 | 15.00 | 20.00 | 15.00 | 20.00 |
| Cetyl alcohol | 2.20 | 2.20 | 2.20 | 2.20 | 2.20 | 2.20 |
| Stearyl alcohol | 3.10 | 3.10 | 3.10 | 3.10 | 3.10 | 3.10 |
| White petrolatum | 1.00 | 3.00 | 2.00 | 3.00 | 6.00 | 3.00 |
| Polysorbate 60 | 3.40 | 3.40 | 3.40 | 3.40 | 3.00 | 3.00 |
| Sorbitan Monostearate | 0.60 | 0.60 | 0.60 | 0.60 | 1.00 | 1.00 |
| Glycerin | 2.00 | 2.00 | 5.00 | 2.00 | 5.00 | 3.00 |
| Xanthan gum | 0.50 | 0.50 | 0.50 | 0.50 | 0.75 | 0.75 |
| Purified water | 68.23 | 66.23 | 64.23 | 61.23 | 59.98 | 59.98 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 1.75 | 1.75 | 1.75 | 1.75 | 1.75 | 1.75 |
| Total | 100.00 | 100.00 | 100.00 | 100.00 | 100.00 | 100.00 |

| Excipients Formulation | % w/w 81 | % w/w 82 | % w/w 83 | % w/w 84 | % w/w 85 | % w/w 86 |
|---|---|---|---|---|---|---|
| Fatty acid* | 15.00 | 15.00 | 15.00 | 25.00 | 18.0 | 25.00 |
| Cetyl alcohol | 2.20 | 2.20 | 2.20 | 2.20 | 2.20 | 2.70 |
| Stearyl alcohol | 3.10 | 3.10 | 3.10 | 3.10 | 3.10 | 3.80 |
| White petrolatum | 3.00 | 6.00 | 6.00 | 3.00 | 5.00 | 3.00 |
| Polysorbate 60 | 3.40 | 3.40 | 3.00 | 3.40 | 3.00 | 3.40 |
| Sorbitan Monostearate | 0.60 | 0.60 | 1.00 | 0.50 | 1.00 | 0.60 |
| Glycerin | 2.00 | 5.00 | 5.00 | 2.00 | 5.00 | 2.00 |
| Xanthan gum | 0.50 | 0.50 | 0.50 | 0.50 | 0.50 | 0.50 |
| Purified water | 66.23 | 60.23 | 60.23 | 56.33 | 58.23 | 55.03 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 1.75 | 1.75 | 1.75 | 1.75 | 1.75 | 1.75 |
| Total | 100.00 | 100.00 | 100.00 | 100.00 | 100.00 | 100.00 |

| Excipients Formulation | % w/w 87 | % w/w 88 | % w/w 89 | % w/w 90 | % w/w 91 | % w/w 92 |
|---|---|---|---|---|---|---|
| Fatty acid* | 25.00 | 15.00 | 20.00 | 20.00 | 20.00 | 20.00 |
| Cetyl alcohol | 2.20 | 2.00 | 2.20 | 2.20 | 2.20 | 2.20 |
| Stearyl alcohol | 3.10 | 2.00 | 3.10 | 3.10 | 3.10 | 3.10 |
| White petrolatum | 3.00 | 3.40 | 5.00 | 3.00 | 5.00 | 3.00 |
| Polysorbate 60 | 3.40 | 3.80 | 3.40 | 3.40 | 3.40 | 3.40 |
| Sorbitan Monostearate | 0.60 | 0.2 | 0.60 | 0.60 | 0.60 | 0.60 |
| Glycerin | 2.00 | 3.00 | 2.00 | 5.00 | 5.00 | 2.00 |
| Xanthan gum | 1.00 | 0.30 | 0.50 | 0.50 | 0.50 | 0.50 |
| Purified water | 55.73 | 66.33 | 59.23 | 58.23 | 56.23 | 61.23 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 1.75 | 1.75 | 1.75 | 1.75 | 1.75 | 1.75 |
| Total | 100.00 | 100.00 | 100.00 | 100.00 | 100.00 | 100.00 |

| Excipients Formulation | % w/w 93 | % w/w 94 | % w/w 95 | % w/w 96 | % w/w 97 | % w/w 98 |
|---|---|---|---|---|---|---|
| Fatty acid* | 10.00 | 12.50 | 25.00 | 10.00 | 15.00 | 20.00 |
| Cetyl alcohol | 2.20 | 2.20 | 2.70 | 4.00 | 4.00 | 2.20 |
| Stearyl alcohol | 3.10 | 3.10 | 3.80 | 2.00 | 2.00 | 3.10 |
| White petrolatum | 5.00 | 5.00 | 3.00 | 3.40 | 2.80 | 3.00 |
| Polysorbate 60 | 3.40 | 3.40 | 3.40 | 3.80 | 3.00 | 3.00 |
| Sorbitan Monostearate | 0.60 | 0.60 | 0.60 | 1.00 | 1.00 | 1.00 |
| Glycerin | 5.00 | 5.00 | 2.00 | 1.00 | 3.00 | 3.00 |
| Xanthan gum | 0.50 | 0.50 | 0.50 | 0.30 | 0.70 | 0.75 |
| Purified water | 65.98 | 63.48 | 54.78 | 70.28 | 64.28 | 59.73 |
| Benzyl alcohol | 2.00 | 2.00 | 2.00 | 2.00 | 2.00 | 2.00 |

TABLE 11-continued

Lower Dosage Strength Imiquimod Cream Formulations 21-254

| | | | | | | |
|---|---|---|---|---|---|---|
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 2.00 | 2.00 | 2.00 | 2.00 | 2.00 | 2.00 |
| Total | 100.00 | 100.00 | 100.00 | 100.00 | 100.00 | 100.00 |

| Excipients Formulation | % w/w 99 | % w/w 100 | % w/w 101 | % w/w 102 | % w/w 103 | % w/w 104 |
|---|---|---|---|---|---|---|
| Fatty acid* | 10.00 | 12.50 | 25.00 | 10.00 | 15.00 | 25.00 |
| Cetyl alcohol | 2.20 | 2.20 | 2.70 | 4.00 | 4.00 | 2.70 |
| Stearyl alcohol | 3.10 | 3.10 | 3.80 | 2.00 | 2.00 | 3.80 |
| White petrolatum | 5.00 | 5.00 | 3.00 | 3.40 | 2.80 | 3.00 |
| Polysorbate 60 | 3.40 | 3.40 | 3.40 | 3.80 | 3.00 | 3.40 |
| Sorbitan Monostearate | 0.60 | 0.60 | 0.60 | 1.00 | 1.00 | 0.60 |
| Glycerin | 5.00 | 5.00 | 2.00 | 1.00 | 3.00 | 2.00 |
| Xanthan gum | 0.50 | 0.50 | 0.50 | 0.30 | 0.70 | 0.50 |
| Purified water | 65.98 | 63.48 | 54.78 | 70.28 | 64.28 | 54.78 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 2.00 | 2.00 | 2.00 | 2.00 | 2.00 | 2.00 |
| Total | 100.00 | 100.00 | 100.00 | 100.00 | 100.00 | 100.00 |

| Excipients Formulation | % w/w 105 | % w/w 106 | % w/w 107 | % w/w 108 | % w/w 109 | % w/w 110 |
|---|---|---|---|---|---|---|
| Fatty acid* | 25.00 | 15.00 | 20.00 | 20.00 | 20.00 | 20.00 |
| Cetyl alcohol | 2.20 | 2.00 | 2.20 | 2.20 | 2.20 | 2.20 |
| Stearyl alcohol | 3.10 | 2.00 | 3.10 | 3.10 | 3.10 | 3.10 |
| White petrolatum | 3.00 | 3.40 | 5.00 | 3.00 | 5.00 | 3.00 |
| Polysorbate 60 | 3.40 | 3.80 | 3.40 | 3.40 | 3.40 | 3.40 |
| Sorbitan Monostearate | 0.60 | 0.2 | 0.60 | 0.60 | 0.60 | 0.60 |
| Glycerin | 2.00 | 3.00 | 2.00 | 5.00 | 5.00 | 2.00 |
| Xanthan gum | 1.00 | 0.30 | 0.50 | 0.50 | 0.50 | 0.50 |
| Purified water | 55.48 | 66.08 | 58.98 | 57.98 | 55.98 | 60.98 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 2.00 | 2.00 | 2.00 | 2.00 | 2.00 | 2.00 |
| Total | 100.00 | 100.00 | 100.00 | 100.00 | 100.00 | 100.00 |

| Excipients Formulation | % w/w 111 | % w/w 112 | % w/w 113 | % w/w 114 | % w/w 115 | % w/w 116 |
|---|---|---|---|---|---|---|
| Fatty acid* | 15.00 | 12.50 | 25.00 | 15.00 | 10.00 | 20.00 |
| Cetyl alcohol | 2.20 | 2.20 | 2.20 | 2.00 | 2.00 | 2.20 |
| Stearyl alcohol | 3.10 | 3.10 | 3.10 | 2.00 | 2.40 | 3.10 |
| White petrolatum | 6.00 | 5.00 | 3.00 | 3.40 | 2.80 | 3.00 |
| Polysorbate 60 | 3.00 | 3.00 | 3.40 | 3.80 | 3.80 | 3.00 |
| Sorbitan Monostearate | 1.00 | 1.00 | 0.60 | 0.20 | 1.00 | 1.00 |
| Glycerin | 5.00 | 5.00 | 2.00 | 3.00 | 3.00 | 3.00 |
| Xanthan gum | 1.00 | 0.50 | 1.00 | 0.30 | 0.30 | 0.75 |
| Purified water | 60.23 | 63.23 | 55.23 | 66.83 | 70.23 | 59.48 |
| Benzyl alcohol | 1.00 | 2.00 | 2.00 | 1.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 2.25 | 2.25 | 2.25 | 2.25 | 2.25 | 2.25 |
| Total | 100.00 | 100.00 | 100.00 | 100.00 | 100.00 | 100.00 |

| Excipients Formulation | % w/w 117 | % w/w 118 | % w/w 119 | % w/w 120 | % w/w 121 | % w/w 122 |
|---|---|---|---|---|---|---|
| Fatty acid* | 15.00 | 12.50 | 25.00 | 15.00 | 10.00 | 25.00 |
| Cetyl alcohol | 2.20 | 2.20 | 2.20 | 2.00 | 2.00 | 2.70 |
| Stearyl alcohol | 3.10 | 3.10 | 3.10 | 2.00 | 2.40 | 3.80 |
| White petrolatum | 6.00 | 5.00 | 3.00 | 3.40 | 2.80 | 3.00 |
| Polysorbate 60 | 3.00 | 3.00 | 3.40 | 3.80 | 3.80 | 3.40 |
| Sorbitan Monostearate | 1.00 | 1.00 | 0.60 | 0.20 | 1.00 | 0.60 |
| Glycerin | 5.00 | 5.00 | 2.00 | 3.00 | 3.00 | 2.00 |
| Xanthan gum | 1.00 | 0.50 | 1.00 | 0.30 | 0.30 | 0.50 |
| Purified water | 60.23 | 63.23 | 55.23 | 66.83 | 70.23 | 54.53 |
| Benzyl alcohol | 1.00 | 2.00 | 2.00 | 1.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 2.25 | 2.25 | 2.25 | 2.25 | 2.25 | 2.25 |
| Total | 100.00 | 100.00 | 100.00 | 100.00 | 100.00 | 100.00 |

| Excipients Formulation | % w/w 123 | % w/w 124 | % w/w 125 | % w/w 126 | % w/w 127 | % w/w 128 |
|---|---|---|---|---|---|---|
| Fatty acid* | 25.00 | 15.00 | 20.00 | 20.00 | 20.00 | 20.00 |
| Cetyl alcohol | 2.20 | 2.00 | 2.20 | 2.20 | 2.20 | 2.20 |
| Stearyl alcohol | 3.10 | 2.00 | 3.10 | 3.10 | 3.10 | 3.10 |
| White petrolatum | 3.00 | 3.40 | 5.00 | 3.00 | 5.00 | 3.00 |
| Polysorbate 60 | 3.40 | 3.80 | 3.40 | 3.40 | 3.40 | 3.40 |
| Sorbitan Monostearate | 0.60 | 0.2 | 0.60 | 0.60 | 0.60 | 0.60 |
| Glycerin | 2.00 | 3.00 | 2.00 | 5.00 | 5.00 | 2.00 |
| Xanthan gum | 1.00 | 0.30 | 0.50 | 0.50 | 0.50 | 0.50 |
| Purified water | 55.23 | 65.83 | 58.73 | 57.73 | 55.73 | 60.73 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 2.25 | 2.25 | 2.25 | 2.25 | 2.25 | 2.25 |
| Total | 100.00 | 100.00 | 100.00 | 100.00 | 100.00 | 100.00 |

| Excipients Formulation | % w/w 129 | % w/w 130 | % w/w 131 | % w/w 132 | % w/w 133 | % w/w 134 |
|---|---|---|---|---|---|---|
| Fatty acid* | 15.00 | 15.00 | 15.00 | 20.00 | 15.00 | 20.00 |
| Cetyl alcohol | 2.20 | 2.20 | 2.20 | 2.20 | 2.20 | 2.20 |
| Stearyl alcohol | 3.10 | 3.10 | 3.10 | 3.10 | 3.10 | 3.10 |
| White petrolatum | 2.50 | 3.00 | 2.00 | 3.00 | 6.00 | 3.00 |
| Polysorbate 60 | 3.40 | 3.40 | 3.40 | 3.40 | 3.00 | 3.00 |
| Sorbitan Monostearate | 0.60 | 0.60 | 0.60 | 0.60 | 1.00 | 1.00 |
| Glycerin | 2.00 | 2.00 | 5.00 | 2.00 | 5.00 | 3.00 |
| Xanthan gum | 0.50 | 0.50 | 0.50 | 0.50 | 0.75 | 0.75 |
| Purified water | 65.98 | 65.48 | 63.48 | 60.48 | 59.23 | 59.23 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 2.50 | 2.50 | 2.50 | 2.50 | 2.50 | 2.50 |
| Total | 100.00 | 100.00 | 100.00 | 100.00 | 100.00 | 100.00 |

| Excipients Formulation | % w/w 135 | % w/w 136 | % w/w 137 | % w/w 138 | % w/w 139 | % w/w 140 |
|---|---|---|---|---|---|---|
| Fatty acid* | 15.00 | 15.00 | 15.00 | 25.00 | 18.0 | 25.00 |
| Cetyl alcohol | 2.20 | 2.20 | 2.20 | 2.20 | 2.20 | 2.70 |
| Stearyl alcohol | 3.10 | 3.10 | 3.10 | 3.10 | 3.10 | 3.80 |
| White petrolatum | 3.00 | 6.00 | 6.00 | 3.00 | 5.00 | 3.00 |
| Polysorbate 60 | 3.40 | 3.40 | 3.00 | 3.40 | 3.00 | 3.40 |
| Sorbitan Monostearate | 0.60 | 0.60 | 1.00 | 0.50 | 1.00 | 0.60 |
| Glycerin | 2.00 | 5.00 | 5.00 | 2.00 | 5.00 | 2.00 |
| Xanthan gum | 0.50 | 0.50 | 0.50 | 0.50 | 0.50 | 0.50 |
| Purified water | 65.48 | 59.48 | 59.48 | 55.58 | 57.48 | 54.28 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 2.50 | 2.50 | 2.50 | 2.50 | 2.50 | 2.50 |
| Total | 100.00 | 100.00 | 100.00 | 100.00 | 100.00 | 100.00 |

TABLE 11-continued

Lower Dosage Strength Imiquimod Cream Formulations 21-254

| Excipients Formulation | % w/w 141 | % w/w 142 | % w/w 143 | % w/w 144 | % w/w 145 | % w/w 146 |
|---|---|---|---|---|---|---|
| Fatty acid* | 25.00 | 15.00 | 20.00 | 20.00 | 20.00 | 20.00 |
| Cetyl alcohol | 2.20 | 2.00 | 2.20 | 2.20 | 2.20 | 2.20 |
| Stearyl alcohol | 3.10 | 2.00 | 3.10 | 3.10 | 3.10 | 3.10 |
| White petrolatum | 3.00 | 3.40 | 5.00 | 3.00 | 5.00 | 3.00 |
| Polysorbate 60 | 3.40 | 3.80 | 3.40 | 3.40 | 3.40 | 3.40 |
| Sorbitan Monostearate | 0.60 | 0.2 | 0.60 | 0.60 | 0.60 | 0.60 |
| Glycerin | 2.00 | 3.00 | 2.00 | 5.00 | 5.00 | 2.00 |
| Xanthan gum | 1.00 | 0.30 | 0.50 | 0.50 | 0.50 | 0.50 |
| Purified water | 54.98 | 65.58 | 58.48 | 57.48 | 55.48 | 60.48 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 2.50 | 2.50 | 2.50 | 2.50 | 2.50 | 2.50 |
| Total | 100.00 | 100.00 | 100.00 | 100.00 | 100.00 | 100.00 |

| Excipients Formulation | % w/w 147 | % w/w 148 | % w/w 149 | % w/w 150 | % w/w 151 | % w/w 152 |
|---|---|---|---|---|---|---|
| Fatty acid* | 15.00 | 18.00 | 15.00 | 20.00 | 12.50 | 20.00 |
| Cetyl alcohol | 2.00 | 2.00 | 2.00 | 2.00 | 2.20 | 2.20 |
| Stearyl alcohol | 2.00 | 2.00 | 2.40 | 2.40 | 3.10 | 3.10 |
| White petrolatum | 3.40 | 2.80 | 3.40 | 2.80 | 5.00 | 3.00 |
| Polysorbate 60 | 3.00 | 3.80 | 3.00 | 3.00 | 3.40 | 3.00 |
| Sorbitan Monostearate | 1.00 | 1.00 | 0.20 | 0.20 | 0.60 | 1.00 |
| Glycerin | 3.00 | 2.00 | 1.00 | 3.00 | 6.00 | 3.00 |
| Xanthan gum | 0.30 | 0.70 | 0.70 | 0.30 | 0.50 | 0.75 |
| Purified water | 65.08 | 62.48 | 67.08 | 61.08 | 61.48 | 58.73 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 3.00 | 3.00 | 3.00 | 3.00 | 3.00 | 3.00 |
| Total | 100.00 | 100.00 | 100.00 | 100.00 | 100.00 | 100.00 |

| Excipients Formulation | % w/w 153 | % w/w 154 | % w/w 155 | % w/w 156 | % w/w 157 | % w/w 158 |
|---|---|---|---|---|---|---|
| Fatty acid* | 15.00 | 18.00 | 15.00 | 20.00 | 12.50 | 25.00 |
| Cetyl alcohol | 2.00 | 2.00 | 2.00 | 2.00 | 2.20 | 2.70 |
| Stearyl alcohol | 2.00 | 2.00 | 2.40 | 2.40 | 3.10 | 3.80 |
| White petrolatum | 3.40 | 2.80 | 3.40 | 2.80 | 5.00 | 3.00 |
| Polysorbate 60 | 3.00 | 3.80 | 3.00 | 3.00 | 3.40 | 3.40 |
| Sorbitan Monostearate | 1.00 | 1.00 | 0.20 | 0.20 | 0.60 | 0.60 |
| Glycerin | 3.00 | 2.00 | 1.00 | 3.00 | 6.00 | 2.00 |
| Xanthan gum | 0.30 | 0.70 | 0.70 | 0.30 | 0.50 | 0.50 |
| Purified water | 65.08 | 62.48 | 67.08 | 61.08 | 61.48 | 53.78 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 3.00 | 3.00 | 3.00 | 3.00 | 3.00 | 3.00 |
| Total | 100.00 | 100.00 | 100.00 | 100.00 | 100.00 | 100.00 |

| Excipients Formulation | % w/w 159 | % w/w 160 | % w/w 161 | % w/w 162 | % w/w 163 | % w/w 164 |
|---|---|---|---|---|---|---|
| Fatty acid* | 25.00 | 15.00 | 20.00 | 20.00 | 20.00 | 20.00 |
| Cetyl alcohol | 2.20 | 2.00 | 2.20 | 2.20 | 2.20 | 2.20 |
| Stearyl alcohol | 3.10 | 2.00 | 3.10 | 3.10 | 3.10 | 3.10 |
| White petrolatum | 3.00 | 3.40 | 5.00 | 3.00 | 5.00 | 3.00 |
| Polysorbate 60 | 3.40 | 3.80 | 3.40 | 3.40 | 3.40 | 3.40 |
| Sorbitan Monostearate | 0.60 | 0.2 | 0.60 | 0.60 | 0.60 | 0.60 |
| Glycerin | 2.00 | 3.00 | 2.00 | 5.00 | 5.00 | 2.00 |
| Xanthan gum | 1.00 | 0.30 | 0.50 | 0.50 | 0.50 | 0.50 |
| Purified water | 54.48 | 65.08 | 57.98 | 56.98 | 54.98 | 59.98 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 3.00 | 3.00 | 3.00 | 3.00 | 3.00 | 3.00 |
| Total | 100.00 | 100.00 | 100.00 | 100.00 | 100.00 | 100.00 |

| Excipients Formulation | % w/w 165 | % w/w 166 | % w/w 167 | % w/w 168 | % w/w 169 | % w/w 170 |
|---|---|---|---|---|---|---|
| Fatty acid* | 15.00 | 20.00 | 15.00 | 20.00 | 10.00 | 20.00 |
| Cetyl alcohol | 2.00 | 2.00 | 4.00 | 4.00 | 2.20 | 2.20 |
| Stearyl alcohol | 2.00 | 2.40 | 2.40 | 2.40 | 3.10 | 3.10 |
| White petrolatum | 3.40 | 2.80 | 2.50 | 3.40 | 5.00 | 3.00 |
| Polysorbate 60 | 3.00 | 3.00 | 3.00 | 3.80 | 3.40 | 3.00 |
| Sorbitan Monostearate | 1.00 | 0.20 | 1.00 | 1.00 | 0.60 | 1.00 |
| Glycerin | 3.00 | 3.00 | 1.00 | 3.00 | 5.00 | 3.00 |
| Xanthan gum | 0.30 | 0.30 | 0.30 | 0.70 | 0.50 | 0.75 |
| Purified water | 64.83 | 60.83 | 65.33 | 57.23 | 64.73 | 58.48 |
| Benzyl alcohol | 2.00 | 2.00 | 2.00 | 1.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 3.25 | 3.25 | 3.25 | 3.25 | 3.25 | 3.25 |
| Total | 100.00 | 100.00 | 100.00 | 100.00 | 100.00 | 100.00 |

| Excipients Formulation | % w/w 171 | % w/w 172 | % w/w 173 | % w/w 174 | % w/w 175 | % w/w 176 |
|---|---|---|---|---|---|---|
| Fatty acid* | 15.00 | 20.00 | 15.00 | 20.00 | 10.00 | 25.00 |
| Cetyl alcohol | 2.00 | 2.00 | 4.00 | 4.00 | 2.20 | 2.70 |
| Stearyl alcohol | 2.00 | 2.40 | 2.40 | 2.40 | 3.10 | 3.80 |
| White petrolatum | 3.40 | 2.80 | 2.50 | 3.40 | 5.00 | 3.00 |
| Polysorbate 60 | 3.00 | 3.00 | 3.00 | 3.80 | 3.40 | 3.40 |
| Sorbitan Monostearate | 1.00 | 0.20 | 1.00 | 1.00 | 0.60 | 0.60 |
| Glycerin | 3.00 | 3.00 | 1.00 | 3.00 | 5.00 | 2.00 |
| Xanthan gum | 0.30 | 0.30 | 0.30 | 0.70 | 0.50 | 0.50 |
| Purified water | 64.83 | 60.83 | 65.33 | 57.23 | 64.73 | 53.53 |
| Benzyl alcohol | 2.00 | 2.00 | 2.00 | 1.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 3.25 | 3.25 | 3.25 | 3.25 | 3.25 | 3.25 |
| Total | 100.00 | 100.00 | 100.00 | 100.00 | 100.00 | 100.00 |

| Excipients Formulation | % w/w 177 | % w/w 178 | % w/w 179 | % w/w 180 | % w/w 181 | % w/w 182 |
|---|---|---|---|---|---|---|
| Fatty acid* | 25.00 | 15.00 | 20.00 | 20.00 | 20.00 | 20.00 |
| Cetyl alcohol | 2.20 | 2.00 | 2.20 | 2.20 | 2.20 | 2.20 |
| Stearyl alcohol | 3.10 | 2.00 | 3.10 | 3.10 | 3.10 | 3.10 |
| White petrolatum | 3.00 | 3.40 | 5.00 | 3.00 | 5.00 | 3.00 |
| Polysorbate 60 | 3.40 | 3.80 | 3.40 | 3.40 | 3.40 | 3.40 |
| Sorbitan Monostearate | 0.60 | 0.2 | 0.60 | 0.60 | 0.60 | 0.60 |
| Glycerin | 2.00 | 3.00 | 2.00 | 5.00 | 5.00 | 2.00 |
| Xanthan gum | 1.00 | 0.30 | 0.50 | 0.50 | 0.50 | 0.50 |
| Purified water | 54.23 | 64.83 | 59.98 | 56.73 | 54.73 | 59.73 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 3.25 | 3.25 | 3.25 | 3.25 | 3.25 | 3.25 |
| Total | 100.00 | 100.00 | 100.00 | 100.00 | 100.00 | 100.00 |

| Excipients Formulation | % w/w 183 | % w/w 184 | % w/w 185 | % w/w 186 | % w/w 187 | % w/w 188 |
|---|---|---|---|---|---|---|
| Fatty acid* | 15.00 | 10.00 | 12.50 | 19.00 | 20.00 | 20.00 |
| Cetyl alcohol | 2.00 | 2.20 | 2.20 | 2.20 | 2.20 | 2.20 |
| Stearyl alcohol | 2.40 | 3.10 | 3.10 | 3.10 | 3.10 | 3.10 |
| White petrolatum | 3.40 | 5.00 | 5.00 | 3.00 | 3.00 | 3.00 |
| Polysorbate 60 | 3.00 | 3.40 | 4.00 | 3.40 | 3.40 | 3.00 |

TABLE 11-continued

Lower Dosage Strength Imiquimod Cream Formulations 21-254

| Excipients | % w/w | % w/w | % w/w | % w/w | % w/w | % w/w |
|---|---|---|---|---|---|---|
| Sorbitan Monostearate | 0.20 | 0.60 | 0.60 | 0.60 | 0.60 | 1.00 |
| Glycerin | 1.00 | 4.00 | 5.00 | 2.00 | 6.00 | 3.00 |
| Xanthan gum | 0.70 | 0.50 | 0.50 | 0.50 | 0.50 | 0.75 |
| Purified water | 66.58 | 65.48 | 61.38 | 60.48 | 56.48 | 58.23 |
| Benzyl alcohol | 2.00 | 2.00 | 2.00 | 2.00 | 1.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 3.50 | 3.50 | 3.50 | 3.50 | 3.50 | 3.50 |
| Total | 100.00 | 100.00 | 100.00 | 100.00 | 100.00 | 100.00 |

| Excipients Formulation | % w/w 189 | % w/w 190 | % w/w 191 | % w/w 192 | % w/w 193 | % w/w 194 |
|---|---|---|---|---|---|---|
| Fatty acid* | 15.00 | 10.00 | 12.50 | 19.00 | 20.00 | 25.00 |
| Cetyl alcohol | 2.00 | 2.20 | 2.20 | 2.20 | 2.20 | 2.70 |
| Stearyl alcohol | 2.40 | 3.10 | 3.10 | 3.10 | 3.10 | 3.80 |
| White petrolatum | 3.40 | 5.00 | 5.00 | 3.00 | 3.00 | 3.00 |
| Polysorbate 60 | 3.00 | 3.40 | 4.00 | 3.40 | 3.40 | 3.40 |
| Sorbitan Monostearate | 0.20 | 0.60 | 0.60 | 0.60 | 0.60 | 0.60 |
| Glycerin | 1.00 | 4.00 | 5.00 | 2.00 | 6.00 | 2.00 |
| Xanthan gum | 0.70 | 0.50 | 0.50 | 0.50 | 0.50 | 0.50 |
| Purified water | 66.58 | 65.48 | 61.38 | 60.48 | 56.48 | 53.28 |
| Benzyl alcohol | 2.00 | 2.00 | 2.00 | 2.00 | 1.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 3.50 | 3.50 | 3.50 | 3.50 | 3.50 | 3.50 |
| Total | 100.00 | 100.00 | 100.00 | 100.00 | 100.00 | 100.00 |

| Excipients Formulation | % w/w 195 | % w/w 196 | % w/w 197 | % w/w 198 | % w/w 199 | % w/w 200 |
|---|---|---|---|---|---|---|
| Fatty acid* | 25.00 | 15.00 | 20.00 | 20.00 | 20.00 | 20.00 |
| Cetyl alcohol | 2.20 | 2.00 | 2.20 | 2.20 | 2.20 | 2.20 |
| Stearyl alcohol | 3.10 | 2.00 | 3.10 | 3.10 | 3.10 | 3.10 |
| White petrolatum | 3.00 | 3.40 | 5.00 | 3.00 | 5.00 | 3.00 |
| Polysorbate 60 | 3.40 | 3.80 | 3.40 | 3.40 | 3.40 | 3.40 |
| Sorbitan Monostearate | 0.60 | 0.2 | 0.60 | 0.60 | 0.60 | 0.60 |
| Glycerin | 2.00 | 3.00 | 2.00 | 5.00 | 5.00 | 2.00 |
| Xanthan gum | 1.00 | 0.30 | 0.50 | 0.50 | 0.50 | 0.50 |
| Purified water | 53.98 | 64.58 | 57.48 | 56.48 | 54.48 | 59.48 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 3.50 | 3.50 | 3.50 | 3.50 | 3.50 | 3.50 |
| Total | 100.00 | 100.00 | 100.00 | 100.00 | 100.00 | 100.00 |

| Excipients Formulation | % w/w 201 | % w/w 202 | % w/w 203 | % w/w 204 | % w/w 205 | % w/w 206 |
|---|---|---|---|---|---|---|
| Fatty acid* | 20.00 | 20.00 | 25.00 | 18.75 | 20.00 | 21.25 |
| Cetyl alcohol | 4.00 | 2.20 | 2.20 | 2.20 | 2.20 | 2.20 |
| Stearyl alcohol | 2.40 | 3.10 | 3.10 | 3.10 | 3.10 | 3.10 |
| White petrolatum | 2.80 | 3.00 | 3.00 | 5.00 | 5.00 | 3.75 |
| Polysorbate 60 | 3.00 | 3.40 | 3.40 | 3.00 | 3.40 | 3.40 |
| Sorbitan Monostearate | 1.00 | 0.60 | 0.60 | 1.00 | 0.60 | 0.60 |
| Glycerin | 1.00 | 2.00 | 2.00 | 5.00 | 5.00 | 5.00 |
| Xanthan gum | 0.30 | 0.50 | 0.50 | 0.50 | 0.50 | 0.50 |
| Purified water | 64.53 | 59.23 | 54.23 | 55.48 | 54.23 | 54.23 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 3.75 | 3.75 | 3.75 | 3.75 | 3.75 | 3.75 |
| Total | 100.00 | 100.00 | 100.00 | 100.00 | 100.00 | 100.00 |

| Excipients Formulation | % w/w 207 | % w/w 208 | % w/w 209 | % w/w 210 | % w/w 211 | % w/w 212 |
|---|---|---|---|---|---|---|
| Fatty acid* | 20.00 | 20.00 | 20.00 | 25.00 | 18.75 | 25.00 |
| Cetyl alcohol | 2.20 | 2.20 | 2.20 | 2.20 | 2.20 | 2.70 |
| Stearyl alcohol | 3.10 | 3.10 | 3.10 | 3.10 | 3.10 | 3.80 |
| White petrolatum | 3.00 | 6.00 | 6.00 | 3.00 | 5.00 | 3.00 |
| Polysorbate 60 | 3.40 | 3.40 | 3.00 | 3.40 | 3.00 | 3.40 |
| Sorbitan Monostearate | 0.60 | 0.60 | 1.00 | 0.50 | 1.00 | 0.60 |
| Glycerin | 2.00 | 5.00 | 5.00 | 2.00 | 5.00 | 2.00 |
| Xanthan gum | 0.50 | 0.50 | 0.50 | 0.50 | 0.50 | 0.50 |
| Purified water | 59.23 | 53.23 | 53.23 | 54.33 | 55.48 | 53.03 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 3.75 | 3.75 | 3.75 | 3.75 | 3.75 | 3.75 |
| Total | 100.00 | 100.00 | 100.00 | 100.00 | 100.00 | 100.00 |

| Excipients Formulation | % w/w 213 | % w/w 214 | % w/w 215 | % w/w 216 | % w/w 217 | % w/w 218 |
|---|---|---|---|---|---|---|
| Fatty acid* | 25.00 | 20.00 | 20.00 | 20.00 | 20.00 | 21.00 |
| Cetyl alcohol | 2.20 | 4.00 | 2.20 | 2.20 | 2.20 | 2.20 |
| Stearyl alcohol | 3.10 | 2.40 | 3.10 | 3.10 | 3.10 | 3.10 |
| White petrolatum | 3.00 | 3.40 | 5.00 | 3.00 | 5.00 | 5.00 |
| Polysorbate 60 | 3.40 | 3.80 | 3.40 | 3.40 | 3.40 | 3.40 |
| Sorbitan Monostearate | 0.60 | 1.00 | 0.60 | 0.60 | 0.60 | 0.60 |
| Glycerin | 2.00 | 3.00 | 2.00 | 5.00 | 5.00 | 5.00 |
| Xanthan gum | 1.00 | 0.70 | 0.50 | 0.50 | 0.50 | 0.50 |
| Purified water | 53.73 | 55.73 | 57.23 | 56.23 | 54.23 | 53.23 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 3.75 | 3.75 | 3.75 | 3.75 | 3.75 | 3.75 |
| Total | 100.00 | 100.00 | 100.00 | 100.00 | 100.00 | 100.00 |

| Excipients Formulation | % w/w 219 | % w/w 220 | % w/w 221 | % w/w 222 | % w/w 223 | % w/w 224 |
|---|---|---|---|---|---|---|
| Fatty acid* | 20.00 | 25.00 | 22.50 | 20.00 | 20.00 | 22.50 |
| Cetyl alcohol | 2.20 | 2.70 | 2.20 | 4.00 | 2.20 | 2.20 |
| Stearyl alcohol | 3.10 | 3.80 | 3.10 | 2.40 | 3.10 | 3.10 |
| White petrolatum | 6.00 | 3.00 | 3.00 | 3.40 | 5.00 | 4.00 |
| Polysorbate 60 | 3.00 | 3.40 | 3.40 | 3.80 | 3.40 | 3.40 |
| Sorbitan Monostearate | 1.00 | 0.60 | 0.60 | 1.00 | 0.60 | 0.60 |
| Glycerin | 5.00 | 2.00 | 2.00 | 3.00 | 2.00 | 2.00 |
| Xanthan gum | 0.50 | 0.50 | 1.00 | 0.70 | 0.50 | 0.50 |
| Purified water | 52.98 | 52.78 | 55.98 | 55.48 | 56.98 | 55.48 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 4.00 | 4.00 | 4.00 | 4.00 | 4.00 | 4.00 |
| Total | 100.00 | 100.00 | 100.00 | 100.00 | 100.00 | 100.00 |

| Excipients Formulation | % w/w 225 | % w/w 226 | % w/w 227 | % w/w 228 | % w/w 229 | % w/w 230 |
|---|---|---|---|---|---|---|
| Fatty acid* | 20.00 | 25.00 | 22.50 | 20.00 | 20.00 | 22.50 |
| Cetyl alcohol | 2.20 | 2.70 | 2.20 | 4.00 | 2.20 | 2.20 |
| Stearyl alcohol | 3.10 | 3.80 | 3.10 | 2.40 | 3.10 | 3.10 |
| White petrolatum | 6.00 | 3.00 | 3.00 | 3.40 | 5.00 | 4.00 |
| Polysorbate 60 | 3.00 | 3.40 | 3.40 | 3.80 | 3.40 | 3.40 |
| Sorbitan Monostearate | 1.00 | 0.60 | 0.60 | 1.00 | 0.60 | 0.60 |
| Glycerin | 5.00 | 2.00 | 2.00 | 3.00 | 2.00 | 2.00 |
| Xanthan gum | 0.50 | 0.50 | 1.00 | 0.70 | 0.50 | 0.50 |
| Purified water | 52.98 | 52.78 | 55.98 | 55.48 | 56.98 | 55.48 |
| Benzyl alcohol | 2.00 | 2.00 | 2.00 | 2.00 | 2.00 | 2.00 |

TABLE 11-continued

Lower Dosage Strength Imiquimod Cream Formulations 21-254

| | | | | | | |
|---|---|---|---|---|---|---|
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 4.00 | 4.00 | 4.00 | 4.00 | 4.00 | 4.00 |
| Total | 100.00 | 100.00 | 100.00 | 100.00 | 100.00 | 100.00 |

| Excipients Formulation | % w/w 231 | % w/w 232 | % w/w 233 | % w/w 234 | % w/w 235 | % w/w 236 |
|---|---|---|---|---|---|---|
| Fatty acid* | 25.00 | 15.00 | 20.00 | 20.00 | 20.00 | 20.00 |
| Cetyl alcohol | 2.20 | 2.00 | 2.20 | 2.20 | 2.20 | 2.20 |
| Stearyl alcohol | 3.10 | 2.00 | 3.10 | 3.10 | 3.10 | 3.10 |
| White petrolatum | 3.00 | 3.40 | 5.00 | 3.00 | 5.00 | 3.00 |
| Polysorbate 60 | 3.40 | 3.80 | 3.40 | 3.40 | 3.40 | 3.40 |
| Sorbitan Monostearate | 0.60 | 0.2 | 0.60 | 0.60 | 0.60 | 0.60 |
| Glycerin | 2.00 | 3.00 | 2.00 | 5.00 | 5.00 | 2.00 |
| Xanthan gum | 1.00 | 0.30 | 0.50 | 0.50 | 0.50 | 0.50 |
| Purified water | 53.48 | 64.08 | 56.98 | 55.98 | 53.98 | 58.98 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 4.00 | 4.00 | 4.00 | 4.00 | 4.00 | 4.00 |
| Total | 100.00 | 100.00 | 100.00 | 100.00 | 100.00 | 100.00 |

| Excipients Formulation | % w/w 237 | % w/w 238 | % w/w 239 | % w/w 240 | % w/w 241 | % w/w 242 |
|---|---|---|---|---|---|---|
| Fatty acid* | 15.00 | 15.00 | 15.00 | 20.00 | 15.00 | 20.00 |
| Cetyl alcohol | 2.20 | 2.20 | 2.20 | 2.20 | 2.20 | 2.20 |
| Stearyl alcohol | 3.10 | 3.10 | 3.10 | 3.10 | 3.10 | 3.10 |
| White petrolatum | 1.00 | 3.00 | 2.00 | 3.00 | 6.00 | 3.00 |
| Polysorbate 60 | 3.40 | 3.40 | 3.40 | 3.40 | 3.00 | 3.00 |
| Sorbitan Monostearate | 0.60 | 0.60 | 0.60 | 0.60 | 1.00 | 1.00 |
| Glycerin | 2.00 | 2.00 | 5.00 | 2.00 | 5.00 | 3.00 |
| Xanthan gum | 0.50 | 0.50 | 0.50 | 0.50 | 0.75 | 0.75 |
| Purified water | 65.73 | 63.73 | 61.73 | 58.73 | 57.48 | 57.48 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 4.25 | 4.25 | 4.25 | 4.25 | 4.25 | 4.25 |
| Total | 100.00 | 100.00 | 100.00 | 100.00 | 100.00 | 100.00 |

| Excipients Formulation | % w/w 243 | % w/w 244 | % w/w 245 | % w/w 246 | % w/w 247 | % w/w 248 |
|---|---|---|---|---|---|---|
| Fatty acid* | 15.00 | 15.00 | 15.00 | 25.00 | 18.0 | 25.00 |
| Cetyl alcohol | 2.20 | 2.20 | 2.20 | 2.20 | 2.20 | 2.70 |
| Stearyl alcohol | 3.10 | 3.10 | 3.10 | 3.10 | 3.10 | 3.80 |
| White petrolatum | 3.00 | 6.00 | 6.00 | 3.00 | 5.00 | 3.00 |
| Polysorbate 60 | 3.40 | 3.40 | 3.00 | 3.40 | 3.00 | 3.40 |
| Sorbitan Monostearate | 0.60 | 0.60 | 1.00 | 0.50 | 1.00 | 0.60 |
| Glycerin | 2.00 | 5.00 | 5.00 | 2.00 | 5.00 | 2.00 |
| Xanthan gum | 0.50 | 0.50 | 0.50 | 0.50 | 0.50 | 0.50 |
| Purified water | 63.73 | 57.73 | 57.73 | 53.83 | 55.73 | 52.53 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 4.25 | 4.25 | 4.25 | 4.25 | 4.25 | 4.25 |
| Total | 100.00 | 100.00 | 100.00 | 100.00 | 100.00 | 100.00 |

| Excipients Formulation | % w/w 249 | % w/w 250 | % w/w 251 | % w/w 252 | % w/w 253 | % w/w 254 |
|---|---|---|---|---|---|---|
| Fatty acid* | 25.00 | 15.00 | 20.00 | 20.00 | 20.0 | 20.00 |
| Cetyl alcohol | 2.20 | 2.00 | 2.20 | 2.20 | 2.20 | 2.20 |
| Stearyl alcohol | 3.10 | 2.00 | 3.10 | 3.10 | 3.10 | 3.10 |
| White petrolatum | 3.00 | 3.40 | 5.00 | 3.00 | 5.00 | 3.00 |
| Polysorbate 60 | 3.40 | 3.80 | 3.40 | 3.40 | 3.40 | 3.40 |
| Sorbitan Monostearate | 0.60 | 0.20 | 0.60 | 0.60 | 0.60 | 0.60 |
| Glycerin | 2.00 | 3.00 | 2.00 | 5.00 | 5.00 | 2.00 |
| Xanthan gum | 1.00 | 0.30 | 0.50 | 0.50 | 0.50 | 0.50 |
| Purified water | 53.23 | 63.83 | 56.73 | 55.73 | 53.73 | 58.73 |
| Benzyl alcohol | 2.00 | 2.00 | 2.00 | 2.00 | 2.00 | 2.00 |
| Methylparaben | 0.20 | 0.20 | 0.20 | 0.20 | 0.20 | 0.20 |
| Propylparaben | 0.02 | 0.02 | 0.02 | 0.02 | 0.02 | 0.02 |
| Imiquimod | 4.25 | 4.25 | 4.25 | 4.25 | 4.25 | 4.25 |
| Total | 100.00 | 100.00 | 100.00 | 100.00 | 100.00 | 100.00 |

*The Fatty acid referenced in this Table 11 can be, for example, linoleic acid (la), stearic acid (sa), palmitic acid (pa), isostearic acid (isa), unrefined oleic acid (uoa), refined oleic acid, such as super refined oleic acid (roa), or mixtures thereof.

The materials listed below in this Example 21 are combined, according to the following procedure to make cream formulations in the above Table 11 of this Example 21.

The work area, all vessels and equipment is initially cleaned prior to commencing manufacture. A 2 L glass container and paddle stirrer blade are placed onto a balance and the weight is recorded. The paddle is then removed from the vessel. The isostearic acid and benzyl alcohol are weighed directly into the 2 L glass container. The imiquimod is then weighed into the 2 L glass container and a spatula is used to ensure the imiquimod is wetted with the isostearic acid and benzyl alcohol mixture. The 2 L container is then heated in a water bath to about 55±5° C. while stirring with a Heidolph mixer (Note: aluminum foil is placed around the top of the vessel and the paddle for the mixer, to limit evaporation). The solution is visually inspected to confirm the imiquimod has fully dissolved prior to mixing with cetyl alcohol, stearyl alcohol, white petrolatum, polysorbate 60 and sorbitan monostearate.

Cetyl alcohol, stearyl alcohol, white petrolatum, polysorbate 60 and sorbitan monostearate are then weighed directly into the 2 L container and mixing is continued at about 55±5° C. until the oil phase is completely in solution. Separately, about 2 L of water are placed into a beaker and heated to 55±5° C. while stirring with a magnetic follower. Briefly, about 500 ml of the heated water is transferred into a 1 L beaker and placed into the water bath maintained at about 55±5° C.

Half of the amount of glycerin required for the final formulation is then weighed into the beaker along with the total amount of methylparaben and propylparaben to the water (where both methyl and propyl paraben are weighed into weighing boats first, a pipette is used to remove a portion of the heated water to wash out the weighing boats to ensure total transfer of both the propyl- and methylparaben into the aqueous phase). The mixture is continuously stirred at about 55±5° C. (this is the aqueous phase).

The remaining glycerin is then added to a 28 ml vial and the xanthan gum is added and mixed using a small overhead mixer (1KA®-Werke Lab Egg) with paddle attachment for about 10 min.

The glycerin and xanthan mixture are then added slowly into the vortex of the aqueous phase, and a further aliquot of about 20 ml of heated water is used to rinse the vessel out into the water phase to ensure complete transfer.

The water phase is then heated and mixed at about 55±5° C. until the xanthan gum mixture is fully and evenly dispersed into the aqueous phase. The temperatures of both the water phase and oil phase are both maintained at about 55±5° C.

The aqueous phase is then transferred into the oil phase and the speed of the Heidolph mixer is increased during addition.

The mixture is then homogenized on high speed for about 3 min and transferred immediately back to the Heidolph mixture; however, the contents of the homogenized sample, about 2 L, are mixed at about room temperature and allowed to cool to about 35° C.

The container and contents and the paddle from the overhead mixer are then re-weighed and the weight of the paddle and 2 L beaker, as determined above, are subtracted to determine the total weight of the formulation remaining.

The total weight (about 1 kg) of the cream is then made up to weight with heated water (Note: water evaporated during heating, which needs to be corrected at this point). The mixture is then transferred back onto the Heidolph mixer at about room temperature and mixed until the temperature of the formulation is below about 28° C. The lid of the container is then placed onto the vessel and stored at room temperature.

While the procedure above describes making an imiquimod cream using isostearic acid as the fatty acid, it is believed that this procedure may be applicable for preparing imiquimod creams based upon other fatty acids, such as those described in Table 11 above.

The lower dosage strength formulations of this Example 21 are believed to be stable and consistent with the specifications for the commercially available Aldara® (imiquimod) 5% cream. More preferably, low dosage formulations of this Example 21, especially as to those lower dosage strength formulations wherein the vehicle comprises an isostearic acid as the fatty acid, are believed to have the following:

(1) Stability. The imiquimod formulations of the present invention, when they are measured on HPLC at 25° C./60% RH, 30° C./65% RH and 40° C./75% RH over, one, two, three and six months, demonstrate stability consistent with the Aldara® 5% imiquimod cream;

(2) Degradation Products. No degradation products are detected in the formulations of the present invention, at its current recommended storage temperatures of about 4-25° C. In addition, there are no degradation products detected at any of the temperatures or time points mentioned under "Stability" above, when analyzed at about 318 nm.

(3) Homogeneity. The amount of imiquimod that is recovered from the formulations at any of the above-mentioned temperatures and time points is between about 90 to about 110% w/w thereby demonstrating good homogeneity;

(4) Benzyl Alcohol Content. The formulations of the present invention are also within specifications for the Aldara® (imiquimod) 5% cream, i.e., between 1.0% w/w and 2.1% w/w, at any of the above-mentioned temperatures and time points as to benzyl alcohol content.

(5) Microscopic Stability. There is no change in the particle size and no crystals are detected in the formulations of the present invention when they are stored at 25° C./60% RH and analyzed over a six month period;

(6) Macroscopic Stability. There are no obvious physical changes in the formulations of the present invention when they are stored at 25° C./60% RH and analyzed over a six month period;

(7) Viscosity. The formulations of the present invention are within the range of the specifications for the Aldara® (imiquimod) 5% cream, i.e., between 2000 cPs and 35,000 cPs, when they are stored at 25° C./60% RH and analyzed over a six month period; pH Stability. The formulations of the present invention are within the range of the specifications for the Aldara® (imiquimod) 5% cream, i.e., between pH 4.0 and pH 5.5) when they are stored at 25° C./60°% RH and analyzed over a six month period;

(8) Preservative Efficacy Test ("PET"). The formulations of the present invention demonstrate sufficient reductions in colony forming unit counts for each of the organisms with which the formulations are inoculated, i.e., S. aureus, E. coli, Ps. Aeruginosa, C. albicans, and A. niger, at 2-8° C. and 40° C. over a 28 day test period and meet the requirements specified in both the USP and EP;

(9) Imiquimod In vitro Release. The Aldara® (imiquimod) 5% cream releases statistically significant ($p<0.05$) higher amounts of imiquimod over a 3 hour time period in comparison to the lower dosage strength formulations of the present invention through a synthetic membrane, e.g., Microporous polyethylene film 3M No. 9711 CoTran™. There is no statistical difference ($p<0.05$) in the total cumulative amount of imiquimod that is released from any of the 3.75% w/w imiquimod formulations. There is no statistical difference ($p<0.05$) in the total cumulative amount of imiquimod that is released from any of the 2.5% w/w imiquimod formulations. The Aldara® (imiquimod) 5% cream also statistically significantly ($p<0.05$) releases imiquimod at a faster rate over a 3 hour time period in comparison to the lower dosage strength formulations of the present invention through a synthetic membrane, e.g., Microporous polyethylene film 3M No. 9711 CoTran™. There is no statistical difference ($p<0.05$) between the imiquimod release rates for any of the 3.75% w/w imiquimod formulations. There is no statistical difference ($p<0.05$) between the imiquimod release rates for any of the 2.5% w/w imiquimod formulations. Thus, the greater the amount of imiquimod in a formulation, the faster and greater the total amount of imiquimod that is released from such formulation that the amount and rate of release of imiquimod are concentration dependant and that the rates and amounts of release of imiquimod from the formulations of the present invention are linear and dose proportionate to the Aldara® 5% imiquimod cream;

(10) Imiquimod In vitro Skin Permeation (Franz Cell Study). With respect to statistical analyses, there is no statistical difference between the lower dosage strength formulations of the present invention and the Aldara® (imiquimod) 5% cream as to the amount of imiquimod recovered from the receiver fluid, epidermis and dermis combined. Nonetheless, there is a statistically significant ($p<0.05$) dose proportionate difference between the amount of imiquimod recovered from each of the matrices with respect to the concentration of imiquimod in the lower dosage strength formulations of the present invention and the Aldara® (imiquimod) 5% cream for both un-absorbed and stratum corneum. Thus there is a linear dose release between the amount of imiquimod that is applied and recovered in each of the matrices, i.e., receiver fluid, unabsorbed dose, stratum corneum, epidermis and dermis.

ANOVA statistical analysis at 95% confidence level is used to analyze the stability data generated, including the data generated for the membrane and skin permeation experiments.

It is also believed that the formulations of the present invention, including the formulations identified in this Example 21, have Hydrophilic-lipophilic balance (HLB) values between about 12 and 15, and more preferably between about 12.4 and about 13.4.

Attachment I

[000312] Stability Study GW 805-01

A. Percentage of imiquimod recovered from each formulation when the formulations were stored through 9 month period at 25°C/60% RH and 40°C/75% RH Imiquimod Content Specification: 90 – 110% LC

| Formulations | | Albion 2.5% (15 ml) | Albion 2.5% (7.5 ml) | Nova 2.5% (15 ml) | Nova 2.5% (7.5 ml) | Albion 3.75 % (15 ml) | Albion 3.75 % (7.5 ml) | Nova 3.75% (15 ml) | Nova 3.75% (7.5 ml) |
|---|---|---|---|---|---|---|---|---|---|
| t = 0 h | | 99.80 ± 0.26 | 99.39 ± 0.97 | 99.36 ± 0.99 | 98.68 ± 0.14 | 97.81 ± 0.61 | 97.96 ± 0.53 | 98.62 ± 0.56 | 100.60 ± 1.80 |
| t = 1 month | 25°C | 100.09 ± 0.95 | 100.70 ± 1.91 | 100.60 ± 1.26 | 99.71 ± 0.63 | 99.08 ± 0.96 | 99.34 ± 0.42 | 99.51 ± 0.54 | 97.61 ± 1.92 |
| | 40°C | 101.75 ± 2.22 | 100.67 ± 0.53 | 100.20 ± 1.53 | 100.79 ± 1.46 | 98.72 ± 0.79 | 101.78 ± 2.96 | 09.98 ± 0.27 | 99.78 ± 0.87 |
| t = 2 months | 25°C | 100.92 ± 1.68 | 100.86 ± 4.61 | 102.73 ± 1.33 | 102.44 ± 1.03 | 103.15 ± 0.77 | 103.51 ± 1.84 | 102.10 ± 0.85 | 104.38 ± 0.30 |
| | 40°C | 100.85 ± 0.60 | 103.47 ± 2.79 | 104.52 ± 1.17 | 103.70 ± 1.45 | 102.87 ± 0.96 | 102.26 ± 0.53 | 103.83 ± 0.19 | 104.70 ± 0.41 |
| t = 3 months* | 25°C | Not tested | Not tested | Not tested | Not tested | 102.12 ± 0.53 | 102.53 ± 0.72 | Not tested | Not tested |
| | 40°C | Not tested | Not tested | Not tested | Not tested | 103.21 ± 0.64 | 102.87 ± 0.58 | Not tested | Not tested |
| t = 3 months | 25°C | 101.85 ± 0.38 | 101.31 ± 1.95 | 102.76 ± 0.34 | 102.23 ± 0.35 | 102.06 ± 0.27 | 102.25 ± 0.92 | 101.07 ± 0.25 | 102.28 ± 0.36 |
| | 40°C | 100.52 ± 1.47 | 102.83 ± 0.28 | 104.70 ± 2.70 | 103.64 ± 1.37 | 103.28 ± 0.42 | 103.06 ± 0.73 | 102.65 ± 1.11 | 1,03.63 ± 2.00 |
| t = 6 months | 25°C | 101.85 ± 0.98 | 100.75 ± 0.40 | Not tested | Not tested | 99.03 ± 0.46 | 101.02 ± 0.13 | Not tested | Not tested |
| | 40°C | 101.72 ± 0.80 | 102.58 ± 0.20 | Not tested | Not tested | 99.31 ± 0.77 | 101.03 ± 1.01 | Not tested | Not tested |
| t = 9 months | 25°C | 101.27 ± 0.60 | 102.94 ± 1.81 | No further testing required | | 102.49 ± 1.72 | 101.31 ± 2.00 | No further testing required | |

Stability Study GW 805-01

B. Amount (%w/w) of benzyl alcohol recovered from each of the formulation when the formulations were stored through 9 month period at 25°C/60% RH and 40°C/75% RH Benzyl Alcohol Specification: 1.0 to 2.1% w/w

| Formulations | | Albion 2.5% (15 ml) | Albion 2.5% (7.5 ml) | Nova 2.5% (15 ml) | Nova 2.5% (7.5 ml) | Albion 3.75 % (15 ml) | Albion 3.75 % (7.5 ml) | Nova 3.75% (15 ml) | Nova 3.75% (7.5 ml) |
|---|---|---|---|---|---|---|---|---|---|
| t = 0 h | | 2.01 ± 0.02 | 2.00 ± 0.03 | 1.98 ± 0.01 | 1.96 ± 0.05 | 2.09 ± 0.14 | 2.00 ± 0.02 | 2.05 ± 0.03 | 2.07 ± 0.03 |
| t = 1 month | 25°C | 2.00 ± 0.06 | 2.05 ± 0.06 | 2.01 ± 0.03 | 1.97 ± 0.06 | 2.02 ± 0.04 | 2.03 ± 0.06 | 2.02 ± 0.06 | 1.94 ± 0.01 |
| | 40°C | 1.87 ± 0.04 | 1.87 ± 0.04 | 1.84 ± 0.02 | 1.94 ± 0.27 | 1.88 ± 0.05 | 1.92 ± 0.11 | 1.96 ± 0.18 | 1.91 ± 0.04 |
| t = 2 months | 25°C | 1.86 ± 0.05 | 1.87 ± 0.11 | 1.92 ± 0.01 | 1.87 ± 0.04 | 1.89 ± 0.04 | 1.85 ± 0.10 | 1.92 ± 0.04 | 1.96 ± 0.03 |
| | 40°C | 1.65 ± 0.03 | 1.68 ± 0.05 | 1.71 ± 0.02 | 1.72 ± 0.01 | 1.77 ± 0.03 | 1.71 ± 0.05 | 1.77 ± 0.03 | 1.77 ± 0.03 |
| t = 3 months* | 25°C | Not tested | Not tested | Not tested | Not tested | 1.87 ± 0.03 | 1.87 ± 0.03 | Not tested | Not tested |
| | 40°C | Not tested | Not tested | Not tested | Not tested | 1.71 ± 0.06 | 1.76 ± 0.05 | Not tested | Not tested |
| t = 3 months | 25°C | 1.89 ± 0.02 | 1.90 ± 0.03 | 1.92 ± 0.02 | 1.90 ± 0.04 | 1.91 ± 0.05 | 1.87 ± 0.02 | 1.96 ± 0.04 | 1.97 ± 0.03 |
| | 40°C | 1.61 ± 0.03 | 1.64 ± 0.01 | 1.66 ± 0.03 | 1.68 ± 0.03 | 1.79 ± 0.02 | 1.77 ± 0.02 | 1.78 ± 0.01 | 1.80 ± 0.05 |
| t = 6 months | 25°C | 1.86 ± 0.02 | 1.87 ± 0.03 | Not tested | Not tested | 1.91 ± 0.01 | 1.94 ± 0.03 | Not tested | Not tested |
| | 40°C | 1.43 ± 0.02 | 1.40 ± 0.03 | Not tested | Not tested | 1.61 ± 0.03 | 1.61 ± 0.01 | Not tested | Not tested |
| t = 9 months | 25°C | 1.70 ± 0.01 | 1.63 ± 0.07 | No further testing required | | 1.84 ± 0.03 | 1.81 ± 0.03 | No further testing required | |

Stability Study GW 805-01

C. Amount (%w/w) of methylparaben recovered from each of the formulation when the formulations were stored through 9 month period at 25°C/60% RH and 40°C/75% RH

Methylparaben Specification: 0.18 – 0.22% w/w

| Formulations | | Albion 2.5% (15 ml) | Albion 2.5% (7.5 ml) | Nova 2.5% (15 ml) | Nova 2.5% (7.5 ml) | Albion 3.75 % (15 ml) | Albion 3.75 % (7.5 ml) | Nova 3.75% (15 ml) | Nova 3.75% (7.5 ml) |
|---|---|---|---|---|---|---|---|---|---|
| t = 0 h | | 0.194 ± 0.000 | 0.194 ± 0.000 | 0.193 ± 0.000 | 0.192 ± 0.001 | 0.199 ± 0.007 | 0.191 ± 0.000 | 0.193 ± 0.000 | 0.196 ± 0.002 |
| t = 1 month | 25°C | 0.205 ± 0.001 | 0.205 ± 0.005 | 0.204 ± 0.002 | 0.204 ± 0.001 | 0.202 ± 0.002 | 0.204 ± 0.003 | 0.204 ± 0.002 | 0.197 ± 0.003 |
| | 40°C | 0206 ± 0.005 | 0.203 ± 0.004 | 0.201 ± 0.003 | 0.213 ± 0.021 | 0.202 ± 0.002 | 0.206 ± 0.005 | 0.208 ± 0.014 | 0.199 ± 0.003 |
| t = 2 months | 25°C | 0.201 ± 0.002 | 0.191 ± 0.009 | 0.201 ± 0.003 | 0.201 ± 0.004 | 0.200 ± 0.002 | 0.200 ± 0.001 | 0.197 ± 0.002 | 0205 ± 0.002 |
| | 40°C | 0.199 ± 0.003 | 0.202 ± 0.003 | 0.202 ± 0.002 | 0.201 ± 0.001 | 0.199 ± 0.002 | 0.197 ± 0.003 | 0.200 ± 0.000 | 0.199 0.002 |
| t = 3 months* | 25°C | Not tested | Not tested | Not tested | Not tested | 0.198 ± 0.003 | 0.193 ± 0.005 | Not tested | Not tested |
| | 40°C | Not tested | Not tested | Not tested | Not tested | 0.194 ± 0.005 | 0.201 ± 0.009 | Not tested | Not tested |
| t = 3 months | 25°C | 0.197 ± 0.001 | 0.197 ± 0.004 | 0.197 ± 0.001 | 0.194 ± 0.001 | 0.197 ± 0.001 | 0.198 ± 0.001 | 0.194 ± 0.000 | 0.195 ± 0.000 |
| | 40°C | 0.194 ± 0.003 | 0.197 ± 0.001 | 0.193 ± 0.000 | 0.194 ± 0.004 | 0.199 ± 0.002 | 0.198 ± 0.001 | 0.195 ± 0.002 | 0.198 ± 0.004 |
| t = 6 months | 25°C | 0.208 ± 0.003 | 0.209 ± 0.002 | Not tested | Not tested | 0.205 ± 0.002 | 0.205 ± 0.001 | Not tested | Not tested |
| | 40°C | 0.205 ± 0.003 | 0.206 ± 0.002 | Not tested | Not tested | 0.206 ± 0.002 | 0.206 ± 0.001 | Not tested | Not tested |
| t = 9 months | 25°C | 0.203 ± 0.001 | 0.196 ± 0.006 | No further testing required | No further testing required | 0.206 ± 0.004 | 0.206 ± 0.003 | No further testing required | No further testing required |

* Samples pulled one week earlier than 3 month time point as requested by Graceway.

Stability Study GW 805-01

D. Amount (%w/w) of propylparaben recovered from each of the formulation when the formulations were stored through 9 month period at 25°C/60% RH and 40°C/75% RH Propylparaben Specification: 0.018% – 0.022% w/w

| Formulations | | Albion 2.5% (15 ml) | Albion 2.5% (7.5 ml) | Nova 2.5% (15 ml) | Nova 2.5% (7.6 ml) | Albion 3.75% (15 ml) | Albion 3.75% (7.5 ml) | Nova 3.75% (15 ml) | Nova 3.75% (7.5 ml) |
|---|---|---|---|---|---|---|---|---|---|
| t = 0 h | | 0.0183 ± 0.000 | 0.0185 ± 0.000 | 0.0186 ± 0.000 | 0.0182 ± 0.000 | 0.0190 ± 0.001 | 0.0181 ± 0.001 | 0.0183 ± 0.000 | 0.0184 ± 0.000 |
| t = 1 month | 25°C | 0.0194 ± 0.001 | 0.0201 ± 0.001 | 0.0196 ± 0.001 | 0.0186 ± 0.000 | 0.0183 ± 0.000 | 0.0188 ± 0.001 | 0.0194 ± 0.001 | 0.0189 ± 0.000 |
| | 40°C | 0.0198 ± 0.001 | 0.0190 ± 0.000 | 0.0184 ± 0.000 | 0.0203 ± 0.002 | 0.0193 ± 0.000 | 0.0197 ± 0.001 | 0.0188 ± 0.001 | 0.0190 ± 0.001 |
| t = 2 months | 25°C | 0.0199 ± 0.001 | 0.0203 ± 0.000 | 0.0200 ± 0.000 | 0.0198 ± 0.001 | 0.0193 ± 0.000 | 0.0196 ± 0.001 | 0.0195 ± 0.000 | 0.0200 0.002 |
| | 40°C | 0.0200 ± 0.000 | 0.0199 ± 0.001 | 0.0202 ± 0.000 | 0.0198 ± 0.001 | 0.0196 ± 0.001 | 0.0187 ± 0.001 | 0.0200 ± 0.000 | 0.0190 ± 0.001 |
| t = 3 months* | 25°C | Not tested | Not tested | Not tested | Not tested | 0.0193 ± 0.001 | 0.0200 ± 0.001 | Not tested | Not tested |
| | 40°C | Not tested | Not tested | Not tested | Not tested | 0.0201 ± 0.001 | 0.0195 ± 0.000 | Not tested | Not tested |
| t = 3 months | 25°C | 0.0207 ± 0.001 | 0.0200 ± 0.000 | 0.0204 ± 0.001 | 0.0202 ± 0.000 | 0.0201 ± 0.000 | 0.0201 ± 0.000 | 0.0207 ± 0.001 | 0.0212 ± 0.001 |
| | 40°C | 0.0207 ± 0.000 | 0.0212 ± 0.001 | 0.0206 ± 0.000 | 0.02101 0.000 | 0.0205 ± 0.001 | 0.0204 ± 0.001 | 0.0199 ± 0.001 | 0.0205 ± 0.001 |
| t = 6 months | 25°C | 0.0197 ± 0.001 | 0.0198 ± 0.000 | Not tested | Not tested | 0.0197 ± 0.002 | 0.0184 ± 0.001 | Not tested | Not tested |
| | 40°C | 0.0195 ± 0.001 | 0.0205 ± 0.001 | Not tested | Not tested | 0.0201 ± 0.001 | 0.0188 ± 0.001 | Not tested | Not tested |
| t = 9 months | 25°C | 0.0203 ± 0.001 | 0.0194 ± 0.001 | No further testing required | | 0.0202 ± 0.000 | 0.0201 ± 0.000 | No further testing required | |

Stability Study GW 805-01

E. The pH of each formulation when stored through 9 month period at 25°C/60% RH and 40°C/75% RH pH Specifications: 4.0 to 5.5

| Formulations | t = 0 h | t = 1 month | | t = 2 months | | t = 3 months | | t = 6 months | | t = 9 months |
|---|---|---|---|---|---|---|---|---|---|---|
| | | 25°C | 40°C | 25°C | 40°C | 25°C | 40°C | 25°C | 40°C | 25°C |
| Albion 2.5 % (15 ml) | 5.001 | 4.824 | 4.811 | 4.8 | 4.721 | 4.911 | 4.784 | 4.773 | 4.719 | 4.769 |
| Albion 2.5 % (7.5 ml) | 4.967 | 4.869 | 4.809 | 4.828 | 4.676 | 4.873 | 4.59 | 4.878 | 4.713 | 4.795 |
| Nova 2.5 % (15 ml) | 5.009 | 4.889 | 4.73 | 4.844 | 4.686 | 4.737 | 4.795 | N/A | N/A | N/A |
| Nova 2.5 % (7.5 ml) | 5.017 | 4.834 | 4.758 | 4.818 | 4.68 | 4.693 | 4.838 | N/A | N/A | N/A |
| Albion 3.75 % (15 ml) | 5.092 | 5.025 | 5.024 | 5.032 | 4.947 | 5.137 | 5.04 | 5.028 | 5.008 | 4.655 |
| Albion 3.75 % (7.5 ml) | 5.024 | 5.022 | 5.031 | 5.041 | 4.91 | 5.169 | 5.048 | 5.005 | 5.012 | 4.772 |
| Nova 3.75 % (15 ml) | 5.087 | 5.037 | 4.996 | 5.042 | 5.001 | 5.113 | 5.032 | N/A | N/A | N/A |
| Nova 3.75 % (7.5 ml) | 5.012 | 5.002 | 5.033 | 4.931 | 4.875 | 5.157 | 5.037 | N/A | N/A | N/A |

Stability Study GW 805-01

F.  The results of the viscosity measurements for the formulations stored through 9 month period at 25°C/60% RH and 40°C/75% RH

Viscosity specification: 2,000 to 35,000 cPs for Bohlin

| Formulation | t = 0 | t = 1 month | | t = 2 months | | t = 3 months | | t = 6 months | | t = 9 months |
|---|---|---|---|---|---|---|---|---|---|---|
| | | 25°C | 40°C | 25°C | 40°C | 25°C | 40°C | 25°C | 40°C | 25°C |
| Albion 2.5 % (15 ml) | 11517.5 | 9712 | 7050 | 9478 | 4218 | 7512 | 3719.5 | 7399.7 | 2394.5 | 5096.5 |
| Albion 2.5 % (7.5 ml) | 11657 | 10344 | 6386.5 | 7489 | 4121 | 6590.5 | 3363 | 6502 | 2404.5 | 4243 |
| Nova 2.5 % (15 ml) | 10653.5 | 12802.5 | 7345 | 7924 | 4726 | 6681.5 | 3727 | N/A | N/A | N/A |
| Nova 2.5 % (7.5 ml) | 10668 | 11685 | 7853.5 | 8296.5 | 4819.5 | 7302.5 | 3849.5 | N/A | N/A | N/A |
| Albion 3.75 % (15 ml) | 11632.5 | 13673.5 | 8950 | 10903.5 | 5848 | 9448.7 | 5207.5 | 8268 | 2703 | 6489 |
| Albion 3.75 % (7.5 ml) | 12384.5 | 13562.5 | 8393 | 9285.5 | 5870 | 10038 | 5790 | 8709.5 | 2877.5 | 6108 |
| Nova 3.75 % (15 ml) | 12658 | 14657 | 9510.5 | 10222 | 5452 | 10165.5 | 4767 | N/A | N/A | N/A |
| Nova 3.75 % (7.5 ml) | 12689 | 13156 | 9510.5 | 10450.5 | 5482 | 9380.5 | 4933.5 | N/A | N/A | N/A |

As the bulk cream was aged at the time of filing (~2 months), the viscosity of the cream filled in to the pump had lower viscosity Stability Study GW 805-01

G. Amount (%w/w) of 4-hydroxy imiquimod from each formulation stored through 9 month period at 25°C/60% RH and 40°C/75% RH 4-hydroxy Imiquimod Specification: NMT 0.3% w/w

| Formulations | | Albion 2.5% (15 ml) | Albion 2.5% (7.5 ml) | Nova 2.5% (15 ml) | Nova 2.5% (7.5 ml) | Albion 3.75 % (15 ml) | Albion 3.75 % (7.5 ml) | Nova 3.75% (15 ml) | Nova 3.75% (7.5 ml) |
|---|---|---|---|---|---|---|---|---|---|
| t = 0 h | | NMT 0.1% w/w | NMT 0.1% w/w | NMT 0.1% w/w | NMT 0.1% w/w | NMT 0.1% w/w | NMT 0.1% w/w | NMT 0.1% w/w | NMT 0.1% w/w |
| t = 1 month | 25°C | NMT 0.1% w/w | NMT 0.1% w/w | NMT 0.1% w/w | NMT 0.1% w/w | NMT 0.1% w/w | NMT 0.1% w/w | NMT 0.1% w/w | NMT 0.1% w/w |
| | 40°C | NMT 0.1% w/w | NMT 0.1% w/w | NMT 0.1% w/w | NMT 0.1% w/w | NMT 0.1% w/w | NMT 0.1% w/w | NMT 0.1% w/w | NMT 0.1% w/w |
| t = 2 months | 25°C | NMT 0.1% w/w | NMT 0.1% w/w | NMT 0.1% w/w | NMT 0.1% w/w | NMT 0.1% w/w | NMT 0.1% w/w | NMT 0.1% w/w | NMT 0.1% w/w |
| | 40°C | NMT 0.1% w/w | NMT 0.1% w/w | NMT 0.1% w/w | NMT 0.1% w/w | NMT 0.1% w/w | NMT 0.1% w/w | NMT 0.1% w/w | NMT 0.1% w/w |
| t = 3 months* | 25°C | Not tested | Not tested | Not tested | Not tested | NMT 0.1% w/w | NMT 0.1% w/w | Not tested | Not tested |
| | 40°C | Not tested | Not tested | Not tested | Not tested | NMT 0.1% w/w | NMT 0.1% w/w | Not tested | Not tested |
| t = 3 months | 25°C | NMT 0.1% w/w | NMT 0.1% w/w | NMT 0.1% w/w | NMT 0.1% w/w | NMT 0.1% w/w | NMT 0.1% w/w | NMT 0.1% w/w | NMT 0.1% w/w |
| | 40°C | NMT 0.1% w/w | NMT 0.1% w/w | NMT 0.1% w/w | NMT 0.1% w/w | NMT 0.1% w/w | NMT 0.1% w/w | NMT 0.1% w/w | NMT 0.1% w/w |
| t = 6 months | 25°C | NMT 0.1% w/w | NMT 0.1% w/w | Not tested | Not tested | NMT 0.1% w/w | NMT 0.1% w/w | Not tested | Not tested |
| | 40°C | NMT 0.1% w/w | NMT 0.1% w/w | Not tested | Not tested | NMT 0.1% w/w | NMT 0.1% w/w | Not tested | Not tested |

| t = 9 months | 25°C | NMT 0.1% w/w | NMT 0.1% w/w | No further testing required | NMT 0.1% w/w | NMT 0.1% w/w | No further testing required |

Stability Study GW 805-01

G.  Amount of n-oxide for the formulations stored through 9 month period at 25°C/60% RH Specification: Run and Record

| Formulations | | Albion 2.5% (15 ml) | Albion 2.5% (7.5 ml) | Nova 2.5% (15 ml) | Nova 2.5% (7.5 ml) | Albion 3.75% (15 ml) | Albion 3.75 % (7.5 ml) | Nova 3.75% (15 ml) | Nova 3.75% (7.5 ml) |
|---|---|---|---|---|---|---|---|---|---|
| t = 0 h | | | | | | | | | |
| t = 1 month | 25°C | | | | | | | | |
| | 40°C | | | | | | | | |
| t = 2 months | 25°C | | | | | | | | |
| | 40°C | | | | Not tested | | | | |
| t = 3 months* | 25°C | | | | | | | | |
| | 40°C | | | | | | | | |
| t = 3 months | 25°C | | | | | | | | |
| | 40°C | | | | | | | | |
| t = 6 months | 25°C | | | | | | | | |
| | 40°C | | | | | | | | |
| t = 9 months | 25°C | None detected | None detected | No further testing required | | None detected | None detected | No further testing required | |

Attachment II

[000313] <u>Stability Study GW 906-01</u>

A. Percentage of imiquimod recovered from each formulation when the formulations were stored through 9 month period at 25°C/60% RH and 40°C/75% RH Imiquimod Content Specification: 90 – 110% LC

| Time point and storage temperature | | Albion 5 % (15 ml) | Albion 5 % (7.5 ml) | Nova 5 % (15 ml) | Nova 5 % (7.5 ml) |
|---|---|---|---|---|---|
| t = 0 h | | 103.19 ± 0.14 | 101.94 ± 0.10 | 101.64 ± 0.74 | 102.05 ± 0.66 |
| t = 1 month | 25°C | 101.36 ± 1.30 | 98.27 ± 0.86 | 98.37 ± 0.85 | 100.74 ± 0.33 |
| | 40°C | 95.35 ± 0.34 | 98.21 ± 0.79 | 96.61 ± 0.38 | 95.11 ± 0.42 |
| t = 2 months | 25°C | 99.79 ± 0.36 | 99.21 ± 0.49 | 99.38 ± 1.15 | 99.84 ± 1.15 |
| | 40°C | 99.66 ± 0.08 | 98.76 ± 0.46 | 99.71 ± 0.55 | 100.66 ± 0.45 |
| t = 3 months | 25°C | 101.33 ± 0.91 | 101.87 ± 0.68 | 101.92 ± 1.30 | 102.24 ± 0.93 |
| | 40°C | 101.51 ± 0.16 | 101.86 ± 0.56 | 102.04 ± 0.79 | 102.54 ± 1.02 |
| t = 6 months | 25°C | 102.87 ± 0.51 | 102.09 ± 0.60 | Not tested | |
| | 40°C | 102.69 ± 0.36 | 101.83 ± 0.59 | | |
| t = 9 months | 25°C | 105.59 ± 0.98 | 105.57 ± 0.23 | | |

Stability Study GW 906-01

C. Amount (%w/w) of benzyl alcohol recovered from each of the formulation were stored through 9 month period at 25°C/60% RH and 40°C/75% RH

Benzyl Alcohol Specification: 1.0 to 2.1% w/w

| Time point and storage temperature | | Albion 5 % (15 ml) | Albion 5 % (7.5 ml) | Nova 5 % (15 ml) | Nova 5 % (7.5 ml) |
|---|---|---|---|---|---|
| t = 0 h | | 1.97 ± 0.01 | 1.95 ± 0.02 | 1.94 ± 0.03 | 1.94 ± 0.02 |
| t = 1 month | 25°C | 1.85 ± 0.04 | 1.79 ± 0.03 | 1.84 ± 0.02 | 1.85 ± 0.04 |
| | 40°C | 1.69 ± 0.05 | 1.73 ± 0.05 | 1.71 ± 0.05 | 1.71 ± 0.05 |
| t = 2 months | 25°C | 1.74 ± 0.01 | 1.73 ± 0.01 | 1.73 ± 0.02 | 1.73 ± 0.01 |
| | 40°C | 1.56 ± 0.02 | 1.54 ± 0.01 | 1.58 ± 0.01 | 1.57 ± 0.01 |
| t = 3 months | 25°C | 1.80 ± 0.02 | 1.80 ± 0.03 | 1.80 ± 0.05 | 1.82 ± 0.01 |
| | 40°C | 158 ± 0.02 | 1.56 ± 0.01 | 1.58 ± 0.02 | 1.57 ± 0.01 |
| t = 6 months | 25°C | 1.83 ± 0.02 | 1.82 ± 0.00 | Not tested | |
| | 40°C | 1.45 ± 0.02 | 1.42 ± 0.05 | | |
| t = 9 months | 25°C | 1.73 ± 0.00 | 1.73 ± 0.04 | | |

Stability Study GW 906-01

D. Amount (%w/w) of methylparaben recovered from each formulation when the formulations were stored through 9 month period at 25°C/60% RH and 40°C/75% RH Methylparaben Specification: 0.18% - 0.22 w/w

| Time point and storage temperature | | Albion 5 % (15 ml) | Albion 5 % (7.5 ml) | Nova 5 % (15 ml) | Nova 5 % (7.5 ml) |
|---|---|---|---|---|---|
| t = 0 h | | 0.204 ± 0.003 | 0.202 ± 0.000 | 0.201 ± 0.001 | 0.202 ± 0.002 |
| t = 1 month | 25°C | 0.203 ± 0.004 | 0.200 ± 0.003 | 0.199 ± 0.001 | 0.202 ± 0.002 |
| | 40°C | 0.193 ± 0.004 | 0.198 ± 0.003 | 0.196 ± 0.001 | 0.193 ± 0.001 |
| t = 2 months | 25°C | 0.200 ± 0.001 | 0.199 ± 0.002 | 0.199 ± 0.002 | 0.198 ± 0.002 |
| | 40°C | 0.202 ± 0.000 | 0.202 ± 0.002 | 0.201 ± 0.000 | 0.201 ± 0.001 |
| t = 3 months | 25°C | 0.207 ± 0.002 | 0.207 ± 0.002 | 0.207 ± 0.005 | 0.206 ± 0.002 |
| | 40°C | 0.206 ± 0.000 | 0.206 ± 0.001 | 0.206 ± 0.001 | 0.205 ± 0.002 |
| t = 6 months | 25°C | 0.209 ± 0.002 | 0.207 ± 0.001 | Not tested | |
| | 40°C | 0.207 ± 0.001 | 0.205 ± 0.001 | | |
| t = 9 months | 25°C | 0.207 ± 0.001 | 0.207 ± 0.003 | | |

Stability Study GW 906-01

D. Amount (%w/w) of propylparaben recovered from each formulation when the formulations were stored through 9 month period at 25°C/60% RH and 40°C/75% RH

Propylparaben Specification: 0.018% - 0.022 w/w

| Time point and storage temperature | | Albion 5 % (15 ml) | Albion 5 % (7.5 ml) | Nova 5 % (15 ml) | Nova 5 % (7.5 ml) |
|---|---|---|---|---|---|
| t = 0 h | | 0.0202 ± 0.001 | 0.0197 ± 0.000 | 0.201 ± 0.001 | 0.0198 ± 0.000 |
| t = 1 month | 25°C | 0.0195 ± 0.001 | 0.0190 ± 0.001 | 0.0187 ± 0.001 | 0.0190 ± 0.001 |
| | 40°C | 0.0180 ± 0.001 | 0.0188 ± 0.000 | 0.0180 ± 0.000 | 0.0181 ± 0.001 |
| t = 2 months | 25°C | 0.0196 ± 0.001 | 0.0191 ± 0.001 | 0.0190 ± 0.001 | 0.0197 ± 0.000 |
| | 40°C | 0.0194 ± 0.001 | 0.0193 ± 0.000 | 0.0190 ± 0.000 | 0.0194 ± 0.001 |
| t = 3 months | 25°C | 0.0197 ± 0.001 | 0.0211 ± 0.001 | 0.0197 ± 0.001 | 0.0205 ± 0.000 |
| | 40°C | 0.0203 ± 0.001 | 0.0201 ± 0.001 | 0.0204 ± 0.000 | 0.0203 ± 0.001 |
| t = 6 months | 25°C | 0.0203 ± 0.001 | 0.0186 ± 0.000 | Not tested | Not tested |
| | 40°C | 0.0195 ± 0.000 | 0.0192 ± 0.001 | Not tested | Not tested |
| t = 9 months | 25°C | 0.0204 ± 0.000 | 0.0206 ± 0.001 | Not tested | Not tested |

Stability Study GW 906-01

E. The pH of each formulation when stored through 9 month period at 25°C/60% RH and 40°C/75% RH pH Specifications: 4.0 to 5.5

| Time point and storage temperature | | Albion 5% (15 ml) | Albion 5% (7.5 ml) | Nova 5% (15 ml) | Nova 5% (7.5 ml) |
|---|---|---|---|---|---|
| t = 0 h | | 5.078 | 5.078 | 5.104 | 5.077 |
| t = 1 month | 25°C | 5.012 | 5.014 | 5.029 | 5.004 |
| | 40°C | 4.958 | 4.955 | 4.958 | 4.98 |
| t = 2 months | 25°C | 5.015 | 5.038 | 4.98 | 5.097 |
| | 40°C | 4.995 | 5.008 | 5.006 | 5.007 |
| t = 3 months | 25°C | 4.998 | 4.9353 | 4.954 | 5.043 |
| | 40°C | 4.841 | 4.805 | 4.942 | 4.864 |
| t = 6 months | 25°C | 5.012 | 4.997 | Not tested | |
| | 40°C | 4.958 | 4.944 | | |
| t = 9 months | 25°C | 5.017 | 4.993 | | |

Stability Study GW 906-01

F. The results of the viscosity measurements for the formulations stored through 9 month period at 25°C/60% RH and 40°C/75% RH

Viscosity Specification: 2,000 to 35,000 cPs for Bohlin

| Formulation | t= 0 | t=1 month | | t=2 months | | t=3 months | | t=6 months | | t = 9 months |
|---|---|---|---|---|---|---|---|---|---|---|
| | | 25°C | 40°C | 25°C | 40°C | 25°C | 40°C | 25°C | 40°C | 25°C |
| Albion 5 % (15 ml) | 8616.5 | 9896 | 8586 | 7924 | 4959 | 8194 | 3991.5 | 7507.5 | 3559 | 5842.5 |
| Albion 5 % (7.5 ml) | 9246.5 | 10804.5 | 8784 | 8019.5 | 5115.5 | 8304.5 | 4640.5 | 8105 | 3562.5 | 6436.5 |
| Nova 5 % (15 ml) | 9299.5 | 11259.5 | 8265.5 | 7700.5 | 5161 | 8544.5 | 3814.5 | Not tested | Not tested | Not tested |
| Nova 5 % (7.5 ml) | 8900 | 10571.5 | 8228.5 | 7751.5 | 4675 | 8410.5 | 4226.5 | Not tested | Not tested | Not tested |

Stability Study GW 906-01

G. Amount (%w/w) of 4-hydroxy imiquimod from each formulation stored through 9 month period at 25°C/60% RH and 40°C/75% RH

4-hydroxy Imiquimod Specification: NMT 0.3% w/w

| Time point and storage temperature | | Percentage (% w/w) of 4-hydroxy imiquimod n in the formulation | | | | |
|---|---|---|---|---|---|---|
| | | Albion 5 % (15 ml) | Albion 5 % (7.5 ml) | Nova 5 % (15 ml) | Nova 5 % (7.5 ml) | 5 % ref sample |
| t = 0 h | | NMT 0.1% w/w | NMT 0.1% w/w | NMT 0.1% w/w | NMT 0.1% w/w | NMT 0.1% w/w |
| t = 1 month | 25°C | NMT 0.1% w/w | NMT 0.1% w/w | NMT 0.1% w/w | NMT 0.1% w/w | |
| | 40°C | NMT 0.1% w/w | NMT 0.1% w/w | NMT 0.1% w/w | NMT 0.1% w/w | |
| t = 2 months | 25°C | NMT 0.1% w/w | NMT 0.1% w/w | NMT 0.1% w/w w | NMT 0.1% w/w | |
| | 40°C | NMT 0.1% w/w | NMT 0.1% w/w | NMT 0.1% w/w | NMT 0.1% w/w | |
| t = 3 months | 25°C | NMT 0.1% w/w | NMT 0.1% w/w | NMT 0.1% w/w | NMT 0.1% w/w | |
| | 40°C | NMT 0.1% w/w | NMT 0.1% w/w | NMT 0.1% w/w | NMT 0.1% w/w | |
| t = 6 months | 25°C | NMT 0.1% w/w | NMT 0.1% w/w | Not tested | Not tested | |
| | 40°C | NMT 0.1% w/w | NMT 0.1% w/w | Not tested | Not tested | |
| t = 9 months | 25°C | NMT 0.1% w/w | NMT 0.1% w/w | Not tested | Not tested | |

* Samples from the same batch of formulation, sub-aliquoted into glass vials for the comparison against the Albion pumps (7.5 g and 15 g fill).

Stability Study GW 906-01

H. Amount of n-oxide for the formulations stored through 9 month period at 25°C/60% RH

Specification: Run and Record

| Time point and storage temperature | | Detection of n-oxide in the formulation | | | |
|---|---|---|---|---|---|
| | | Albion 5 % (15 ml) | Albion 5 % (7.5 ml) | Nova 5 % (15 ml) | Nova 5 % (7.5 ml) |
| t = 0 h | | | | | |
| t = 1 month | 25°C | | | | |
| | 40°C | | | | |
| t = 2 months | 25°C | | Not tested | | |
| | 40°C | | | | |
| t = 3 months | 25°C | | | | |
| | 40°C | | | | |
| t = 6 months | 25°C | | | | |
| | 40°C | | | | |
| t = 9 months | 25°C | None detected | None detected | Not tested | Not tested |

Attachment III

[000314] Stability Study GW 907-01

A. Percentage of imiquimod recovered from each formulation compared to theoretical when stored through 9 month period at 25°C/60% RH and 40°C/75% RH

Imiquimod Content Specification: 90-110% LC

| Time point | Temperature storage | Formulations (% recovered compared to theoretical) | | | | | |
|---|---|---|---|---|---|---|---|
| | | Albion 2.5 % | Albion 3.75 % | Albion 5 % | Ref 2.5 % | Ref 3.75 % | Ref 5 % |
| t = 0 h | | 102.29 ± 0.55 | 101.88 ± 1.13 | 102.80 ± 0.09 | 102.49 ± 0.50 | 102.93 ± 0.83 | 103.39 ± 1.44 |
| t = 1 month | 25°C | 102.93 ± 0.64 | 102.43 ± 0.81 | 102.99 ± 1.97 | | | |
| | 40 °C | 102.92 ± 1.28 | 100.29 ± 0.42 | 102.24 ± 0.39 | | | |
| | 40 °C (3M) | 102.69 ± 0.36 | 101.13 ± 0.23 | 101.73 ± 0.44 | | | |
| t = 2 months | 25 °C | 102.81 ± 1.17 | 102.40 ± 1.06 | 102.59 ± 0.30 | | | |
| | 40 °C | 103.39 ± 0.61 | 102.73 ± 0.80 | 102.85 ± 0.44 | | | |
| t = 3 months | 25 °C | 103.11 ± 0.78 | 101.29 ± 0.24 | 102.87 ± 0.85 | | | |
| | 40 °C | 102.07 ± 1.10 | 101.80 ± 0.36 | 100.72 ± 2.41 | | | |
| t = 6 months | 25 °C | 104.25 ± 1.66 | 100.71 ± 4.41 | 103.64 ± 0.79 | | | |
| | 40 °C | 104.68 ± 0.55 | 104.29 ± 0.57 | 104.36 ± 0.91 | | | |
| t = 9 months | 25 °C | 102.59 ± 1.25 | 102.75 ± 0.10 | 101.81 ± 1.08 | | | |

Where 'Ref' samples are from the same batch of each representative formulation, sub-aliquoted in to glass vials for comparison against pumps.

Stability Study GW 907-01

B. Amount (%w/w) of benzyl alcohol recovered from each of the formulation when stored through 9 month period at 25°C/60% RH and 40°C/75% RH Benzyl Alcohol Specification: 1.0 to 2.1% w/w

| Time point | Temperature storage | Amount (%w/w) of benzyl alcohol recovered from each of the formulation | | | | | |
|---|---|---|---|---|---|---|---|
| | | Albion 2.5 % | Albion 3.75 % | Albion 5 % | Ref 2.5 % | Ref 3.75 % | Ref 5 % |
| t = 0 h | | 1.83 ± 0.02 | 1.88 ± 0.03 | 1.78 ± 0.01 | 1.79 ± 0.03 | 1.89 ± 0.03 | 1.75 ± 0.03 |
| t = 1 month | 25°C | 1.78 ± 0.03 | 1.75 ± 0.06 | 1.82 ± 0.01 | | | |
| | 40 °C | 1.77 ± 0.02 | 1.74 ± 0.01 | 1.69 ± 0.01 | | | |
| | 40 °C (3M) | 1.76 ± 0.02 | 1.85 ± 0.00 | 1.72 ± 0.01 | | | |
| t = 2 months | 25 °C | 1.83 ± 0.05 | 1.92 ± 0.04 | 1.79 ± 0.03 | | | |
| | 40 °C | 1.63 ± 0.04 | 1.76 ± 0.03 | 1.68 ± 0.06 | | | |
| t = 3 months | 25 °C | 1.75 ± 0.01 | 1.82 ± 0.01 | 1.74 ± 0.01 | | | |
| | 40 °C | 1.55 ± 0.02 | 1.66 ± 0.04 | 1.53 ± 0.88 | | | |
| t = 6 months | 25 °C | 1.69 ± 0.05 | 1.76 ± 0.02 | 1.66 ± 0.02 | | | |
| | 40 °C | 1.33 ± 0.00 | 1.47 ± 0.02 | 1.38 ± 0.02 | | | |
| t = 9 months | 25 °C | 1.65± 0.01 | 1.74±0.02 | 1.65 ± 0.03 | | | |

Where 'Ref samples are from the same batch of each representative formulation, sub-aliquoted in to glass vials for comparison against pumps.

Stability Study GW 907-01

C. Amount (%w/w) of methylparaben recovered from each of the formulation when stored through 9 month period at 25°C/60% RH and 40°C/75% RH Methylparaben Specification: 0.18% - 0.22% w/w

| Time point | Temperature storage | Amount (%w/w) of methylparaben recovered from each formulation | | | | | |
|---|---|---|---|---|---|---|---|
| | | Albion 2.5 % | Albion 3.75 % | Albion 5 % | Ref 2.5 % | Ref 3.75 % | Ref 5 % |
| t = 0 h | | 0.201 ± 0.002 | 0.200 ± 0.002 | 0.201 ± 0.000 | 0.200 ± 0.000 | 0.201 ± 0.002 | 0.202 ± 0.003 |
| t = 1 month | 25 °C | 0.195 ± 0.002 | 0.192 ± 0.001 | 0.191 ± 0.004 | | | |
| | 40 °C | 0.203 ± 0.002 | 0.188 ± 0.002 | 0.203 ± 0.001 | | | |
| | 40 °C (3m) | 0.202 ± 0.001 | 0.200 ± 0.001 | 0.201 ± 0.002 | | | |
| t = 2 months | 25 °C | 0.205 ± 0.002 | 0.205 ± 0.003 | 0.208 ± 0.002 | | | |
| | 40 °C | 0.204 ± 0.002 | 0.204 ± 0.001 | 0.205 ± 0.003 | | | |
| t = 3 months | 25 °C | 0.204 ± 0.002 | 0.200 ± 0.001 | 0.202 ± 0.001 | | | |
| | 40 °C | 0.200 ± 0.001 | 0.201 ± 0.004 | 0.197 ± 0.005 | | | |
| t = 6 months | 25 °C | 0.207 ± 0.005 | 0.202 ± 0.005 | 0.205 ± 0.002 | | | |
| | 40 °C | 0.204 ± 0.002 | 0.205 ± 0.001 | 0.203 ± 0.002 | | | |
| t = 9 months | 25 °C | 0.211±.001 | 0.207±.001 | 0.21±.001 | | | |

Where 'Ref samples are from the same batch of each representative formulation, sub-aliquoted in to glass vials for comparison against pumps.

Stability Study GW 907-01

D. Amount (%w/w) of propylparaben recovered from each formulation when stored through 9 month period at 25°C/60% RH and 40°C/75% RH

Propylparaben Specification: 0.018% - 0.022% w/w

| Time point | Temperature storage | Amount (%w/w) of propylparaben recovered from each formulation | | | | | |
|---|---|---|---|---|---|---|---|
| | | Albion 2.5 % | Albion 3.75 % | Albion 5 % | Ref 2.5 % | Ref 3.75 % | Ref 5 % |
| t = 0 h | | 0.0190 ± 0.001 | 0.0185 ± 0.000 | 0.0191 ± 0.001 | 0.0187 ± 0.000 | 0.0193 ± 0.000 | 0.0189 ± 0.000 |
| t = 1 month | 25 C | 0.0199 ± 0.001 | 0.0179 ± 0.000 | 0.0202 ± 0.000 | | | |
| | 40 °C | 0.0201 ± 0.000 | 0.0210 ± 0.001 | 0.0208 ± 0.001 | | | |
| | 40 °C (3M) | 0.0194 ± 0.000 | 0.0200 ± 0.000 | 0.0198 ± 0.001 | | | |
| t = 2 months | 25 °C | 0.0196 ± 0.001 | 0.0202 ± 0.002 | 0.0202 ± 0.002 | | | |
| | 40 °C | 0.0189 ± 0.001 | 0.0216 ± 0.001 | 0.0183 ± 0.000 | | | |
| t = 3 months | 25 °C | 0.0224 ± 0.001 | 0.0209 ± 0.000 | 0.0200 ± 0.002 | | | |
| | 40 °C | 0.0213 ± 0.000 | 0.0202 ± 0.000 | 0.0192 ± 0.002 | | | |
| t = 6 months | 25 °C | 0.0194 ± 0.001 | 0.0183 ± 0.002 | 0.0188 ± 0.001 | | | |
| | 40 °C | 0.0194 ± 0.000 | 0.0191 ± 0.000 | 0.0193 ± 0.000 | | | |
| t = 9 months | 25 °C | 0.0191±0.000 | 0.0197±.000 | 0.0192±.000 | | | |

Where 'Ref' samples are from the same batch of each representative formulation, sub-aliquoted in to glass vials for comparison against pumps Stability Study GW 907-01

E. The pH of each formulation when stored through 9 month period at 25°C/60% RH and 40°C/75% RH pH Specifications: 4.0 to 5.5

| Time point | Temperature storage | pH | | | | | |
|---|---|---|---|---|---|---|---|
| | | Albion 2.5 % | Albion 3.75 % | Albion 5 % | Ref 2.5 % | Ref 3.75 % | Ref 5 % |
| t = 0 h | | 4.926 | 5.017 | 5.032 | 4.794 | 5.111 | 5.085 |
| t = 1 month | 25 °C | 4.852 | 5.184 | 5.12 | | | |
| | 40 °C | 4.844 | 5.044 | 4.971 | | | |
| | 40 °C (3M) | 4.928 | 5.108 | 5.079 | | | |
| t = 2 months | 25°C | 4.864 | 5.075 | 4.985 | | | |
| | 40 °C | 4.926 | 5.017 | 5.032 | | | |
| t = 3 months | 25°C | 4.471 | 5.130 | 5.163 | | | |
| | 40 °C | 4.854 | 5.153 | 5.134 | | | |
| t = 6 months | 25°C | 4.774 | 4.969 | 4.985 | | | |
| | 40 °C | 4.732 | 4.976 | 4.980 | | | |
| t = 9 months | 25 °C | 4.778 | 4.971 | 4.990 | | | |

Where 'Ref samples are from the same batch of each representative formulation, sub-aliquoted in to glass vials for comparison against pumps.

Stability Study GW 907-01

F. The results of the viscosity measurements for the formulations stored through 9 month period at 25°C/60% RH and 40°C/75% RH

Viscosity Specification: 2,000 to 35,000 cPs for Bohlin

| Time point | Temperature storage | Bohlin Viscosity (cPs) (based on 3M method) | | | | | |
|---|---|---|---|---|---|---|---|
| | | Albion 2.5 % | Albion 3.75 % | Albion 5 % | Ref 2.5 % | Ref 3.75 % | Ref 5 % |
| t = 0 h | | 7955.5 | 9816 | 8521 | 9038 | 11195 | 9629 |
| t = 1 month | 25 °C | 8897.5 | 10412 | 8803 | | | |
| | 40 °C | 8142.5 | 10746 | 8472.5 | | | |
| t = 2 months | 25 °C | 9132.5 | 10339 | 8570 | | | |
| | 40 °C | 4700.5 | 6626.5 | 5498.5 | | | |
| t = 3 months | 25 °C | 8241 | 8330.5 | 7430 | | | |
| | 40 °C | 3513.5 | 5397.5 | 4323 | | | |
| t = 6 months | 25 °C | 5440 | 7349 | 6580.5 | | | |
| | 40 °C | 2588 | 2993.5 | 3134 | | | |
| t = 9 months | 25 °C | 3093 | 3622.5 | 4485 | | | |

Where 'Ref' samples are from the same batch of each representative formulation, sub-aliquoted in to glass vials for comparison against pumps.

Stability Study GW 907-01

G. Amount (%w/w) of 4-hydroxy imiquimod from each formulation stored through 9 month period at 25°C/60% RH and 40°C/75% RH

4-hydroxy Imiquimod Specification: NMT 0.3% w/w

| Time point | Temperature storage | Amount (%w/w) of 4-hydroxy imiquimod recovered from each of the formulation ||||||
|---|---|---|---|---|---|---|---|
| | | Albion 2.5 % | Albion 3.75 % | Albion 5 % | Ref 2.5 % | Ref 3.75 % | Ref 5 % |
| t = 0 h | | NMT 0.1% w/w | NMT 0.1% w/w | NMT 0.1% w/w | NMT 0.1% w/w | NMT 0.1% w/w | NMT 0.1% w/w |
| t = 1 month | 25 °C | NMT 0.1% w/w | NMT 0.1% w/w | NMT 0.1% w/w | | | |
| | 40 °C | NMT 0.1% w/w | NMT 0.1% w/w | NMT 0.1% w/w | | | |
| t = 2 months | 25 °C | NMT 0.1% w/w | NMT 0.1% w/w | NMT 0.1% w/w | | | |
| | 40 °C | NMT 0.1% w/w | NMT 0.1% w/w | NMT 0.1% w/w | | | |
| t = 3 months | 25 °C | NMT 0.1% w/w | NMT 0.1% w/w | NMT 0.1% w/w | | | |
| | 40 °C | NMT 0.1% w/w | NMT 0.1% w/w | NMT 0.1% w/w | | | |
| t = 6 months | 25 °C | NMT 0.1% w/w | NMT 0.1% w/w | NMT 0.1% w/w | | | |
| | 40 °C | NMT 0.1% w/w | NMT 0.1% w/w | NMT 0.1% w/w | | | |
| t = 9 months | 25 °C | NMT 0.1% w/w | NMT 0.1% w/w | NMT 0.1% w/w | | | |

Where 'Ref' samples are from the same batch of each representative formulation, sub-aliquoted in to glass vials for comparison against pumps.

Stability Study GW 907-01

H.   Amount of n-oxide for the formulations stored through 9 month period at 25°C/60% RH and 40°C/75% RH Specification: Run and Record

| Time point | Temperature storage | Albion 2.5 % | Albion 3.75 % | Albion 5 % |
|---|---|---|---|---|
| t = 0 h | | | | |
| t = 1 month | 25 °C | | | |
| | 40 °C | | | |
| t = 2 months | 25 °C | Not tested | | |
| | 40 °C | | | |
| t = 3 months* | 25 °C | | | |
| | 40 °C | | | |
| t = 6 months | 25 °C | None detected | None detected | None detected |
| | 40 °C | None detected | None detected | None detected |
| t = 9 months | 25 °C | None detected | None detected | None detected |

Attachment IV

[000315] <u>Stability Study GW 921-01</u>

A. Percentage of imiquimod recovered from each formulation compared to theoretical when stored through 6 month period at 25°C/60% RH and 40°C/75% RH

Imiquimod Content Specification 90 -110% LC

| Time point | Temperature storage | Albion 3.75 % 7.5 g fill | Albion 3.75 % 15 g fill % | Ref 3.75 %* |
|---|---|---|---|---|
| t = 0 h | | 101.23 ± 0.57 | 102.00 ± 1.03 | 102.16 ± 1.64 |
| t = 1 month | 25 °C | 102.85 ± 0.36 | 102.64 ± 0.73 | 102.72 ± 0.38 |
| | 40 °C | 102.05 ± 0.20 | 100.83 ± 1.36 | 103.33 ± 0.27 |
| t = 2 months | 25 °C | 101.73 ± 1.08 | 100.03 ± 0.50 | 101.00 ± 0.56 |
| | 40 °C | 100.89 ± 0.20 | 100.41 ± 0.41 | 101.94 ± 0.39 |
| t = 3 months | 25 °C | 100.80 ± 0.90 | 100.21 ± 0.55 | 102.34 ± 1.17 |
| | 40 °C | 103.02 ± 1.46 | 102.75 ± 1.26 | 103.69 ± 1.28 |
| t = 6 months | 25 °C | 100.49 ± 0.82 | 101.31 ± 0.97 | 101.64 ± 1.12 |
| | 40 °C | 102.33 ± 0.20 | 102.38 ± 0.97 | 102.06 ± 1.06 |

* Samples from the same batch of formulation, sub-aliquoted into glass vials for the comparison against the Albion pumps (7.5 g and 15 g fill).

Stability Study GW 921-01

B. Amount (%w/w) of benzyl alcohol recovered from each formulation when stored through 6 month period at 25°C/60% RH and 40°C/75% RH Benzyl Alcohol Specification: 1.0 to 2.1% w/w

| Time point | Temperature storage | Albion 3.75 % 7.5 g fill | Albion 3.75 % 15 g fill | Ref 3.75 %* |
|---|---|---|---|---|
| t = 0 h | | 1.85 ± 0.03 | 1.89 ± 0.03 | 1.85 ± 0.01 |
| t = 1 month | 25°C | 1.89 ± 0.03 | 1.88 ± 0.04 | 1.91 ± 0.03 |
| | 40 °C | 1.78 ± 0.02 | 1.81 ± 0.02 | 1.86 ± 0.02 |
| t = 2 months | 25 °C | 1.81 ± 0.05 | 1.82 ± 0.04 | 1.82 ± 0.02 |
| | 40 °C | 1.70 ± 0.04 | 1.69 ± 0.01 | 1.71 ± 0.01 |
| t = 3 months | 25 °C | 1.80 ± 0.02 | 1.80 ± 0.07 | 1.77 ± 0.20 |
| | 40 °C | 1.57 ± 0.05 | 1.62 ± 0.05 | 1.65 ± 0.01 |
| t = 6 months | 25 °C | 1.66 ± 0.07 | 1.69 ± 0.02 | 1.74 ± 0.03 |
| | 40 °C | 1.37 ± 0.04 | 1.41 ± 0.02 | 1.55 ± 0.03 |

* Samples from the same batch of formulation, sub-aliquoted into glass vials for the comparison against the Albion pumps (7.5 g and 15 g fill).

Stability Study GW 921-01

C. Amount (%w/w) of methylparaben recovered from each formulation when stored through a 6 month period at 25°C/60% RH and 40°C/75% RH

Methylparaben Specification: 0.18% - 0.22% w/w

| Time point | Temperature storage | Albion 3.75 % 7.5 g fill | Albion 3.75 % 15 g fill % | Ref 3.75 %* |
|---|---|---|---|---|
| t = 0 h | | 0.201 ± 0.000 | 0.203 ± 0.002 | 0.205 ± 0.003 |
| t = 1 month | 25°C | 0.207 ± 0.003 | 0.204 ± 0.001 | 0.207 ± 0.001 |
| | 40 °C | 0.203 ± 0.002 | 0.201 ± 0.003 | 0.207 ± 0.001 |
| t = 2 months | 25 °C | 0.202 ± 0.008 | 0.203 ± 0.004 | 0.202 ± 0.002 |
| | 40 °C | 0.206 ± 0.005 | 0.202 ± 0.001 | 0.205 ± 0.001 |
| t = 3 months | 25 °C | 0.208 ± 0.003 | 0.208 ± 0.007 | 0.205 ± 0.005 |
| | 40 °C | 0.203 ± 0.005 | 0.205 ± 0.005 | 0.208 ± 0.004 |
| t = 6 months | 25 °C | 0.199 ± 0.006 | 0.203 ± 0.004 | 0.204 ± 0.003 |
| | 40 °C | 0.201 ± 0.003 | 0.198 ± 0.005 | 0.207 ± 0.003 |

* Samples from the same batch of formulation, sub-aliquoted into glass vials for the comparison against the Albion pumps (7.5 g and 15 g fill).

Stability Study GW 921-01

D. Amount (%w/w) of propylparaben recovered from each formulation when stored through a 6 month period at 25°C/60% RH and 40°C/75% RH

Propylparaben Specification: 0.018% - 0.022% w/w

| Time point | Temperature storage | Albion 3.75 % 7.5 g fill | Albion 3.75 % 15 g fill % | Ref 3.75 %* |
|---|---|---|---|---|
| t = 0 h | | 0.0189 ± 0.001 | 0.0196 ± 0.000 | 0.0214 ± 0.002 |
| t = 1 month | 25 °C | 0.0200 ± 0.001 | 0.0193 ± 0.000 | 0.0199 ± 0.000 |
| | 40 °C | 0.0198 ± 0.001 | 0.0195 ± 0.000 | 0.0198 ± 0.000 |
| t = 2 months | 25 °C | 0.0202 ± 0.001 | 0.0190 ± 0.001 | 0.0192 ± 0.001 |
| | 40 °C | 0.0194 ± 0.000 | 0.0185 ± 0.001 | 0.0194 ± 0.001 |
| t = 3 months | 25 °C | 0.0209 ± 0.000 | 0.2060 ± 0.001 | 0.0208 ± 0.000 |
| | 40 °C | 0.0205 ± 0.002 | 0.0208 ± 0.001 | 0.0208 ± 0.000 |
| t = 6 months | 25 °C | 0.0195 ± 0.000 | 0.0197 ± 0.001 | 0.0203 ± 0.001 |
| | 40 °C | 0.0208 ± 0.001 | 0.0200 ± 0.000 | 0.0202 ± 0.001 |

* Samples from the same batch of formulation, sub-aliquoted into glass vials for the comparison against the Albion pumps (7.5 g and 15 g fill).

Stability Study GW 921-01

E.  The pH of each formulation when stored through a 6 month period at 25°C/60% RH and 40°C/75% RH pH Specifications: 4.0 to 5.5

| Time point | Temperature storage | pH | | |
|---|---|---|---|---|
| | | Albion 3.75 % 7.5 g fill | Albion 3.75 % 15 g fill % | Ref 3.75 %* |
| t = 0 h | | 5.138 | 5.059 | 5.039 |
| t = 1 month | 25 °C | 5.059 | 5.072 | |
| | 40 °C | 5.052 | 5.052 | |
| t = 2 months | 25 °C | 5.000 | 5.033 | |
| | 40 °C | 4.991 | 4.921 | |
| t = 3 months | 25 °C | 4.967 | 5.104 | |
| | 40 °C | 5.016 | 5.030 | |
| t = 6 months | 25 °C | 5.200 | 5.156 | |
| | 40 °C | 5.011 | 4.980 | |

* Samples from the same batch of formulation, sub-aliquoted into glass vials for the comparison against the Albion pumps (7.5 g and 15 g fill).

Stability Study GW 921-01

F. The results of the viscosity measurements for the formulation stored through a 6 month period at 25°C/60% RH and 40°C/75% RH Viscosity Specification: 2,000 to 35,000 cPs for Bohlin

| Time point | Temperature storage | Bohlin Viscosity (cPs) (based on 3M method) | |
|---|---|---|---|
| | | Albion 3.75 % 7.5 g fill | Albion 3.75 % 15 g fill % |
| t = 0 h | | 10786 | 10027 |
| t = 1 month | 25 °C | 9303 | 9138 |
| | 40 °C | 7161 | 6956 |
| t = 2 months | 25 °C | 8268 | 8340 |
| | 40 °C | 6309 | 6328 |
| t = 3 months | 25 °C | 7428 | 6621 |
| | 40 °C | 6249 | 6613 |
| t = 6 months | 25 °C | 5450 | 5310 |
| | 40 °C | 2808 | 2727 |

Stability Study GW 921-01

G. Amount (%w/w) of 4-hydroxy Imiquimod from each formulation stored through a 6 month period at 25°C/60% RH and 40°C/75% RH 4-hydroxy Imiquimod Specification: NMT 0.3% w/w

| Time point | Temperature storage | Amount (%w/w) of 4-hydroxy imiquimod recovered from each formulation | | |
|---|---|---|---|---|
| | | Albion 3.75 % 7.5 g fill | Albion 3.75 % 15 g fill % | Ref 3.75 %* |
| t = 0 h | | NMT 0.1% w/w | NMT 0.1% w/w | NMT 0.1% w/w |
| t = 1 month | 25 °C | NMT 0.1% w/w | NMT 0.1% w/w | NMT 0.1% w/w |
| | 40 °C | NMT 0.1% w/w | NMT 0.1% w/w | NMT 0.1% w/w |
| t = 2 months | 25 °C | NMT 0.1% w/w | NMT 0.1% w/w | NMT 0.1% w/w |
| | 40 °C | NMT 0.1% w/w | NMT 0.1% w/w | NMT 0.1% w/w |
| t = 3 months | 25 °C | NMT 0.1% w/w | NMT 0.1% w/w | NMT 0.1% w/w |
| | 40 °C | NMT 0.1% w/w | NMT 0.1% w/w | NMT 0.1% w/w |
| t = 6 months | 25 °C | NMT 0.1% w/w | NMT 0.1% w/w | NMT 0.1% w/w |
| | 40 °C | NMT 0.1% w/w | NMT 0.1% w/w | NMT 0.1% w/w |

* Samples from the same batch of formulation, sub-aliquoted into glass vials for the comparison against the Albion pumps (7.5 g and 15 g fill).

Stability Study GW 921-01

H. Imiquimod raw data (top, middle and bottom extractions) Percentage of imiquimod recovered from each formulation (top, middle and bottom) compared to theoretical when stored through a 6 month period at 25°C/60% RH and 40°C/75% RH

Imiquimod Content Specification: 90 to 110% LC

| Time point | Temperature storage | Formulations (% recovered compared to theoretical) | | | | | | | | |
|---|---|---|---|---|---|---|---|---|---|---|
| | | Albion 3.75 % 7.5 g fill | | | Albion 3.75 % 15 g fill % | | | Ref 3.75 %* | | |
| | | Top | Middle | Bottom | Top | Middle | Bottom | Top | Middle | Bottom |
| t = 0 h | | 101.89 | 100.94 | 100.86 | 101.58 | 101.23 | 103.17 | 101.78 | 100.74 | 103.95 |
| t = 1 month | 25°C | 102.45 | 102.95 | 103.15 | 102.00 | 102.49 | 103.44 | 102.68 | 102.37 | 103.12 |
| | 40 °C | 102.14 | 101.82 | 102.18 | 99.37 | 102.04 | 101.09 | 103.10 | 103.26 | 13/63 |
| t = 2 months | 25 °C | 102.87 | 100.73 | 101.57 | 100.41 | 99.46 | 100.21 | 100.77 | 101.64 | 100.59 |
| | 40 °C | 100.94 | 100.67 | 101.06 | 99.94 | 100.65 | 100.63 | 101.53 | 102.30 | 102.00 |
| t = 3 months | 25 °C | 100.57 | 100.04 | 101.80 | 100.16 | 99.69 | 100.79 | 103.31 | 102.67 | 101.05 |
| | 40 °C | 104.33 | 101.44 | 103.28 | 104.20 | 101.93 | 102.12 | 104.15 | 104.67 | 102.25 |
| t = 6 months | 25 °C | 100.60 | 101.24 | 99.62 | 101.65 | 102.07 | 100.21 | 102.24 | 100.35 | 102.33 |
| | 40 °C | 102.50 | 102.38 | 102.10 | 103.47 | 101.62 | 102.04 | 102.18 | 103.06 | 100.94 |

Stability Study GW 921-01

I. Benzyl alcohol raw data (top, middle and bottom extractions) Amount (%w/w) of benzyl alcohol recovered from each of the formulation (top, middle and bottom) when stored through a 6 month period at 25°C/60% RH and 40°C/75% RH Benzyl Alcohol Specification: 1.0 to 2.1% w/w

| Time point | Temperature storage | Amount (%w/w) of benzyl alcohol recovered from each formulation | | | | | | | | |
|---|---|---|---|---|---|---|---|---|---|---|
| | | Albion 3.75 % 7.5 g fill | | | Albion 3.75 % 15 g fill % | | | Ref 3.75 %* | | |
| | | Top | Middle | Bottom | Top | Middle | Bottom | Top | Middle | Bottom |
| t = 0 h | | 1.82 | 1.85 | 1.87 | 1.89 | 1.85 | 1.92 | 1.87 | 1.86 | 1.83 |
| t = 1 month | 25°C | 1.85 | 1.91 | 1.90 | 1.83 | 1.89 | 1.91 | 1.92 | 1.88 | 1.93 |
| | 40 °C | 1.77 | 1.79 | 1.80 | 1.79 | 1.83 | 1.80 | 1.85 | 1.84 | 1.88 |
| t = 2 months | 25 °C | 1.86 | 1.76 | 1.83 | 1.82 | 1.78 | 1.86 | 1.84 | 1.80 | 1.81 |
| | 40 °C | 1.69 | 1.67 | 1.75 | 1.68 | 1.68 | 1.70 | 1.72 | 1.70 | 1.71 |
| t = 3 months | 25 °C | 1.78 | 1.80 | 1.82 | 1.73 | 1.84 | 1.85 | 1.79 | 1.76 | 1.76 |
| | 40 °C | 1.58 | 1.51 | 1.61 | 1.66 | 1.56 | 1.64 | 1.65 | 1.64 | 1.66 |
| t = 6 months | 25 °C | 1.69 | 1.71 | 1.58 | 1.67 | 1.69 | 1.71 | 1.72 | 1.77 | 1.73 |
| | 40 °C | 1.40 | 1.40 | 1.33 | 1.43 | 1.38 | 1.41 | 1.52 | 1.57 | 1.55 |

* Samples from the same batch of formulation, sub-aliquoted into glass vials for the comparison against the Albion pumps (7.5 g and 15 g fill).

Stability Study GW 921-01

J. Methylparaben raw data (top, middle and bottom extractions) Amount (%w/w) of methylparaben recovered from each of the formulations (top, middle and bottom) when stored through a 6 month period at 25°C/60% RH and 40°C/75% RH Methylparaben Specification: 0.18% - 0.22% w/w

| Time point | Temperature storage | Amount (%w/w) of methylparaben recovered from each formulation | | | | | | | | |
|---|---|---|---|---|---|---|---|---|---|---|
| | | Albion 3.75 % 7.5 g fill | | | Albion 3.75 % 15 g fill % | | | Ref 3.75 %* | | |
| | | Top | Middle | Bottom | Top | Middle | Bottom | Top | Middle | Bottom |
| t = 0 h | | 0.20 | 0.20 | 0.20 | 0.20 | 0.20 | 0.21 | 0.20 | 0.20 | 0.21 |
| t = 1 month | 25°C | 0.20 | 0.21 | 0.21 | 0.20 | 0.20 | 0.21 | 0.21 | 0.21 | 0.21 |
| | 40 °C | 0.20 | 0.20 | 0.20 | 0.20 | 0.20 | 0.20 | 0.21 | 0.21 | 0.21 |
| t = 2 months | 25 °C | 0.21 | 0.20 | 0.20 | 0.20 | 0.20 | 0.21 | 0.20 | 0.20 | 0.20 |
| | 40 °C | 0.20 | 0.20 | 0.21 | 0.20 | 0.20 | 0.20 | 0.20 | 0.21 | 0.20 |
| t = 3 months | 25 °C | 0.21 | 0.21 | 0.21 | 0.20 | 0.21 | 0.21 | 0.21 | 0.20 | 0.20 |
| | 40 °C | 0.20 | 0.20 | 0.21 | 0.21 | 0.20 | 0.21 | 0.21 | 0.21 | 0.20 |
| t = 6 months | 25 °C | 0.20 | 0.20 | 0.19 | 0.20 | 0.20 | 0.21 | 0.20 | 0.21 | 0.20 |
| | 40 °C | 0.20 | 0.20 | 0.20 | 0.20 | 0.19 | 0.20 | 0.20 | 0.21 | 0.21 |

* Samples from the same batch of formulation, sub-aliquoted into glass vials for the comparison against the Albion pumps (7.5 g and 15 g fill).

Stability Study GW 921-01

K. Propylparaben raw data (top, middle and bottom extractions) Amount (%w/w) of propylparaben recovered from each of the formulation (top, middle and bottom) when stored through a 6 month period at 25°C/60% RH and 40°C/75% RH Propylparaben Specification: 0.018% - 0.022% w/w

| Time point | Temperature storage | Amount (%w/w) of propylparaben recovered from each formulation | | | | | | | | |
|---|---|---|---|---|---|---|---|---|---|---|
| | | Albion 3.75 % 7.5 g fill | | | Albion 3.75 % 15 g fill % | | | Ref 3.75 %* | | |
| | | Top | Middle | Bottom | Top | Middle | Bottom | Top | Middle | Bottom |
| t = 0 h | | 0.0207 | 0.0187 | 0.0184 | 0.0184 | 0.0192 | 0.0200 | 0.0219 | 0.0198 | 0.0195 |
| t = 1 month | 25°C | 0.0193 | 0.0201 | 0.0205 | 0.0188 | 0.0193 | 0.0196 | 0.0200 | 0.0197 | 0.0202 |
| | 40 °C | 0.0191 | 0.0202 | 0.0193 | 0.0193 | 0.0199 | 0.0194 | 0.0196 | 0.0201 | 0.0196 |
| t = 2 months | 25 °C | 0.0211 | 0.0200 | 0.0194 | 0.0200 | 0.0192 | 0.0184 | 0.0197 | 0.0187 | 0.0185 |
| | 40 °C | 0.0187 | 0.0191 | 0.0197 | 0.0193 | 0.0188 | 0.0195 | 0.0201 | 0.0188 | 0.0193 |
| t = 3 months | 25 °C | 0.0208 | 0.0207 | 0.0210 | 0.0195 | 0.0215 | 0.0207 | 0.0211 | 0.0204 | 0.0201 |
| | 40 °C | 0.0214 | 0.0189 | 0.0211 | 0.0217 | 0.0201 | 0.0207 | 0.0213 | 0.0209 | 0.0204 |
| t = 6 months | 25 °C | 0.0193 | 0.0199 | 0.0192 | 0.0204 | 0.0199 | 0.0187 | 0.0208 | 0.0198 | 0.0205 |
| | 40 °C | 0.0198 | 0.0217 | 0.0208 | 0.0195 | 0.0203 | 0.0201 | 0.0196 | 0.0212 | 0.0197 |

* Samples from the same batch of formulation, sub-aliquoted into glass vials for the comparison against the Albion pumps (7.5 g and 15 g fill).

Stability Study GW 921-01

L. N-oxide raw data (top, middle and bottom extractions) Amount (%w/w) of n-oxide recovered from each formulation (top, middle and bottom) when stored through a 6 month period at 25°C/60% RH and 40°C/75% RH

Specification: Run and Record

| Time point | Temperature storage | Amount (%w/w) of n oxide recovered from each formulation ||||||
| | | Albion 3.75 % 7.5 g fill ||| Albion 3.75 % 15 g fill % |||
| | | Top | Middle | Bottom | Top | Middle | Bottom |
|---|---|---|---|---|---|---|---|
| t = 0 h | | | | | | | |
| t = 1 month | 25°C | | | | | | |
| | 40 °C | | | | | | |
| t = 2 months | 25 °C | Not tested |||||| 
| | 40 °C | | | | | | |
| t = 3 months | 25 °C | | | | | | |
| | 40 °C | | | | | | |
| t = 6 months | 25 °C | None detected | None detected | None detected | None detected | None detected | None detected |
| | 40 °C | None detected | None detected | None detected | None detected | None detected | None detected |

Attachment V

[000316] Report Analysis

Sample ID: Albion 30 mL Pump with Cocoon

Test Method: USP 32/NF 27 <661> Physicochemical Tests — Plastics
Reference Standard: Not Applicable
Test Results: Below
Comment: The sample meets USP 32/NF 27 specifications for the tests conducted.

TEST RESULTS

PHYSICOCHEMICAL TESTS — PLASTICS

Nonvolatile Residue USP <661>

| EXTRACTANT | TEST RESULT | SPECIFICATION |
|---|---|---|
| Water @ 70°C for 24 hours | 1 mg | Not More Than 15 mg |

Residue on Ignition USP <281>

Meets the USP Specifications.

Specification: It is not necessary to perform this test when the nonvolatile residue does not exceed 5 mg as noted for the $H_2O$ extraction medium for plastics.

Heavy Metals USP <661>

The color in the sample tube was lighter than the color in the standard tube (less than 1 ppm).

Specification: Any brown color produced within 10 minutes in the tube containing the extract of the sample does not exceed that in the tube containing the standard lead solution (1 ppm).

Buffering Capacity USP <661>

| mL of 0.010 N Hydrochloric Acid (Sample) | 0.03 |
|---|---|
| mL of 0.010 N Sodium Hydroxide (Blank) | 0.06 |
| Total (mL) | 0.09 |
| Reported (mL) | ~0.1 |

Specification: The total of the two volumes required for titration between sample and blank is not greater than 10.0 mL.

[000317]                    Attachment VI

ALBION 30 ml piston (LDPE) restitution 7.5ml     (AIRLESS)

(Imiquimod 3.75% cream)

TEST RESULTS (See also Fig. 8)

| (Imiquimod 3.75% cream) | | device #62 | device #63 | device #64 | device #65 | device #66 | device #67 | device #68 | device #69 | device #70 | device #71 |
|---|---|---|---|---|---|---|---|---|---|---|---|
| | PRIMING | 3 | 3 | 3 | 3 | 3 | 3 | 3 | 3 | 3 | 3 |
| FIRST 2-WEEK CYCLE | | 1 dose | 1 dose | 1 dose | 1 dose | 1 dose | 1 dose | 1 dose | 1 dose | 1 dose | 1 dose |
| | Day 1 | 235 | 236 | 233 | 227 | 234 | 234 | 228 | 230 | 232 | 230 |
| | Day 2 | 236 | 238 | 233 | 235 | 236 | 235 | 233 | 233 | 235 | 236 |
| | Day 3 | 236 | 241 | 235 | 235 | 239 | 234 | 230 | 235 | 237 | 237 |
| | Day 4 | 235 | 242 | 237 | 235 | 240 | 237 | 234 | 235 | 239 | 238 |
| | Day 5 | 236 | 240 | 236 | 235 | 239 | 236 | 235 | 235 | 238 | 238 |
| | Day 6 | 237 | 241 | 237 | 237 | 240 | 238 | 237 | 238 | 239 | 240 |
| | Day 7 | 234 | 242 | 235 | 238 | 239 | 236 | 235 | 232 | 238 | 235 |
| | Day 8 | 240 | 243 | 239 | 240 | 241 | 239 | 238 | 236 | 238 | 241 |
| | Day 9 | 240 | 242 | 238 | 236 | 239 | 239 | 237 | 231 | 239 | 235 |
| | Day 10 | 239 | 240 | 237 | 237 | 243 | 239 | 239 | 239 | 239 | 239 |
| | Day 11 | 237 | 242 | 240 | 238 | 241 | 238 | 236 | 235 | 240 | 217 |
| | Day 12 | 240 | 244 | 242 | 241 | 242 | 238 | 232 | 240 | 241 | 239 |
| | Day 13 | 240 | 239 | 237 | 235 | 240 | 237 | 237 | 239 | 239 | 237 |
| | Day 14 | 236 | 240 | 239 | 237 | 240 | 238 | 236 | 238 | 240 | 238 |
| Rest or Static Period (Second 2-week Cycle) | | | | | | | | | | | |
| THIRD 2-WEEK CYCLE | | 1 dose | 1 dose | 1 dose | 1 dose | 1 dose | 1 dose | 1dose | 1 dose | 1 dose | |
| | Day 29 | 237 | 232 | 235 | 231 | 232 | 231 | 230 | 234 | 233 | 229 |
| | Day 30 | 242 | 244 | 240 | 240 | 240 | 237 | 238 | 242 | 242 | 237 |
| | Day 31 | 243 | 241 | 239 | 237 | 239 | 238 | 237 | 239 | 241 | 239 |
| | Day 32 | 244 | 244 | 237 | 242 | 240 | 240 | 239 | 242 | 241 | 223 |
| | Day 33 | 239 | 243 | 238 | 238 | 240 | 240 | 235 | 239 | 240 | 237 |
| | Day 34 | 239 | 243 | 241 | 241 | 243 | 235 | 235 | 240 | 239 | 241 |
| | Day 35 | 240 | 240 | 241 | 240 | 241 | 240 | 236 | 239 | 240 | 238 |
| | Day 36 | 241 | 240 | 240 | 236 | 241 | 237 | 236 | 236 | 237 | 240 |
| | Day 37 | 240 | 238 | 236 | 237 | 239 | 230 | 238 | 233 | 237 | 234 |
| | Day 38 | 240 | 241 | 237 | 240 | 235 | 236 | 236 | 240 | 237 | 237 |
| | Day 39 | 239 | 226 | 238 | 240 | 238 | 239 | 238 | 236 | 231 | 234 |
| | Day 40 | 239 | 235 | 235 | 239 | 237 | 238 | 232 | 236 | 223 | 235 |
| | Day 41 | 238 | 240 | 237 | 234 | 239 | 238 | 234 | 236 | 237 | 233 |
| | Day 42 | 238 | 239 | 235 | 236 | 239 | 239 | 236 | 232 | 236 | 232 |

ALBION 30 ml piston (LDPE) restitution 1.5ml  AIRLESS (Imiquimod 3.75%)

TEST RESULTS (See also Fig. 9)

|  |  | device #62 | device #63 | device #64 | device #65 | device #66 | device #67 | device #68 | device #69 | device #70 | device #71 |
|---|---|---|---|---|---|---|---|---|---|---|---|
|  | PRIMING | 3 | 3 | 3 | 3 | 3 | 3 | 3 | 3 | 3 | 2 |
|  |  | dose 1 | dose 1 | dose 1 | dose 1 | dose 1 | dose 1 | dose 1 | dose 1 | dose 1 | dose 1 |
| FIRST 2-WEEK CYCLE | Day 1 | 235 | 234 | 232 | 233 | 235 | 236 | 235 | 231 | 234 | 236 |
| | Day 2 | 237 | 239 | 237 | 237 | 239 | 235 | 239 | 235 | 233 | 238 |
| | Day 3 | 238 | 238 | 239 | 238 | 240 | 238 | 240 | 238 | 234 | 241 |
| | Day 4 | 239 | 234 | 240 | 236 | 241 | 240 | 241 | 237 | 237 | 239 |
| | Day 5 | 240 | 240 | 240 | 235 | 239 | 238 | 241 | 237 | 239 | 242 |
| | Day 6 | 237 | 238 | 240 | 236 | 241 | 236 | 238 | 235 | 241 | 240 |
| | Day 7 | 239 | 242 | 240 | 231 | 241 | 238 | 236 | 237 | 237 | 239 |
| | Day 8 | 238 | 243 | 241 | 243 | 243 | 239 | 242 | 237 | 242 | 243 |
| | Day 9 | 239 | 239 | 241 | 239 | 243 | 240 | 239 | 239 | 239 | 244 |
| | Day 10 | 237 | 238 | 238 | 240 | 243 | 240 | 240 | 241 | 238 | 244 |
| | Day 11 | 235 | 240 | 240 | 240 | 242 | 240 | 239 | 238 | 240 | 240 |
| | Day 12 | 238 | 238 | 241 | 243 | 243 | 239 | 242 | 238 | 240 | 243 |
| | Day 13 | 236 | 241 | 243 | 242 | 244 | 238 | 241 | 233 | 238 | 242 |
| | Day 14 | 238 | 242 | 240 | 241 | 247 | 240 | 241 | 238 | 239 | 242 |
|  |  |  |  |  |  |  |  |  |  |  |  |
|  | Rest or Static Period (Second 2-week Cycle) | | | | | | | | | | |

|  |  | dose 1 | dose 1 | dose 1 | dose 1 | dose 1 | dose 1 | dose 1 | dose 1 | dose 1 | dose 1 |
|---|---|---|---|---|---|---|---|---|---|---|---|
| THIRD 2-WEEK CYCLE | Day 29 | 234 | 238 | 239 | 228 | 243 | 236 | 236 | 234 | 234 | 239 |
| | Day 30 | 243 | 242 | 238 | 242 | 248 | 240 | 242 | 236 | 240 | 244 |
| | Day 31 | 243 | 244 | 241 | 242 | 248 | 240 | 242 | 239 | 242 | 242 |
| | Day 32 | 241 | 245 | 242 | 242 | 247 | 240 | 242 | 237 | 239 | 244 |
| | Day 33 | 241 | 243 | 241 | 242 | 250 | 242 | 242 | 240 | 240 | 243 |
| | Day 34 | 242 | 244 | 242 | 243 | 247 | 240 | 242 | 239 | 242 | 246 |
| | Day 35 | 243 | 243 | 241 | 242 | 242 | 239 | 243 | 241 | 239 | 245 |
| | Day 36 | 240 | 245 | 241 | 241 | 243 | 239 | 242 | 238 | 241 | 243 |
| | Day 37 | 241 | 239 | 241 | 239 | 242 | 240 | 240 | 237 | 240 | 242 |
| | Day 38 | 241 | 244 | 240 | 243 | 241 | 240 | 240 | 236 | 242 | 242 |
| | Day 39 | 241 | 244 | 241 | 242 | 245 | 241 | 242 | 237 | 241 | 244 |
| | Day 40 | 241 | 245 | 241 | 242 | 242 | 240 | 243 | 236 | 240 | 244 |
| | Day 41 | 242 | 244 | 242 | 241 | 242 | 241 | 243 | 238 | 241 | 242 |
| | Day 42 | 242 | 244 | 242 | 241 | 243 | 240 | 241 | 238 | 241 | 243 |

Attachment VII

Figure 10:
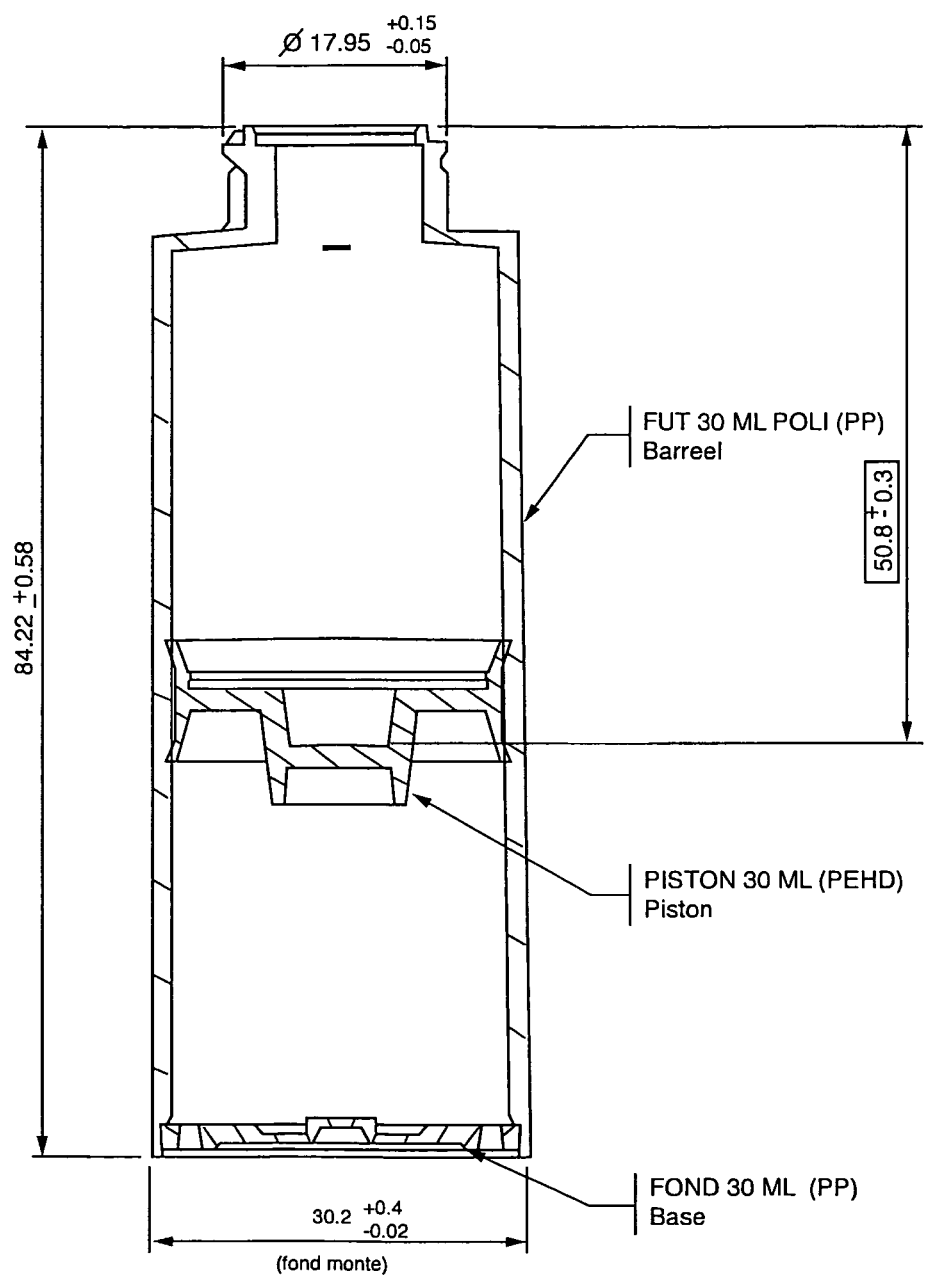
FIG. 10 is a cross-sectional view of a further embodiment of a lower or first subassembly used in the dispensing package of the present invention, which includes a hollow body along with the take-up piston and base closure member (see also Attachment VII below)
Figure 11:
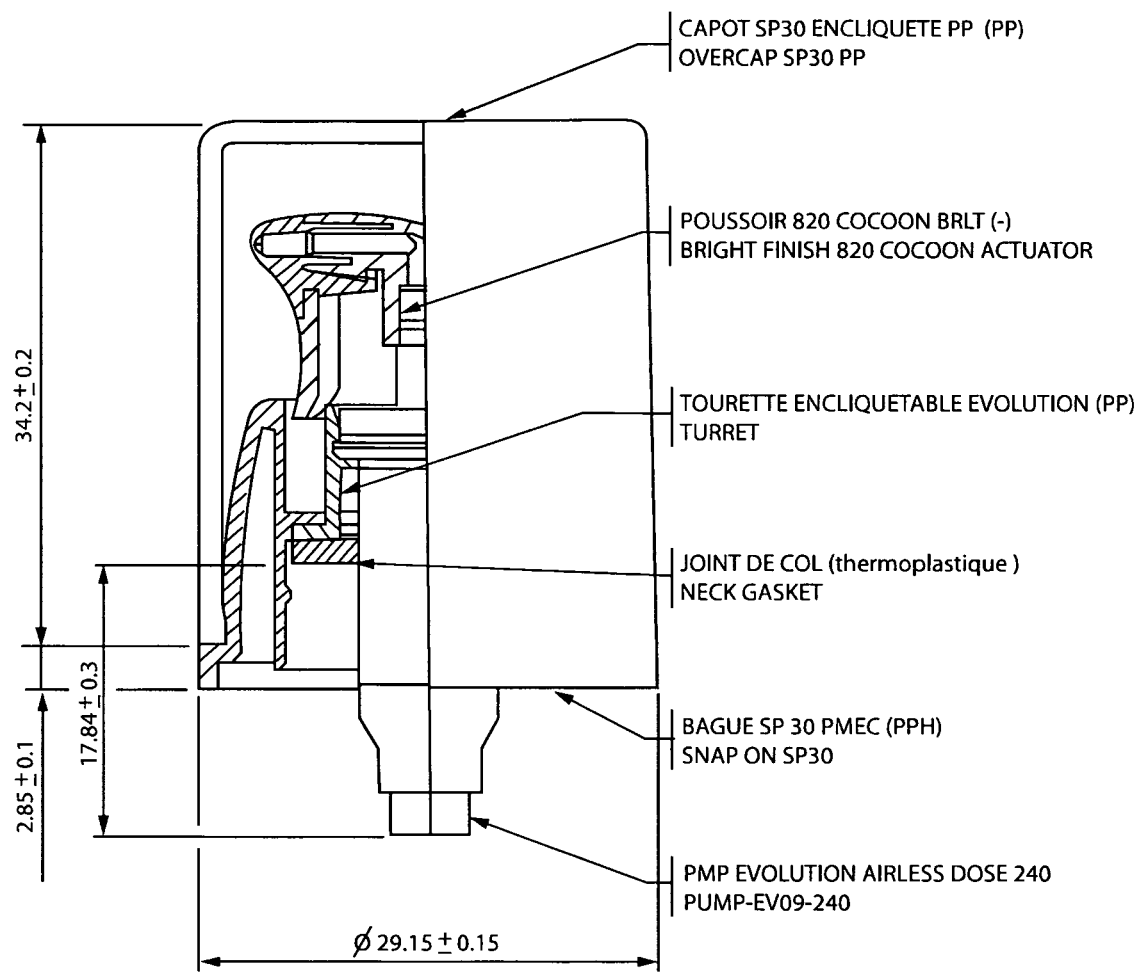
FIG. 11 is a partial cross-sectional view of a further embodiment of an upper or second subassembly used in the dispensing package of the present invention, which includes a dispensing head, a finger-operable pump, a holding member and a cap (no compressed neck gasket)(see also Attachment VII below).

[000318] Airlessystems Product Description (See also FIGs. 10 and 11)

Product: EH EVO9/240 30 ALBION PP BC PR 820 PP BC COCOON BC CA PP BC

| Components | Materials | Suppliers |
|---|---|---|
| cap | PPR 7220 | TOTAL Petrochemicals |
|  | White colorant standard : PP00121522 | Clariant |
| actuator | PPH :5060 + | TOTAL Petrochemicals |
|  | White colorant standard : PP00121522 + | Clariant |
|  | ENGAGE 8401 + | DOW CHEMICALS COMPANY |
|  | SL PE ER 7.5 | POLYTECHS |
| snap-on | PPH: 5060 + | TOTAL Petrochemicals |
|  | White colorant standard: PP00121522 | Clariant |
| neck gasket | F217-5 | TECKNIPLEX |
| pump EV09/240: |  |  |
| body | PST Valox HX312C-1H1001 or | SABIC |
|  | PBT: ORGATER TMFOD | PALMAROLE |
| Clapper | PEHD : Hostalen GC 7260 | BASELL |
| return spring | stainless steel 1.4310 | UGITECH |
| turret | PPH 5060 | TOTAL Petrochemicals |
| spring holder | PPH 5060 | TOTAL Petrochemicals |
| piston | PEHD : Hostalen GC7260 | BASELL |
| virote | PPH 5060 | TOTAL Petrochemicals |
|  | + Silicone Silibione oils 70047 V300 | BLUE STAR SILICONE |
| stem | PBT : TMFOD Orgater or | PALMAROLE |
|  | PBT : Valoxi-HX312C-1H1001 | SABIC |

Attachment VIII

[000319]     Aldara® (imiquimod) 5% Cream

HIGHLIGHTS OF PRESCRIBING INFORMATION

These highlights do not include all the information needed to use Aldara® safely and effectively. See full prescribing information for Aldara®.

Aldara® (imiquimod) Cream
For topical use only
Initial U.S. Approval: 1997

---------------------------------- INDICATIONS AND USAGE ----------------------------------

Aldara® Cream is indicated for the topical treatment of:

- Clinically typical, nonhyperkeratotic, nonhypertrophic actinic keratoses (AK) on the face or scalp in immunocompetent adults (1.1)
- Biopsy-confirmed, primary superficial basal cell carcinoma (sBCC) in immunocompetent adults; maximum tumor diameter of 2.0 cm on trunk, neck, or extremities (excluding hands and feet), only when surgical methods are medically less appropriate and patient follow-up can be reasonably assured (1.2)
- External genital and perianal warts/condyloma acuminata in patients 12 years old or older (1.3)

Limitations of Use:   Efficacy was not demonstrated for molluscum contagiosum in children aged 2-12 (1.4, 8.4)

-------------------------------- DOSAGE AND ADMINISTRATION --------------------------------

Aldara® Cream is not for oral, ophthalmic, or intravaginal use.(2)

- Actinic keratosis: 2 times per week for a full 16 weeks (2.1)
- Superficial basal cell carcinoma: 5 times per week for a full 6 weeks (2.2)
- External genital warts (EGW):  3 times per week until total clearance or a maximum of 16 weeks (2.3)

---------------------------------DOSAGE FORMS AND STRENGTHS---------------------------------

Aldara® (imiquimod) Cream, 5%, is supplied in single-use packets (12 per box), each of which contains 250 mg of the cream, equivalent to 12.5 mg of imiquimod. (3)

---------------------------------------- CONTRAINDICATIONS ----------------------------------------

- None (4)

---------------------------------WARNINGS AND PRECAUTIONS---------------------------------

- Intense local inflammatory reactions can occur (e.g., skin weeping, erosion). Dosing interruption may be required (2, 5.1, 6)

- Flu-like systemic signs and symptoms including malaise, fever, nausea, myalgias and rigors may occur. Dosing interruption may be required (2, 5.2, 6)

- Avoid exposure to sunlight and sunlamps. Wear sunscreen daily (5.3).

- Safety and efficacy have not been established for repeat courses of treatment to the same area for AK. (5.4)

- Aldara® Cream is not recommended for treatment of BCC subtypes other than the superficial variant, i.e., sBCC. (5.5)

- Treatment of urethral, infra-vaginal, cervical, rectal or intra-anal viral disease is not recommended. (5.6)

- Safety and efficacy in immunosuppressed patients have not been established (1.5)

---------------------------------------- ADVERSE REACTIONS ----------------------------------------

Most common adverse reactions (incidence >28%) are application site reactions or local skin reactions: itching, burning, erythema, flaking/scaling/dryness, scabbing/crusting, edema, induration, excoriation, erosion, ulceration. Other reported reactions ($\geq$ 1%) include fatigue, fever, and headache (6.1, 6.2, 6.3)

To report SUSPECTED ADVERSE REACTIONS, contact Graceway Pharmaceuticals, LLC at 1-800-328-0255 or FDA at 1-800-FDA-1 088 or *www.fda.gov/medwatch.*

See 17 for PATIENT COUNSELING INFORMATION and FDA- approved patient labeling.

Revised: March 2007

PRESCRIBING INFORMATION: CONTENTS*

1 INDICATIONS AND USAGE 1.1 Actinic Keratosis 1.2 Superficial Basal Cell Carcinoma 1.3 External Genital Warts 1.4 Limitations of Use 1.5 Unevaluated Populations

2 DOSAGE AND ADMINISTRATION 2.1 Actinic Keratosis 2.2 Superficial Basal Cell Carcinoma 2.3 External Genital Warts

3 DOSAGE FORMS AND STRENGTHS

4 CONTRAINDICATIONS

5 WARNINGS AND PRECAUTIONS 5.1 Local Inflammatory Reactions 5.2 Systemic Reactions 5.3 Ultraviolet Light Exposure 5.4 Unevaluated Uses: Actinic Keratosis 5.5 Unevaluated Uses: Superficial Basal Cell Carcinoma 5.6 Unevaluated Uses: External Genital Warts

6 ADVERSE REACTIONS 6.1 Clinical Trials Experience: Actinic Keratosis 6.2 Clinical Trials Experience: Superficial Basal Cell Carcinoma 6.3 Clinical Trials Experience: External Genital Warts 6.4 Clinical Trials Experience: Dermal Safety Studies 6.5 Postmarketing Experience

8 USE IN SPECIFIC POPULATIONS 8.1 Pregnancy 8.3 Nursing Mothers 8.4 Pediatric Use 8.5 Geriatric Use

10 OVER DOSAGE

11 DESCRIPTION

12 CLINICAL PHARMACOLOGY 12.1 Mechanism of Action 12.2 Pharmacodynamics 12.3 Pharmacokinetics

13 NONCLINICAL TOXICOLOGY 13.1 Carcinogenesis, Mutagenesis, Impairment of Fertility

14 CLINICAL STUDIES 14.1 Actinic Keratosis 14.2 Superficial Basal Cell Carcinoma 14.3 External Genital Warts

16 HOW SUPPLIED/STORAGE AND HANDLING

17 PATIENT COUNSELING INFORMATION 17.1 General Information: All Indications 17.2 Local Skin Reactions: All Indications 17.3 Systemic Reactions: All Indications 17.4 Patients Being Treated for Actinic Keratosis (AK)

17.5 Patients Being Treated for Superficial Basal Cell Carcinoma (sBCC)

17.6 Patients Being Treated for External Genital Warts 17.7 FDA-Approved Patient Labeling

*Sections or subsections omitted from the full prescribing information are not listed.

FULL PRESCRIBING INFORMATION

1    INDICATIONS AND USAGE 1.1    Actinic Keratosis

Aldara® Cream is indicated for the topical treatment of clinically typical, nonhyperkeratotic, nonhypertrophic actinic keratoses on the face or scalp in immunocompetent adults.

1.2    Superficial Basal Cell Carcinoma

Aldara® Cream is indicated for the topical treatment of biopsy-confirmed, primary superficial basal cell carcinoma (sBCC) in immunocompetent adults, with a maximum tumor diameter of 2.0 cm, located on the trunk (excluding anogenital skin), neck, or extremities (excluding hands and feet), only when surgical methods are medically less appropriate and patient follow-up can be reasonably assured.

The histological diagnosis of <u>superficial</u> basal cell carcinoma should be established prior to treatment, since safety and efficacy of Aldara® Cream have not been established for other types of basal cell carcinomas, including nodular and morpheaform (fibrosing or sclerosing) types.

1.3 External Genital Warts

Aldara® Cream is indicated for the treatment of external genital and perianal warts/condyloma acuminata in patients 12 years or older.

1.4 Limitations of Use

Aldara® Cream has been evaluated in children ages 2 to 12 years with molluscum contagiosum and these studies failed to demonstrate efficacy. *[see Use in Specific Populations (8.4)]*.

1.5 Unevaluated Populations

The safety and efficacy of Aldara® Cream in immunosuppressed patients have not been established.

Aldara® Cream should be used with caution in patients with pre-existing autoimmune conditions.

The efficacy and safety of Aldara® Cream have not been established for patients with Basal Cell Nevus Syndrome or Xeroderma Pigmentosum.

2 DOSAGE AND ADMINISTRATION

The application frequency for Aldara® Cream is different for each indication.

Aldara® Cream is not for oral, ophthalmic, or intravaginal use.

2.1 Actinic Keratosis

Aldara® Cream should be applied 2 times per week for a full 16 weeks to a defined treatment area on the face or scalp (but not both concurrently). The treatment area is defined as one contiguous area of approximately 25 $cm^2$ (e.g., 5 cm x 5 cm) on the face (e.g. forehead or one cheek) or on the scalp. Examples of 2 times per week application schedules are Monday and Thursday, or Tuesday and Friday. Aldara® Cream should be applied to the entire treatment area and rubbed in until the Aldara® Cream is no longer visible. No more than one packet of Aldara® Cream should be applied to the contiguous treatment area at each application. Aldara® Cream should be applied prior to normal sleeping hours and left on the skin for approximately 8 hours, after which time the Aldara® Cream should be removed by washing the area with mild soap and water. The prescriber should demonstrate the proper application technique to maximize the benefit of Aldara® Cream therapy.

It is recommended that patients wash their hands before and after applying Aldara® Cream. Before applying the Aldara® Cream, the patient should wash the treatment area with mild soap and water and allow the area to dry thoroughly (at least 10 minutes).

Contact with the eyes, lips and nostrils should be avoided.

Local skin reactions in the treatment area are common. *[see Adverse Reactions (6.1, 6.5)]* A rest period of several days may be taken if required by the patient's discomfort or severity of the local skin reaction. However, the treatment period should not be extended beyond 16 weeks due to missed doses or rest periods. Response to treatment cannot be adequately assessed until resolution of local skin reactions. Lesions that do not respond to treatment should be carefully re-evaluated and management reconsidered.

Aldara® Cream is packaged in single-use packets, with 12 packets supplied per box. Patients should be prescribed no more than 3 boxes (36 packets) for the 16-week treatment period. Unused packets should be discarded. Partially-used packets should be discarded and not reused.

2.2    Superficial Basal Cell Carcinoma

Aldara® Cream should be applied 5 times per week for a full 6 weeks to a biopsy-confirmed superficial basal cell carcinoma. An example of a 5 times per week application schedule is to apply Aldara® Cream, once per day, Monday through Friday. Aldara® Cream should be applied prior to normal sleeping hours and left on the skin for approximately 8 hours, after which time the Aldara® Cream should be removed by washing the area with mild soap and water. The prescriber should demonstrate the proper application technique to maximize the benefit of Aldara® Cream therapy.

It is recommended that patients wash their hands before and after applying Aldara® Cream. The patient should wash the treatment area with mild soap and water before applying the cream, and allow the area to dry thoroughly.

The target tumor should have a maximum diameter of 2 cm and be located on the trunk (excluding anogenital skin), neck, or extremities (excluding hands and feet). The treatment area should include a 1 cm margin of skin around the tumor. Sufficient cream should be applied to cover the treatment area, including 1 centimeter of skin surrounding the tumor. Aldara® Cream should be rubbed into the treatment area until the cream is no longer visible.

Table 1. Amount of Aldara® Cream to Use for sBCC

| Target Tumor Diameter | Size of Cream Droplet to be Used (diameter) | Approximate Amount of Aldara® to be Used |
|---|---|---|
| 0.5 to < 1.0 cm | 4 mm | 10 mg |
| 1.0 to < 1.5 cm | 5 mm | 25 mg |
| 1.5 to 2.0 cm | 7 mm | 40 mg |

Contact with the eyes, lips and nostrils should be avoided.

Local skin reactions in the treatment area are common. *[see Adverse Reactions (6.2, 6.5)]* A rest period of several days may be taken if required by the patient's discomfort or severity of the local skin reaction.

Early clinical clearance cannot be adequately assessed until resolution of local skin reactions (e.g. 12 weeks post-treatment). Local skin reactions or other findings (e.g. infection) may require that a patient be seen sooner than the post-treatment assessment for clinical clearance. If there is clinical evidence of persistent tumor at the post-treatment assessment for clinical clearance, a biopsy or other alternative intervention should be considered. Lesions that do not respond to therapy should be carefully re-evaluated and management reconsidered; the safety and efficacy of a repeat course of Aldara® Cream treatment have not been established. If any suspicious lesion arises in the treatment area at any time after a determination of clinical clearance, the patient should seek a medical evaluation. *[see Clinical Studies (14.2)]*.

Aldara® Cream is packaged in single-use packets, with 12 packets supplied per box. Patients should be prescribed no more than 3 boxes (36 packets) for the 6-week treatment period. Unused packets should be discarded. Partially-used packets should be discarded and not reused.

2.3 External Genital Warts

Aldara® Cream should be applied 3 times per week to external genital/perianal warts. Aldara® Cream treatment should continue until there is total clearance of the genital/perianal warts or for a maximum of 16 weeks. Examples of 3 times per week application schedules are: Monday, Wednesday, Friday or Tuesday, Thursday, Saturday. Aldara® Cream should be applied prior to normal sleeping hours and left on the skin for 6 -10 hours, after which time the Aldara® Cream should be removed by washing the area with mild soap and water. The prescriber should demonstrate the proper application technique to maximize the benefit of Aldara® Cream therapy.

It is recommended that patients wash their hands before and after applying Aldara® Cream. A thin layer of Aldara® Cream should be applied to the wart area and rubbed in until the Aldara® Cream is no longer visible. The application site should not be occluded. Following the treatment period the Aldara® Cream should be removed by washing the treated area with mild soap and water.

Local skin reactions at the treatment site are common. *[see Adverse Reactions (6.3, 6.5)]*. A rest period of several days may be taken if required by the patient's discomfort or severity of the local skin reaction. Treatment may resume once the reaction subsides. Non-occlusive dressings such as cotton gauze or cotton underwear may be used in the management of skin reactions.

Aldara® Cream is packaged in single-use packets which contain sufficient Aldara® Cream to cover a wart area of up to 20 $cm^2$; use of excessive amounts of Aldara® Cream should be avoided.

3 DOSAGE FORMS AND STRENGTHS

Aldara® (imiquimod) Cream, 5%, is supplied in single-use packets each of which contains 250 mg of the cream, equivalent to 12.5 mg of imiquimod. Aldara® Cream is supplied in boxes of 12 packets each.

4 CONTRAINDICATIONS

None.

5 WARNINGS AND PRECAUTIONS

5.1 Local Inflammatory Reactions

Intense local inflammatory reactions including skin weeping or erosion can occur after few applications of Aldara® Cream and may require an interruption of dosing. *[see Dosage and Administration (2) and Adverse Reactions (6)]*. Aldara® Cream has the potential to exacerbate inflammatory conditions of the skin, including chronic graft versus host disease.

Administration of Aldara® Cream is not recommended until the skin is completely healed from any previous drug or surgical treatment.

5.2 Systemic Reactions

Flu-like signs and symptoms may accompany, or even precede, local inflammatory reactions and may include malaise, fever, nausea, myalgias and rigors. An interruption of dosing should be considered. *[see Adverse Reactions (6)]*

5.3 Ultraviolet Light Exposure

Exposure to sunlight (including sunlamps) should be avoided or minimized during use of Aldara® Cream because of concern for heightened sunburn susceptibility. Patients should be warned to use protective clothing (e.g., a hat) when using Aldara® Cream. Patients with sunburn should be advised not to use Aldara® Cream until fully recovered. Patients who may have considerable sun exposure, e.g. due to their occupation, and those patients with inherent sensitivity to sunlight should exercise caution when using Aldara® Cream.

Aldara® Cream shortened the time to skin tumor formation in an animal photococarcinogenicity study *[see Nonclinical Toxicology (13.1)]*. The enhancement of ultraviolet carcinogenicity is not necessarily dependent on phototoxic mechanisms. Therefore, patients should minimize or avoid natural or artificial sunlight exposure.

5.4 Unevaluated Uses: Actinic Keratosis

Safety and efficacy have not been established for Aldara® Cream in the treatment of actinic keratosis with repeated use, i.e. more than one treatment course, in the same area.

The safety of Aldara® Cream applied to areas of skin greater than 25 cm$^2$ (e.g. 5 cm X 5 cm) for the treatment of actinic keratosis has not been established *[see Clinical Pharmacology (12.3)]*.

5.5 Unevaluated Uses: Superficial Basal Cell Carcinoma

The safety and efficacy of Aldara® Cream have not been established for other types of basal cell carcinomas (BCC), including nodular and morpheaform (fibrosing or sclerosing) types. Aldara® Cream is not recommended for treatment of BCC subtypes other than the superficial variant (i.e., sBCC). Patients with sBCC treated with Aldara® Cream should have regular follow-up of the treatment site. *[see Clinical Studies (14.2)]*.

The safety and efficacy of treating sBCC lesions on the face, head and anogenital area have not been established.

5.6  Unevaluated Uses: External Genital Warts

Aldara® Cream has not been evaluated for the treatment of urethral, intra-vaginal, cervical, rectal, or intra-anal human papilloma viral disease.

6  ADVERSE REACTIONS

Because clinical trials are conducted under widely varying conditions, adverse reaction rates observed in the clinical trials of a drug cannot be directly compared to rates in the clinical trials of another drug and may not reflect the rates observed in practice.

6.1  Clinical Trials Experience: Actinic Keratosis

The data described below reflect exposure to Aldara® Cream or vehicle in 436 subjects enrolled in two double-blind, vehicle-controlled studies. Subjects applied Aldara® Cream or vehicle to a 25 $cm^2$ contiguous treatment area on the face or scalp 2 times per week for 16 weeks.

Table 2: Selected Adverse Reactions Occurring in > 1% of Aldara®-Treated Subjects and at a Greater Frequency than with Vehicle in the Combined Studies (Actinic Keratosis)

| Aldara® Cream Preferred Term | Aldara® Cream (n=215) | Vehicle (n= 221) |
|---|---|---|
| Application Site Reaction | 71 (33%) | 32 (14%) |
| Upper Resp Tract Infection | 33 (15%) | 27 (12%) |
| Sinusitis | 16 (7%) | 14 (6%) |
| Headache | 11 (5%) | 7 (3%) |
| Carcinoma Squamous | 8 (4%) | 5 (2%) |
| Diarrhea | 6 (3%) | 2 (1%) |
| Eczema | 4 (2%) | 3 (1%) |
| Back Pain | 3 (1%) | 2 (1%) |
| Fatigue | 3 (1%) | 2 (1%) |
| Fibrillation Atrial | 3 (1%) | 2 (1%) |
| Infection Viral | 3 (1%) | 2 (1%) |
| Dizziness | 3 (1%) | 1 (<1%) |
| Vomiting | 3 (1%) | 1 (<1%) |
| Urinary Tract Infection | 3 (1%) | 1 (<1%) |
| Fever | 3 (1%) | 0 (0%) |
| Rigors | 3 (1%) | 0 (0%) |
| Alopecia | 3 (1%) | 0 (0%) |

Table 3: Application Site Reactions Reported by > 1% of Aldara®-Treated Subjects and at a Greater Frequency than with Vehicle in the Combined Studies (Actinic Keratosis)

| Included Term | Aldara® Cream n=215 | Vehicle n=221 |
|---|---|---|
| Itching | 44 (20%) | 17 (8%) |
| Burning | 13 (6%) | 4 (2%) |
| Bleeding | 7 (3%) | 1 (<1%) |
| Stinging | 6 (3%) | 2 (1%) |
| Pain | 6 (3%) | 2 (1%) |
| Induration | 5 (2%) | 3 (1%) |
| Tenderness | 4 (2%) | 3 (1%) |
| Irritation | 4 (2%) | 0 (0%) |

Local skin reactions were collected independently of the adverse reaction "application site reaction" in an effort to provide a better picture of the specific types of local reactions that might be seen. The most frequently reported local skin reactions were erythema, flaking/scaling/dryness, and scabbing/crusting. The prevalence and severity of local skin reactions that occurred during controlled studies are shown in the following table.

Table 4: Local Skin Reactions in the Treatment Area as Assessed by the Investigator

| | (Actinic Keratosis) Aldara® Cream (n=215) | | Vehicle n=220 | |
|---|---|---|---|---|
| | All Grades* | Severe | All Grades* | Severe |
| Erythema | 209 (97%) | 38 (18%) | 206 (93%) | 5 (2%) |
| Flaking/Scaling/Dryness | 199 (93%) | 16 (7%) | 199 (91%) | 7 (3%) |
| Scabbing/Crusting | 169 (79%) | 18 (8%) | 92 (42%) | 4 (2%) |
| Edema | 106 (49%) | 0 (0%) | 22 (10%) | 0 (0%) |
| Erosion/Ulceration | 103 (48%) | 5 (2%) | 20 (9%) | 0 (0%) |
| Weeping/Exudate | 45 (22%) | 0 (0%) | 3 (1%) | 0 (0%) |
| Vesicles | 19 (9%) | 0 (0%) | 2 (1%) | 0 (0%) |

*Mild, Moderate, or Severe

The adverse reactions that most frequently resulted in clinical intervention (e.g., rest periods, withdrawal from study) were local skin and application site reactions. Overall, in the clinical studies, 2% (5/215) of subjects discontinued for local skin/application site reactions. Of the 215 subjects treated, 35 subjects (16%) on Aldara® Cream and 3 of 220 subjects (1%) on vehicle cream had at least one rest period. Of these Aldara® Cream subjects, 32 (9 1%) resumed therapy after a rest period.

In the AK studies, 22 of 678 (3.2%) of Aldara®-treated subjects developed treatment site infections that required a rest period off Aldara® Cream and were treated with antibiotics (19 with oral and 3 with topical).

Of the 206 Aldara® subjects with both baseline and 8-week post-treatment scarring assessments, 6 (2.9%) had a greater degree of scarring scores at 8-weeks post-treatment than at baseline.

6.2 Clinical Trials Experience: Superficial Basal Cell Carcinoma

The data described below reflect exposure to Aldara® Cream or vehicle in 364 subjects enrolled in two double-blind, vehicle-controlled studies. Subjects applied Aldara® Cream or vehicle 5 times per week for 6 weeks. The incidence of adverse reactions reported by > 1% of subjects during the studies is summarized below.

Table 5: Selected Adverse Reactions Reported by > 1% of Aldara®-Treated Subjects and at a Greater Frequency than with Vehicle in the Combined Studies (Superficial Basal Cell Carcinoma)

| Preferred Term | Aldara® Cream (n=185) N% | Vehicle (n=179) N % |
|---|---|---|
| Application Site Reaction | 52 (28%) | 5 (3%) |
| Headache | 14 (8%) | 4 (2%) |
| Back Pain | 7 (4%) | 1 (<1%) |
| Upper Resp Tract Infection | 6 (3%) | 2 (1%) |
| Rhinitis | 5 (3%) | 1 (<1%) |
| Lymphadenopathy | 5 (3%) | 1 (<1%) |
| Fatigue | 4 (2%) | 2 (1%) |
| Sinusitis | 4 (2%) | 1 (<1%) |
| Dyspepsia | 3 (2%) | 2 (1%) |
| Coughing | 3 (2%) | 1 (<1%) |
| Fever | 3 (2%) | 0 (0%) |
| Dizziness | 2 (1%) | 1 (<1%) |
| Anxiety | 2 (1%) | 1 (<1%) |
| Pharyngitis | 2 (1%) | 1 (<1%) |
| Chest Pain | 2 (1%) | 0 (0%) |
| Nausea | 2 (1%) | 0 (0%) |

The most frequently reported adverse reactions were local skin and application site reactions including erythema, edema, induration, erosion, flaking/scaling, scabbing/crusting, itching and burning at the application site. The incidence of application site reactions reported by > 1% of the subjects during the 6 week treatment period is summarized in the table below.

Table 6: Application Site Reactions Reported by > 1% of Aldara®-Treated Subjects and at a Greater Frequency than with Vehicle in the Combined Studies (Superficial Basal Cell Carcinoma)

| Included Term | Aldara® Cream n=185 | Vehicle n=179 |
|---|---|---|
| Itching | 30 (16%) | 1 (1%) |
| Burning | 11 (6%) | 2 (1%) |
| Pain | 6 (3%) | 0 (0%) |
| Bleeding | 4 (2%) | 0 (0%) |
| Erythema | 3 (2%) | 0 (0%) |
| Papule(s) | 3 (2%) | 0 (0%) |
| Tenderness | 2 (1%) | 0 (0%) |
| Infection | 2 (1%) | 0 (0%) |

Local skin reactions were collected independently of the adverse reaction "application site reaction" in an effort to provide a better picture of the specific types of local reactions that might be seen. The prevalence and severity of local skin reactions that occurred during controlled studies are shown in the following table.

Table 7: Local Skin Reactions in the Treatment Area as Assessed by the Investigator (Superficial Basal Cell Carcinoma)

| | Aldara® Cream n=184 | | Vehicle n=178 | |
|---|---|---|---|---|
| | All Grades* | Severe | All Grades* | Severe |
| Erythema | 184 (100%) | 57 (31%) | 173 (97%) | 4 (2%) |
| Flaking/Scaling | 167 (91%) | 7 (4%) | 135 (76%) | 0 (0%) |
| Induration | 154 (84%) | 11 (6%) | 94 (53%) | 0 (0%) |
| Scabbing/Crusting | 152 (83%) | 35 (19%) | 61 (34%) | 0 (0%) |
| Edema | 143 (78%) | 13 (7%) | 64 (36%) | 0 (0%) |
| Erosion | 122 (66%) | 23 (13%) | 25 (14%) | 0 (0%) |
| Ulceration | 73 (40%) | 11 (6%) | 6 (3%) | 0 (0%) |
| Vesicles | 57 (31%) | 3 (2%) | 4 (2%) | 0 (0%) |

*Mild, Moderate, or Severe

The adverse reactions that most frequently resulted in clinical intervention (e.g., rest periods, withdrawal from study) were local skin and application site reactions; 10% (19/1 85) of subjects received rest periods. The average number of doses not received per subject due to rest periods was 7 doses with a range of 2 to 22 doses; 79% of subjects (15/19) resumed therapy after a rest period. Overall, in the clinical studies, 2% (4/185) of subjects discontinued for local skin/application site reactions.

In the sBCC studies, 17 of 1266 (1.3%) Aldara® -treated subjects developed treatment site infections that required a rest period and treatment with antibiotics.

6.3 Clinical Trials Experience: External Genital Warts

In controlled clinical trials for genital warts, the most frequently reported adverse reactions were local skin and application site reactions.

Some subjects also reported systemic reactions. Overall, 1.2% (4/327) of the subjects discontinued due to local skin/application site reactions. The incidence and severity of local skin reactions during controlled clinical trials are shown in the following table.

Table 8: Local Skin Reactions in the Treatment Area as Assessed by the Investigator
(External Genital Warts)

| | Aldara® Cream | | | | Vehicle | | | |
|---|---|---|---|---|---|---|---|---|
| | Females n=114 | | Males n=156 | | Females n=99 | | Males n=157 | |
| | All Grades* | Severe | All Grades* | Severe | All Grades* | Severe | All Grades* | Severe |
| Erythema | 74 (65%) | 4 (4%) | 90 (58%) | 6 (4%) | 21 (21%) | 0 (0%) | 34 (22%) | 0 (0%) |
| Erosion | 35 (31%) | 1 (1%) | 47 (30%) | 2 (1%) | 8 (8%) | 0 (0%) | 10 (6%) | 0 (0%) |
| Excoriation/ Flaking | 21 (18%) | 0 (0%) | 40 (26%) | 1 (1%) | 8 (8%) | 0 (0%) | 12 (8%) | 0 (0%) |
| Edema | 20 (18%) | 1 (1%) | 19 (12%) | 0 (0%) | 5 (5%) | 0 (0%) | 1 (1%) | 0 (0%) |
| Scabbing | 4 (4%) | 0 (0%) | 20 (13%) | 0 (0%) | 0 (0%) | 0 (0%) | 4 (3%) | 0 (0%) |
| Induration | 6 (5%) | 0 (0%) | 11 (7%) | 0 (0%) | 2 (2%) | 0 (0%) | 3 (2%) | 0 (0%) |
| Ulceration | 9 (8%) | 3 (3%) | 7 (4%) | 0 (0%) | 1 (1%) | 0 (0%) | 1 (1%) | 0 (0%) |
| Vesicles | 3 (3%) | 0 (0%) | 3 (2%) | 0 (0%) | 0 (0%) | 0 (0%) | 0 (0%) | 0 (0%) |

*Mild, Moderate, or Severe

Remote site skin reactions were also reported. The severe remote site skin reactions reported for females were erythema (3%), ulceration (2%), and edema (1%); and for males, erosion (2%), and erythema, edema, induration, and excoriation/flaking (each 1%). Selected adverse reactions judged to be probably or possibly related to Aldara® Cream are listed below.

Table 9: Selected Treatment Related Reactions (External Genital Warts)

|  | Females | | Males | |
|---|---|---|---|---|
|  | Aldara® Cream n=117 | Vehicle n=103 | Aldara® Cream n=156 | Vehicle n=158 |
| Application Site Disorders: Application Site Reactions Wart Site: | | | | |
| Itching | 38 (32%) | 21 (20%) | 34 (22%) | 16 (10%) |
| Burning | 30 (26%) | 12 (12%) | 14 (9%) | 8 (5%) |
| Pain | 9 (8%) | 2 (2%) | 3 (2%) | 1 (1%) |
| Soreness | 3 (3%) | 0 (0%) | 0 (0%) | 1 (1%) |
| Fungal Infection* | 13 (11%) | 3 (3%) | 3 (2%) | 1 (1%) |
| Systemic Reactions: | | | | |
| Headache | 5 (4%) | 3 (3%) | 8 (5%) | 3 (2%) |
| Influenza-like symptoms | 4 (3%) | 2 (2%) | 2 (1%) | 0 (0%) |
| Myalgia | 1 (1%) | 0 (0%) | 2 (1%) | 1 (1%) |

*Incidences reported without regard to causality with Aldara® Cream.

Adverse reactions judged to be possibly or probably related to Aldara® Cream and reported by more than 1% of subjects included:

Application Site Disorders: burning, hypopigmentation, irritation, itching, pain, rash, sensitivity, soreness, stinging, tenderness Remote Site Reactions: bleeding, burning, itching, pain, tenderness, tinea cruris Body as a Whole: fatigue, fever, influenza-like symptoms Central and Peripheral Nervous System Disorders: headache Gastro-Intestinal System Disorders: diarrhea Musculo-Skeletal System Disorders: myalgia.

6.4  Clinical Trials Experience: Dermal Safety Studies

Provocative repeat insult patch test studies involving induction and challenge phases produced no evidence that Aldara® Cream causes photoallergenicity or contact sensitization in healthy skin; however, cumulative irritancy testing revealed the potential for Aldara® Cream to cause irritation, and application site reactions were reported in the clinical studies *[see Adverse Reactions (6)]*.

6.5  Postmarkefing Experience

The following adverse reactions have been identified during post-approval use of Aldara® Cream. Because these reactions are reported voluntarily from a population of uncertain size, it is not always possible to reliably estimate their frequency or establish a causal relationship to drug exposure.

Body as a Whole: angioedema.

Cardiovascular: capillary leak syndrome, cardiac failure, cardiomyopathy, pulmonary edema, arrhythmias (tachycardia, atrial fibrillation, palpitations), chest pain, ischemia, myocardial infarction, syncope.

Endocrine: thyroiditis.

Hematological: decreases in red cell, white cell and platelet counts (including idiopathic thrombocytopenic purpura), lymphoma.

Hepatic: abnormal liver function.

Neuropsychiatric: agitation, cerebrovascular accident, convulsions (including febrile convulsions), depression, insomnia, multiple sclerosis aggravation, paresis, suicide.

Respiratory: dyspnea.

Urinary System Disorders: proteinuria.

Skin and Append ges: exfoliative dermatitis, erythema multiforme, hyperpigmentation.

Vascular: Henoch-Schonlein purpura syndrome.

8  USE IN SPECIFIC POPULATIONS 8.1  Pregnancy

Pregnancy Category C:

Note: The Maximum Recommended Human Dose (MRHD) was set at 2 packets per treatment of Aldara® Cream (25 mg imiquimod) for the animal multiple of human exposure ratios presented in this label. If higher doses than 2 packets of Aldara® Cream are used clinically, then the animal multiple of human exposure would be reduced for that dose. A non-proportional increase in systemic exposure with increased dose of Aldara® Cream was noted in the clinical pharmacokinetic study conducted in actinic keratosis subjects *[see Clinical*

*Pharmacology (12.3)]*. The AUC after topical application of 6 packets of Aldara® Cream was 8 fold greater than the AUC after topical application of 2 packets of Aldara® Cream in actinic keratosis subjects. Therefore, if a dose of 6 packets per treatment of Aldara® Cream was topically administered to an individual, then the animal multiple of human exposure would be either 1/3 of the value provided in the label (based on body surface area comparisons) or 1/8 of the value provided in the label (based on AUC comparisons). The animal multiples of human exposure calculations were based on weekly dose comparisons for the carcinogenicity studies described in this label. The animal multiples of human exposure calculations were based on daily dose comparisons for the reproductive toxicology studies described in this label.

Systemic embryofetal development studies were conducted in rats and rabbits. Oral doses of 1, 5 and 20 mg/kg/day imiquimod were administered during the period of organogenesis (gestational days 6 - 15) to pregnant female rats. In the presence of maternal toxicity, fetal effects noted at 20 mg/kg/day (577X MRHD based on AUC comparisons) included increased resorptions, decreased fetal body weights, delays in skeletal ossification, bent limb bones, and two fetuses in one litter (2 of 1567 fetuses) demonstrated exencephaly, protruding tongues and low-set ears. No treatment related effects on embryofetal toxicity or teratogenicity were noted at 5 mg/kg/day (98X MRHD based on AUC comparisons).

Intravenous doses of 0.5, 1 and 2 mg/kg/day imiquimod were administered during the period of organogenesis (gestational days 6 — 18) to pregnant female rabbits. No treatment related effects on embryofetal toxicity or teratogenicity were noted at 2 mg/kg/day (1 .5X MRHD based on BSA comparisons), the highest dose evaluated in this study, or 1 mg/kg/day (407X MRHD based on AUC comparisons).

A combined fertility and peri- and post-natal development study was conducted in rats. Oral doses of 1, 1.5, 3 and 6 mg/kg/day imiquimod were administered to male rats from 70 days prior to mating through the mating period and to female rats from 14 days prior to mating through parturition and lactation. No effects on growth, fertility, reproduction or post-natal development were noted at doses up to 6 mg/kg/day (87X MRHD based on AUC comparisons), the highest dose evaluated in this study. In the absence of maternal toxicity, bent limb bones were noted in the F1 fetuses at a dose of 6 mg/kg/day (87X MRHD based on AUC comparisons). This fetal effect was also noted in the oral rat embryofetal development study conducted with imiquimod. No treatment related effects on teratogenicity were noted at 3 mg/kg/day (41X MRHD based on AUC comparisons).

There are no adequate and well-controlled studies in pregnant women. Aldara® Cream should be used during pregnancy only if the potential benefit justifies the potential risk to the fetus.

8.3 Nursing Mothers

It is not known whether imiquimod is excreted in human milk following use of Aldara® Cream. Because many drugs are excreted in human milk, caution should be exercised when Aldara® Cream is administered to nursing women.

8.4 Pediatric Use

AK and sBCC are not conditions generally seen within the pediatric population. The safety and efficacy of Aldara® Cream for AK or sBCC in patients less than 18 years of age have not been established.

Safety and efficacy in patients with external genital/perianal warts below the age of 12 years have not been established.

Aldara® Cream was evaluated in two randomized, vehicle-controlled, double-blind trials involving 702 pediatric subjects with molluscum contagiosum (MC) (470 exposed to Aldara® Cream; median age 5 years, range 2-12 years). Subjects applied Aldara® Cream or vehicle 3 times weekly for up to 16 weeks. Complete clearance (no MC lesions) was assessed at Week 18. In Study 1, the complete clearance rate was 24% (52/217) in the Aldara® Cream group compared with 26% (28/106) in the vehicle group. In Study 2, the clearance rates were 24% (60/253) in the Aldara® Cream group compared with 28% (35/126) in the vehicle group. These studies failed to demonstrate efficacy.

Similar to the studies conducted in adults, the most frequently reported adverse reaction from 2 studies in children with molluscum contagiosum was application site reaction. Adverse events which occurred more frequently in Aldara®-treated subjects compared with vehicle-treated subjects generally resembled those seen in studies in indications approved for adults and also included otitis media (5% Aldara® Cream vs. 3% vehicle) and conjunctivitis (3% Aldara® Cream vs. 2% vehicle).

Erythema was the most frequently reported local skin reaction. Severe local skin reactions reported by Aldara®-treated subjects in the pediatric studies included erythema (28%), edema (8%), scabbing/crusting (5%), flaking/scaling (5%), erosion (2%) and weeping/exudate (2%).

Systemic absorption of imiquimod across the affected skin of 22 subjects aged 2 to 12 years with extensive MC involving at least 10% of the total body surface area was observed after single and multiple doses at a dosing frequency of 3 applications per week for 4 weeks. The investigator determined the dose applied, either 1, 2 or 3 packets per dose, based on the size of the treatment area and the subject's weight. The overall median peak serum drug concentrations at the end of week 4 was between 0.26 and 1.06 ng/ml except in a 2-year old female who was administered 2 packets of study drug per dose, had a Cmax of 9.66 ng/mL after multiple dosing. Children aged 2-5 years received doses of 12.5 mg (one packet) or 25 mg (two packets) of imiquimod and had median multiple-dose peak serum drug levels of approximately 0.2 or 0.5 ng/mL, respectively. Children aged 6-12 years received doses of 12.5 mg, 25 mg, or 37.5 mg (three packets) and had median multiple dose serum drug levels of approximately 0.1, 0.15, or 0.3 ng/mL, respectively. Among the 20 subjects with evaluable laboratory assessments, the median WBC count decreased by $1.4*10^9$/L and the median absolute neutrophil count decreased by $1.42*10^9$/L.

8.5 Geriatric Use

Of the 215 subjects treated with Aldara® Cream in the AK clinical studies, 127 subjects (59%) were 65 years and older, while 60 subjects (28%) were 75 years and older. Of the 185 subjects treated with Aldara® Cream in the sBCC clinical studies, 65 subjects (35%) were 65 years and older, while 25 subjects (14%) were 75 years and older. No overall differences in safety or effectiveness were observed between these subjects and younger subjects. No other clinical experience has identified differences in responses between the elderly and younger subjects, but greater sensitivity of some older individuals cannot be ruled out.

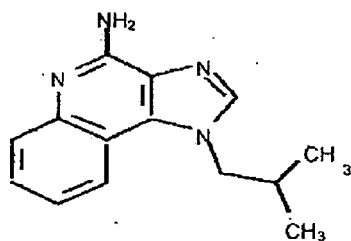

10 OVER DOSAGE

Topical overdosing of Aldara® Cream could result in an increased incidence of severe local skin reactions and may increase the risk for systemic reactions.

The most clinically serious adverse event reported following multiple oral imiquimod doses of >200 mg (equivalent to imiquimod content of >16 packets) was hypotension, which resolved following oral or intravenous fluid administration.

11 DESCRIPTION

Aldara® (imiquimod 5%) Cream is an immune response modifier for topical administration. Each gram contains 50 mg of imiquimod in an off-white oil-in-water vanishing cream base consisting of isostearic acid, cetyl alcohol, stearyl alcohol, white petrolatum, polysorbate 60, sorbitan monostearate, glycerin, xanthan gum, purified water, benzyl alcohol, methylparaben, and propylparaben.

Chemically, imiquimod is 1-(2-methylpropyl)-1$H$-imidazo,[4,5-c]quinolin-4-amine. Imiquimod has a molecular formula of $C_{14}H_{16}N_4$ and a molecular weight of 240.3. Its structural formula is:

12 CLINICAL PHARMACOLOGY

12.1 Mechanism of Action

The mechanism of action of Aldara® Cream in treating AK and sBCC lesions is unknown.

12.2 Pharmacodynamics

*Actinic Keratosis*

In a study of 18 subjects with AK comparing Aldara® Cream to vehicle, increases from baseline in week 2 biomarker levels were reported for CD3, CD4, CD8, CD11c, and CD68 for Aldara® Cream treated subjects; however, the clinical relevance of these findings is unknown.

*Superficial Basal Cell Carcinoma*

An open label study in six subjects with sBCC suggests that treatment with Aldara® Cream may increase the infiltration of lymphocytes, dendritic cells, and macrophages into the tumor lesion; however, the clinical significance of these findings is unknown.

*External Genital Warts*

Imiquimod has no direct antiviral activity in cell culture. A study in 22 subjects with genital/perianal warts comparing Aldara® Cream and vehicle shows that Aldara® Cream induces mRNA encoding cytokines including interferon- at the treatment site. In addition HPVL1 mRNA and HPV DNA are significantly decreased following treatment. However, the clinical relevance of these findings is unknown.

12.3 Pharmacokinetics

Systemic absorption of imiquimod across the affected skin of 58 subjects with AK was observed with a dosing frequency of 3 applications per week for 16 weeks. Mean peak serum drug concentrations at the end of week 16 were approximately 0.1, 0.2, and 3.5 ng/mL for the applications to face (12.5 mg imiquimod, 1 single-use packet), scalp (25 mg, 2 packets) and hands/arms (75 mg, 6 packets), respectively.

Table 10: Mean Serum Imiquimod Concentration in Adults Following Administration of the Last Topical Dose During Week 16 (Actinic Keratosis)

| Amount of Aldara® Cream applied | Mean peak serum imiquimod concentration [$C_{max}$] |
|---|---|
| 12.5 mg (1 packet) | 0.1 ng/mL |
| 25mg (2 packets) | 0.2 ng/mL |
| 75 mg (6 packets) | 3.5 ng/mL |

The application surface area was not controlled when more than one packet was used. Dose proportionality was not observed. However it appears that systemic exposure may be more dependent on surface area of application than amount of applied dose. The apparent half-life was approximately 10 times greater with topical dosing than the 2 hour apparent half-life seen following subcutaneous dosing, suggesting prolonged retention of drug in the skin_ Mean urinary recoveries of imiquimod and metabolites combined were 0.08 and 0.15% of the applied dose in the group using 75 mg (6 packets) for males and females, respectively following 3 applications per week for 16 weeks.

Systemic absorption of imiquimod was observed across the affected skin of 12 subjects with genital/perianal warts, with an average dose of 4.6 mg. Mean peak drug concentration of approximately 0.4 ng/mL was seen during the study. Mean urinary recoveries of imiquimod and metabolites combined over the whole course of treatment, expressed as percent of the estimated applied dose, were 0.11 and 2.41% in the males and females, respectively.

13  NONCLINICAL TOXICOLOGY 13.1  Carcinogenesis, Mutagenesis, Impairment of Fertility In an oral (gavage) rat carcinogenicity study, imiquimod was administered to Wistar rats on a 2X/week (up to 6 mg/kg/day) or daily (3 mg/kg/day) dosing schedule for 24 months. No treatment related tumors were noted in the oral rat carcinogenicity study up to the highest doses tested in this study of 6 mg/kg administered 2X/week in female rats (87X MRHD based on weekly AUC comparisons), 4 mg/kg administered 2X/week in male rats (75X MRHD based on weekly AUC comparisons) or 3 mg/kg administered 7X/week to male and female rats (153X MRHD based on weekly AUC comparisons).

In a dermal mouse carcinogenicity study, imiquimod cream (up to 5 mg/kg/application imiquimod or 0.3% imiquimod cream) was applied to the backs of mice 3X/week for 24 months. A statistically significant increase in the incidence of liver adenomas and carcinomas was noted in high dose male mice compared to control male mice (251X MRHD based on weekly AUC comparisons). An increased number of skin papillomas was observed in vehicle cream control group animals at the treated site only. The quantitative composition of the vehicle cream used in the dermal mouse carcinogenicity study is the same as the vehicle cream used for Aldara® Cream, minus the active moiety (imiquimod).

In a 52-week dermal photoco-carcinogenicity study, the median time to onset of skin tumor formation was decreased in hairless mice following chronic topical dosing (3X/week; 40 weeks of treatment followed by 12 weeks of observation) with concurrent exposure to UV radiation (5 days per week) with the Aldara® Cream vehicle alone. No additional effect on tumor development beyond the vehicle effect was noted with the addition of the active ingredient, imiquimod, to the vehicle cream.

Imiquimod revealed no evidence of mutagenic or clastogenic potential based on the results of five in vitro genotoxicity tests (Ames assay, mouse lymphoma L5178Y assay, Chinese hamster ovary cell chromosome aberration assay, human lymphocyte chromosome aberration assay and SHE cell transformation assay) and three in vivo genotoxicity tests (rat and hamster bone marrow cytogenetics assay and a mouse dominant lethal test).

Daily oral administration of imiquimod to rats, throughout mating, gestation, parturition and lactation, demonstrated no effects on growth, fertility or reproduction, at doses up to 87X MRHD based on AUC comparisons.

14 CLINICAL STUDIES

14.1 Actinic Keratosis

In two double-blind, vehicle-controlled clinical studies, 436 subjects with AK were randomized to treatment with either Aldara® Cream or vehicle cream 2 times per week for 16 weeks. The studies enrolled subjects with 4 to 8 clinically typical, visible, discrete, nonhyperkeratotic, nonhypertrophic AK lesions within a 25 cm$^2$ contiguous treatment area on either the face or scalp. The 25 cm$^2$ contiguous treatment area could be of any dimensions e.g., 5 cm x 5 cm, 3 cm by 8.3 cm, 2 cm by 12.5 cm. Study subjects ranged from 37 to 88 years of age (median 66 years) and 55% had Fitzpatrick skin type I or II. All Aldara®-treated subjects were Caucasians.

On a scheduled dosing day, the study cream was applied to the entire treatment area prior to normal sleeping hours and left on for approximately 8 hours. Twice weekly dosing was continued for a total of 16 weeks. The clinical response of each subject was evaluated 8 weeks after the last scheduled application of study cream. Efficacy was assessed by the complete clearance rate, defined as the proportion of subjects at the 8-week post-treatment visit with no (zero) clinically visible AK lesions in the treatment area. Complete clearance included clearance of all baseline lesions, as well as any new or sub-clinical AK lesions which appeared during therapy.

Complete and partial clearance rates are shown in the table below. The partial clearance rate was defined as the percentage of subjects in whom 75% or more baseline AK lesions were cleared.

Table 11: Clearance Rates (AK)

| Study | Complete Clearance Rates (100% AK Lesions Cleared) | |
|---|---|---|
| | Aldara® Cream | Vehicle |
| Study AK1 | 46% (49/107) | 3% (3/110) |
| Study AK2 | 44% (48/108) | 4% (4/111) |

Partial and Complete Clearance Rates (75% or More Baseline AK Lesions Cleared)

| Study | Aldara® Cream | Vehicle |
|---|---|---|
| Study AK1 | 60% (64/107) | 10% (11/110) |
| Study AK2 | 58% (63/108) | 14% (15/111) |

Sub-clinical AK lesions may become apparent in the treatment area during treatment with Aldara® Cream. During the course of treatment, 48% (103/215) of subjects experienced an increase in AK lesions relative to the number present at baseline within the treatment area. Subjects with an increase in AK lesions had a similar response to those with no increase in AK lesions.

14.2 Superficial Basal Cell Carcinoma

In two double-blind, vehicle-controlled clinical studies, 364 subjects with primary sBCC were treated with Aldara® Cream or vehicle cream 5 times per week for 6 weeks. Target tumors were biopsy-confirmed sBCC and had a minimum area of 0.5 cm$^2$ and a maximum diameter of 2.0 cm (4.0 cm$^2$). Target tumors were not to be located within 1.0 cm of the hairline, or on the anogenital area or on the hands or feet, or to have any atypical features. The population ranged from 31-89 years of age (median 60 years) and 65% had Fitzpatrick skin type I or II. On a scheduled dosing day, study cream was applied to the target tumor and approximately 1 cm (about 1/3 inch) beyond the target tumor prior to normal sleeping hours, and 5 times per week dosing was continued for a total of 6 weeks. The target tumor area was clinically assessed 12 weeks after the last scheduled application of study cream. The entire target tumor was then excised and examined histologically for the presence of tumor.

Efficacy was assessed by the complete response rate defined as the proportion of subjects with clinical (visual) and histological clearance of the sBCC lesion at 12 weeks post-treatment.

Of Aldara®-treated subjects, 6% (11/178) who had both clinical and histological assessments post-treatment, and who appeared to be clinically clear had evidence of tumor on excision of the clinically-clear treatment area.

Data on composite clearance (defined as both clinical and histological clearance) are shown in the table below.

Table 12: Composite Clearance Rates at 12 Weeks Post-Treatment for Superficial Basal Cell Carcinoma

| Study | Aldara® Cream | Vehicle Cream |
|---|---|---|
| Study sBCC1 | 70% (66/94) | 2% (2/89) |
| Study sBCC2 | 80% (73/91) | 1% (1/90) |
| Total | 75% (139/185) | 2% (3/179) |

A separate 5-year, open-label study is ongoing to assess the recurrence of sBCC treated with Aldara® Cream applied once daily 5 days per week for 6 weeks. Target tumor inclusion criteria were the same as for the studies described above. At 12-weeks post-treatment, subjects were clinically evaluated for evidence of persistent sBCC (no histological assessment). Subjects with no clinical evidence of sBCC entered the long-term follow-up period. At the 12 week post-treatment assessment, 90% (163/182) of the subjects enrolled had no clinical evidence of sBCC at their target site and 162 subjects entered the long-term follow-up period for up to 5 years. Two year (24 month) follow-up data are available from this study and are presented in the table below:

Table 13: Estimated Clinical Clearance Rates for Superficial Basal Cell Carcinoma

| | Follow-up Period | | | |
|---|---|---|---|---|
| Follow-up visit after 12-week post-treatment assessment | No. of Subjects who remained clinically clear | No. of Subjects with sBCC recurrence | No. of Subjects who discontinued at this visit with no sBCC[a] | Estimated Rate of Subjects who Clinically Cleared and remained Clear[b] |
| Month 3 | 153 | 4 | 5 | 87% |
| Month 6 | 149 | | | 85% |
| Month 12 | 143 | 4 | 0 | 84% |
| Month 24 | 139 | | | 79% |

[a] Reasons for discontinuation included death, non-compliance, entry criteria violations, personal reasons, and treatment of nearby sBCC tumor.
[b] Estimated rate of subjects who clinically cleared and remained clear are estimated based on the time to event analysis employing the life table method beginning with the rate of clinical clearance at 12 weeks post-treatment.

14.3 External Genital Warts

Figure 12:
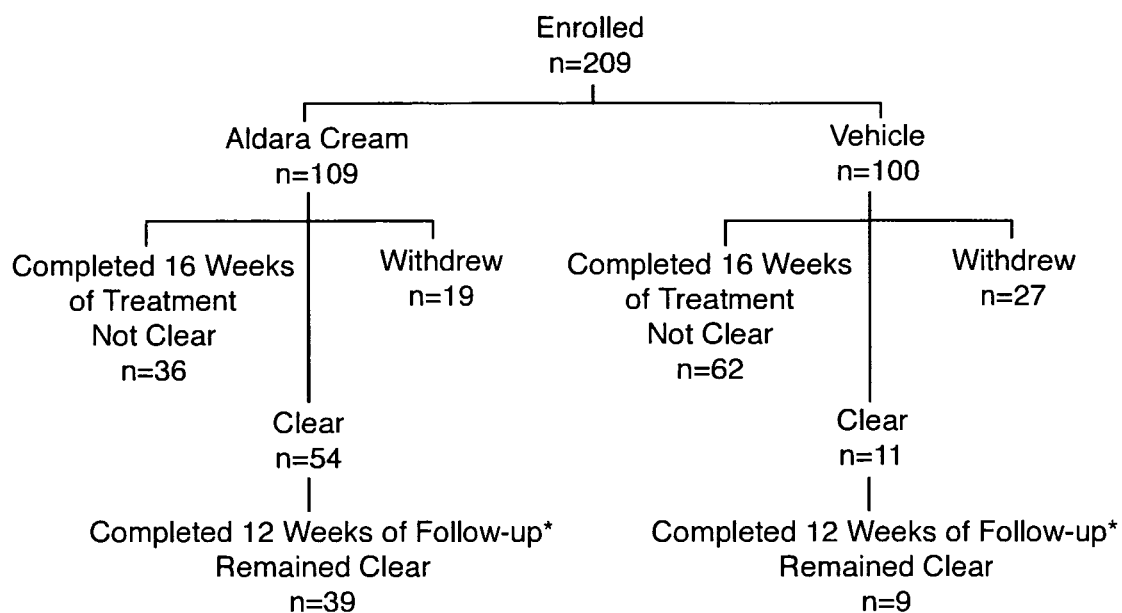
FIG. 12 is a graphic representation of subject accountability (external genital warts).

In a double-blind, placebo-controlled clinical study, 209 otherwise healthy subjects 18 years of age and older with genital/perianal warts were treated with Aldara® Cream or vehicle control times per week for a maximum of 16 weeks. The median baseline wart area was 69 mm$^2$ (range 8 to 5525 mm$^2$). Subject accountability is shown in FIG. 12.

Data on complete clearance are listed in the table below. The median time to complete wart clearance was 10 weeks.

Table 14: Complete Clearance Rates (External Genital Warts)- Study EGW1

| Treatment | Subjects with Complete Clearance of Warts | Subjects Without Follow-up | Subjects with Warts Remaining at Week 16 |
|---|---|---|---|
| Overall | | | |
| Aldara® Cream (n =109) | 54 (50%) | 19 (17%) | 36 (33%) |
| Vehicle (n =100) | 11 (11%) | 27 (27%) | 62 (62%) |
| Females | | | |
| Aldara® Cream (n =46) | 33 (72%) | 5 (11%) | 8 (17%) |
| Vehicle (n =40) | 8 (20%) | 13 (33%) | 19 (48%) |
| Males | | | |
| Aldara® Cream (n =63) | 21 (33%) | 14 (22%) | 28 (44%) |
| Vehicle (n = 60) | 3 (5%) | 14 (23%) | 43 (72%) |

16 HOW SUPPLIED/STORAGE AND HANDLING

Aldara® (imiquimod) Cream, 5%, is supplied in single-use packets which contain 250 mg of the cream. Available as: box of 12 packets NDC 29336-610-12. Store at 4 - 25°C (39 - 77°F)

Avoid freezing.

*Keep out of reach of children.*

17 PATIENT COUNSELING INFORMATION See *FDA-Approved Patient Labeling (17.7)*

17.1 General Information: All Indications

Aldara® Cream should be used as directed by a physician. *[see Dosage and Administration (2)]* Aldara® Cream is for external use only. Contact with the eyes, lips and nostrils should be avoided. *[see Indications and Usage (1) and Dosage and Administration (2)]*

The treatment area should not be bandaged or otherwise occluded. Partially-used packets should be discarded and not reused. The prescriber should demonstrate the proper application technique to maximize the benefit of Aldara® Cream therapy.

It is recommended that patients wash their hands before and after applying Aldara® Cream.

17.2 Local Skin Reactions: All Indications

Patients may experience local skin reactions during treatment with Aldara® Cream (even with normal dosing). Potential local skin reactions include erythema, edema, vesicles, erosions/ulcerations, weeping/exudate, flaking/scaling/dryness, and scabbing/crusting. These reactions can range from mild to severe in intensity and may extend beyond the application site onto the surrounding skin. Patients may also experience application site reactions such as itching and/or burning. *[see Adverse Reactions (6)]*

Local skin reactions may be of such an intensity that patients may require rest periods from treatment. Treatment with Aldara® Cream can be resumed after the skin reaction has subsided, as determined by the physician. Patients should contact their physician promptly if they experience any sign or symptom at the application site that restricts or prohibits their daily activity or makes continued application of the Aldara® Cream difficult.

Because of local skin reactions, during treatment and until healed, the treatment area is likely to appear noticeably different from normal skin. Localized hypopigmentation and hyperpigmentation have been reported following use of Aldara® Cream. These skin color changes may be permanent in some patients.

17.3 Systemic Reactions: All Indications

Patients may experience flu-like systemic signs and symptoms during treatment with Aldara® Cream (even with normal dosing). Systemic signs and symptoms may include malaise, fever, nausea, myalgias and rigors. *[see Adverse Reactions (6)]* An interruption of dosing should be considered.

17.4 Patients Being Treated for Actinic Keratosis (AK)

Dosing is 2 times per week for a full 16 weeks, unless otherwise directed by the physician. However, the treatment period should not be extended beyond 16 weeks due to missed doses or rest periods. *[see Dosage and Administration (2.1)]*

It is recommended that the treatment area be washed with mild soap and water 8 hours following Aldara® Cream application.

Most patients using Aldara® Cream for the treatment of AK experience erythema, flaking/scaling/dryness and scabbing/crusting at the application site with normal dosing. [see *Adverse Reactions (6.1)*].

Use of sunscreen is encouraged, and patients should minimize or avoid exposure to natural or artificial sunlight (tanning beds or UVA/B treatment) while using Aldara® Cream. *[see Warnings and Precautions (5.3)]*

Sub-clinical AK lesions may become apparent in the treatment area during treatment and may subsequently resolve. *[see Clinical Studies (16.1)]*

17.5  Patients Being Treated for Superficial Basal Cell Carcinoma (sBCC)

Dosing is 5 times per week for a full 6 weeks, unless otherwise directed by the physician. However, the treatment period should not be extended beyond 6 weeks due to missed doses or rest periods. *[see Dosage and Administration (2.2)]*

It is recommended that the treatment area be washed with mild soap and water 8 hours following Aldara® Cream application. *[see Dosage and Administration (2.2)]*

Most patients using Aldara® Cream for the treatment of sBCC experience erythema, edema, induration, erosion, scabbing/crusting and flaking/scaling at the application site with normal dosing. [see *Adverse Reactions (6.2)*]

Use of sunscreen is encouraged, and patients should minimize or avoid exposure to natural or artificial sunlight (tanning beds or UVA/B treatment) while using Aldara® Cream. *[see Warnings and Precautions (5.7)]*

The clinical outcome of therapy can be determined after resolution of application site reactions and/or local skin reactions.

Patients with sBCC treated with Aldara® Cream should have regular follow-up to re-evaluate the treatment site. *[see Clinical Studies (16.2)]*

17.6  Patients Being Treated for External Genital Warts

Dosing is 3 times per week to external genital/perianal warts. Aldara® Cream treatment should continue until there is total clearance of the genital/perianal warts or for a maximum of 16 weeks.

It is recommended that the treatment area be washed with mild soap and water 6-10 hours following Aldara® Cream application.

It is common for patients to experience local skin reactions such as erythema, erosion, excoriation/flaking, and edema at the site of application or surrounding areas. Most skin reactions are mild to moderate.

Sexual (genital, anal, oral) contact should be avoided while Aldara® Cream is on the skin. Application of Aldara® Cream in the vagina is considered internal and should be avoided. Female patients should take special care if applying the Aldara® Cream at the opening of the vagina because local skin reactions on the delicate moist surfaces can result in pain or swelling, and may cause difficulty in passing urine.

Uncircumcised males treating warts under the foreskin should retract the foreskin and clean the area daily.

New warts may develop during therapy, as Aldara® Cream is not a cure.
The effect of Aldara® Cream on the transmission of genital/perianal warts is unknown. Aldara® Cream may weaken condoms and vaginal diaphragms, therefore concurrent use is not recommended.

Should severe local skin reaction occur, the Aldara® Cream should be removed by washing the treatment area with mild soap and water.

17.7 FDA-Approved Patient Labeling

Patient Information

ALDARA® [al dar' a] Cream, 5% (Imiquimod)

IMPORTANT: Not for mouth, eye, or vaginal use

Read the Patient Information that comes with Aldara® Cream before you start using it and each time you get a refill. There may be new information. This leaflet does not take the place of talking with your healthcare provider about your medical condition or treatment. If you do not understand the information, or have any questions about Aldara® Cream, talk with your healthcare provider or pharmacist.

What is Aldara® Cream?

Aldara® Cream is a skin use only (topical) medicine used to treat:
- external genital and perianal warts in people 12 years and older
- actinic keratosis in adults with normal immune systems. Actinic keratosis is caused by too much sun exposure.
- superficial basal cell carcinoma in adults with normal immune systems when surgical methods are less appropriate. This skin cancer needs to be diagnosed by your healthcare provider.

Aldara® Cream is used in different ways for the three different skin conditions it is used to treat. It is very important that you follow the instructions for your skin condition. Talk to your healthcare provider if you have questions.

Aldara® Cream does not work for everyone. Aldara® Cream will not cure your genital or perianal warts. New warts may develop during treatment with Aldara® Cream. It is not known if Aldara® Cream can stop you from spreading genital or perianal warts to other people. For your own health and the health of others, it is important to practice safer sex. Talk to your healthcare provider about safer sex practices.

Who should not use Aldara® Cream?
- Aldara® Cream has not been studied in children under 12 years old for external genital and perianal warts.
- Aldara® Cream has not been studied in children under 18 years old for actinic keratosis or superficial basal cell carcinoma. Children usually do not get actinic keratosis or basal cell carcinoma.

Before using Aldara® Cream, tell your healthcare provider:
- about all your medical conditions, including if you
  - are pregnant or planning to become pregnant. It is not known if Aldara® Cream can harm your unborn baby.
  - are breastfeeding. It is not known if Aldara® Cream passes into your milk and if it can harm your baby.
- about all the medicines you take including prescription and nonprescription medicines, vitamins and herbal supplements. Especially tell your healthcare provider if you have had other treatments for genital or perianal warts, or actinic keratosis, or superficial basal cell carcinoma. Aldara® Cream should not be used until your skin has healed from other treatments.

How should I use Aldara® Cream?

- Use Aldara® Cream exactly as prescribed by your healthcare provider. Aldara® Cream is for skin use only. Do not take by mouth or use in or near your eyes, lips or nostrils. Do not use Aldara® Cream unless your healthcare provider has taught you the right way to use it. Talk to your healthcare provider if you have any questions.

- Aldara® Cream is used for several skin conditions. Use Aldara® Cream only on the area of your body to be treated. Your healthcare provider will tell you where to apply Aldara® Cream and how often and for how long to apply it for your condition. Do not use Aldara® Cream longer than prescribed. Using too much Aldara® Cream, or using it too often, or for too long can increase your chances for having a severe skin reaction or other side effect. Talk to your healthcare provider if Aldara® Cream does not work for you.

For external genital and perianal warts, Aldara® Cream is usually used once a day for 3 days a week:

- Monday, Wednesday and Friday, or
- Tuesday, Thursday and Saturday

For these conditions, Aldara® Cream is usually left on the skin for 6 to 10 hours. Treatment should continue until the warts are completely gone, or up to 16 weeks.

For actinic keratosis, Aldara® Cream is usually used once a day for 2 days a week, 3 to 4 days apart, such as:

- Monday and Thursday, or
- Tuesday and Friday

For this condition, Aldara® Cream is usually left on the skin for about 8 hours. Treatment should continue for the full 16 weeks even if all actinic keratoses appear to be gone, unless you are told otherwise by your healthcare provider. The area you treat with Aldara® Cream should be no larger than approximately the size of your forehead or one cheek (for example 2 inches by 2 inches), unless otherwise directed by your healthcare provider.

For superficial basal cell carcinoma, Aldara® Cream is usually used once a day for 5 days a week:

- Monday, Tuesday, Wednesday, Thursday and Friday

For this condition, Aldara® Cream is usually left on the skin for about 8 hours. Your healthcare provider will show you how much Aldara® Cream to apply to your superficial basal cell carcinoma. You should also apply Aldara® Cream to a small area of skin all around the superficial basal cell carcinoma. This small area of skin should be about the size of your fingertip. Treatment should continue for the full 6 weeks, even if the superficial basal cell carcinoma appears to be gone, unless you are told otherwise by your healthcare provider.

Applying Aldara® Cream

Aldara® Cream should be applied just before your bedtime.
- Wash the area to be treated with mild soap and water. Allow the area to dry.
  - Uncircumcised males treating warts under their penis foreskin must pull their foreskin back and clean before treatment, and clean daily during the weeks of treatment.
- Wash your hands
- Open a new packet of Aldara® Cream just before use
- Apply a thin layer of Aldara® Cream only to the affected area or areas to be treated. Do not use more Aldara® Cream than is needed to cover the treatment area.
- Rub the Aldara® Cream in all the way to the affected area or areas.
  - Do not get Aldara® Cream in your eyes.
  - Do not get Aldara® Cream in the anus when applying to perianal warts.
  - Female patients treating genital warts must be careful when applying Aldara® Cream around the vaginal opening. Female patients should take special care if applying the Aldara® Cream at the opening of the vagina because local skin reactions on the delicate moist surfaces can cause pain or swelling, and may cause problems passing urine. Do not put Aldara® Cream in your vagina or on the skin around the genital wart.
- Do not cover the treated area with an airtight bandage. Cotton gauze dressings can be used. Cotton underwear can be worn after applying Aldara® Cream to the genital or perianal area.

- Safely throw away the open packet of Aldara® Cream so that children and pets cannot get it. The open packet should be thrown away even if all the Aldara® Cream was not completely used.
- After applying Aldara® Cream, wash your hands well.
- Leave the Aldara® Cream on the affected area or areas for the time prescribed by your healthcare provider. The length of time that Aldara® Cream is left on the skin is not the same for the different skin conditions that Aldara® Cream is used to treat. Do not bathe or get the treated area wet before the right time has passed. Do not leave Aldara® Cream on your skin longer than prescribed.
- After the right amount of time has passed, wash the treated area or areas with mild soap and water.
- If you forget to apply Aldara®Cream, apply the missed dose of Aldara® Cream as soon as you remember and then continue on your regular schedule.
- If you get Aldara® Cream in your mouth or in your eyes rinse well with water right away.

What should I avoid while using Aldara® Cream?

- Do not cover the treated site with bandages or other closed dressings. Cotton gauze dressings are okay to use, if needed. Cotton underwear can be worn after treating the genital or perianal area.
- Do not apply Aldara® Cream in or near the eyes, lips or nostrils, or in the vagina or anus.
- Do not use sunlamps or tanning beds, and avoid sunlight as much as possible during treatment with Aldara® Cream. Use sunscreen and wear protective clothing if you go outside during daylight.
- Do not have sexual contact including genital, anal, or oral sex when Aldara® Cream is on your genital or perianal skin. Aldara® Cream may weaken condoms and vaginal diaphragms. This means they may not work as well to prevent pregnancy. For your own health and the health of others, it is important to practice safer sex. Talk to your healthcare provider about safer sex practices.

What are the possible side effects of Aldara® Cream?

The most common side effects with Aldara® Cream are skin reactions at the treatment site including:

- redness
- swelling
- a sore, blister, or ulcer
- skin that becomes hard or thickened
- skin peeling
- scabbing and crusting
- itching
- burning
- changes in skin color that do not always go away Actinic Keratosis During treatment and until the skin has healed, your skin in the treatment area is likely to appear noticeably different from normal skin. Side effects, such as redness, scabbing, itching and burning are common at the site where Aldara® Cream is applied, and sometimes the side effects go outside of the area where Aldara® Cream was applied. Swelling, small open sores and drainage may also be experienced with use of Aldara® Cream. You may also experience itching and/or burning. Actinic keratoses that were not seen before may appear during treatment and may later go away. If you have questions regarding treatment or skin reactions, please talk with your healthcare provider.

Superficial Basal Cell Carcinoma

During treatment and until the skin has healed, your skin in the treatment area is likely to appear noticeably different from normal skin. Side effects, such as redness, swelling and a sore are common at the site where Aldara® Cream is applied. You may also experience itching or burning. Your healthcare provider will need to check the area that was treated after your treatment is finished to make sure that the skin cancer is gone. Superficial basal cell carcinoma can come back. The chances of it coming back are higher as time passes. It is very important to have regular follow-up visits with your healthcare provider to check the area to make sure your skin cancer has not come back. Ask your healthcare provider how often you should have your skin checked. Talk with your healthcare provider if you have questions about your treatment or skin reactions.

External Genital and Perianal Warts

Patients should be aware that new warts may develop during treatment, as Aldara® Cream is not a cure. Many people see reddening or swelling on or around the application site during the course of treatment. If you have questions regarding treatment or local skin reactions, please talk with your healthcare provider.

You have a higher chance for severe skin reactions if you use too much Aldara® Cream or use it the wrong way. Stop Aldara® Cream right away and call your healthcare provider if you get any skin reactions that affect your daily activities, or that do not go away. Sometimes, Aldara® Cream must be stopped for a while to allow your skin to heal. Talk to your healthcare provider if you have questions about your treatment or skin reactions.

Other side effects of Aldara® Cream include headache, back pain, muscle aches, tiredness, flu-like symptoms, swollen lymph nodes, diarrhea, and fungal infections.

If the reactions seem excessive, if either skin breaks down or sores develop during the first week of treatment, if flu-like symptoms develop or if you begin to not feel well at anytime, contact your healthcare provider.

These are not all the side effects of Aldara® Cream. For more information, ask your healthcare provider or pharmacist.

How do I store Aldara® Cream?
- Store Aldara® Cream at 39 - 77° F (4 - 25° C). Do not freeze.
- Safely throw away Aldara® Cream that is out of date or that you do not need.
- Keep Aldara® Cream and all medicines out of the reach of children.

General information about Aldara® Cream

Medicines are sometimes prescribed for conditions that are not mentioned in patient information leaflets. Do not use Aldara® Cream for a condition for which it was not prescribed. Do not give Aldara® Cream to other people, even if they have the same symptoms you have.

This leaflet summarizes the most important information about Aldara® Cream. If you would like more information, talk with your healthcare provider. You can ask your pharmacist or healthcare provider for information about Aldara® Cream that is written for the healthcare provider. If you have other questions about Aldara® Cream, call 1-888-2-ALDARA.

What are the ingredients in Aldara® Cream?

Active Ingredient: imiquimod

Inactive ingredients: isostearic acid, cetyl alcohol, stearyl alcohol, white petrolatum, polysorbate 60, sorbitan monostearate, glycerin, xanthan gum, purified water, benzyl alcohol, methylparaben, and propylparaben.

Manufactured by:

3M Health Care Limited

Loughborough LE1 1 1EP England

Distributed by:

Graceway Pharmaceuticals, LLC Bristol, TN 37620

Attachment IX

[000320] Zyclara®[zi-clar-a](imiquimod) 3.75% Cream

HIGHLIGHTS OF PRESCRIBING INFORMATION FOR ACTINIC KERATOSIS

These highlights do not include all the information needed to use ZYCLARA® Cream safely and effectively. See full prescribing information for Zyclara® Cream.

ZYCLARA® (imiquimod), Cream, 3.75%
For topical use only
Initial U.S. Approval: 1997

---------------------------------- INDICATIONS AND USAGE ----------------------------------

ZYCLARA® Cream is indicated for the topical treatment of clinically typical visible or palpable actinic keratoses of the face or balding scalp in immunocompetent adults. (1.1)

---------------------------------- DOSAGE AND ADMINISTRATION ----------------------------------

ZYCLARA® Cream is not for oral, ophthalmic, or intravaginal use. (2)
- daily to the skin of the affected area (either the face or balding scalp) for two 2-week treatment cycles separated by a 2-week no-treatment period. (2.1)

---------------------------------- DOSAGE FORMS AND STRENGTHS ----------------------------------
Cream, 3.75%, white to fainty yellow cream. (3)

---------------------------------- CONTRAINDICATIONS ----------------------------------
- None. (4)

---------------------------------- WARNINGS AND PRECAUTIONS ----------------------------------
- Intense local inflammatory reactions can occur (e.g., skin weeping, erosion). Dosing interruption may be required (2, 5.1, 6)

- Flu-like systemic signs and symptoms including fatigue, nausea, fever, myalgias, arthralgias, and chills. Dosing interruption may be required (2, 5.2, 6)
- Avoid exposure to sunlight and sunlamps (5.3). Wear sunscreen daily (17.4).
- Avoid concomitant use of Zyclara® Cream and any other imiquimod cream.

---------------------------------------- ADVERSE REACTIONS ----------------------------------------

Most common Adverse Reactions (incidence >50%) are local skin reactions, erythema, edema, weeping/exudate, flaking/scaling/dryness, scabbing/crusting and erosion/ulceration (6.2). Other reported reactions (occurring in $\geq 2\%$ of ZYCLARA®-Treated Subjects) include headache, fatigue, nausea and fever (6.1).

To report SUSPECTED ADVERSE REACTIONS, contact Graceway Pharmaceuticals, LLC at 1-800-328-0255 or FDA at 1-800-FDA-1088 or www.fda.gov/medwatch.

See 17 for PATIENT COUNSELING INFORMATION and FDA-approved patient labeling.

Issued" March 2010

FULL PRESCRIBING INFORMATION: CONTENTS\*

1  INDICATIONS AND USAGE
   1.1 Actinic Keratosis
   1.2 Unevaluated Populations 2  DOSAGE AND ADMINISTRATION
   2.1 Actinic Keratosis

3  DOSAGE FORMS AND STRENGTHS

4  CONTRAINDICATIONS

5  WARNINGS AND PRECAUTIONS
   5.1 Local Skin Reactions 5.2 Systemic Reactions 5.3 Ultraviolet Light Exposure

6 ADVERSE REACTIONS 6.1 Clinical Trials Experience 6.2 Postmarketing Experience

8 USE IN SPECIFIC POPULATIONS 8.1 Pregnancy 8.3 Nursing Mothers 8.4 Pediatric Use 8.5 Geriatric Use

10 OVER DOSAGE

11 DESCRIPTION

12 CLINICAL PHARMACOLOGY 12.1 Mechanism of Action 12.2 Pharmacodynamics 12.3 Pharmacokinetics

13 NONCLINICAL TOXICOLOGY 13.1 Carcinogenesis, Mutagenesis, Impairment of Fertility

14 CLINICAL STUDIES

16 HOW SUPPLIED/STORAGE AND HANDLING

17 PATIENT COUNSELING INFORMATION 17.1 Instructions for Administration 17.2 Local Skin Reactions 17.3 Systemic Reactions 17.4 Recommended Administration

*Sections or subsections omitted from the full prescribing information are not listed

FULL PRESCRIBING INFORMATION

1    INDICATIONS AND USAGE 1.1    Actinic Keratosis

ZYCLARA® Cream is indicated for the topical treatment of clinically typical visible or palpable actinic keratosis (AK), of the face or balding scalp in immunocompetent adults.

1.2    Unevaluated Populations

Safety and efficacy have nor been established for ZYCLARA® Cream in the treatment of actinic keratoses with more than one 2-cycle treatment course in the same area.

The safety and efficacy of ZYCLARA® Cream in immunosuppressed patients have not been established.

The safety and efficacy have not been established for ZYCLARA® Cream in the treatment of patients with xeroderma pigmentosum.

The safety and efficacy have not been established for ZYCLARA® Cream in the treatment of superficial basal cell carcinoma.

The safety and efficacy have not been established for ZYCLARA® Cream in the treatment of external genital warts.

ZYCLARA® Cream should be used with caution in patients with pre-existing autoimmune conditions.

2    DOSAGE AND ADMINISTRATION

ZYCLARA® Cream is not for oral, ophthalmic, or intravaginal use.

2.1    Actinic Keratosis

ZYCLARA® Cream should be applied once daily before bedtime to the skin of the affected area (either the face or balding scalp) for two 2-week treatment cycles separated by a 2-week no-treatment period. ZYCLARA® Cream should be applied as a thin film to the entire treatment area and rubbed in until the Zyclara® Cream is no longer visible. Up to 2 packets of ZYCLARA® Cream may be applied to the treatment area at each application. ZYCLARA® Cream should be left on the skin for approximately 8 hours, after which time the cream should be removed by washing the area with mild soap and water. The prescriber should demonstrate the proper application technique to maximize the benefit of ZYCLARA® Cream therapy.

Patients should wash their hands before and after applying ZYCLARA® Cream.

Avoid use in or on the lips and nostrils. Do not use in or near the eyes.

Local skin reactions in the treatment area are common. *[see Adverse Reactions (6.1, 6.2)]* A rest period of several days may be taken if required by the patient's discomfort or severity of the local skin reaction. However, neither 2-week treatment cycle should be extended due to missed doses or rest periods. A transient increase in AK lesion counts may be observed during treatment. Response to treatment cannot be adequately assessed until resolution of local skin reactions. The patient should continue dosing as prescribed. Treatment should continue for the full treatment course even if all actinic keratoses appear to be gone. Lesions that do not respond to treatment should be carefully re-evaluated and management reconsidered.

ZYCLARA® Cream is packaged in single-use packets, with 28 packets supplied per box. Patients should be prescribed no more than 56 packets for the total 2-cycle treatment course. Unused packets should be discarded. Partially-used packets should be discarded and not reused.

3    DOSAGE FORMS AND STRENGTHS

Cream, 3.75%, white to faintly yellow cream.

4    CONTRAINDICATIONS

None.

5    WARNINGS AND PRECAUTIONS 5.1    Local Skin Reactions

Intense local skin reactions including skin weeping or erosion can occur after a few applications of ZYCLARA® Cream and may require an interruption of dosing. *[see Dosage and Administration (2) and Adverse Reactions (6)].* ZYCLARA® Cream has the potential to exacerbate inflammatory conditions of the skin, including chronic graft versus host disease.

Administration of ZYCLARA® Cream is not recommended until the skin is healed from any previous drug or surgical treatment.

Concomitant use of ZYCLARA® Cream and any other imiquimod cream, in the same treatment area, should be avoided since they contain the same active ingredient (imiquimod) and may increase the risk for and severity of local skin reactions.

5.2 Systemic Reactions

Flu-like signs and symptoms may accompany, or even precede, local skin reactions and may include fatigue, nausea, fever, myalgias, arthralgias, and chills. An interruption of dosing and an assessment of the patient should be considered. [see Adverse Reactions (6)]

Lymphadenopathy occurred in 2% of subjects treated with ZYCLARA® Cream [see Adverse Reactions (6)]. This reaction resolved in all subjects by 4 weeks after completion of treatment.

The safety of concomitant use of ZYCLARA® Cream and any other imiquimod creams has not been established and should be avoided since they contain the same active ingredient (imiquimod) and may increase the risk for and severity of systemic reactions.

5.3 Ultraviolet Light Exposure

Exposure to sunlight (including sunlamps) should be avoided or minimized during use of ZYCLARA® Cream because of concern for heightened sunburn susceptibility. Patients should be warned to use protective clothing (e.g., a hat) when using ZYCLARA® Cream. Patients with sunburn should be advised not to use ZYCLARA® Cream until fully recovered. Patients who may have considerable sun exposure, e.g. due to their occupation, and those patients with inherent sensitivity to sunlight should exercise caution when using ZYCLARA® Cream.

In an animal photoco-carcinogenicity study, imiquimod cream shortened the time to skin tumor formation *[see Nonclinical Toxicology (13.1)]*. The enhancement of ultraviolet carcinogenicity is not necessarily dependent on phototoxic mechanisms. Therefore, patients should minimize or avoid natural or artificial sunlight exposure.

6 ADVERSE REACTIONS

Because clinical trials are conducted under widely varying conditions, adverse reaction rates observed in the clinical trials of a drug cannot be directly compared to rates in the clinical trials of another drug and may not reflect the rates observed in practice.

6.1  Clinical Trials Experience:

The data described below reflect exposure to ZYCLARA® Cream or placebo in 319 subjects enrolled in two double-blind, vehicle-controlled studies. Subjects applied up to two packets of ZYCLARA® Cream or vehicle daily to the skin of the affected area (either entire face or balding scalp) for two 2-week treatment cycles separated by a 2-week no-treatment period.

Table 1: Selected Adverse Reactions Occurring in > 2% of ZYCLARA®-Treated Subjects and at a Greater Frequency Than With Vehicle in the Combined Studies

| Preferred Term | ZYCLARA® Cream 3.75% (N=160) | Vehicle (N=159) |
|---|---|---|
| Headache | 10 (6%) | 5 (3%) |
| Application site pruritus | 7 (4%) | 1 (< 1%) |
| Fatigue | 7 (4%) | 0 (0%) |
| Nausea | 6 (3%) | 2 (1%) |
| Application site irritation | 5 (3%) | 0 (0%) |
| Application site pain | 5 (3%) | 0 (0%) |
| Pyrexia | 5 (3%) | 0 (0%) |
| Anorexia | 4 (3%) | 0 (0%) |
| Dizziness | 4 (3%) | 0 (0%) |
| Herpes simplex | 4 (3%) | 1 (< 1%) |
| Pain | 4 (3%) | 0 (0%) |
| Chest pain | 3 (2%) | 0 (0%) |
| Diarrhea | 3 (2%) | 0 (0%) |
| Lymphadenopathy | 3 (2%) | 0 (0%) |

Table 2: Local Skin Reactions in the Treatment Area in ZYCLARA®)-Treated Subjects as Assessed by the Investigator

|  | ZYCLARA® Cream 3.75% (N=160) | | Placebo (N=159) | |
| --- | --- | --- | --- | --- |
|  | All Grades* | Severe | All Grades* | Severe |
| Erythema | 154 (96%) | 40 (25%) | 124 (78%) | 0 (0%) |
| Scabbing/Crusting | 149 (93%) | 22 (14%) | 72 (45%) | 0 (0%) |
| Flaking/Scaling/Dryness | 147 (92%) | 13 (8%) | 123 (77%) | 2 (1%) |
| Edema | 120 (75%) | 9 (6%) | 31 (19%) | 0 (0%) |
| Erosion/Ulceration | 99 (62%) | 17 (11%) | 14 (9%) | 0 (0%) |
| Weeping/Exudate | 81 (51%) | 9 (6%) | 6 (4%) | 0 (0%) |

*All Grades: mild, moderate or severe

Local skin reactions may extend beyond treatment area.

Overall, in the clinical trials, 11% (17/160) of subjects on ZYCLARA® Cream and 0% on vehicle cream required rest periods due to adverse reactions.

Other adverse reactions observed in subjects treated with ZYCLARA® Cream include: application site bleeding, application site swelling, arthralgia, cheilitis, chills, dermatitis, herpes zoster, influenza-like illness, insomnia, lethargy, myalgia, pancytopenia, pruritus, squamous cell carcinoma, and vomiting.

6.2 Clinical Trials Experience: Dermal Safety Studies

There are currently no postmarketing adverse reactions reported for ZYCLARA® Cream.

The following adverse reactions have been identified during post-approval use of Aldara® (imiquimod) Cream, 5%. Because these reactions are reported voluntarily from a population of uncertain size, it is not always possible to reliably estimate their frequency or establish a causal relationship to drug exposure.

Body as a Whole: angioedema.

Cardiovascular: capillary leak syndrome, cardiac failure, cardiomyopathy, pulmonary edema, arrhythmias (tachycardia, supraventricular tachycardia, atrial fibrillation, palpitations), chest pain, ischemia, myocardial infarction, syncope.

Endocrine: thyroiditis.

Gastro-Intestinal System Disorders: abdominal pain.

6.3 Postmarketing Experience with Aldara® (imiquimod) Cream, 5%

The following adverse reactions have been identified during post-approval use of Aldara® (imiquimod) Cream, 5%. Because these reactions are reported voluntarily from a population of uncertain size, it is not always possible to reliably estimate their frequency or establish a causal relationship to drug exposure.

Body as a Whole: angioedema.

Cardiovascular: capillary leak syndrome, cardiac failure, cardiomyopathy, pulmonary edema, arrhythmias (tachycardia, atrial fibrillation, palpitations), chest pain, ischemia, myocardial infarction, syncope.

Endocrine: thyroiditis.

Hematological: decreases in red cell, white cell and platelet counts (including idiopathic thrombocytopenic purpura), lymphoma.

Hepatic: abnormal liver function.

Infections and Infestations: herpes simplex.

Neuropsychiatric: agitation, cerebrovascular accident, convulsions (including febrile convulsions), depression, insomnia, multiple sclerosis aggravation, paresis, suicide.

Respiratory: dyspnea.

Urinary System Disorders: proteinuria, urinary retention, dysuria.

Skin and Appendages: exfoliative dermatitis, erythema multiforme, hyperpigmentation, hypertrophic scar.

Vascular: Henoch-Schonlein purpura syndrome

8  USE IN SPECIFIC POPULATIONS

8.1  Pregnancy

Pregnancy Category C:

There are no adequate and well-controlled studies in pregnant women. ZYCLARA® Cream should be used during pregnancy only if the potential benefit justifies the potential risk to the fetus.

Note: The animal multiples of human exposure calculations were based on daily dose comparisons for the reproductive toxicology studies described in this label. The animal multiples of human exposure were based on weekly dose comparisons for the carcinogenicity studies described in this label. For the animal multiple of human exposure ratios presented in this label, the Maximum Recommended Human Dose (MRHD) was set at 2-packets (500 mg cream) per treatment of ZYCLARA® Cream (imiquimod 3.75%, 18.75 mg imiquimod).

Systemic embryofetal development studies were conducted in rats and rabbits. Oral doses of 1, 5, and 20 mg/kg/day imiquimod were administered during the period of organogenesis (gestational days 6 - 15) to pregnant female rats. In the presence of maternal toxicity, fetal effects noted at 20 mg/kg/day (190X MRHD based on AUC comparisons) included increased resorptions, decreased fetal body weights, delays in skeletal ossification, bent limb bones, and two fetuses in one litter (2 of 1567 fetuses) demonstrated exencephaly, protruding tongues, and low-set ears. No treatment related effects on embryofetal toxicity or teratogenicity were noted at 5 mg/kg/day (32X MRHD based on AUC comparisons).

Intravenous doses of 0.5, 1, and 2 mg/kg/day imiquimod were administered during the period of organogenesis (gestational days 6 - 18) to pregnant female rabbits. No treatment-related effects on embryofetal toxicity or teratogenicity were noted at 2 mg/kg/day (2.1X MRHD based on BSA comparisons), the highest dose evaluated in this study, or 1 mg/kg/day (134X MRHD based on AUC comparisons).

A combined fertility and peri- and post-natal development study was conducted in rats. Oral doses of 1, 1.5, 3, and 6 mg/kg/day imiquimod were administered to male rats from 70 days prior to mating through the mating period and to female rats from 14 days prior to mating through parturition and lactation. No effects on growth, fertility, reproduction, or post-natal development were noted at doses up to 6 mg/kg/day (29X MRHD based on AUC comparisons), the highest dose evaluated in this study. In the absence of maternal toxicity, bent limb bones were noted in the F1 fetuses at a dose of 6 mg/kg/day (29X MRHD based on AUC comparisons). This fetal effect was also noted in the oral rat embryofetal development study conducted with imiquimod. No treatment-related effects on teratogenicity were noted at 3 mg/kg/day (14X MRHD based on AUC comparisons).

8.3 Nursing Mothers

It is not known whether imiquimod is excreted in human milk following use of ZYCLARA® Cream. Because many drugs are excreted in human milk, caution should be exercised when ZYCLARA® Cream is administered to nursing women.

8.4 Pediatric Use

AK is not a condition generally seen within the pediatric population. The safety and efficacy of ZYCLARA® Cream for AK in patients less than 18 years of age has not been established.

8.5 Geriatric Use

Of the 160 subjects treated with ZYCLARA® Cream in the clinical studies, 78 subjects were 65 years or older. No overall differences in safety or effectiveness were observed between these subject and younger subjects.

10 OVER DOSAGE

Topical overdosing of ZYCLARA® Cream could result in an increased incidence of severe local skin reactions and may increase the risk for systemic reactions.

Hypotension was reported in a clinical trial following multiple oral imiquimod doses of >200 mg (equivalent to the ingestion of imiquimod content of >21 packets of ZYCLARA® Cream). This resolved following oral or intravenous fluid administration.

11 DESCRIPTION

ZYCLARA® Cream is intended for topical administration. Each gram contains 37.5 mg of imiquimod in a white to faintly yellow oil-in-water vanishing cream base consisting of isostearic acid, cetyl alcohol, stearyl alcohol, white petrolatum, polysorbate 60, sorbitan monostearate, glycerin, xanthan gum, purified water, benzyl alcohol, methylparaben, and propylparaben.

Chemically, imiquimod is 1-(2-methylpropyl)-1$H$-imidazo[4,5-c]quinolin-4-amine. Imiquimod has a molecular formula of $C_{14}H_{16}N_4$ and a molecular weight of 240.3. Its structural formula is:

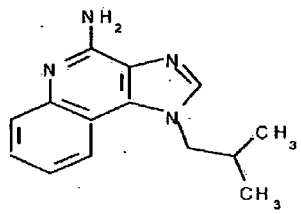

12 CLINICAL PHARMACOLOGY

12.1 Mechanism of Action

The mechanism of action of ZYCLARA® Cream in treating AK lesions is unknown.

12.2 Pharmacodynamics

The pharmacodynamics of ZYCLARA® are unknown.

Imiquimod is a Toll-like receptor 7 agonist that activates immune cells. Topical application to skin is associated with increases in markers for cytokines and immune cells.

In a study of 18 subjects with AK comparing Aldara® (imiquimod) Cream, 5% to vehicle, increases from baseline in week 2 biomarker levels were reported for CD3, CD4, CD8, CD11 c, and CD68 for Aldara® (imiquimod) Cream, 5% treated subjects; however, the clinical relevance of these findings is unknown.

12.3 Pharmacokinetics

Following dosing with 2 packets once daily (18.75 mg imiquimod/day) for up to three weeks, systemic absorption of imiquimod was observed in all subjects when ZYCLARA® Cream was applied to the face and/or scalp in 17 subjects with at least 10 AK lesions. The mean peak serum imiquimod concentration at the end of the trial was approximately 0.323 ng/mL. The median time to maximal concentrations (T max ) occurred at 9 hours after dosing. Based on the plasma half-life of imiquimod observed at the end of the study, 29.3±17.0 hours, steady-state concentrations can be anticipated to occur by day 7 with once daily dosing.

13 NONCLINICAL TOXICOLOGY

13.1 Carcinogenesis, Mutagenesis, Impairment of Fertility

In an oral (gavage) rat carcinogenicity study, imiquimod was administered to Wistar rats on a 2X/week (up to 6 mg/kg/day) or daily (3 mg/kg/day) dosing schedule for 24 months. No treatment related tumors were noted in the oral rat carcinogenicity study up to the highest doses tested in this study of 6 mg/kg administered 2X/week in female rats (8.2X MRHD based on weekly AUC comparisons), 4 mg/kg administered 2X/week in male rats (7.1X MRHD) based on weekly AUC comparisons) or 3 mg/kg administered 7X/week to male and female rats (14X MRHD based on weekly AUC comparisons).

In a dermal mouse carcinogenicity study, imiquimod cream (up to 5 mg/kg/application imiquimod or 0.3% imiquimod cream) was applied to the backs of mice 3X/week for 24 months. A statistically significant increase in the incidence of liver adenomas and carcinomas was noted in high dose male mice compared to control male mice (24X MRHD based on weekly AUC comparisons). An increased number of skin papillomas was observed in vehicle cream control group-animals at the treated site only.

In a 52-week dermal photo-carcinogenicity study, the median time to onset of skin tumor formation was decreased in hairless mice following chronic topical dosing (3X/week; 40 weeks of treatment followed by 12 weeks of observation) with concurrent exposure to UV radiation (5 days per week) with vehicle alone. No additional effect on tumor development beyond the vehicle effect was noted with the addition of the active ingredient, imiquimod, to the vehicle cream.

Imiquimod revealed no evidence of mutagenic or clastogenic potential based on the results of five in vitro genotoxicity tests (Ames assay, mouse lymphoma L5178Y assay, Chinese hamster ovary cell chromosome aberration assay, human lymphocyte chromosome aberration assay and SHE cell transformation assay) and three in vivo genotoxicity tests (rat and hamster bone marrow cytogenetics assay and a mouse dominant lethal test).

Daily oral administration of imiquimod to rats, throughout mating, gestation, parturition and lactation, demonstrated no effects on growth, fertility or reproduction, at doses up to 29X MRHD based on AUC comparisons.

14   CLINICAL STUDIES 14.1   Actinic Keratosis

In two double-blind, randomized, vehicle-controlled clinical studies, 319 subjects with AK were treated with ZYCLARA® Cream, or vehicle cream. Studies enrolled subjects >18 years of age with 5-20 typical visible or palpable AK lesions of the face or scalp. Study cream was applied to either the entire face (excluding ears) or balding scalp once daily for two 2-week treatment cycles separated by a 2-week no-treatment period. Subjects then continued in the study for an 8-week follow-up period during which they returned for clinical observations and safety monitoring. Study subjects ranged from 36 to 90 years of age and 54% had Fitzpatrick skin type I or II. All ZYCLARA® Cream-treated subjects were Caucasians.

On a scheduled dosing day, up to two packets of the study cream were applied to the entire treatment area prior to normal sleeping hours and left on for approximately 8 hours. Efficacy was assessed by AK lesion counts at the 8-week post-treatment visit. All AKs in the treatment area were counted, including baseline lesions as well as lesions which appeared during therapy.

Complete clearance required absence of any lesions including those that appeared during therapy in the treatment area. Complete and partial clearance rates are shown in the tables below. Partial clearance rate was defined as the percentage of subjects in whom the number of baseline AKs was reduced by 75% or more. The partial clearance rate was measured relative to the numbers of AK lesions at baseline.

Table 3: Rates of Subject with Complete Clearance at 8 Weeks Post Treatment

|  | ZYCLARA® Cream 3.75% | Vehicle Cream |
|---|---|---|
| Study 1 | 25.9% (21/81) | 2.5% (2/80) |
| Study 2 | 45.6% (36/79) | 10.1% (8/79) |

Table 4: Rates of Subjects with Partial Clearance ($\geq$75%) at 8 Weeks Post Treatment

|  | ZYCLARA® Cream 3.75% | Vehicle Cream |
|---|---|---|
| Study 1 | 45.7% (37/81) | 18.8% (15/80) |
| Study 2 | 73.4% (58/79) | 26.6% (21/79) |

During the course of treatment, 86% (138/160) of subjects experienced a transient increase in lesions evaluated as actinic keratoses relative to the number present at baseline within the treatment area.

16  HOW SUPPLIED/STORAGE AND HANDLING

ZYCLARA® (imiquimod) Cream, 3.75%, is supplied in single-use packets which contain 250 mg of the cream. Available as: box of 28 packets NDC 29336-710-28. Store at 25°C (77°F); excursions permitted to 15° to 30°C (59° to 86°F) [See USP Controlled Room Temperature].

Avoid freezing.

*Keep out of reach of children.*

17  PATIENT COUNSELING INFORMATION

*See FDA-Approved Patient Labeling (17.7)*

17.1  General Information:

ZYCLARA® Cream should be used as directed by a physician. *[see Dosage and Administration (2)]* ZYCLARA® Cream is for external use only. Contact with the eyes, lips and nostrils should be avoided. *[see Indications and Usage (1) and Dosage and Administration (2)].*

The treatment area should not be bandaged or otherwise occluded. Partially-used packets should be discarded and not reused. The prescriber should demonstrate the proper application technique to maximize the benefit of ZYCLARA® Cream therapy.

It is recommended that patients wash their hands before and after applying ZYCLARA® Cream.

17.2  Local Skin Reactions:

*Patients* may experience local skin reactions during treatment with ZYCLARA® Cream. Potential local skin reactions include erythema, edema, erosions/ulcerations, weeping/exudate, flaking/scaling/dryness, and scabbing/crusting. These reactions can range from mild to severe in intensity and may extend beyond the application site onto the surrounding skin. Patients may also experience application site reactions such as itching, irritation or pain. *[see Adverse Reactions (6)]*

Local skin reactions may be of such an intensity that patients may require rest periods from treatment. Treatment with ZYCLARA® Cream can be resumed after the skin reaction has subsided, as determined by the physician. However, each treatment cycle should not be extended beyond 2 weeks due to missed doses or rest periods. Patients should contact their physician promptly if they experience any sign or symptom at the application site that restricts or prohibits their daily activity or makes continued application of the ZYCLARA® Cream difficult.

Because of local skin reactions, during treatment and until healed, the treatment area is likely to appear noticeably different from normal skin. Localized hypopigmentation and hyperpigmentation have been reported following use of imiquimod cream. These skin color changes may be permanent in some patients.

17.3 Systemic Reactions:

Patients may experience flu-like systemic signs and symptoms during treatment with ZYCLARA® Cream. Systemic signs and symptoms may include fatigue, nausea, fever, myalgia, arthralgia, and chills. *[see Adverse Reactions (6)]* An interruption of dosing and assessment of the patient should be considered.

17.4 Recommended Administration

Dosing is once daily before bedtime to the skin of the affected area (either the full face or balding scalp) for two 2-week treatment cycles separated by a 2-week no-treatment period. However, the treatment period should not be extended beyond two 2-week treatment cycles due to missed doses or rest periods. *[see Dosage and Administration (2.1).*

It is recommended that patients wash their hands before and after applying ZYCLARA® Cream. Before applying the ZYCLARA® Cream, the patient should wash the treatment area with mild soap and water and allow the area to dry thoroughly.

It is recommended that the treatment area be washed with mild soap and water 8 hours following ZYCLARA® Cream application.

Most patients using ZYCLARA® Cream for the treatment of AK experience erythema, flaking/scaling/dryness and scabbing/crusting at the application site with normal dosing. [see Adverse Reactions (6.1)].

Use of sunscreen is encouraged, and patients should minimize or avoid exposure to natural or artificial sunlight (tanning beds or UVA/B treatment) while using ZYCLARA® Cream. *[see Warnings and Precautions (5.3)].*

Sub-clinical AK lesions may become apparent in the treatment area during treatment and may subsequently resolve. *[see Clinical Studies (14.1)].*

17.7 FDA-Approved Patient Labeling

Patient Information

ZYCLARA® [imiquimod] Cream, 3.75% (Imiquimod)

IMPORTANT: Not for mouth, eye, or vaginal use

Read the Patient Information that comes with ZYCLARA® Cream before you start using it and each time you get a refill. There may be new information. This leaflet does not take the place of talking with your healthcare provider about your medical condition or treatment. If you do not understand the information, or have any questions about ZYCLARA® Cream, talk with your healthcare provider or pharmacist.

What is ZYCLARA® Cream?

ZYCLARA® Cream is a skin use only (topical) medicine used to treat:

- actinic keratosis in adults with normal immune systems. Actinic keratosis is caused by too much sun exposure.

ZYCLARA® Cream does not work for everyone.

Who should not use ZYCLARA® Cream?

- ZYCLARA® Cream has not been studied in children under 18 years old. Children usually do not get actinic keratoses.

Before using ZYCLARA® Cream, tell your healthcare provider:

- about all your medical conditions, including if you
  - are pregnant or planning to become pregnant. It is not known if ZYCLARA® Cream can harm your unborn baby.
  - are breastfeeding. It is not known if ZYCLARA® Cream passes into your milk and if it can harm your baby.
- about all the medicines you take including prescription and non-prescription medicines, vitamins and herbal supplements. Especially tell your healthcare provider if you have had other treatments for actinic keratosis. ZYCLARA® Cream should not be used until your skin has healed from other treatments.

How should I use ZYCLARA® Cream?

- Use ZYCLARA® Cream exactly as prescribed by your healthcare provider. ZYCLARA® Cream is for skin use only. Do not take by mouth or use in or near your eyes, lips or nostrils. Do not use ZYCLARA® Cream unless your healthcare provider has taught you the right way to use it. Talk to your healthcare provider if you have any questions.
- Your healthcare provider will tell you where to apply ZYCLARA® Cream and how often and for how long to apply it for your condition. Do not use ZYCLARA® Cream longer than prescribed. Using too much ZYCLARA® Cream, or using it too often, or for too long can increase your chances for having a severe skin reaction or other side effect. Talk to your healthcare provider if ZYCLARA® Cream does not work for you.
- ZYCLARA® Cream is applied once a day for two-weeks. There is no treatment for the next two weeks. ZYCLARA® Cream is then applied once a day for another two-weeks.

ZYCLARA® Cream is usually left on the skin for about 8 hours. Treatment should continue for the full treatment course even if all actinic keratosis appear to be gone, unless you are told otherwise by your healthcare provider. ZYCLARA® Cream should be used to treat either the whole face or balding scalp.

Applying ZYCLARA® Cream

ZYCLARA® Cream should be applied just before your bedtime.
- Wash the area to be treated with mild soap and water. Allow the area to dry.
- Wash your hands
- Open a new packet(s) of ZYCLARA® Cream just before use
- Apply a thin layer of ZYCLARA® Cream only to the affected area or areas to be treated. Do not use more ZYCLARA® Cream than is needed to cover the treatment area. Do not use more than two packets for each application.
- Rub the ZYCLARA® Cream in all the way to the affected area or areas.
  - Do not get ZYCLARA® Cream in or around your eyes.
- Safely throw away the open packet of ZYCLARA® Cream so that children and pets cannot get it. The open packet should be thrown away even if all the ZYCLARA® Cream was not completely used.
- After applying ZYCLARA® Cream, wash your hands well.

- Leave the ZYCLARA® Cream on the affected area or areas for the time prescribed by your healthcare provider. Do not bathe or get the treated area wet before the right time has passed. Do not leave ZYCLARA® Cream on your skin longer than prescribed.
- After about 8 hours, wash the treated area or areas with mild soap and water.
- If you forget to apply ZYCLARA® Cream, continue on your regular schedule and do not make up the missed dose(s).
- If you get ZYCLARA® Cream in your mouth or in your eyes rinse well with water right away.

What should I avoid while using ZYCLARA® Cream?

- Do not cover the treated site with bandages or other closed dressings. Cotton gauze dressings are okay to use, if needed.
- Do not apply ZYCLARA® Cream in or near the eyes, lips or nostrils,.
- Do not use sunlamps or tanning beds, and avoid sunlight as much as possible during treatment with ZYCLARA® Cream. Use sunscreen and wear protective clothing if you go outside during daylight.
- What are the possible side effects of ZYCLARA® Cream?

Side effects with ZYCLARA® Cream may include skin reactions at the treatment site such as:

- redness
- swelling
- a sore, blister, or ulcer
- skin that becomes hard or thickened
- skin peeling
- scabbing and crusting
- itching
- burning
- changes in skin color that do not always go away During treatment and until the skin has healed, your skin in the treatment area is likely to appear noticeably different from normal skin. Side effects, such as redness, scabbing, itching and burning are common at the site where ZYCLARA® Cream is applied, and sometimes the side effects go outside of the area where ZYCLARA® Cream was applied. Swelling, small open sores and drainage may also be experienced with use of ZYCLARA® Cream. You may also experience itching, irritation or pain. Actinic keratoses that were not seen before may appear during treatment and may later go away. If you have questions regarding treatment or skin reactions, please talk with your healthcare provider.

You have a higher chance for severe skin reactions if you use too much ZYCLARA® Cream or use it the wrong way. Stop ZYCLARA® Cream right away and call your healthcare provider if you get any skin reactions that affect your daily activities, or that do not go away. Sometimes, ZYCLARA® Cream must be stopped for a while to allow your skin to heal. Talk to your healthcare provider if you have questions about your treatment or skin reactions.

Other side effects of ZYCLARA® Cream include headache, back pain, muscle aches, joint aches, tiredness, flu-like symptoms, swollen lymph nodes, nausea and diarrhea.

If the reactions seem excessive, if either skin breaks down or sores develop during the first week of treatment, if flu-like symptoms develop or if you begin to not feel well at anytime, stop applying ZYCLARA® Cream and contact your healthcare provider.

These are not all the side effects of ZYCLARA® Cream. For more information, ask your healthcare provider or pharmacist.

How do I store ZYCLARA® Cream?

Store ZYCLARA® Cream at 39-77° F (4-25° C). Do not freeze.

- Safely throw away ZYCLARA® Cream that is out of date or that you do not need.
- Keep ZYCLARA® Cream and all medicines out of the reach of children.

General information about ZYCLARA® Cream

Medicines are sometimes prescribed for conditions that are not mentioned in patient information leaflets. Do not use ZYCLARA® Cream for a condition for which it was not prescribed. Do not give ZYCLARA® Cream to other people, even if they have the same symptoms you have.

This leaflet summarizes the most important information about ZYCLARA® Cream. If you would like more information, talk with your healthcare provider. You can ask your pharmacist or healthcare provider for information about ZYCLARA® Cream that is written for the healthcare provider. If you have other questions about ZYCLARA® Cream, call 1-800-328-0255.

What are the ingredients in ZYCLARA® Cream?

Active Ingredient: imiquimod

Inactive ingredients: isostearic acid, cetyl alcohol, stearyl alcohol, white petrolatum, polysorbate 60, sorbitan monostearate, glycerin, xanthan gum, purified water, benzyl alcohol, methylparaben, and propylparaben.

Manufactured by
3M Health Care Limited
Loughborough LE11 1EP England
Distributed by
Graceway Pharmaceuticals, LLC
Bristol, TN 37620

Attachment X

[000321] Zyclara® [zi-clar-a] (imiquimod) 3.75% Cream

HIGHLIGHTS OF PRESCRIBING INFORMATION FOR GENITAL AND PERIANAL WARTS

These highlights do not include all the information needed to use ZYCLARA® Cream safely and effectively. See full prescribing information for Zyclara® Cream.

ZYCLARA® (imiquimod), Cream, 3.75%
For topical use only
Initial U.S. Approval:

--------------------------------------- INDICATIONS AND USAGE ---------------------------------------

Zyclara® Cream is indicated for the treatment of external genital and perianal warts/condyloma acuminata in patients 12 years or older (11)

--------------------------------- DOSAGE AND ADMINISTRATION ---------------------------------

Zyclara® Cream is not for oral, ophthalmic, infra-anal or intravaginal use.(2)
- External Genital Warts: daily to the external genital/perianal warts until total clearance or up to 8 weeks (2.1)

--------------------------------- DOSAGE FORMS AND STRENGTHS ---------------------------------

Zyclara® (imiquimod) Cream, 3.75%, is supplied in single-use packets 28 per Dose Pack, each of which contains 250 mg of the cream, equivalent to 9.4 mg of imiquimod. (3)

FULL PRESCRIBING INFORMATION: CONTENTS*

1. INDICATIONS AND USAGE

Unevaluated Populations

2. DOSAGE AND ADMINISTRATION

3. DOSAGE FORMS AND STRENGTHS

4. CONTRAINDICATIONS

5. WARNINGS AND PRECAUTIONS
    5.1 Local Skin Reactions
    5.2 Systemic Reactions
    5.3 Ultraviolet Light Exposure
    5.4 Unevaluation Uses: External Genital Warts 6. ADVERSE REACTIONS
    6.1 Clinical Trials Experience
    6.2 Dermal Safety Trials Experience
    6.3 Postmarketing Experience ---------------------------------------- CONTRAINDICATIONS ----------------------------------------

- None (4)

---------------------------------- WARNINGS AND PRECAUTIONS ----------------------------------

- Intense local inflammatory reactions can occur (e.g., skin weeping, erosion). Dosing interruption may be required (2, 5.1, 6)
- Flue-like signs and symptoms may accompany, or even precede, local skin reactions and may include fatigue, fever, mylagia, malaise and nausea. Dosing interruption may be required (2, 5.2, 6)
- Avoid exposure to sunlight and sunlamps to the affected areas (5.3).
- Treatment of urethral, intra-vaginal, cervical, rectal or intra-anal viral disease is not recommended. (5.)

---------------------------------------- ADVERSE REACTIONS ----------------------------------------

Table 1: Local Skin Reactions in the Treatment Area Assessed by the Investigator, Table 1: Local Skin Reactions in the Treatment Area Assessed by the Investigator Table 2: Treatment Related Adverse Reactions occurring in > 1% of Zyclara® — Treated Subjects and at a Greater Frequency than with Placebo in either gender. (6)

To report SUSPECTED ADVERSE REACTIONS, contact Graceway Pharmaceuticals, LLC at 1-800-328-0255 or FDA at 1-800-FDA-1088 or *www.fda.gov/medwatch.*

See 17 for PATIENT COUNSELING INFORMATION and FDA-approved patient labeling.

8. USE IN SPECIFIC POPULATIONS
    8.1 Pregnancy
    8.3 Nursing Mothers
    8.4 Pediatric Use
    8.5 Geriatric Use

10. OVER DOSAGE

11. DESCRIPTION

12 CLINICAL PHARMACOLOGY
    12.1 Mechanism of Action
    12.2 Pharmacodynamics
    12.3 Pharmacokinetics 13 NONCLINICAL TOXICOLOGY
    13.1 Carcinogenesis, Mutagenesis, Impairment of Fertility

14. CLINICAL STUDIES
16 HOW SUPPLIED/STORAGE AND HANDLING

17    PATIENT COUNSELING INFORMATION 17.1 Instructions for Administration:

17.2 Local Skin Reactions:

17.3 Systemic Reactions:

17.4 Recommended Administration 17.7 FDA-Approved Patient Labeling

*Sections or subsections omitted from the Full Prescribing Information are not listed.

FULL PRESCRIBING INFORMATION

1    INDICATIONS AND USAGE

Zyclara® Cream is indicated for the treatment of external genital and perianal warts/condyloma acuminata, whether present at the start of therapy or emerging during therapy, in patients 12 years or older.

1.1    Unevaluated Populations

The safety and efficacy of Zyclara® Cream in immunosuppressed patients have not been established.

Zyclara® Cream should be used with caution in patients with pre-existing autoimmune conditions.

2    DOSAGE AND ADMINISTRATION

Zyclara® Cream is not for oral, ophthalmic, infra-anal, or intravaginal use. Zyclara® Cream should be applied once-a-day to the external genital/perianal warts. Zyclara® Cream should be used for up to 8 weeks. Zyclara® Cream should be applied prior to normal sleeping hours and left on the skin for approximately 8 hours, after which time the Zyclara® Cream should be removed by washing the area with mild soap and water. The prescriber should demonstrate the proper application technique to maximize the benefit of Zyclara® Cream therapy.

It is recommended that patients wash their hands before and after applying Zyclara® Cream.

A thin layer of Zyclara® Cream should be applied to the areas of existing and emerging warts and rubbed in until the Zyclara® Cream is no longer visible. The application site should not be occluded. Following the treatment period the Zyclara® Cream should be removed by washing the treated area with mild soap and water.

Local skin reactions at the treatment site are common. *[see Adverse Reactions (6.2)]* A rest period of several days may be taken if required by the patient's discomfort or severity of the local skin reaction. Treatment may resume once the reaction subsides. Non-occlusive dressings such as cotton gauze or cotton underwear may be used in the management of skin reactions.

Zyclara® Cream is packaged in single-use packets with 28 packets supplied per box, which contain sufficient Zyclara® Cream to cover the wart areas; use of excessive amounts of Zyclara® Cream should be avoided. Patients should be prescribed no more than 2 Dose Packs (56 packets) for the treatment course. Unused packets should be discarded. Partially-used packets should be discarded and not reused.

3   DOSAGE FORMS AND STRENGTHS

Zyclara® (imiquimod) Cream, 3.75%, is supplied in single-use packets each of which contains 250 mg of the cream, equivalent to 9.4 mg of imiquimod. Zyclara® Cream is supplied in a Dose Pack of 28 packets each.

4   CONTRAINDICATIONS
None.

5   WARNINGS AND PRECAUTIONS
5.1   Local Skin Reactions

Intense local skin reactions including skin weeping or erosion can occur after a few applications of Zyclara® Cream and may require an interruption of dosing. *[see Dosage and Administration (2) and Adverse Reactions (6)]*. Zyclara® Cream has the potential to exacerbate inflammatory conditions of the skin, including chronic graft versus host disease.

Administration of Zyclara® Cream is not recommended until the skin is healed from any previous drug or surgical treatment.

5.2   Systemic Reactions

Flu-like signs and symptoms may accompany, or even precede, local skin reactions and may include fatigue, fever, myalgia, malaise and nausea. An interruption of dosing and an assessment of the patient should be considered. *[see Adverse Reactions (6)]*

5.3 Ultraviolet Light Exposure

In an animal photo-carcinogenicity study, imiquimod cream shortened the time to skin tumor formation *[see Nonclinical Toxicology (13.1)]*. The enhancement of ultraviolet carcinogenicity is not necessarily dependent on phototoxic mechanisms. Therefore, patients should minimize or avoid natural or artificial sunlight exposure to the affected areas.

5.4 Unevaluated Uses

Zyclara® Cream has not been evaluated for the treatment of urethral, intra-vaginal, cervical, rectal, or intra-anal human papilloma viral disease.

6 ADVERSE REACTIONS

Clinical trials are conducted under widely varying conditions. Adverse reaction rates observed in the clinical trials of a drug cannot be directly compared to rates in the clinical trials of another drug and may not reflect the rates observed in practice.

6.1 Clinical Trials Experience

In two double-blind, placebo-controlled studies for genital warts, 602 subjects applied up to one packet of Zyclara® Cream or placebo daily for up to 8 weeks. The most frequently reported adverse reactions were local skin and application site reactions.

Overall, fewer than 1% (3/400) of the subjects treated with Zyclara® Cream discontinued due to local skin/application site reactions. The incidence and severity of local skin reaction during controlled clinical studies are shown in Table 1 below.

Table 1: Local Skin Reactions in the Treatment Area Assessed by the Investigator

|  | Zyclara® Cream | | | | Placebo | | | |
|---|---|---|---|---|---|---|---|---|
|  | Females n=217 | | Males n=183 | | Females n=106 | | Males n=96 | |
|  | All Grades* | Severe | All Grades* | Severe | All Grades* | Severe | All Grades* | Severe |
| Erythema | 74% | 10% | 78% | 10% | 23% | 0% | 37% | 1% |
| Edema (induration) | 41% | 2% | 48% | 2% | 8% | 0% | 9% | 0% |
| Weeping/Exudate | 35% | 1% | 39% | 3% | 5% | 0% | 0% | 0% |
| Flaking/Sealing/Dryness | 26% | 0% | 39% | 0% | 11% | 0% | 11% | 0% |
| Scabbing/Crusting | 18% | <1% | -34% | 1% | 6% | 0% | 2% | 0% |
| Erosion/Ulceration | 36% | 13% | 42% | 10% | 7% | 1% | 2% | 0% |

*Mild, Moderate, or Severe

Local skin reactions were recorded as adverse events if they extended beyond the treatment area, if they required any medical intervention, or they resulted in patient discontinuation from the study.

Selected treatment related adverse reactions are listed below.

Table 2: Treatment Related Adverse Reactions Occurring in > 1% of Zyclara® – Treated Subjects and at a Greater Frequency than with Placebo in either gender

|  | Females | | Males | |
|---|---|---|---|---|
|  | Zyclara® Cream | Placebo | Zyclara® Cream | Placebo |
| Preferred Term | n=217 | n=106 | n=183 | n=96 |
| Application site pain | 7.8% | 0% | 5.5% | 1.0% |
| Application site irritation | 5.5% | 0.9% | 6.0% | 1.0% |
| Application site pruritus | 3.2% | 1.9% | 1.6% | 0% |
| Application site bleeding | 1.4% | 0.9% | 1.5% | 0% |
| Application site discharge | 1.4% | 0% | 0.5% | 0% |
| Application site erythema | 1.4% | 0% | 0% | 0% |

| | | | | |
|---|---|---|---|---|
| Application site reaction | 0.9% | 0% | 1.1% | 0% |
| Application site rash | 0.9% | 0% | 1.1% | 0% |
| Scrotal pain | 0% | 0% | 1.6% | 0% |
| Application site excoriation | 0% | 0% | 1.1% | 0% |
| Secretion discharge | 0% | 0% | 1.1% | 0% |
| Scrotal erythema | 0% | 0% | 1.1% | 0% |
| Scrotal ulcer | 0% | 0% | 1.1% | 0% |
| Scrotal edema | 0% | 0% | 1.1% | 0% |
| Pruritus genital | 0% | 0% | 1.1% | 0% |
| Application site cellulitis | 0% | 0% | 1.1% | 0% |

Systemic adverse reactions considered treatment related in clinical trials involving Zyclara® Cream included pain, pyrexia (fever), influenza, and myalgia.

Adverse reactions seen in clinical trials for external genital warts involving 5% imiquimod cream included: tinea cruris, application site soreness, hypopigmentation, sensitivity, stinging and tenderness.

Other systemic adverse reactions considered treatment related in clinical trials for external genital warts involving 5% imiquimod cream included: headache, influenza-like symptoms, fatigue, malaise, nausea, and diarrhea.

6.2 Dermal Safety Trials Experience

Provocative repeat insult patch test studies involving induction and challenge phases produced no evidence that imiquimod cream causes photoallergenicity or contact sensitization in healthy skin; however, cumulative irritancy testing revealed the potential for imiquimod cream to cause irritation, and application site reactions were reported in the clinical studies. *[see Adverse Reactions (6)]*

6.3 Postmarketing Experience

The following adverse reactions have been identified during post-approval use of Aldara® (imiquimod) Cream, 5%. Because these reactions are reported voluntarily from a population of uncertain size, it is not always possible to reliably estimate their frequency or establish a causal relationship to drug exposure.

Application Site Disorders: tingling at the application site.

Body as a Whole: angioedema.

Cardiovascular: capillary leak syndrome, cardiac failure, cardiomyopathy, pulmonary edema, arrhythmias (tachycardia, atrial fibrillation, palpitations), chest pain, ischemia, myocardial infarction, syncope.

Endocrine: thyroiditis.

Gastro-Intestinal System Disorders: abdominal pain.

Hematological: decreases in red cell, white cell and platelet counts (including idiopathic thrombocytopenic purpura), lymphoma.

Hepatic: abnormal liver function.

Infections and Infestations: herpes simplex.

Musculo-Skeletal System Disorders: arthralgia.

Neuropsychiatric: agitation, cerebrovascular accident, convulsions (including febrile convulsions), depression, insomnia, multiple sclerosis aggravation, paresis, suicide.

Respiratory: dyspnea.

Urinary System Disorders: proteinuria.

Skin and Appendages: exfoliative dermatitis, erythema multiforme, hyperpigmentation, hypertrophic scar.

Vascular: Henoch-Schonlein purpura syndrome.

8  USE IN SPECIFIC POPULATIONS 8.1  Pregnancy

Pregnancy Category C:

There are no adequate and well-controlled studies in pregnant women. Zyclara® Cream should be used during pregnancy only if the potential benefit justifies the potential risk to the fetus.

Note: The animal multiples of human exposure calculations were based on daily dose comparisons in this label. For the animal multiple of human exposure ratios presented in this label, the Maximum Recommended Human Dose (MRHD) was set at 1 packet (250 mg cream) per treatment of Zyclara® Cream (imiquimod 3.75%, 9.375 mg imiquimod).

Systemic embryofetal development studies were conducted in rats and rabbits. Oral doses of 1, 5 and 20 mg/kg/day imiquimod were administered during the period of organogenesis (gestational days 6 — 15) to pregnant female rats. In the presence of maternal toxicity, fetal effects noted at 20 mg/kg/day (375X MRHD based on AUC comparisons) included increased resorptions, decreased fetal body weights, delays in skeletal ossification, bent limb bones, and two fetuses in one litter (2 of 1567 fetuses) demonstrated exencephaly, protruding tongues and low-set ears. No treatment related effects on embryofetal toxicity or teratogenicity were noted at 5 mg/kg/day (73X MRHD based on AUC comparisons).

Intravenous doses of 0.5, 1 and 2 mg/kg/day imiquimod were administered during the period of organogenesis (gestational days 6 — 18) to pregnant female rabbits. No treatment related effects on embryofetal toxicity or teratogenicity were noted at 2 mg/kg/day (2.1X MRHD based on BSA comparisons), the highest dose evaluated in this study, or 1 mg/kg/day (234X MRHD based on AUC comparisons).

A combined fertility and peri- and post-natal development study was conducted in rats. Oral doses of 1, 1.5, 3 and 6 mg/kg/day imiquimod were administered to male rats from 70 days prior to mating through the mating period and to female rats from 14 days prior to mating through parturition and lactation. No effects on growth, fertility, reproduction or post-natal development were noted at doses up to 6 mg/kg/day (50X MRHD based on AUC comparisons), the highest dose evaluated in this study. In the absence of maternal toxicity, bent limb bones were noted in the F1 fetuses at a dose of 6 mg/kg/day (50X MRHD based on AUC comparisons). This fetal effect was also noted in the oral rat embryofetal development study conducted with imiquimod. No treatment related effects on teratogenicity were noted at 3 mg/kg/day (24X MRHD based on AUC comparisons).

8.3    Nursing Mothers

It is not known whether imiquimod is excreted in human milk following use of Zyclara® Cream. Because many drugs are excreted in human milk, caution should be exercised when Zyclara® Cream is administered to nursing women.

8.4    Pediatric Use

Safety and efficacy in patients with external genital/perianal warts below the age of 12 years have not been established.

8.5    Geriatric Use

Of the 399 subjects treated with Zyclara® Cream in the EGW clinical studies, 5 subjects (1%) were 65 years or older. Data were too sparse to evaluate treatment effects in this population. No other clinical experience has identified differences in responses between the elderly and younger subjects, but greater sensitivity of some older individuals cannot be ruled out.

10  OVER DOSAGE

Topical overdosing of Zyclara® Cream could result in an increased incidence of severe local skin reactions and may increase the risk for systemic reactions.

The most clinically serious adverse event reported following multiple oral imiquimod doses of >200 mg (equivalent to imiquimod content of > 21 packets of Zyclara® Cream) was hypotension, which resolved following oral or intravenous fluid administration.

11  DESCRIPTION

Zyclara® Cream is a toll-like receptor agonist for topical administration. Each gram contains 37.5 mg of imiquimod in an off-white oil-in-water vanishing cream base consisting of isostearic acid, cetyl alcohol, stearyl alcohol, white petrolatum, polysorbate 60, sorbitan monostearate; glycerin, xanthan gum, purified water, benzyi alcohol, methylparaben; and propylparaben.

Chemically, imiquimod is 1-(2-methylpropyl)-1$H$-imidazo [4,5-c] quinolin-4-amine. Imiquimod has a molecular foiinula of $C_{14}H_{16}N_4$ and a molecular weight of 240.3. Its structural formula is:

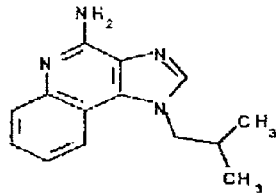

12  CLINICAL PHARMACOLOGY

12.1  Mechanism of Action

The mechanism of action of Zyclara® Cream is unknown.

12.2  Pharmacodynamics

Imiquimod has no direct antiviral activity in cell culture. A study in 22 subjects with genital/perianal warts comparing imiquimod cream 5% and vehicle shows that imiquimod induces mRNA encoding cytokines including interferon-α at the treatment site. In addition HPVL1 mRNA and HPV DNA are significantly decreased following treatment. However, the clinical relevance of these findings is unknown.

12.3 Pharmaeokinetics

Systemic absorption of imiquimod (up to 9.4 mg [one packet]) across the affected skin of 18 subjects with EGW was observed with once daily dosing for 3 weeks. The mean peak serum drug concentration at Day 21 was 0.488 ng/mL.

13 NONCLINICAL TOXICOLOGY 13.1 Carcinogenesis, Mutagenesis, Impairment of Fertility In an oral (gavage) rat carcinogenicity study, imiquimod was administered to Wistar rats on a 2X/week (up to 6 mg/kg/day) or daily (3 mg/kg/day) dosing schedule for 24 months. No treatment related tumors were noted in the oral rat carcinogenicity study up to the highest doses tested in this study of 6 mg/kg administered 2X/week in female rats (50X MRHD based on AUC comparisons), 4 mg/kg administered 2X/week in male rats (40X MRHD) or 3 mg/kg administered 7X/week to male and female rats (25X MRHD).

In a dermal mouse carcinogenicity study, imiquimod cream (up to 5 mg/kg/application imiquimod or 0.3% imiquimod cream) was applied to the backs of mice 3X/week for 24 months. A statistically significant increase in the incidence of liver adenomas and carcinomas was noted in high dose male mice compared to control male mice (96X MIRED based on AUC comparisons). An increased number of skin papillomas was observed in vehicle cream control group animals at the treated site only.

In a 52-week dermal photo-carcinogenicity study, the median time to onset of skin tumor formation was decreased in hairless mice following chronic topical dosing (3X/week; 40 weeks of treatment followed by 12 weeks of observation) with concurrent exposure to UV radiation (5 days per week) with vehicle alone. No additional effect on tumor development beyond the vehicle effect was noted with the addition of the active ingredient, imiquimod, to the vehicle cream.

Imiquimod revealed no evidence of mutagenic or elastogenic potential based on the results of five in vitro genotoxicity tests (Ames assay, mouse lymphoma L5178Y assay, Chinese hamster ovary cell chromosome aberration assay, human lymphocyte chromosome aberration assay and SHE cell transformation assay) and three in vivo genotoxicity tests (rat and hamster bone marrow cytogenetics assay and a mouse dominant lethal test).

Daily oral administration of imiquimod to rats, throughout mating, gestation, parturition and lactation, demonstrated no effects on growth, fertility or reproduction, at doses up to 57X MRHD based on AUC comparisons.

14   CLINICAL STUDIES

In two double-blind, randomized, placebo-controlled clinical studies, 601 subjects with EGW were treated with 3.75% imiquimod cream, or a matching placebo cream. Studies enrolled subjects aged from 15 to 81 years. The baseline wart area ranged from 6 to 5579 $mm^2$ and the baseline wart count ranged from 2 to 48 warts. Most subjects had two or more treated anatomic areas at Baseline. Anatomic areas included: inguinal, perineal, and perianal areas (both genders); the glans penis, penis shaft, scrotum, and foreskin (in men); and the vulva (in women). Up to one packet of study cream was applied once daily to each wart identified at Baseline and any new wart that appeared during the treatment period. The study cream was applied to all warts prior to normal sleeping hours and left on for approximately 8 hours. Subjects continued applying the study cream for up to 8 weeks or until they achieved complete clearance of all (baseline and new) warts in all anatomic areas. Subjects not achieving complete wart clearance by the Week 8 visit (end of treatment, EOT), were evaluated for up to 8 weeks or until they achieved complete clearance during an additional 8 week no-treatment period. Subjects who achieved complete clearance of all warts at any time until the Week 16 visit entered a 12 week follow-up for recurrence period.

Efficacy was assessed by wart counts (those present at Baseline and new warts appearing during the study) at EOS (i.e., up to 16 weeks from Baseline).

Complete clearance required clearance of all warts in all anatomic areas. Partial clearance rate was defined as the proportion of subjects with at least a 75% reduction in the number of baseline warts at EOS. Percent reductions were measured relative to the numbers of warts at Baseline. Complete and partial clearance rates, and percent reductions in wart counts from baseline are shown in the table below (by overall rate and by gender).

Table 3: Efficacy Endpoints

|  | Zyclara® Cream 3.75% | Placebo Cream |
|---|---|---|
| Complete Clearance Rate | | |
| Overall | 28.3% (113/399) | 9.4% (19/202) |
| Females | 36.6% (79/216) | 14.2% (15/106) |
| Males | 18.6% (34/183) | 4.2% (4/96) |
| Partial Clearance Rate | | |
| Overall | 38.3% (153/399) | 11.9% (24/202) |
| Females | 47.7% (103/216) | 17.0% (18/106) |
| Males | 27.3% (50/183) | 6.3% (6/96) |
| Percent Reduction of EGW (Median) | | |
| Overall | 50.0% | 0.0 |
| Females | 70.7% | 0.0 |
| Males | 23.3% | 0.0 |

The numbers of subjects who remained clear of EGW at the end of 12 week follow-up for recurrence period are shown in Table 4 below:

Table 4: Sustained Complete Clearance

|  | Zyclara® Cream, 3.75% | Placebo Cream |
|---|---|---|
| Cleared and entered Follow-up | 102 | 13 |
| Remained Clear | 71 | 12 |

16  HOW SUPPLIED/STORAGE AND HANDLING

Zyclara® (imiquimod) Cream, 3.75%, is supplied in single-use packets which contain 250 mg of the cream. Available as: Dose Pack of 28 packets NDC 29336-710-28.

Store at 25°C (77°F); excursions permitted to 15° to 30°C (59° to 86°F) [See USP Controlled Room Temperature].

Avoid freezing.

*Keep out of reach of children.*

17  PATIENT COUNSELING INFORMATION

*See FDA-Approved Patient Labeling (17. 7)*

17.1  Instructions for Administration:

Zyclara® Cream should be used as directed by a physician. *[see Dosage and Administration (2)]* Zyclara® Cream is for external use only. Contact with the eyes, lips and nostrils should be avoided. *[see Indications and Usage (1) and Dosage and Administration (2)]*

The treatment area should not be bandaged or otherwise occluded. Partially-used packets should be discarded and not reused. The prescriber should demonstrate the proper application technique to maximize the benefit of Zyclara® Cream therapy.

It is recommended that patients wash their hands before and after applying Zyclara® Cream.

17.2  Local Skin Reactions:

Patients may experience local skin reactions during treatment with Zyclara® Cream. Potential local skin reactions include erythema, edema, erosions/ulcerations, weeping/exudate, flaking/scaling/dryness, and scabbing/crusting. These reactions can range from mild to severe in intensity and may extend beyond the application site onto the surrounding skin. Patients may also experience application site reactions such as itching, irritation or pain. *[see Adverse Reactions (6)]*

Local skin reactions may be of such an intensity that patients may require rest periods from treatment. Treatment with Zyclara® Cream can be resumed after the skin reaction has subsided, as determined by the physician. Treatment should not be extended beyond 8 weeks due to missed doses or rest periods. Patients should contact their physician promptly if they experience any sign or symptom at the application site that restricts or prohibits their daily activity or makes continued application of the Zyclara® Cream difficult.

Because of local skin reactions, during treatment and until healed, the treatment area is likely to appear noticeably different from normal skin. Localized hypopigmentation and hyperpigmentation have been reported following use of imiquimod cream. These skin color changes may be permanent in some patients.

17.3  Systemic Reactions:

Patients may experience flu-like systemic signs and symptoms during treatment with Zyclara® Cream. Systemic signs and symptoms may include fatigue, fever, myalgia, malaise, and nausea. *[see Adverse Reactions (6)]* An interruption of dosing and assessment of the patient should be considered.

17.4 Recommended Administration

Dosing is once daily before bedtime to the skin of the affected wart areas. Zyclara® Cream treatment should continue until there is total clearance of the genital/perianal warts or for up to 8 weeks.

It is recommended that the treatment area be washed with mild soap and water approximately 8 hours following Zyclara® Cream application.

It is common for patients to experience local skin reactions such as erythema, erosion, excoriation/flaking, and edema at the site of application or surrounding areas. Most skin reactions are mild to moderate.

Sexual (genital, anal, oral) contact should be avoided while Zyclara® Cream is on the skin. Application of Zyclara® Cream in the vagina is considered internal and should be avoided. Female patients should take special care if applying the Zyclara® Cream at the opening of the vagina because local skin reactions on the delicate moist surfaces can result in pain or swelling, and may cause difficulty in passing urine.

Uncircumcised males treating warts under the foreskin should retract the foreskin and clean the area daily.

New warts may develop during therapy, as Zyclara® Cream is not a cure.

The effect of Zyclara® Cream on the transmission of genital/perianal warts is unknown. Zyclara® Cream may weaken condoms and vaginal diaphragms, therefore concurrent use is not recommended.

Should severe local skin reaction occur, the Zyclara® Cream should be removed by washing the treatment area with mild soap and water.

17.7 FDA-Approved Patient Labeling 17.8 Patient Information

Zyclara® [imiquimod] Cream, 3.75% (Imiquimod)

IMPORTANT: Not for mouth, eye, or vaginal use

Read the Patient Information that comes with Zyclara® Cream before you start using it and each time you get a refill. There may be new information. This leaflet does not take the place of talking with your healthcare provider about your medical condition or treatment. If you do not understand the information, or have any questions about Zyclara® Cream, talk with your healthcare provider or pharmacist.

What is Zyclara® Cream?

- Zyclara® Cream is a skin use only (topical) medicine used to treat external genital and perianal warts in people 12 years and older.

Zyclara® Cream does not work for everyone.

- Zyclara® Cream may not completely cure your genital or perianal warts. New warts may develop during treatment with Zyclara® Cream. It is not known if Zyclara® Cream can stop you from spreading genital or perianal warts to other people. For your own health and the health of others, it is important to practice safer sex. Talk to your healthcare provider about safer sex practices.

Who should not use Zyclara® Cream?

- Zyclara® Cream has not been studied in children under 12 years old for external genital and perianal warts.

Before using Zyclara® Cream, tell your healthcare provider:

- about all your medical conditions, including if you
    - are pregnant or planning to become pregnant. It is not known if Zyclara® Cream can harm your unborn baby.
    - are breastfeeding. It is not known if Zyclara® Cream passes into your milk and if it can harm your baby.
- about all the medicines you take including prescription and non-prescription medicines, vitamins and herbal supplements. Especially tell your healthcare provider if you have had other treatments for genital or perianal warts. Zyclara® Cream should not be used until your skin has healed from other treatments.

How should I use Zyclara® Cream?

- Use Zyclara® Cream exactly as prescribed by your healthcare provider. Zyclara® Cream is for skin use only. Do not take by mouth and do not get Zyclara® Cream in or near your eyes, lips or nostrils. Do not use Zyclara® Cream unless your healthcare provider has taught you the right way to use it. Talk to your healthcare provider if you have any questions.
- Your healthcare provider will tell you where to apply Zyclara® Cream and how often and for how long to apply it for your condition. Do not use Zyclara® Cream longer than prescribed. Using too much Zyclara® Cream, or using it too often, or for too long can increase your chances for having a severe skin reaction or other side effect. Talk to your healthcare provider if Zyclara® Cream does not work for you.
- Zyclara® Cream is applied once a day.

Zyclara® Cream is usually left on the skin for approximately 8 hours. Treatment should continue until the warts are completely gone or for up to 8 weeks.

Applying Zyclara® Cream

Zyclara® Cream should be applied just before your bedtime.
- Wash the area to be treated with mild soap and water. Allow the area to dry.
  - Uncircumcised males treating warts under their penis foreskin must pull their foreskin back and clean before treatment and clean daily during the weeks of treatment.
- Wash your hands
- Open a new packet of Zyclara® Cream just before use.
- Apply a thin layer of Zyclara® Cream only to the affected area or areas to be treated. Do not use more Zyclara® Cream than is needed to cover the treatment area. Do not use more than one packet for each application.
- Rub the cream in all the way to the affected area or areas.
- Do not get Zyclara® Cream in or around your eyes or mouth.
- Do not get Zyclara® Cream in the anus when applying to perianal warts.
- Female patients treating genital warts must be careful when applying Zyclara® Cream around the vaginal opening. Female patients should take special care if applying the Zyclara® Cream at the opening of the vagina because local skin reactions on the delicate moist surfaces can cause pain or swelling, and may cause problems passing urine. Do not put Zyclara® Cream in your vagina.

- Do not cover the treated area with an airtight bandage. Cotton gauze dressings can be used. Cotton underwear can be worn after applying Zyclara® Cream to the genital or perianal area.
- Safely throw away the open packet of Zyclara® Cream so that children and pets cannot get it. The open packet should be thrown away even if all the Zyclara® Cream was not completely used.
- After applying Zyclara® Cream, wash your hands well.
- Leave the Zyclara® Cream on the affected area or areas for the time prescribed by your healthcare provider. Do not bathe or get the treated area wet before the right time has passed. Do not leave Zyclara® Cream on your skin longer than prescribed.
- After about 8 hours, wash the treated area or areas with mild soap and water.
- If you forget to apply Zyclara® Cream, continue on your regular schedule and do not make up the missed dose(s).
- If you get Zyclara® Cream in your mouth or in your eyes rinse well with water right away.

What should I avoid while using Zyclara® Cream?

- Do not cover the treated site with bandages or other closed dressings. Cotton gauze dressings are okay to use, if needed. Cotton underwear can be worn after treating the genital or perianal area.
- Do not get Zyclara® Cream in or near the eyes, lips or nostrils.
- Do not put Zyclara® Cream in your vagina or anus.
- Do not use sunlamps or tanning beds, and avoid sunlight to the treated area as much as possible during treatment with Zyclara® Cream.
- Do not have sexual contact including genital, anal, or oral sex when Zyclara® Cream is on your genital or perianal skin. Zyclara® Cream may weaken condoms and vaginal diaphragms. This means they may not work as well to prevent pregnancy. For your own health and the health of others, it is important to practice safer sex. Talk to your healthcare provider about safer sex practices.

What are the possible side effects of Zyclara® Cream?

Side effects with Zyclara® Cream may include skin reactions at the treatment site such as:

- redness
- swelling
- a sore, blister, or ulcer
- skin that becomes hard or thickened
- skin peeling
- scabbing and crusting
- itching
- burning
- changes in skin color that do not always go away During treatment and until the skin has healed, your skin in the treatment area is likely to appear noticeably different from normal skin. Side effects, such as redness, scabbing, itching and burning are common at the site where Zyclara® Cream is applied, and sometimes the side effects go outside of the area where Zyclara® Cream was applied. Swelling, small open sores and drainage may also be experienced with use of Zyclara® Cream. You may also experience itching, irritation or pain. Patients should be aware that new warts may develop during treatment, as Zyclara® Cream may not be a cure. Many people see reddening or swelling on or around the application site during the course of treatment. If you have questions regarding treatment or local skin reactions, please talk with your healthcare provider.

You have a higher chance for severe skin reactions if you use too much Zyclara® Cream or use it the wrong way. Stop Zyclara® Cream right away and call your healthcare provider if you get any skin reactions that affect your daily activities, or that do not go away. Sometimes, Zyclara® Cream must be stopped for a while to allow your skin to heal. Talk to your healthcare provider if you have questions about your treatment or skin reactions.

Other side effects of Zyclara® Cream include pain, fever, muscle aches, and may also include headache, back pain, joint aches, tiredness, flu-like symptoms, nausea, and diarrhea.

If the reactions seem excessive, if either skin breaks down or sores develop during the first week of treatment, if flu-like symptoms develop or if you begin to not feel well at anytime, stop applying Zyclara® Cream and contact your healthcare provider.

These are not all the side effects of Zyclara® Cream. For more information, ask your healthcare provider or pharmacist.

How do I store Zyclara® Cream?

- Store Zyclara® Cream at 77°F (25°C). [59° to 86°F; 15° to 30°C]. Do not freeze.
- Safely throw away Zyclara® Cream that is out of date or that you do not need.
- Keep Zyclara® Cream and all medicines out of the reach of children.

General information about Zyclara® Cream

Medicines are sometimes prescribed for conditions that are not mentioned in patient information leaflets. Do not use Zyclara® Cream for a condition for which it was not prescribed. Do not give Zyclara® Cream to other people, even if they have the same symptoms you have.

This leaflet summarizes the most important information about Zyclara® Cream. If you would like more information, talk with your healthcare provider. You can ask your pharmacist or healthcare provider for information about Zyclara® Cream that is written for the healthcare provider. If you have other questions about Zyclara® Cream, call 1-800-328-0255.

What are the ingredients in Zyclara® Cream?

Active Ingredient: imiquimod

Inactive ingredients: isostearic acid, cetyl alcohol, stearyl alcohol, white petrolatum, polysorbate 60, sorbiran monostearate, glycerin, xanthan gum, purified water, benzyl alcohol, methylparaben, and propylparaben.

Manufactured by:
3M Health Care Limited, Loughborough LE11 1EP England
Distributed by:
Graceway Pharmaceuticals, LLC, Bristol, TN 37620

Attachment XI

[000322]  CANADA PRODUCT MONOGRAPH

(Actinic Keratosis)

ZYCLARA®

(imiquimod) Cream, 3.75%

250 mg single-dose packet

Immune response modifier

Graceway Pharmaceuticals

252 Pall Mall St., Suite 302

London, Ontario

Canada

N6A 5P6

Date of Preparation:

January 13, 2009

Submission Control No: Not yet assigned

TABLE OF CONTENTS

PART I: HEALTH PROFESSIONAL INFORMATION ............................................................. 229
    SUMMARY PRODUCT INFORMATION ......................................................................... 229
    INDICATIONS AND CLINICAL USE ............................................................................... 229
    CONTRAINDICATIONS ..................................................................................................... 229
    WARNINGS AND PRECAUTIONS ................................................................................... 229
    ADVERSE REACTIONS ..................................................................................................... 232
    DRUG INTERACTIONS .................................................................................................... 234
    DOSAGE AND ADMINISTRATION ................................................................................. 235
    OVERDOSAGE ................................................................................................................... 236
    ACTION AND CLINICAL PHARMACOLOGY ............................................................... 236
    STORAGE AND STABILITY ............................................................................................. 237
    DOSAGE FORMS, COMPOSITION AND PACKAGING ................................................ 237

PART II: SCIENTIFIC INFORMATION ............................................................................... 239
    PHARMACEUTICAL INFORMATION ............................................................................. 239
    CLINICAL TRIALS ............................................................................................................ 240
    DETAILED PHARMACOLOGY ........................................................................................ 241
    TOXICOLOGY ................................................................................................................... 243
    REFERENCES .................................................................................................................... 245

PART III: CONSUMER INFORMATION ............................................................................. 248

ZYCLARA®

(imiquimod) Cream, 3.75%

PART I: HEALTH PROFESSIONAL INFORMATION FOR ACTINIC KERATOSIS
SUMMARY PRODUCT INFORMATION

| Route of Administration | Dosage Form / Strength | Clinically Relevant Nonmedicinal Ingredients |
|---|---|---|
| Topical | Cream / 9.4 mg imiquimod per 250 mg single-dose packet (3.75 % w/w) | *For a complete listing see Dosage Forms, Composition and Packaging section.* |

INDICATIONS AND CLINICAL USE

Zyclara® Cream is indicated for the topical treatment of clinically typical visible or palpable actinic keratoses (AK) of the entire face or balding scalp in adults.

CONTRAINDICATIONS

Zyclara® Cream is contraindicated in individuals with a history of sensitivity reactions to any of its components. It should be discontinued if hypersensitivity to any of its ingredients is noted.

WARNINGS AND PRECAUTIONS

General

The efficacy of Zyclara® in the prevention of squamous cell carcinoma (SCC) associated with AK has not been established (see PHARMACOLOGY, Clinical Studies).

Hypersensitivity reactions (urticaria) and erythema multiform have been reported in patients receiving imiquimod Cream. Causality has not been established and no other reports of similar cases have been reported in post-marketing surveillance. Zyclara® Cream should be discontinued immediately if these events occur.

The efficacy and safety of Zyclara® Cream have not been established for patients with Basal Cell Nevus Syndrome or Xeroderma Pigmentosum.

The safety and efficacy of Zyclara® Cream in immunosuppressed patients have not been established.

Local Skin Reactions

Intense local skin reactions including skin weeping or erosion can occur after a few applications of Zyclara® Cream and may require an interruption of dosing. *(see Dosage and Administration and Adverse* Reactions) Zyclara® Cream has the potential to exacerbate inflammatory conditions of the skin, including chronic graft versus host disease.

Local skin reactions such as erythema, erosion, excoriation/flaking, and edema are common.

Should a severe local skin reaction occur, the Zyclara® Cream should be removed by washing the treatment area with mild soap and water. Treatment with Zyclara® can be resumed after the skin reaction has subsided.

Provocative repeat insult patch test studies involving induction and challenge phases produced no evidence that imiquimod cream causes photoallergenicity or contact sensitization in healthy skin; however, cumulative irritancy testing revealed the potential for imiquimod cream to cause irritation, and application site reactions were reported in clinical studies *(see Adverse Reactions)*.

Systemic Reactions

Flu-like signs and symptoms may accompany, or even precede, local skin reactions and may include fatigue, nausea, fever, myalgias, arthralgias, and chills. An interruption of dosing and an assessment of the patient should be considered. *(see Adverse Reactions)*

Ultraviolet Light Exposure

Exposure to sunlight (including sunlamps) should be avoided or minimized during use of Zyclara® Cream because of concern for heightened sunburn susceptibility. Patients should be warned to use protective clothing (e.g. hat) when using Zyclara® Cream. Patients with sunburn should be advised not to use Zyclara® Cream until fully recovered. Patients who may have considerable sun exposure, e.g., due to their occupation, and those patients with inherent sensitivity to sunlight should exercise caution when using Zyclara® Cream. Phototoxicity has not been adequately assessed for Zyclara® Cream. The enhancement of ultraviolet carcinogenicity is not necessarily dependent on phototoxic mechanisms. Despite the absence of observed phototoxicity in humans *(see PHARMACOLOGY, Clinical Studies)*, imiquimod cream shortened the time to skin tumour formation in an animal photoco-carcinogenicity study *(see Carcinogenesis, Mutagenesis, Impairment of Fertility)*. Therefore, it is prudent for patients to minimize or avoid natural or artificial sunlight exposure.

Carcinogenesis and Mutagenesis

Two-year bioassays in Wistar rats (up to 3 mg/kg orally per day) and CD-1 mice (up to 4.5 mg/kg applied topically 3 times per week) showed no evidence of a carcinogenic effect in male and female rats and female mice. Liver tumours were increased in male mice exposed to the highest dose concentration, compared to the unexposed controls. However, the number of tumours was within the range seen historically for male CD-1 mice. It is generally accepted that an increase in liver tumours in male mice, in the absence of other neoplastic responses in mice or rats, is not indicative of a carcinogenic risk for humans.

In a photocarcinogenicity study in hairless mice, animals received Zyclara® Cream 3 times per week at imiquimod concentrations of 0.03%, 0.1% and 0.3% and were irradiated with solar ultraviolet light for 5 days each week for 40 weeks and observed an additional 12 weeks.

Vehicle cream enhanced UVR-induced skin tumour development. Zyclara® Cream had no additional effect on tumour development beyond the vehicle effect (i.e., the addition of the active ingredient, imiquimod, to the vehicle cream did not result in an additional effect beyond the vehicle effect on tumour development).

Special Populations

Pregnant Women: Imiquimod was not teratogenic in rat or rabbit teratology studies. In rats at a high maternally toxic dose (28 times human dose on a mg/m$^2$ basis), reduced pup weights and delayed ossification were observed. However, there are no adequate and well-controlled studies in pregnant women. Because animal reproduction studies are not always predictive of human response, this drug should be used during pregnancy only if the potential benefit justifies the potential risk to the fetus.

Nursing Women: It is not known whether topically applied imiquimod is excreted in human milk. Because many drugs are excreted in human milk, caution should be exercised when Zyclara® Cream is administered to nursing women.

Pediatrics (< 18 years of age): Actinic keratosis is not a condition generally seen within the pediatric population. Safety and efficacy in patients below the age of 18 years have not been established.

Geriatrics (> 65 years of age): Of the 160 subjects treated with Zyclara® Cream in the clinical studies, 78 subjects were 65 years or older. No overall differences in safety or effectiveness were observed between these subject and younger subjects. No other clinical experience has identified differences in responses between the elderly and younger subjects, but greater sensitivity of some older individuals cannot be ruled out.

ADVERSE REACTIONS
Adverse Drug Reaction Overview

Because clinical trials are conducted under widely varying conditions, adverse reaction rates observed in the clinical trials of a drug cannot be directly compared to rates in the clinical trials of another drug and may not reflect the rates observed in practice.

Clinical Trial Adverse Drug Reactions

The data described below reflect exposure to Zyclara® Cream or placebo in 319 subjects enrolled in two double-blind, placebo-controlled studies. Subjects applied Zyclara® Cream or placebo daily to the skin of the affected area (either the entire face or balding scalp) for two 2-week treatment cycles separated by a 2-week no treatment period.

Table 1: Adverse Reactions Occurring in > 1% of Zyclara®-Treated Subjects and at a Greater Frequency than with Placebo in the Combined Studies

| Preferred Term | Zyclara® Cream, 3.75% (N=160) | Placebo (N=159) |
|---|---|---|
| Headache | 10 (6.3%) | 5 (3.1%) |
| Application site pruritus | 7 (4.4%) | 1 (0.6%) |
| Fatigue | 7 (4.4%) | 0 (0%) |
| Nausea | 6 (3.8%) | 2 (1.3%) |
| Application site irritation | 5 (3.1%) | 0 (0%) |
| Application site pain | 5 (3.1%) | 0 (0%) |
| Pyrexia | 5 (3.1%) | 0 (0%) |
| Anorexia | 4 (2.5%) | 0 (0%) |
| Dizziness | 4 (2.5%) | 0 (0%) |
| Herpes simplex | 4 (2.5%) | 1 (0.6%) |
| Pain | 4 (2.5%) | 0 (0%) |
| Chest pain | 3 (1.9%) | 0 (0%) |
| Diarrhea | 3 (1.9%) | 0 (0%) |
| Lymphadenopathy | 3 (1.9%) | 0 (0%) |
| Application Site Swelling | 2 (1.3%) | 0 (0%) |
| Arthralgia | 2 (1.3%) | 0 (0%) |
| Blood glucose increased | 2 (1.3%) | 0 (0%) |
| Dermatitis | 2 (1.3%) | 0 (0%) |
| Food poisoning | 2 (1.3%) | 0 (0%) |
| Insomnia | 2 (1.3%) | 0 (0%) |
| Seborrhoeic keratosis | 2 (1.3%) | 0 (0%) |
| Squamous cell carcinoma | 2 (1.3%) | 1 (0.6%) |
| Vomiting | 2 (1.3%) | 1 (0.6%) |

Table 2: Application Site Reactions in Zyclara®-Treated Subjects as Assessed by the Investigator

| Included Term | Zyclara®- Cream, 3.75%* (N=160) | Placebo* (N-159) |
|---|---|---|
| Any application site reaction | 17 (10.6%) | 2 (1.3%) |
| Application site pruritus | 7 (4.4%) | 1 (0.6%) |
| Application site irritation | 5 (3.1%) | 0 (0%) |
| Application site pain | 5 (3.1%) | 0 (0%) |
| Application site swelling | 2 (1.3%) | 0 (0%) |
| Application site paraesthesia | 1 (0.6%) | 1 (0.6%) |

| Application site scar | 1 (0.6%) | 0 (0%) |

* up to 2 packets daily

Local skin reactions were collected independently of the adverse event "application site reaction" in an effort to provide a better picture of the specific types of local reactions that might be seen. The most frequently reported local skin reactions were erythema, flaking/scaling/dryness, and scabbing/crusting. The prevalence and severity of local skin reactions that occurred during controlled studies are shown in the following table.

Table 3: Local Skin Reactions in the Treatment Area in Zyclara®-Treated Subjects as Assessed by the Investigator

|  | Zyclara® Cream, 3.75% (N = 160) | | Placebo (N = 159) | |
| --- | --- | --- | --- | --- |
|  | All Grades | Severe | All Grades | Severe |
| Erythema | 154 (96.3%) | 40 (25.2%) | 124 (78.0%) | 0 (0.0%) |
| Edema | 120 (75.0%) | 9 (5.7%) | 31 (19.5%) | 0 (0.0%) |
| Weeping/Exudate | 81 (50.6%) | 9 (5.7%) | 6 (3.8%) | 0 (0.0%) |
| Flaking/Scaling/Dryness | 147 (91.9%) | 13 (8.2%) | 123 (77.4%) | 2 (1.3%) |
| Scabbing/Crusting | 149 (93.1%) | 22 (13.8%) | 72 (45.3%) | 0 (0.0%) |
| Erosion/Ulceration | 99 (61.9%) | 17 (10.7%) | 14 (8.8%) | 0 (0.0%) |

Other adverse events observed in subjects treated with Zyclara® Cream in treatment regimens other than two 2-week treatment cycles include: application site bleeding, cheilitis, chills, herpes zoster, influenza-like illness, lethargy, myalgia, pancytopenia and pruritus.

Post-Market Adverse Drug Reactions

There is no post-marketing data available for the Zyclara® Cream, 3.75% product.

DRUG INTERACTIONS

Overview

Interactions between Zyclara® Cream with other drugs have not been established.

DOSAGE AND ADMINISTRATION

Recommended Dose and Dosage Adjustment

Zyclara® Cream should be applied once daily before bedtime to the skin of the affected area (entire face or balding scalp) for two treatment cycles of 2 weeks each separated by a 2-week no-treatment period or as directed by physician.

Administration

Before applying the Zyclara® Cream, the patient should wash the treatment area with mild soap and water and allow the area to dry thoroughly. Zyclara® Cream should be applied as a thin film to the entire treatment area and rubbed in until the Zyclara® Cream is no longer visible. Up to 2 packets of Zyclara® Cream may be applied to the treatment area at each application. Zyclara® Cream should be left on the skin for approximately 8 hours, after which time the Zyclara® Cream should be removed by washing the area with mild soap and water. The prescriber should demonstrate the proper application technique to maximize the benefit of Zyclara® Cream therapy.

Use in or near the eyes, lips and nostrils should be avoided.

Local skin reactions in the treatment area are common. *(see Adverse Reactions)* A rest period of several days may be taken if required by the patients discomfort or severity of the local skin reaction. However, each treatment cycle should not be extended beyond 2 weeks due to missed doses or rest periods. Response to treatment cannot be adequately assessed until resolution of local skin reactions. Lesions that do not respond to treatment should be carefully reevaluated and management reconsidered. Zyclara® Cream is packaged in single-use packets. Partially-used packets should be discarded and not reused. The application site is not to be occluded.

Missed Dose

Each treatment cycle should not be extended beyond 2 weeks due to missed doses or rest periods.

OVERDOSAGE

Overdosage of Zyclara® Cream in humans is unlikely due to minimal percutaneous absorption. Animal studies reveal a rabbit dermal lethal imiquimod dose of greater than 5000 mg/kg. Persistent topical overdosing of Zyclara® Cream could result in an increased incidence of severe local skin reactions and may increase the risk for systemic reactions.

The most clinically serious adverse event reported following multiple oral imiquimod doses of $\geq 200$ mg was hypotension which resolved following oral or intravenous fluid administration.

ACTION AND CLINICAL PHARMACOLOGY

Mechanism of Action

*In vitro* studies have demonstrated that imiquimod induces the release of interferon alpha (IFN-α) and other cytokines from human monocytes/macrophages and keratinocytes. The panel of cytokines induced varied with the cell's tissue origin. Topical *in vivo* application of imiquimod cream on mouse skin resulted in increased concentrations of IFN and tumour necrosis factor (TNF) compared with skin of untreated mice.

Pharmacodynamics

The mechanism of action of imiquimod in treating actinic keratosis (AK) lesions is unknown. While the following have been observed, the clinical significance of these observations in AK is not known. In a study of 58 patients with AK treated with imiquimod 3 times per week, the response of biomarkers sensitive to imiquimod after 16 weeks of dosing increased compared to the response after the first dose. For interleukin-1 antagonist, the median concentration observed following multiple dosing was <2-fold higher than that after single dose administration, for interferon-α was $\leq$3-fold, and for 2'5'-oligoadenylate synthetase was approximately 3-fold.

Pharmacokinetics

Percutaneous absorption of imiquimod has been studied through intact healthy skin, the skin of genital warts, and lesions of sun damaged skin. Percutaneous absorption of [14C]imiquimod was minimal in a study involving six healthy subjects treated with a single topical application (5 mg) of [14C]imiquimod in cream formulation. No radioactivity was detected in the serum (lower limit of quantitation is 1 ng/mL) and < 0.9% of the radiolabelled dose was excreted in the urine and feces following topical application.

Absorption: Zyclara® Cream exhibited low systemic exposure to imiquimod and its metabolites when applied daily for 3 weeks (18.75 mg, 2 packets once daily) to the entire face and/or balding scalp (approximately 200 cm$^2$) of patients with AK (N=17). A mean (median) peak serum drug concentration at the end of week 3 was approximately 0.323 ng/mL. Steady-state levels were achieved in 2 weeks and T$_{max}$), ranged between 6 and 9 hours.

Excretion: The apparent half-life following topical dosing of 3.75% imiquimod cream was calculated as 29 hours after daily administration of 2 packets (18.75 mg) for 3 weeks.

Special Populations and Conditions

Age: No formal pharmacokinetic study was conducted to examine age related differences in the pharmacokinetic profile of imiquimod 3.75% cream.

Gender: During a 3 weeks treatment, the C$_{max}$ and AUC$_{0-24}$ on Day 21 appeared to be similar in female and male subjects and lower in male subjects who applied Zyclara® (imiquimod) Cream, 3.75% balding scalp rather than the face.

STORAGE AND STABILITY

Store between 15-25°C. Avoid freezing.

DOSAGE FORMS, COMPOSITION AND PACKAGING

Zyclara® Cream is supplied in single-use packets which contain 250 mg of the cream. Available as box of XX packets.

Each gram of Zyclara® contains 37.5 mg of imiquimod in an off-white oil-in-water vanishing cream base consisting of isostearic acid, cetyl alcohol, stearyl alcohol, white petrolatum, polysorbate 60, sorbitan monostearate, glycerin, xanthan gum, purified water, benzyl alcohol, methylparaben, and propylparaben.

PART II: SCIENTIFIC INFORMATION

PHARMACEUTICAL INFORMATION

Drug Substance

Proper name: Imiquimod (USAN, INN)

Chemical name: 1-(2-methylpropyl)-1H-imidazo [4,5-c] quinolin-4-amine

Molecular formula and molecular mass: $C_{14}H_{16}N_4$; MW = 240.3

Structural formula:

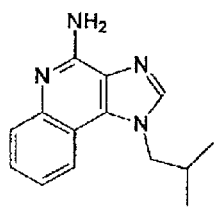

Physicochemical properties:

| | |
|---|---|
| Physical Form: | Crystalline solid that varies in colour from white to off-white or buff. The compound has no odour. |
| Solubility: | Practically insoluble in most common organic solvents and in aqueous systems except at extremely low pH conditions. It can be made soluble to the extent of at least 100 mg/mL in methanol (as a salt) upon the addition of a few drops of hydrochloric or acetic acid. Soluble in fatty acids such as oleic acid and isostearic acid. |
| pKa Value: | The ionization constant for imiquimod was determined by ultraviolet (UV) spectroscopy and pH-solubility to be about 7.5. |

Melting point: 297-299°C with sublimation.

CLINICAL TRIALS

Study demographics and trial design for studies considered pivotal are presented in Table 4.

Table 4: Summary of Patient Demographics for Pivotal Clinical Trials

| Study Number | Study Design | Duration of Treatment | Application Frequency/ Study Cream | No. Subjects in ITT (2.5%/3.75 %/Placebo No. Subjects in PP (2.5%/3.75%/ Placebo) | Sex (M/F) | Age in Years Mean (SD) | No. Discontinued (2.5%/3.75%/Placebo) |
|---|---|---|---|---|---|---|---|
| GW01-0702 | Phase 3, 1:1:1 Imiq 2.5%, Imiq 3.75%: Pla; dbleblind, parallel; subjects with AK. | 2 weeks treatment followed by 2 weeks of no treatment; then, 2 weeks treatment followed by 8 weeks of no treatment | Once daily | 242 (81/81/80) 218 (75/73/70) | 198/44 | 63.7 (10.1) | 3/7/5 |
| GW01-0704 | Phase 3, 1:1:1 Imiq 2.5%, Imiq 3.75%: Pla; dbleblind, parallel; subjects with AK. | 2 weeks treatment followed by 2 weeks of no treatment; then, 2 weeks treatment followed by 8 weeks of no treatment | Once daily | 237 (79/79/79) 207 (67/68/72) | 191/46 | 65.1 (9.9) | 3/4/4 |

AK = actinic keratosis; Imiq = imiquimod; Pla = placebo

In two double-blind, randomized, placebo-controlled clinical studies, 319 subjects with AK were treated with 3.75% imiquimod cream, or a matching placebo cream. Studies enrolled subjects >18 years of age with 5-20 typical visible or palpable AK lesions of the face or scalp in an area that exceeded 25cm$^2$. Study cream was applied to full lace or balding scalp once daily for two 2-week treatment cycles separated by a 2-week no-treatment period. Subjects then continued in the study for an 8-week follow-up period during which they returned for clinical observations and safety monitoring. Study subjects ranged from 36 to 90 years of age and 54% had Fitzpatrick skin type I or II. All Zyclara® Cream-treated subjects were Caucasians.

On a scheduled dosing day, the study cream was applied to the entire treatment area prior to normal sleeping hours and left on for approximately 8 hours. Efficacy was assessed by AK lesion counts at the 8-week post-treatment visit. All AKs in the treatment area were counted, including baseline lesions as well as new or sub-clinical AK lesions which appeared during therapy.

Complete clearance required clearance of all lesions. The partial clearance rate and percent reductions were measured relative to the numbers of AK lesions at Baseline. Partial clearance rate was defined as the proportion of subjects in whom the number of baseline AKs was reduced by 75% or more. Complete and partial clearance rates, and percent reductions in AK counts from baseline are shown in the table below.

Table 5: Efficacy Endpoints[a]

|  | Zyclara® Cream, 3.75% | Placebo Cream | p-value |
|---|---|---|---|
| Complete Clearance Rate | 35.6% (57/160) | 6.3% (10/159) | <0.001 |
| Partial Clearance Rate | 59.4% (95/160) | 22.6% (36/159) | <0.001 |
| Percent Reduction of AKs (median) | 81.8% | 25.0% | <0.001 |

[a] Studies GW01-0702 and GW01-0704

Sub-clinical AK lesions may become apparent in the treatment area during treatment with Zyclara® Cream. During the course of treatment, >85% (138/160) of subjects experienced an increase in AK lesions relative to the number present at baseline within the treatment area. Subjects with an increase in AK lesions had a similar response to those with no increase in AK lesions.

DETAILED PHARMACOLOGY

Pharmacodynamics: Imiquimod is an immune response modifier that is not a nucleoside analogue. Saturable binding studies suggest a membrane receptor for imiquimod exists on responding cells. *In vitro* studies have demonstrated that imiquimod induces the production of IFN and other cytokines from a variety of human and animal cells. In addition, cytokines were produced following dermal application and oral administration in various laboratory animals and in human studies following oral administration of imiquimod. In animal models imiquimod is an effective antiviral and antitumour agent whose activity is principally due to induction of alpha interferon but other cytokines are also involved. Imiquimod induced a local immune response and a decrease in HPV-DNA for genotypes 6 and 11 in patients treating external genital/perianal warts. The immune response was characterized by significant increases in mRNA for IFN-α, 2'5'-oligoadenylate synthetase and IFN-γ in wart tissue. Although these data suggest a sequence of immunologic events initiated by imiquimod therapy, the cause of wart regression seen with imiquimod therapy has not been established.

*In vitro* studies using isolated guinea pig myocardium, showed stimulation with tachyphylaxis development after multiple doses. Moderate to marked inhibition of agonist-induced contractions was observed in isolated guinea pig tracheal strips. Intravenous administration of a bolus dose of imiquimod caused CNS and cardiac stimulation in dogs. Little activity was found in inflammatory rat models. Some local anaesthetic activity, slight effect on locomotor, and slight effect on hexobarbital induced sleep time were observed in the mouse.

Pharmacokinetics and Metabolism: Animal and human dermal pharmacokinetic results indicate that minimal, if any, systemic absorption occurs following dermal application of imiquimod cream. Imiquimod was not quantifiable in the serum of rats dosed topically three times per week at 5 mg/kg for 4 weeks; low levels of metabolite were quantifiable after the last, but not after the first dose. In guinea pigs, after a single large (21 mg/kg) topical dose of [$^{14}$C] imiquimod as a 5% cream, only low concentrations of imiquimod were quantifiable in plasma.

Oral ADME (absorption, distribution, metabolism; elimination) studies in laboratory animals, revealed extensive biotransformation followed by both urinary and biliary excretion of metabolites. Tissue distribution is rapid with clearance after 2 to 3 days with the exception of pigmented tissues - skin and uveal tract of the eye. No evidence of ocular toxicity was found in six month oral rat and monkey imiquimod toxicity studies conducted at high daily doses.

Percutaneous absorption of 5% imiquimod cream following topical application for 8-12 hours was observed across the intact skin of healthy subjects and the affected skin of subjects with either genital warts or AK. In subjects with AK, urinary recovery less than 0.6% of the applied dose was seen. Because of this low percutaneus absorption, serum levels of imiquimod and metabolites were low or undetectable in these subjects.

TOXICOLOGY

Acute Toxicity: Acute dermal toxicity studies in rabbits with unformulated imiquimod under occlusion did not reveal any toxic effects at very high dose levels - 5000 mg/kg. When administered orally, intraperitoneally, subcutaneously or intravenously, single dose studies revealed that imiquimod produced central nervous system (CNS) stimulation and convulsions at lethal doses. However, signs of CNS toxicity did not occur when animals were given lower repeat doses (100 mg/kg or lower).

Table 6

| Species | Route | $LD_{50}$ (mg/kg) |
|---|---|---|
| Mouse | oral | 403 |
|  | intraperitoneal | 879 |
| Rat | oral | 1665 |
|  | intraperitoneal | 763 |
|  | subcutaneous | $\approx 20$ |
| Rabbit | dermal | > 5000 |
| Monkey | oral | > 200 |
|  | intravenous infusion | $\approx 8$ |
|  | intravenous bolus | > 6 |

Irritation/Sensitization Studies: Skin irritation studies in rabbits showed that imiquimod was non-irritating when dosed unformulated at 500 mg or formulated up to 250 mg per site. Unformulated imiquimod produced mild or no eye irritation in rabbits when applied unformulated at 100 mg/eye or formulated up to 5 mg/eye. Formulated imiquimod was not irritating to rat or rabbit vaginal tract when applied every other day for 10 days at 10 and 50 mg/dose respectively. Dermal sensitization studies in guinea pigs showed that the imiquimod cream was not a dermal sensitizer. Comparison of the dermal reaction to imiquimod cream in animal species (rat, mouse, rabbit) with clinical study results, reveals that mouse and rabbit results are comparable to humans. The more severe dermal irritation seen in the rat is not predictive of human response.

Long-Term Toxicity: Two repeat dose dermal toxicity studies in rats showed a compound related but non-dose related dermal irritation. A dose-related decrease in body weight of male rats was also observed. No systemic toxicity was found at doses up to 5 mg/kg three days per week for 4 weeks or at doses up to 2.5 mg/kg three days per week for 16 weeks.

The adverse effects observed for the high doses (10-30 mg/kg) in repeat dose oral toxicity studies in rats and monkeys could be related to exaggerated pharmacological effects of excessive cytokines induction and lymphoid stimulation: reduced body weight gains, anaemia, serum protein changes and death. High repeat daily doses of imiquimod did not produce necrosis in any organ; the compound is not cytotoxic. Recovery animals demonstrated that the adverse effects were readily reversible. An oral no-adverse-effect level of 3 mg/kg/day was determined in both rats and monkeys dosed daily for 6 months.

Carcinogenicity: Two-year bioassays in Wistar rats (up to 3 mg/kg orally per day) and CD-1 mice (up to 4.5 mg/kg applied topically 3 times per week) showed no evidence of a carcinogenic effect in male and female rats and female mice. Liver tumours were increased in male mice exposed to the highest dose concentration, compared to the unexposed controls. However, the number of tumours was within the range seen historically for male CD-1 mice. It is generally accepted that an increase in liver tumours in male mice, in the absence of other neoplastic responses in mice or rats, is not indicative of a carcinogenic risk for humans.

In a photocarcinogenicity study in hairless mice, animals received imiquimod cream 3 times per week at concentrations of 0.03%, 0.1% and 0.3% and were irradiated with solar ultraviolet light for 5 days each week for 40 weeks and observed an additional 12 weeks.

Vehicle cream enhanced UVR-induced skin tumour development. Imiquimod cream had no additional effect on tumour development beyond the vehicle effect (i.e., the addition of the active ingredient, imiquimod, to the vehicle cream did not result in an additional effect beyond the vehicle effect on tumour development).

Mutagenicity: Imiquimod was without effect in a series of eight mutagenicity assays including Ames, mouse lymphoma, CHO chromosome aberration, human lymphocyte chromosome aberration, SHE cell transformation, rat and hamster bone marrow cytogenetics, and mouse dominant lethal test.

REFERENCES

1. Arany I, Tyring S, Stanley MA, Tomai MA, Miller RL, Smith MH et al. Enhancement of the innate and cellular immune response in patients with genital warts treated with topical imiquimod cream 5%. Antiviral Res 1999;43:55-63.

2. Berman B, Bienstock L, Kuritzky L, Mayeaux EJ, Jr., Tyring SK. Actinic keratoses: sequelae and treatments. Recommendations from a consensus panel. J Fam Pract. May 2006;55(5)(suppl):1-8.

3. Bernstein DI, Harrison CJ. Effects of the Immunomodulating Agent R-837 on Acute and Latent Herpes Simplex Virus Type 2 Infections. Antimicro Agents and Chemotherapy 1989; 33(9):1511-1515.

4. Bernstein DI, Miller RL, Harrison CJ. Effects of Therapy with an Immunomodulator (Imiquimod, R-837) Alone and with Acyclovir on Genital HSV-2 Infection in Guinea-Pigs When Begun After Lesion Development. Antiviral Res 1993; 20:45-55.

5. Dahl MV. Imiquimod: An immune response modifier. J Am Acad Dermatol 2000;43(1):S1-5.

6. Edwards L. Imiquimod in clinical practice. J Am Mad Dermatol 2000;43(1):S12-17.

7. Edwards L, Ferenczy A, Eron L, Baker D, Owens ML, Fox TL et al. Self-administered topical 5% imiquimod cream for external anogenital warts. Arch Dermatol 1998;134:25-30.

8. Einspahr JG, Xu MJ, Warneke J, et al. Reproducibility and expression of skin biomarkers in sun-damaged skin and actinic keratoses. *Cancer Epidemiol Biomarkers Prev.* Oct 2006;15(10):1841-1848.

9. Gaspari AA, Sander DN. Immunotherapy of basal cell carcinoma: evolving approaches. Dermatol Surg 2003;29(10):1027-1034.

10. Gollnick H, Barasso R, Jappe U, Ward K, Eul A, Carey-Yard M et al. Safety and efficacy of imiquimod 5% cream in the treatment of penile genital warts in uncircumcised men when applied three times weekly or once per day. Int J STD & AIDS 2001;12:22-28.

11. Harrison CJ, Miller RL, Bernstein DI. Posttherapy Suppression of Genital Herpes Simplex Virus (HSV) Recurrences and Enhancement of HSV-Specific T-Cell Memory by Imiquimod in Guinea Pigs. Antimicro Agents and Chemo 1994; 38(9):2059-2064.

12. Kende M, Lupton HW, Canonico PG. Treatment of Experimental Viral Infections with Immuno-modulators. Adv Biosci 1988; 68:51-63.

13. Miller RL, Birmachu W, Gerster JF et al. Imiquimod Cytokine Induction and Antiviral Activity. Intl Antiviral News 1995; 3(7):111-113.

14. Miller RL, Gerster JF, Owens ML, Slade HB, Tomai MA. Imiquimod applied topically: a novel immune response modifier and new class of drug. Int J Immunopharm 1999;21:1-14.

15. Quatresooz P, Pierard-Franchimont C, Paquet P, et al. Crossroads between actinic keratosis and squamous cell carcinoma, and novel pharmacological issues. *Eur J Dermatoi.* Jan-Feb 2008;18(1):6-10.

16. Sauder DN. Immunomodulatory and pharmacologic properties of imiquimods. J Am Acad Dermatol 2000;43(1):S6-11.

17. Stockfleth E, Kerl H. Guidelines for the management of actinic keratoses. *Eur J Dermatol.* Nov-Dec 2006;16(6):599-606.

18. Testerman TL, Gerster JF, Imbertson LM et al. Cytokine Induction by the Immunomodulators Imiquimod and S-27609. J Leuk Biol 1995; 58:365-372.

19. Torres A, Storey L, Anders M, et al. Microarray analysis of aberrant gene expression in actinic keratosis: effect of the Toll-like receptor-7 agonist imiquimod. *Br J Dermatol.* Dec 2007;157(6):1132-47. Epub Oct 28 2007.

20. Tyring SK. Immune-response modifiers: A new paradigm in the treatment of human papillomavirus. Curr Ther Res 2000;60(9):584-596.

21. Tyring SK, Arany I, Stanley MA, Tomai MA, Miller RL, Smith MH et al. A randomized, controlled, molecular study of condylomata acuminata clearance during treatment with imiquimod. J Infect Dis 1998;178(August):551-555.

22. Valve M, Ortonne JP, Birch-Machin MA, Gupta G. Management of field change in actinic keratosis. *Br J Dermatol.* Dec 2007;157(s2):21-24.

23. Weeks CE, Gibson SJ. Induction of Interferon and Other Cytokines by Imiquimod and its Hydroxylated Metabolite R-842 in Human Blood Cells *In Vitro.* J Interferon Res 1994; 14:81-85.

24. Lebwohl M, Dinehart S, Whiting D, Lee PK, Tawfik N, Jorizzo J, Lee JH, Fox TL et al. Imiquimod 5% cream for the treatment of actinic keratosis: Results from two phase III, randomized, double-blind, parallel group, vehicle-controlled trials. J Am Acad Dermatol May 2004;50(5):714-21.

PART III: CONSUMER INFORMATION

<sup>Pr</sup>Zyclara®

(imiquimod) Cream, 3.75%

This leaflet is part III of a three-part "Product Monograph" published when Zyclara® was approved for sale in Canada and is designed specifically for Consumers. This leaflet is a summary and will not tell you everything about Zyclara®. Contact your doctor or pharmacist if you have any questions about the drug.

ABOUT THIS MEDICATION

What the medication is used for:

Zyclara® is the brand name for imiquimod cream, 3.75%. It is used to treat actinic keratosis (AK) in adults with normal immune systems. Actinic keratosis may be caused by too much sun exposure.

What it does:

Zyclara® cream is an immune response modifier. Zyclara® Cream is a medicine that works by stimulating your body's own immune response.

When it should not be used:

Zyclara® Cream can only be used if a doctor prescribes it for you.

Zyclara® Cream should only be used on the skin.

What the medicinal ingredient is:

Zyclara® Cream contains 37.5 mg of imiquimod per gram.

What the important nonmedicinal ingredients are:

Isostearic acid, cetyl alcohol, stearyl alcohol, white petrolatum, polysorbate 60, sorbitan monostearate, glycerin, xanthan gum, purified water, benzyl alcohol, methylparaben, and propylparaben.

*For a full listing of nonmedicinal ingredients see Part 1 of the product monograph.*

What dosage forms it comes in:

Zyclara® Cream is supplied in single-use packets which contain 250 mg of the cream. It is available as boxes of XX packets.

WARNINGS AND PRECAUTIONS

- Only use on the affected area of your skin.
- Use this Zyclara® Cream the way your doctor showed you.
- Do not rub Zyclara® Cream in your eyes, lips or nostrils.
- If you get Zyclara® Cream in your eyes, wash your eyes out with abundant amounts of water.
- Wear a hat, long sleeves and use sunscreen if you must be out in the sun. Avoid natural or artificial sunlight, for example tanning salons, as much as possible.

Medicines are sometimes prescribed for conditions that are not mentioned in patient information leaflets. Do not use Zyclara® Cream for a condition for which it was not prescribed. Do not give Zyclara® Cream to other people, even if they have the same symptoms you have.

BEFORE you use Zyclara® talk to your doctor or pharmacist if:
- you have ever had any unusual or allergic reaction to Zyclara® Cream.
- you have any allergies.
- you are thinking about having a baby, pregnant (about to have a baby), or breast-feeding your baby.
- you have had any other treatment for your Actinic Keratosis:

- any prescription and over-the-counter drugs you have used.
- any other non-drug treatments you have had for your condition.
- for example, freezing or surgery.

Zyclara® Cream should not be used while pregnant or breast-feeding unless your doctor tells you to.

INTERACTIONS WITH THIS MEDICATION

Drugs that may interact with Zyclara® include: none.

PROPER USE OF THIS MEDICATION

Usual dose:

- Use Zyclara® Cream exactly as prescribed by your healthcare provider. Zyclara® Cream is for skin use only. Do not take by mouth or use in or near your eyes, lips or nostrils. Do not use Zyclara® Cream unless your healthcare provider has taught you the right way to use it. Talk to your healthcare provider if you have any questions.

- Your healthcare provider will tell you where to apply Zyclara® Cream and how often and for how long to apply it for your condition. Do not use Zyclara® Cream longer than prescribed. Using too much Zyclara® Cream, or using it too often, or for too long can increase your chances for having a severe skin reaction or other side effect. Talk to your healthcare provider if Zyclara® Cream does not work for you.

- Zyclara® Cream is applied once a day for two-weeks. There is no treatment for the next two weeks. Zyclara® Cream is then applied once a day for another two-weeks.

- Do not cover the treated site with bandages or other closed dressings. Cotton gauze dressings are okay to use, if needed.

- Do not apply Zyclara® Cream in or near the eyes, lips or nostrils.

- Do not use sunlamps or tanning beds, and avoid sunlight as much as possible during treatment with Zyclara® Cream. Use sunscreen and wear protective clothing if you go outside during daylight.

Zyclara® Cream is usually left on the skin for about 8 hours. Treatment should continue for the full treatment course even if all actinic keratoses appear to be gone, unless you are told otherwise by your healthcare provider. Zyclara® Cream should be used to treat either the whole face or balding scalp.

Applying Zyclara® Cream

Zyclara® Cream should be applied just before your bedtime.
- Wash the area to be treated with mild soap and water. Allow the area to dry.
- Wash your hands
- Open a new packet(s) of Zyclara® Cream just before use
- Apply a thin layer of Zyclara® Cream only to the affected area or areas to be treated. Do not use more Zyclara® Cream than is needed to cover the treatment area. Do not use more than two packets for each application.
- Rub the Zyclara® Cream in all the way to the affected area or areas.
  o Do not get Zyclara® Cream in or around your eyes.
- Safely throw away the open packet of Zyclara® Cream so that children and pets cannot get it. The open packet should be thrown away even if all the Zyclara® Cream was not completely used.
- After applying Zyclara® Cream, wash your hands well.
- Leave the Cream on the affected area or areas for the time prescribed by your healthcare provider. Do not bathe or get the treated area wet before the right time has passed. Do not leave Zyclara® Cream on your skin longer than prescribed.
- After about 8 hours, wash the treated area or areas with mild soap and water.
- If you forget to apply Zyclara® Cream, continue on your regular schedule and do not make up the missed dose(s).
- If you get Zyclara® Cream in your mouth or in your eyes rinse well with water right away.
- Use Zyclara® Cream daily for 2-week treatment cycles, unless otherwise directed by the physician.
- The treatment period should not be extended beyond two 2-week treatment cycles weeks due to missed does or rest periods.

Overdose:

Persistent topical overdosing of Zyclara® Cream could result in an increased incidence of severe local skin reactions and may increase the risk for systemic reactions.

Missed Dose:

If you miss a dose of Zyclara® Cream, wait until the next night to apply it.

SIDE EFFECTS AND WHAT TO DO ABOUT THEM

Side effects with Zyclara® Cream may include skin reactions at the treatment site such as:

- redness
- swelling
- a sore, blister, or ulcer
- skin that becomes hard or thickened
- skin peeling
- scabbing and crusting
- itching
- burning
- changes in skin color that do not always go away During treatment and until the skin has healed, your skin in the treatment area is likely to appear noticeably different from normal skin. Side effects, such as redness, scabbing, itching and burning are common at the site where Zyclara® Cream is applied, and sometimes the side effects go outside of the area where Zyclara® Cream was applied. Swelling, small open sores and drainage may also be experienced with use of Zyclara® Cream. You may also experience itching, irritation or pain. Actinic keratoses that were not seen before may appear during treatment and may later go away. If you have questions regarding treatment or skin reactions, please talk with your healthcare provider.

You have a higher chance for severe skin reactions if you use too much Zyclara® Cream or use it the wrong way. Stop Zyclara® Cream right away and call your healthcare provider if you get any skin reactions that affect your daily activities, or that do not go away. Sometimes, Zyclara® Cream must be stopped for a while to allow your skin to heal. Talk to your healthcare provider if you have questions about your treatment or skin reactions.

Other side effects of Zyclara® Cream include headache, back pain, muscle aches, joint aches, tiredness, flu-like symptoms, swollen lymph nodes, nausea and diarrhea.

If the reactions seem excessive, if either skin breaks down or sores develop during the first week of treatment, if flu-like symptoms develop or if you begin to not feel well at anytime, stop applying Zyclara® Cream and contact your healthcare provider.

These are not all the side effects of Zyclara® Cream. For more information, ask your healthcare provider or pharmacist.

*This is not a complete list of side effects. For any unexpected effects while taking Zyclara®, contact your doctor or pharmacist.*

HOW TO STORE IT

Store Zyclara® Cream between 15-25° C. Do not freeze.

Safely throw away Zyclara® Cream that is out of date or that you do not need.

Keep Zyclara® Cream and all medicines out of the reach of children.

REPORTING SUSPECTED SIDE EFFECTS

To monitor drug safety, Health Canada through the Canada Vigilance Program collects information on serious and unexpected effects of drugs. If you suspect you have had a serious or unexpected reaction to this drug you may notify Canada Vigilance:

Toll-free telephone: 1-866-234-2345

Toll-free fax: 1-866-678-6789

Online: www.healthcanada.gc.ca/medeffect

By email: CanadaVigilance@hcsc.gc.ca

By regular mail:

Canada Vigilance National Office

Marketed Health Products Safety and Effectiveness

Information Bureau

Marketed Health Products Directorate

Health Products and Food Branch

Health Canada

Tunney's Pasture, AL 0701C

Ottawa, ON K1A 0K9

*NOTE: Should you require information related to the management of the side effect, please contact your healthcare provider before notifying Canada Vigilance. The Canada Vigilance Program does not provide medical advice.*

MORE INFORMATION

This document plus the full product monograph, prepared for health professionals can be found at:

http://www.gracewaypharma.ca or by contacting the sponsor, Graceway Pharmaceuticals, at: 1-800-328-0255

This leaflet was prepared by Graceway Pharmaceuticals, 252 Pall Mall St., Suite 302, London, Ontario, N6A 5P6

Last revised: January 13, 2009

Attachment XII

[000323] CANADA PRODUCT MONOGRAPH

(External Genital and Perianal Warts)

PRODUCT MONOGRAPH

ZYCLARA®

(imiquimod) Cream, 3.75%

9.4 mg per 250 mg single-dose packet

Immune response modifier

| | |
|---|---|
| Graceway Pharmaceuticals<br>252 Pall Mall St., Suite 302<br>London, Ontario<br>Canada<br>N6A 5P6 | Date of Preparation:<br>March 24, 2010 |

Submission Control No.:

TABLE OF CONTENTS

PART I: HEALTH PROFESSIONAL INFORMATION..................................................3
    SUMMARY PRODUCT INFORMATION .......................................................3
    INDICATIONS AND CLINICAL USE...............................................................3
    CONTRAINDICATIONS ..................................................................................4
    WARNINGS AND PRECAUTIONS................................................................4
    ADVERSE REACTIONS...................................................................................6
    DRUG INTERACTIONS ..................................................................................8
    DOSAGE AND ADMINISTRATION ..............................................................8
    OVERDOSAGE ...............................................................................................10
    ACTION AND CLINICAL PHARMACOLOGY .........................................10
    STORAGE AND STABILITY.........................................................................11
    DOSAGE FORMS, COMPOSITION AND PACKAGING ..........................11

PART II: SCIENTIFIC INFORMATION ...................................................................12
    PHARMACEUTICAL INFORMATION.......................................................12
    CLINICAL TRIALS........................................................................................13
    DETAILED PHARMACOLOGY ..................................................................15
    TOXICOLOGY ...............................................................................................16
    REFERENCES ................................................................................................19

PART III: CONSUMER INFORMATION ..................................................................21

Zyclara® (imiquimod) Cream, 3.75%

PART I: HEALTH PROFESSIONAL INFORMATION

SUMMARY PRODUCT INFORMATION

| Route of Administration | Dosage Form/ Strength | Clinically Relevant Nonmedicinal Ingredients |
|---|---|---|
| Topical | Cream / 9.4 mg imiquimod per 230 mg single-close packet (3.75 % w/w) | *For a complete listing see Dosage Forms Composition and Packaging, section.* |

INDICATIONS AND CLINICAL USE

Zyclara® Cream is indicated for the treatment of external genital and perianal warts/condyloma acuminate, whether present at the start of therapy or emerging during therapy in patients 12 years or older.

Geriatrics (>65 years of age)

Data from EGW clinical trials was too sparse to evaluate treatment effects in this population (see WARNINGS AND PRECAUTIONS, Geriatrics).

Pediatrics

Safety and efficacy in patients below the age of 12 years have not been established (See WARNINGS AND PRECAUTIONS, Pediatrics).

Immunosuppressed

The safety and efficacy of Zyclara® Cream in immunosuppressed patients have not been established (SEE WARNINGS AND PRECAUTIONS, Immune).

CONTRAINDICATIONS

Zyclara® Cream is contraindicated in individuals with a history of sensitivity reactions to imiquimod or to any of the components in the formulation. It should be discontinued if hypersensitivity to any of its ingredients is noted (See WARNINGS AND PRECAUTIONS, Sensitivity).

WARNINGS AND PRECAUTIONS
General

Zyclara® Cream has not been evaluated for the treatment of urethral, intra vaginal, cervical, rectal, or intra-anal human papilloma viral disease.

Systemic Reactions

Flu-like signs and symptoms may accompany, or even precede, local skin reactions and may include fatigue, nausea, fever, myalgias, arthralgias, and chills. An interruption of dosing or dose adjustment and an assessment of the patient should be considered (See ADVERSE REACTIONS)

Carcinogenesis and Mutagenesis

In a hairless mouse photocarcinogenicity study with solar ultraviolet light irradiation, imiquimod cream enhanced UVR-induced skin tumour development, but not beyond that of the vehicle cream. Vehicle cream alone enhanced ultraviolet; induced skin tumour development (See TOXICOLOGY, Carcinogenicity). It is recommended that patients minimize or avoid natural or artificial sunlight exposure to the treatment area(s) during treatment with Zyclara®.

Immune

The safety and efficacy of Zyclara® Cream in immunosuppressed patients have not been established.

Zyclara® topical Cream should be used with caution in patients with pre-existing autoimmune conditions (including thyroiditis, multiple sclerosis, spondyloarthropathy, psoriasis, ulcerative colitis) (See ADVERSE REACTIONS Post-Market Adverse, Drug Reactions).

Sensitivity

Hypersensitivity reactions (urticaria) and erythema multiforme have been reported in patients receiving, imiquimod cream, however causality has not been established. Zyclara® Cream should be discontinued immediately if these events occur.

Skin

Local skin reactions such as erythema, scabbing/crusting, flaking/scaling/dryness, and edema are common.

Intense local skin reactions including erythema, scabbing/crusting and erosion/ulceration can occur after a few applications of Zyclara® Cream and may require an interruption of dosing (See ADVERSE REACTIONS and DOSAGE AND ADMINISTRATION)

Zyclara® Cream has the potential to exacerbate inflammatory conditions of the skin, including chronic graft versus host disease.

Administration of Zyclara® Cream is not recommended until the skin is healed from any previous drug or surgical treatment.

Should a severe local skin reaction occur, the Zyclara® Cream should be removed by washing the treatment area with mild soap, and water and drying the area thoroughly. Treatment with Zyclara® Cream can be resumed after consultation with the treating physician; and once the skin reaction has subsided.

Special Populations

Pregnant Women: Imiquimod was not teratogenic in rate or rabbit teratology studies. In rats at a high maternally toxic dose (28 times human dose on a mg/m$^2$ basis), reduced pup weights and delayed ossification were observed. However, there are no adequate and well-controlled studies in pregnant women. Because animal reproduction studies are not always predictive of human response; this drug should be used during pregnancy only if the potential benefit justifies the potential risk to the fetus.

Nursing Women: It is not known whether topically applied imiquimod is excreted in human milk. Because many drugs are excreted in human milk, caution should be exercised when Zyclara® Cream is administered to nursing women..

Pediatrics (<18 years of age): Safety and efficacy in patients with external genital/perianal warts below the age of 12 years have not been established.

Geriatrics (>65 years of age): Of the 399 subjects treated with Zyclara® Cream in the EGW clinical studies, 5 subjects (1%) were 65 years or older. Data were too sparse to evaluate treatment effects in this population. No other clinical experience has identified differences in responses between the elderly and younger subjects, but greater sensitivity of some older individuals cannot be ruled out.

ADVERSE REACTIONS

Adverse Drug Reaction Overview

Clinical Trial Adverse Drug Reactions

In two double-blind, placebo-controlled studies for genital warts, 602 subjects applied up to one packet of Zyclara® Cream or placebo daily for up to 8 weeks. The most frequently reported adverse reactions were local skin and application site reactions.

Overall, fewer than 1% (3/400) of the subjects treated with Zyclara® Cream discontinued due to local skin/application site reactions. The incidence and severity of local skin reaction during controlled clinical studies are shown in Table 1.

Table 1: Local Skin Reactions in the Treatment Area Assessed by the Investigator

|  | Zyclara® Cream | | | | Placebo | | | |
|---|---|---|---|---|---|---|---|---|
|  | Females n=217 | | Males n=183 | | Females n=106 | | Males n=96 | |
|  | All Grades * | Severe | All Grades * | Severe | All Grades * | Severe | All Grades * | Severe |
| Erythema | 74% | 10% | 78% | 10% | 23% | 0% | 37% | 1% |
| Edema (induration) | 41% | 2% | 48% | 2% | 8% | 0% | 9% | 0% |
| Weeping/ Exudate | 35% | 1% | 39% | 3% | 5% | 0% | 0% | 0% |
| Flaking/ Scaling/ Dryness | 26% | 0% | 39% | 0% | 11% | 0% | 11% | 0% |
| Scabbing/ Crusting | 18% | <1% | 34% | 1% | 6% | 0% | 2% | 0% |
| Erosion/ Ulceration | 36% | 13% | 42% | 10% | 7% | 1% | 2% | 0% |

*Mild, Moderate, or Severe

Local skin reactions were recorded as adverse events if they extended beyond the treatment area, if they required any medical intervention, or they resulted in patient discontinuation from the study.

Selected treatment related adverse reactions are listed below in Table 2:

Table 2: Treatment Related Adverse Reactions Occurring in > 1% of Zyclara®--Treated Subjects and at a Greater Frequency than with Placebo in either gender

|  | Females | | Males | |
| --- | --- | --- | --- | --- |
| Preferred Term | Zyclara® Cream n=217 | Placebo n=106 | Zyclara® Cream n=183 | Placebo n=96 |
| Application site pain | 7.8% | 0% | 5.5% | 1.0% |
| Application site irritation | 5.5% | 0.9% | 6.0% | 1.0% |
| Application site pruritus | 3.2% | 1.9% | 1.6% | 0% |
| Application site bleeding | 1.4% | 0.9% | 1.5% | 0% |
| Application site discharge | 1.4% | 0% | 0.5% | 0% |
| Application site erythema | 1.4% | 0% | 0% | 0% |
| Application site reaction | 0.9% | 0% | 1.1% | 0% |
| Application site rash | 0.9% | 0% | 1.1% | 0% |
| Scrotal pain | 0% | 0% | 1.6% | 0% |
| Application site excoriation | 0% | 0% | 1.1% | 0% |
| Secretion discharge | 0% | 0% | 1.1% | 0% |
| Scrotal erythema | 0% | 0% | 1.1% | 0% |
| Scrotal ulcer | 0% | 0% | 1.1% | 0% |
| Scrotal edema | 0% | 0% | 1.1% | 0% |
| Pruritus genital | 0% | 0% | 1.1% | 0% |
| Application site cellulitis | 0% | 0% | 1.1% | 0% |

Systemic adverse reactions considered treatment related in clinical trials involving Zyclara® Cream included pain, pyrexia (fever), influenza, and myalgia.

Adverse reactions seen in clinical trials for external genital, warts involving 5% imiquimod cream included: tinea cruris, application site soreness, hypopigmentation, sensitivity, stinging and tenderness.

Other systemic adverse reactions considered treatment related in clinical trials for external genital warts involving 5% imiquimod cream included: headache, influenza-like symptoms fatigue, malaise, nausea, and diarrhea.

Dermal Safety Trials Experience

Provocative repeat insult patch test studies involving induction and challenge phases produced no evidence that imiquimod cream causes photoallergenicity or contact sensitization in healthy skin; however, cumulative irritancy testing revealed the potential for imiquimod Cream to cause irritation, and application site reactions were reported in the clinical studies.

Post-Market Adverse Drug Reactions

Rare reports have been received of either the onset or exacerbation of autoimmune conditions (including thyroiditis, multiple sclerosis, spondyloarthropathy, psoriasis; ulcerative colitis) in association with imiquimod 5% cream therapy.

The following adverse reactions have been identified during post-approval use of Aldara® (imiquimod) Cream, 5%. Because these reactions are reported voluntarily from a population of uncertain size, it is not always possible to reliably estimate their frequency or establish a causal relationship to drug exposure.

Application Site Disorders: tingling at the application site.

Body as a Whole: angioedema.

Cardiovascular: capillary leak syndrome, cardiac failure, cardiomyopathy, pulmonary edema, arrhythmias (tachycardia, atrial fibrillation, palpitations), chest pain, ischemia, myocardial infarction, syncope.

Endocrine: thyroiditis.

Gastro-Intestinal System Disorders: abdominal pain.

Hematological: decreases in red cell, white cell and platelet counts (including idiopathic thrombocytopenic purpura), lymphoma.

Hepatic: abnormal liver function.

Infections and Infestations: herpes simplex.

Musculo-Skeletal System Disorders: arthralgia.

Neuropsychiatric: agitation, cerebrovascular accident, convulsions (including febrile convulsions (including febrile convulsions), depression, insomnia, multiple sclerosis aggravation, paresis, suicide.

Respiratory: dyspnea.

Urinary System Disorders: proteinuria.

Skin and Appendages: exfoliative dermatitis, erythema multiforme, hyperpigmentation, hypertrophic scar.

Vascular: Henoch-Schonlein purpura syndrome.

DRUG INTERACTIONS

Overview

Interactions between Zyclara® Cream with other drugs have not been established.

DOSAGE AND ADMINISTRATION

Recommended Dose and Dosage Adjustment

Zyclara® Cream should be applied once-a-day to the external genital/perianal warts. Zyclara® Cream should be used for up to 8 weeks.

Up to 1 packet of Zyclara® Cream should be applied to the treatment area at each application.

Missed Dose

If a dose is missed, the regular schedule should be continued. Do not make up the missed dose(s).

Each treatment cycle should not be extended due to missed doses or rest periods.

Administration

Zyclara® Cream should be used as directed by a physician. Zyclara® Cream is for external use only. Contact with the eyes, lips and nostrils should be avoided.

It is recommended that patients wash their hands before and after applying Zyclara® Cream.

Zyclara® Cream is not for oral, ophthalmic, intra-anal, or intravaginal use. Zyclara® Cream should be applied once-a-day to the external genital/perianal warts. Zyclara® Cream should be used for up to 8 weeks. Zyclara® Cream should be applied prior to normal sleeping hours and left on the skin for approximately 8 hours, after which time the Zyclara® Cream should be removed by washing the area with mild soap and water. The prescriber should demonstrate the proper application technique to maximize the benefit of Zyclara® Cream therapy.

A <u>thin</u> layer of Zyclara® Cream should be applied to the areas of existing and emerging warts and rubbed in until the Zyclara® Cream is no longer visible. The application site should not be occluded. Following the treatment period, the Zyclara® Cream should be removed by washing the treated area with mild soap and water. Unused packets should be discarded. Partially-used packets should be discarded and not reused.

Local skin reactions at the treatment site are common (see Adverse Reactions). A rest period of several days may be taken if required by the patient's discomfort or severity of the local skin reaction. Treatment may resume once the reaction subsides. Non-occlusive dressings such as cotton gauze or cotton underwear may be used in the management of skin reactions.

Sexual (genital, anal, oral) contact should be avoided while Zyclara® Cream is on the skin. Application of Zyclara® Cream in the vagina is considered internal and should be avoided. Female patients should take special care if applying the Zyclara® Cream at the opening of the vagina because local skin reactions on the delicate moist surfaces can result in pain or swelling, and may cause difficulty in passing urine.

Uncircumcised males treating warts under the foreskin should retract the foreskin and clean the area daily.

New warts may develop during therapy, as Zyclara® Cream is not a cure.

The effect of Zyclara® Cream on the transmission of genital/perianal warts is unknown.

Zyclara® Cream may weaken condoms and vaginal diaphragms, therefore concurrent use is not recommended.

Should severe local skin reaction occur, the Zyclara® Cream should be removed by washing the treatment area with soap and water.

OVERDOSAGE

Overdosage of Zyclara® Cream in humans is unlikely due to minimal percutaneous absorption. Animal studies reveal a rabbit dermal lethal imiquimod dose of greater than 5000 mg/kg. Persistent topical overdosing of Zyclara® Cream could result in an increased incidence of severe local skin reactions and may increase the risk for systemic reactions.

The most clinically serious adverse event reported following multiple oral imiquimod doses of ≥ 200 mg was hypotension which resolved following oral or intravenous fluid administration.

ACTION AND CLINICAL PHARMACOLOGY

Mechanism of Action

*In vitro* studies have demonstrated that imiquimod induces the release of interferon alpha (IFN-α) and other cytokines from human monocytes/macrophages and keratincytes. The panel cytokines induced varied with the cell's tissue origin. Topical *in vivo* application of imiquimod cream on mouse skin resulted in increased concentrations of IFN and tumor necrosis factor (TNF) compared with skin of untreated mice.

Pharmacodynamics

Imiquimod has no direct antiviral activity in cell culture. A study in 22 subjects with genital/perianal warts comparing imiquimod cream 5% and vehicle shows that imiquimod induces mRNA encoding cytokines including interferon-α at the treatment site. In addition HPVL1 mRNA and HPV DNA are significantly decreased following treatment. However, the clinical relevance of these findings is unknown.

Pharmacokinetics

Percutaneous absorption of imiquimod has been studied through intact healthy skin, the skin of genital warts, and lesions of sun damaged skin. Percutaneous absorption of [$^{14}$C]imiquimod was minimal in a study involving six healthy subjects treated with a single topical application (5mg) of [$^{14}$C]imiquimod in cream formulation. No radioactivity [$^{14}$C] was detected in the serum (lower limit of quantitation is 1 ng/mL) and <0.9% of the radiolabelled dose was excreted in the urine and feces following topical application.

Systemic absorption of imiquimod (up to 9.4 mg [one 250 mg packet of 3.75% imiquimod cream]) across the affected skin of 18 subjects with EGW was observed with once daily dosing for 3 weeks. The mean peak serum drug concentration at Day 21 was 0.488 ng/mL.

Special Populations and Conditions

Age: No formal phaimacokinetic study was conducted to examine age related differences in the pharmacokinetic profile of Zyclara® Cream.

Gender: During 3 weeks of treatment, the $AUC_{0\_24}$ on Day 21 appeared to be similar in female and male subjects but $C_{max}$ was higher and reached more quickly in female subjects who applied Zyclara® Cream to external genital warts.

STORAGE AND STABILITY

Store between 15°C and 25°C. Avoid freezing.

DOSAGE FORMS, COMPOSITION AND PACKAGING

Zyclara® Cream is supplied in single-use packets which contain 250 mg of the cream. Available as a box of 28 packets.

Each gram of Zyclara® Cream contains 37.5 mg of imiquimod in an off-white to faintly yellow oil-in-water vanishing cream base consisting of isostearic acid, cetyl alcohol, stearyl alcohol, white petrolatum, polysorbate 60, sorbitan monostearate glycerin, xanthan gum, purified water, benzyl alcohol, methylparaben, and propylparaben.

PART II: SCIENTIFIC INFORMATION

PHARMACEUTICAL INFORMATION

Drug Substance

Common name   Imiquimod (USAN, INN)

Chemical name:   1-(2-methylpropyl)-1$H$-imidazo[4,5-c]quinolin-4-amine

Molecular formula and molecular mass:   $C_{14}H_{16}N_4$, MW = 240.3

Structural formula:

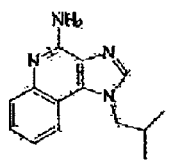

Physicochemical properties:

Physical Form:   Crystalline solid that various in color from white to off-white or buff. The compound has no odor.

Solubility:   Practically insoluble in most common organic solvents and in aqueous systems except at extremely low pH conditions. It can be made soluble to the extent of at least

|  |  |
|---|---|
|  | 100 mg/mL in methanol (as a salt) upon the addition of a few drops of hydrochloric or acetic acid. Soluble in fatty acids such as oleic acid and isostearic acid. |
| pKa Value: | The ionization constant for imiquimod was determined by ultraviolet (UV) spectroscopy and pH-solubility to be about 7.5. |
| Melting point: | 297-299°C with sublimation. |

CLINICAL TRIALS

In two double-blind, randomized, placebo-controlled clinical studies, 601 subjects with EGW were treated with 3.75% imiquimod cream, or a matching placebo cream. Studies enrolled subjects aged from 15 to 81 years. The baseline wart area ranged from 6 to 5579 $mm^2$ and the baseline wart count ranged from 2 to 48 warts. Most Subjects had two or more treated anatomic areas at Baseline. Anatomic areas included: inguinal, perineal, and perianal areas (both genders); the glans penis, penis shaft, scrotum, and foreskin, (in men); and the vulva (in women). Up to one packet of study cream was applied once daily to each wart identified at Baseline and any new wart that appeared during the treatment period. The study cream was applied to all warts prior to normal sleeping hours and left on for approximately 8 hours. Subjects continued applying the study cream for up to 8 weeks or until they achieved complete clearance of all (baseline and new) warts in all anatomic areas. Subjects not achieving complete wart clearance by the Week 8 visit (end of treatment, EOT), were evaluated for up to 8 weeks or until they achieved complete clearance during an additional 8 week no-treatment period. Subjects who achieved complete clearance of all warts at anytime until the Week 16 visit entered a 12 week follow-up for recurrence period.

Efficacy was assessed by wart counts (those present at Baseline and new warts appearing during the study) at EOS (i.e., up to 16 weeks from Baseline). Complete clearance required clearance of all warts in all anatomic areas. Partial clearance rate was defined as the proportion of subjects with at least 75% reduction in the number of baseline warts at EOS. Percent reductions were measured relative to the numbers of warts at Baseline. Complete and partial clearance rates and percent reductions in wart counts from baseline are shown in the table below (by overall rate and by gender).

Table 3: Efficacy Endpoints

|  | Zyclara® Cream, 3.75% | Placebo Cream |
|---|---|---|
| Complete Clearance Rate |  |  |
| Overall | 28.3% (113/399) | 9.4% (19/202) |
| Females | 36.6% (79/216) | 14.2% (15/106) |
| Males | 18.6% (34/183) | 4.2% (4/96) |
| Partial Clearance Rate |  |  |
| Overall | 38.3% (153/399) | 11.9% (24/202) |
| Females | 47.7% (103/216) | 17.0% (18/106) |
| Males | 27.3% (50/183) | 6.3% (6/96) |
| Percent Reduction of EGW (Median) |  |  |
| Overall | 50.0% | 0.0 |
| Females | 70.7% | 0.0 |
| Males | 23.3% | 0.0 |

The numbers of subjects who remained clear of EGW at the end of 12 week follow-up for recurrence period are shown in Table 4 below:

Table 4: Sustained Complete Clearance

|  | Zyclara® Cream, 3.75% | Placebo Cream |
|---|---|---|
| Cleared and entered Follow-up | 102 | 13 |
| Remained Clear | 71 | 12 |

DETAILED PHARMACOLOGY

Pharmacodynamics: Imiquimod is a immune response modifier that is not a nucleoside analogue. Imiquimod is a Toll-like receptor 7 agonist that activates immune cells. Topical application to skin is associated with increases in markers for cytokines and immune cells.

Saturable binding studies suggest a membrane reception for imiquimod exists on responding cells. *In vitro* studies have demonstrated that imiquimod induces the production of IFN and other cytokines from a variety of human and animal cells. In addition, cytokines were produced following dermal application and oral administration in various laboratory animals and in human studies following oral administration of imiquimod. In animal models imiquimod is an effective antiviral and antitumour agent whose activity is principally due to induction of alpha interferon but other cytokines are also involved.

*In vitro* studies using isolated guinea pig myocardium, showed stimulation with tachyphylaxis development after multiple does. Moderate to marked inhibition of agonist-induced contractions was observed in isolated guinea pig tracheal strips. Intravenous administration of a bolus dose of imiquimod caused CNS and cardiac stimulation in dogs. Little activity was found in inflammatory rat models. Some local anesthetic activity, slight effect on locomotor, and slight effect on hexobarbital induced sleep time were observed in the mouse.

Pharmacokinetics and Metabolism: Animal and human dermal pharmacokinetic results indicate that minimal, if any, systemic absorption occurs following dermal application of imiquimod cream. Imiquimod was not quantifiable in the serum of rats dosed topically three times per week at 5 mg/kg for 4 weeks; low levels of metabolite were quantifiable after the last, but not after the first dose. In guinea pigs, after a single large (21 mg/kg) topical dose of [$^{14}$C] imiquimod as a 5% cream, only low concentrations of imiquimod were quantifiable in plasma.

Oral ADME (absorption, distribution, metabolism, elimination) studies in laboratory animals, revealed extensive biotransformation follows by both urinary and biliary excretion of metabolites. Tissue distribution is rapid with clearance after 2 to 3 days with the exception of pigmented tissues — skin and uveal tract of the eye. No evidence of ocular toxicity was found in six month oral rate and monkey imiquimod toxicity studies conducted at high daily doses.

Systemic absorption of imiquimod (up to 9.4 mg [one packet]) across the affected skin of 18 subjects with EGW was observed with once daily dosing for 3 weeks. The mean peak serum drug concentration at Day 21 was 0.488 ng/mL.

TOXICOLOGY

Acute Toxicity: Acute dermal toxicity Studies in rabbits with unformulated imiquimod under occlusion did not reveal any toxic effects at very high dose levels — 5000 mg/kg. When administered orally, intraperitoneally subcutaneously or intravenously, single dose studies revealed that imiquimod produced central nervous system (CNS) stimulation and convulsions at lethal doses. However, signs of CNS toxicity did not occur when animals were given lower repeat doses (100 mg/kg or lower).

Table 5

| Species | Route | |
|---|---|---|
| Mouse | oral | |
| | intraperitoneal | |
| Rat | oral | |
| | intraperitoneal | |
| | subcutaneous | |
| Rabbit | dermal | |

| Monkey | oral | |
| | intravenous infusion | |
| | intravenous bolus | |

Irritation/Sensitization Studies: Skin irritation studies in rabbits showed that imiquimod was non-irritating when dosed unformulated at 500 mg or formulated up to 250 mg per site. Unformulated imiquimod produced mild or no eye irritation in rabbits when applied unformulated at 100 mg/eye or formulated up to 5 mg/eye. Formulated imiquimod was not irritating to rate or rabbit vaginal tract when applied every other day for 10 days at 10 and 50 mg/dose respectively. Dermal sensitization studies in guinea pigs showed that the imiquimod cream was not a dermal sensitizer. Comparison of the dermal reaction to imiquimod cream in animal species (rat, mouse, rabbit) with clinical study results, reveals that mouse and rabbit results are comparable to humans. The more severe dermal irritation seen in the rate is not predictive of human response.

Long-Term Toxicity: Two repeat dose dermal toxicity studies in rats showed a compound related but non-dose related dermal irritation. A dose-related decrease in body weight of male rats was also observed. No systemic toxicity was found at doses up to 5 mg/kg three days per week for 4 weeks or at doses up to 2.5 mg/kg three days per week for 16 weeks.

The adverse effects observed for the high doses (10-30 mg/kg) in repeat dose oral toxicity studies in rats and monkeys could be related to exaggerated pharmacological effects of excessive cytokines induction and lymphoid stimulation reduced body weight gains, anemia, serum protein changes and death. High repeat daily doses of imiquimod did not produce necrosis in any organ; the compound is not cytotoxic. Recovery animals demonstrated that the adverse effects were readily reversible. An oral no-adverse-effect level of 3 mg/kg/day was determined in both rats and monkeys dosed daily for 6 months.

Carcinogenicity: Two-year bioassays in Wistar rats (up to 3 mg/kg orally per day) and CD-1 mice (up to 4.5mg/kg applied topically 3 limes per week) showed no evidence of a carcinogenic effect in male and female rats and female mice. Liver tumors were increased in male mice exposed to the highest dose concentration, compared to the unexposed controls. However, the number of tumors was within the range seen historically for male CD-1 mice. It is generally accepted that an increase in liver tumors in male mice, in the absence of other neoplastic responses in mice or rats, is not indicative of a carcinogenic risk for humans.

In a photocarcinogenicity study in hairless mice, animals received imiquimod cream 3 times per week at concentrations of 0.03%, 0.1% and 0.3% and were irradiated with solar ultraviolet light for 5 days each week for 40 weeks and observed an additional 12 weeks. Vehicle cream enhanced UVR-induced skin tumour development. Imiquimod cream had no additional effect on tumour development beyond the vehicle effect (i.e. the addition of the active ingredient, imiquimod, to the vehicle cream did not result in an additional effect beyond the vehicle effect on tumour development).

Mutagenicity: Imiquimod was without effect in a series of eight mutagenicity assays including Ames, mouse lymphoma, CHO chromosome aberration, human lymphocyte chromosome aberration, SHE cell transformation, rat and hamster bone marrow cytogenetics, and mouse dominant lethal test.

Reproduction and Teratology: Teratology studies in rats and rabbits dosed at 1-20 mg/kg orally and at 0.5-2.0 mg/kg intravenously, did not reveal any teratogenic effects. The high doses in both studies produced some adverse effects in the dams related to maternal toxicity. The maternal toxicity was reflected in the high dose pups, reduced pup weights and delayed ossification in the rate. A radiolabel intravenous study in pregnant rabbits dosed at 1mg/kg between day 6 to 18 of gestation for a total of 13 doses, showed radiolabel in the uteri, placenta, amniotic fluid and fetuses with no preferential concentration in the conceptus.

In a rat general reproduction study which utilized daily oral doses of 1.5-6.0 mg/kg, drug-related toxicity was observed at the high doses in the FO generation with no adverse reproductive effects. Reversible ossification defects were observed in pups at the high dose. No effects were observed in growth, development, behavior, learning/memory or reproduction of second generation. Daily oral administration of imiquimod to rats, at doses up to 8 times recommended human dose on a mg/m² basis throughout mating, gestation, parturition and lactation, demonstrated no impairment of reproduction.

REFERENCES

1. Arany I, Tyring S, Stanley MA, Tomai MA, Miller RL, Smith MH et al. Enhancement of the innate and cellular immune response in patients with genital warts treated with topical imiquimod cream 5%. Antiviral Res 1999;43:55-63.

2. Bernstein DI, Harrison CJ. Effects of the Immunomodulating Agent R-837 on Acute and Latent Herpes Simplex Virus Type 2 Infections. Antimicro Agents and Chemotherapy 1989; 33(9): 1511-1515.

3. Bernstein DI, Miller RL, Harrison CJ. Effects of Therapy with an Immunomodulator (Imiquimod, R-837) Alone and with Acyclovir on Genital HSV-2 Infection in Guinea-Pigs When Begun After Lesion Development. Antiviral Res 1993; 20:45-55.

4. Dahl MV. Imiquimod: An immune response modifier. J Am Acad Dermatol 2000;43(1):S1-5.

5. Edwards L. Imiquimod in clinical practice. J Am Acad Dermatol 2000;43(1): S12-17.

6. Edwards L, Ferenczy A, Eron L, Baker D, Owens ML, Fox TL et al. Self-administered topical 5% imiquimod cream for external anogenital warts. Arch Dermatol 1998;134:25-30.

7. Gibson SJ, Lindh JM, Riter TR, et al. Plasmacytoid dendritic cells produce cytokines and mature in response to the TLR7 agonists, imiquimod and resiquimod. Cell Immunol. 2002;218(1-2); 74-86.

8. Gollnick H, Barasso R, Jappe U, Ward K, Eul A, Carey-Yard M et al. Safety and efficacy of imiquimod 5% cream in the treatment of penile genital warts in uncircumcised men when applied three times weekly or once per day. Int J STD & AIDS 2001;12:22-28.

9. Harrison CJ, Miller RL, Bernstein DI. Posttherapy Suppression of Genital Herpes Simplex Virus (HSV) Recurrences and Enhancement of HSV-Specific T-Cell Memory by Imiquimod in Guinea Pigs. Antimicro Agents and Chemo 1994; 38(9) 2059-2064.

10. Hemmi H, Kaisho T, Takeuchi O, Sato S, Sanjo H, Hoshino K, Horiuchi T, Tomizawa H, Takeda K, Akira S. Small anti-viral compounds activate immune cells *via* the TLR7 MyD88-dependent signaling pathway. Nat Immunol 2002; 3(2): 196-200.

11. Kende M, Lupton HW, Canonico PG. Treatment of Experimental Viral Infections with Immuno-modulators. Adv Biosci 1988; 68:51-63.

12. Miller RL, Birmachu W, Gerster JF et al Imiquimod Cytokine Induction and Antiviral Activity. Intl Antiviral News 1995; 3(7):111-113.

13. Miller RL, Gerster JF, OwensML, Slade HB, Tomai MA. Imiquimod applied topically: a novel immune response modifier and new class of drug. Int J Immunopharm 1999; 21: 1-14.

14. Saucier DN. Immunomodulatory and pharmacologic properties of imiquimods. J Am Acad Dermatol 2000;43(1):S6-11.

15. Testerman TL, Gerster JF, Imbertson LM et al. Cytokine Induction by the Immunomodulators Imiquimod and S-27609. J Leuk Biol 1995; 58:365-372.

16. Tyring SK. Immune-response modifiers: A new paradigm in the treatment of human papillomavirus. Curr Ther Res 2000;60(9):584-596.

17. Tyring SK, Arany I, Stanley MA, Tomai MA, Miller RL, Smith MH et al. A randomized, controlled, molecular study of condylomata acuminata clearance during treatment with imiquimod. J Infect Dis 1998; 178(August):551-555.

18. Weeks CE, Gibson SJ. Induction of Interferon and Other Cytokines by Imiquimod and its Hydroxylated Metabolite R-842 in Human Blood Cells *In Vitro*. J. interferon Res 1994; 14:81-85.

| IMPORTANT PLEASE READ |
|---|

Part III: CONSUMER INFORMATION

ZYCLARA®

(imiquimod) Cream, 3.75%

This leaflet is part III of a three-part "Product Monograph" published when Zyclara® Cream was approved for sale in Canada and is designed specifically for Consumers. This leaflet is a summary and will not tell you everything about Zyclara® Cream. Contact your doctor or pharmacist if you have any questions about the drug.

| ABOUT THIS MEDICATION |
|---|

What the medication is used for:

Zyclara® is the brand name for imiquimod cream, 3.75%. It is used for the treatment of external genital and perianal warts/condyloma acuminata, whether present at the start of therapy or emerging during therapy, in patients 12 years or older.

What it does:

Zyclara® Cream is an immune response modifier. Zyclara® Cream is a medicine that works by stimulating your body's own immune response.

When it should not be used:

Do not use Zyclara® if you are allergic to imiquimod, or other medications that contain imiquimod (e.g. Aldara® Cream), or any of the other ingredients in Zyclara® Cream.

What the medicinal ingredient is:

Imiquimod.

What the important nonmedicinal ingredients are:

Isostearic acid, cetyl alcohol, stearyl alcohol, white petrolatum, polysorbate 60, sorbitan monostearate, glycerin, xanthan gum, purified water, benzyl alcohol, methylparaben, and propylparaben.

What dosage forms it comes in:

Zyclara® Cream contains 37.5 mg imiquimod per gram (3.75%) and is supplied in single-use packets which contain 250 mg of the cream. It is available as boxes of 28 packets.

*Zyclara® Product Monograph*

WARNINGS AND PRECAUTIONS

- Zyclara® should not be used in patients under 12 years of age
- Avoid exposure to of treated area(s) sunlight, sunlamp or tanning-bed during the treatment with Zyclara®
- Zyclara® may cause severe skin reactions
- Zyclara® may also cause flu-like symptoms before or during local skin reactions BEFORE you use Zyclara® talk to your doctor or pharmacist if:
- you have or had other skin cancers or other growths on your body
- you are immunocompromised (have weak immune system)

- you have or have had any other treatment for your external genital/perianal warts, such as freezing or surgery
- you are pregnant or planning to become pregnant
- you are breastfeeding or planning to breastfeed

INTERACTIONS WITH THIS MEDICATION

Tell your doctor or pharmacist about all the medicines you take or have taken, including prescription and non-prescription medicines, vitamins and herbal supplements. It is not known if Zyclara® Cream and other medicines can affect each other.

PROPER USE OF THIS MEDICATION

Use Zyclara® Cream exactly as prescribed by your doctor. Do not use Zyclara® Cream until your doctor has shown you the right way to use it.

Usual adult dose:

Apply Zyclara® Cream to the external genital/perianal warts once a day just before bedtime.

Zyclara® Cream should be used for up to 8 weeks.

How to apply Zyclara® Cream:
Zyclara® Cream should be applied just before your bedtime.
- Wash the area to be treated with mild soap and water. Allow the area to dry.
    - Uncircumcised males treating warts under their penis foreskin must pull their foreskin back and clean before treatment and clean daily during the weeks of treatment.
- Wash your hands
- Open a new packet(s) of Zyclara® Cream just before use.

- Apply a thin layer of Zyclara® Cream only to the affected area or areas to be treated. Do not use more Zyclara® Cream than is needed to cover the treatment area. Do no use more than one packet for each application.
- Rub the Zyclara® Cream in all the way to the affected area or areas.
- Do not get Zyclara® Cream in or around your eyes or mouth.
- Do not get Zyclara® in the anus when applying to perianal warts.
- Female patients treating genital warts must be careful when applying Zyclara® Cream around the vaginal opening. Female patients should take special care if applying the Zyclara® Cream at the opening of the vagina because local skin reactions on the delicate moist surfaces can cause pain or swelling, and may cause problems passing urine. Do not put Zyclara® Cream in your vagina.
- Do not cover the treated area(s) with an airtight bandage. Cotton gauze dressings can be used. Cotton underwear can be worn after applying Zyclara® Cream to the genital or perianal area.
- Safely throw away the open packet of Zyclara® Cream so that children and pets cannot get it. The open packet should be thrown away even if all the Zyclara® Cream was not completely used.
- After applying Zyclara® Cream, wash your hands well with soap and water.
- Leave the Zyclara® Cream on the affected area(s) for about 8 hours or as instructed by your doctor. Do not bathe or get the treated area(s) wet before the right time has passed. Do not leave Zyclara® Cream on your skin longer than prescribed.
- After about 8 hours, wash the treated area(s) with mild soap and water.
- If you get Zyclara® Cream in your mouth or in your eyes rinse well with water right away.

*Zyclara® Product Monograph*

Avoid exposure of the treated area(s) to sunlight, sunlamp or tanning-bed during the treatment with Zyclara®.

Overdose:

If you have used more Zyclara® Cream than you should, contact your doctor, or poison control centre.

Missed Dose:

If you forget to apply Zyclara® Cream, continue on your regular schedule and do not make up the missed dose(s).

SIDE EFFECTS AND WHAT TO DO ABOUT THEM

Side effects with Zyclara® Cream may include skin reactions at the treatment site such as:

- redness
- swelling
- a sore, blister, or ulcer
- skin that becomes hard or thickened
- skin peeling
- scabbing and crusting
- itching
- burning
- changes in skin color that do not always go away During treatment and until skin has healed, you skin in the treatment area is likely to appear noticeably different hoar nornial skin. Side elects at the site where Zyclara® Cream is applied are common. Sometimes the side effects to outside of the area where Zyclara® Cream was applied. Patients should be aware that new warts may develop during treatment, as Zyclara® Cream may not be a cure. You have a higher chance for severe skin reactions if you use too much Zyclara® Cream or use it the wrong way. Stop Zyclara® Cream right away and call your healthcare provider if you get any skin reactions that affect your daily activities, or that do not go away. Sometimes, Zyclara® Cream must be stopped for a while to allow your skin to heal. Talk to your healthcare provider if you have questions about your treatment or skin reactions.

Other side effects of Zyclara® Cream include pain, fever, muscle aches, and may also include headache, back pain, joint aches, tiredness, flu-like symptoms, nausea, and diarrhea.

If the reactions seem excessive, if either skin breaks down or sores develop during the first week of treatment, if flu-like symptoms develop or if you begin to not feel well at anytime, stop applying Zyclara® Cream and contact your healthcare provider.

These are not all the side effects of Zyclara® Cream. For more information, ask your healthcare provider or pharmacist.

HOW TO STORE IT

Store Zyclara® Cream between 15-25°C. Do not freeze.

Safely throw away Zyclara® Cream that is out of date or that you do not need.

Keep Zyclara® Cream and all medicines out of the reach of children.

Zyclara® Product Monograph

REPORTING SUSPECTED SIDE EFFECTS

To monitor drug safety, Health Canada through the Canada Vigilance Program collects information on serious and unexpected effects of drugs. If you suspect you have had a serious or unexpected reaction to this drug you may notify Canada Vigilance:

You can report any suspected adverse reaction associated with the use of health products in the Canada Vigilance Program by one of the following 3 ways:

Report online at www.healthcanada.gc.ca/medeffect.

Call toll-free at 1-866-234-2345

Complete a Canada Vigilance Reporting Form and:

- Fax toll-free to 1-866-678-6789, or
- Mail to: Health Canada

Postal Locator 0701C

Ottawa, ON K1AOK9

Postage paid labels, Canada Vigilance Reporting Form and the adverse reaction reporting Guidelines are available on the MedEffect™ Canada Web site at www.healtheanada.ge.ca/medeffect

*Note: Should you require information related to the management of side effects, contact your health professional. The Canada Vigilance Program does not provide medical advice.*

MORE INFORMATION

This document plus the full product monograph, prepared for health professionals can be found at:

http://www.gracewaypharma.ca or by contacting the sponsor, Graceway Pharmaceuticals at: 1-800-328-0255

This leaflet was prepared by Graceway Pharmaceuticals, 252 Pall Mall St., Suite 302, London, Ontario, N6A 5P6

Attachment XIII

[000324] Zyclara® [zi-clar-a] (imiquimod) 3.75% Cream

HIGHLIGHTS OF PRESCRIBING INFORMATION

These highlights do not include all the information needed to use ZYCLARA® Cream safely and effectively. See full prescribing information for ZYCLARA® Cream for Actinic Keratosis.

ZYCLARA® Cream, 3.75%, is packaged for use in the total 2-cycle treatment course to treat Actinic Keratosis as follows:

(a) 9.4 mg (about 9.375 mg at 3.75%) per 250 mg single unit-dose packets with 28 packets (250mg/packet) supplied per box (two boxes or 56 single unit-dose packets);

(b) two 7.5g pumps (about 282 mg [about 281.25 mg at 3.75%] imiquimod per 7.5 g); or (c) one 15g pump (about 564 mg [about 562.5 mg at 3.75%] imiquimod per 15 g).

ZYCLARA® (imiquimod), Cream, 3.75%

For topical use only

Imiquimod Initial U.S. Approval: 1997

---------------------------------- INDICATIONS AND USAGE ----------------------------------

ZYCLARA® Cream is indicated for the topical treatment of clinically typical, visible or palpable actinic keratoses (AK) of the full face or balding scalp in immunocompetent adults (1.1).

---------------------------------- DOSAGE AND ADMINISTRATION ----------------------------------

ZYCLARA® Cream is not for oral, ophthalmic, or intravaginal use (2).

• Once daily to the skin of the affected area (either the entire face or balding scalp) for two 2-week treatment cycles separated by a 2-week no-treatment period (2.1).

---------------------------------- DOSAGE FORMS AND STRENGTHS ----------------------------------

- Cream, 3.75%, white to faintly yellow cream (3).

---------------------------------------- CONTRAINDINCATIONS ----------------------------------------

- None (4).

--------------------------------- WARNINGS AND PRECAUTIONS ---------------------------------

- Intense local inflammatory reactions can occur (e.g., skin weeping, erosion). Dosing interruption may be required (2, 5.1, 6).
- Flu-like systemic signs and symptoms including fatigue, nausea, fever, myalgias, arthralgias, and chills. Dosing interruption may be required (2, 5.2, 6).
- Avoid exposure to sunlight and sunlamps (5.3). Wear sunscreen daily (17.4).
- Avoid concomitant use of Zyclara® Cream and any other imiquimod cream.

---------------------------------------- ADVERSE REACTIONS ----------------------------------------

Most common Adverse Reactions (incidence >50%) are local skin reactions erythema, edema, weeping/exudate, flaking/scaling/dryness, scabbing/crusting and erosion/ulceration (6.2). Other reported reactions (occurring in >2% of ZYCLARA®-Treated Subjects) include headache, fatigue, nausea and fever (see 6.1).

To report SUSPECTED ADVERSE REACTIONS, contact Graceway Pharmaceuticals, LLC at 1-800-328-0255 or FDA at 1-800-FDA-1088 or www.fda.gov/medwatch.

See 17 for PATIENT COUNSELING INFORMATION and FDA-approved patient labeling.

---

FULL PRESCRIBING INFORMATION: CONTENTS\*

1 INDICATIONS AND USAGE 1.1 Actinic Keratosis 1.2 Unevaluated Populations

2 DOSAGE AND ADMINISTRATION 2.1 Actinic Keratosis

3 DOSAGE FORMS AND STRENGTHS

4 CONTRAINDICATIONS

5 WARNINGS AND PRECAUTIONS 5.1 Local Skin Reactions 5.2 Systemic Reactions 5.3 Ultraviolet Light Exposure 5.4 Unevaluated Uses: Actinic Keratosis

6 ADVERSE REACTIONS 6.1 Clinical Trials Experience 6.2 Postmarketing Experience

8 USE IN SPECIFIC POPULATIONS 8.1 Pregnancy 8.3 Nursing Mothers 8.4 Pediatric Use 8.5 Geriatric Use

10 OVERDOSAGE

11 DESCRIPTION

12 CLINICAL PHARMACOLOGY 12.1 Mechanism of Action 12.2 Pharmacodynamics 12.3 Pharmacokinetics

13 NONCLINICAL TOXICOLOGY 13.1 Carcinogenesis, Mutagenesis, Impairment of Fertility

14 CLINICAL STUDIES

16 HOW SUPPLIED/STORAGE AND HANDLING

17 PATIENT COUNSELING INFORMATION 17.1 Instructions for Administration 17.2 Local Skin Reactions 17.3 Systemic Reactions 17.4 Recommended Administration

*Sections or subsections omitted from the Full Prescribing Information are not listed.

FULL PRESCRIBING INFORMATION

1 INDICATIONS AND USAGE 1.1 Actinic Keratosis

ZYCLARA® Cream is indicated for the topical treatment of clinically typical visible or palpable, actinic keratoses (AK), of the full face or balding scalp in immunocompetent adults.

1.2 Unevaluated Populations

Safety and efficacy have not been established for ZYCLARA® Cream in the treatment of actinic keratosis, with more than one 2-cycle treatment course in the same area.

The safety and efficacy of ZYCLARA® Cream in immunosuppressed patients have not been established.

The safety and efficacy have not been established for ZYCLARA® Cream in the treatment of patients with xeroderma pigmentosum.

The safety and efficacy have not been established for ZYCLARA® Cream in the treatment of superficial basal cell carcinoma.

The safety and efficacy have not been established for ZYCLARA® Cream in the treatment of external genital warts.

ZYCLARA® Cream should be used with caution in patients with pre-existing autoimmune conditions.

2 DOSAGE AND ADMINISTRATION

ZYCLARA® Cream is not for oral, ophthalmic, or intravaginal use.

2.1 Actinic Keratosis

ZYCLARA® Cream should be applied once daily before bedtime to the skin of the affected area (either entire face or balding scalp) for two 2-week treatment cycles separated by a 2-week no-treatment period. ZYCLARA® Cream should be applied as a thin film to the entire treatment area and rubbed in until the ZYCLARA® Cream is no longer visible. Up to 2 packets or 2 full actuations of the pump of ZYCLARA® Cream may be applied to the treatment area at each application. ZYCLARA® Cream should be left on the skin for approximately 8 hours, after which time the ZYCLARA® Cream should be removed by washing the area with mild soap and water. The prescriber should demonstrate the proper application technique to maximize the benefit of ZYCLARA® Cream therapy.

Patients should wash their hands before and after applying ZYCLARA® Cream.

Avoid use in or on the lips and nostrils. Do not use in or near the eyes.

Local skin reactions in the treatment area are common *[see Adverse Reactions (6.1, 6.2)]*. A rest period of several days may be taken if required by the patient's discomfort or severity of the local skin reaction. However, neither 2-week treatment cycle should be extended due to missed doses or rest periods. A transient increase in AK lesion counts may be observed during treatment. Response to treatment cannot be adequately assessed until resolution of local skin reactions. The patient should continue dosing as prescribed. Treatment should continue for the full treatment course even if all actinic keratoses appear to be gone. Lesions that do not respond to treatment should be carefully re-evaluated and management reconsidered.

ZYCLARA® Cream is packaged in single-use packets, with 28 packets (250mg/packet) supplied per box, a 7.5g pump and a 15g pump. Each ZYCLARA® Cream pump actuation delivers a similar amount of cream as one packet. Patients should be prescribed no more than 56 packets, two 7.5g pumps or one 15g pump for the total 2-cycle treatment course. Partially used packets should be discarded and not reused. When the treatment course is complete, any remaining packets or pumps should be discarded.

3     DOSAGE FORMS AND STRENGTHS

Cream, 3.75%, white to faintly yellow cream.

4     CONTRAINDICATIONS

None.

5 WARNINGS AND PRECAUTIONS

5.1 Local Skin Reactions

Intense local skin reactions including skin weeping or erosion can occur after a few applications of ZYCLARA® Cream and may require an interruption of dosing *[see Dosage and Administration (2) and Adverse Reactions (6)]*. ZYCLARA® Cream has the potential to exacerbate inflammatory conditions of the skin, including chronic graft versus host disease. Administration of ZYCLARA® Cream is not recommended until the skin is healed from any previous drug or surgical treatment.

Concomitant use of ZYCLARA® Cream and any other imiquimod creams, in the same treatment area, should be avoided since they contain the same active ingredient (imiquimod) and may increase the risk for and severity of local skin reactions.

5.2 Systemic Reactions

Flu-like signs and symptoms may accompany, or even precede, local skin reactions and may include fatigue, nausea, fever, myalgias, arthralgias, and chills. An interruption of dosing and an assessment of the patient should be considered *[see Adverse Reactions (6)]*.

Lymphadenopathy occurred in 2% of subjects treated with ZYCLARA® Cream *[see Adverse Reactions (6)]*. This reaction resolved in all subjects by 4 weeks after completion of treatment.

The safety of concomitant use of ZYCLARA® Cream and any other imiquimod creams has not been established and should be avoided since they contain the same active ingredient (imiquimod) and may increase the risk for and severity of systemic reactions.

5.3 Ultraviolet Light Exposure

Exposure to sunlight (including sunlamps) should be avoided or minimized during use of ZYCLARA® Cream because of concern for heightened sunburn susceptibility. Patients should be warned to use protective clothing (e.g., a hat) when using ZYCLARA® Cream. Patients with sunburn should be advised not to use ZYCLARA® Cream until fully recovered. Patients who may have considerable sun exposure, e.g. due to their occupation, and those patients with inherent sensitivity to sunlight should exercise caution when using ZYCLARA® Cream.

In an animal photo-carcinogenicity study, imiquimod cream shortened the time to skin tumor formation *[see Nonclinical Toxicology (13.1)]*. The enhancement of ultraviolet carcinogenicity is not necessarily dependent on phototoxic mechanisms. Therefore, patients should minimize or avoid natural or artificial sunlight exposure.

6  ADVERSE REACTIONS

Because clinical trials are conducted under widely varying conditions, adverse reaction rates observed in the clinical trials of a drug cannot be directly compared to rates in the clinical trials of another drug and may not reflect the rates observed in practice.

6.1  Clinical Trials Experience:

The data described below reflect exposure to ZYCLARA® Cream or vehicle in 319 subjects enrolled in two double-blind, vehicle-controlled trials. Subjects applied up to two packets of ZYCLARA® Cream or vehicle daily to the skin of the affected area (either entire face or balding scalp) for two 2-week treatment cycles separated by a 2-week no treatment period.

Table 1: Selected Adverse Reactions Occurring in > 2% of ZYCLARA®-Treated Subjects and at a Greater Frequency than with Vehicle in the Combined Studies

| Preferred Term | ZYCLARA® Cream 3.75% (N=160) | Vehicle (N=159) |
|---|---|---|
| Headache | 10 (6%) | 5 (3%) |
| Application site pruritus | 7 (4%) | 1 (<1%) |
| Fatigue | 7 (4%) | 0 (0%) |
| Nausea | 6 (4%) | 2 (1%) |
| Application site irritation | 5 (3%) | 0 (0%) |
| Application site pain | 5 (3%) | 0 (0%) |
| Pyrexia | 5 (3%) | 0 (0%) |
| Anorexia | 4 (3%) | 0 (0%) |
| Dizziness | 4 (3%) | 0 (0%) |
| Herpes simplex | 4 (3%) | 1 (<1%) |
| Pain | 4 (3%) | 0 (0%) |
| Chest pain | 3 (2%) | 0 (0%) |

| Preferred Term | ZYCLARA® Cream 3.75% (N=160) | Vehicle (N=159) |
|---|---|---|
| Diarrhea | 3 (2%) | 0 (0%) |
| Lymphadenopathy | 3 (2%) | 0 (0%) |

Table 2: Local Skin Reactions in the Treatment Area in ZYCLARA®-Treated Subjects as Assessed by the Investigator

| | ZYCLARA® Cream 3.75% (N=160) | | Vehicle (N=159) | |
|---|---|---|---|---|
| | All Grades* | Severe | All Grades* | Severe |
| Erythema | 154 (96%) | 40 (25%) | 124 (78%) | 0 (0%) |
| Scabbing/Crusting | 149 (93%) | 22 (14%) | 72 (45%) | 0 (0%) |
| Flaking/Scaling/Dryness | 147 (92%) | 13 (8%) | 123 (77%) | 2 (1%) |
| Edema | 120 (75%) | 9 (6%) | 31 (19%) | 0 (0%) |
| Erosion/Ulceration | 99 (62%) | 17 (11%) | 14 (9%) | 0 (0%) |
| Weeping/Exudate | 81 (51%) | 9 (6%) | 6 (4%) | 0 (0%) |

* All Grades: mild, moderate or severe

Local skin reactions may extend beyond treatment area.

Overall, in the clinical trials, 11% (17/160) of subjects on ZYCLARA® Cream and 0% on vehicle cream required rest periods due to adverse reactions.

Other adverse reactions observed in subjects treated with ZYCLARA® Cream include: application site bleeding, application site swelling, arthralgia, cheilitis, chills, dermatitis, herpes zoster, influenza-like illness, insomnia, lethargy, myalgia, pancytopenia, pruritus, squamous cell carcinoma, and vomiting.

6.2 Postmarketing Experience

There are currently no post-marketing adverse reactions reported for Zyclara® Cream.

The following adverse reactions have been identified during post-approval use of Aldara® (imiquimod) Cream, 5%. Because these reactions are reported voluntarily from a population of uncertain size, it is not always possible to reliably estimate their frequency or establish a causal relationship to drug exposure.

Body as a Whole: angioedema.

Cardiovascular: capillary leak syndrome, cardiac failure, cardiomyopathy, pulmonary edema, arrhythmias (tachycardia, supraventricular tachycardia, atrial fibrillation, palpitations), chest pain, ischemia, myocardial infarction, syncope.

Endocrine: thyroiditis.

Gastro-Intestinal System Disorders: abdominal pain.

Hematological: decreases in red cell, white cell and platelet counts (including idiopathic thrombocytopenic purpura), lymphoma Hepatic: abnormal liver function Infections and Infestations: herpes simplex.

Neuropsychiatric: agitation, cerebrovascular accident, convulsions (including febrile convulsions), depression, insomnia, multiple sclerosis aggravation, paresis, suicide.

Respiratory: dyspnea.

Urinary System Disorders: proteinuria, urinary retention, dysuria.

Skin and Appendages: exfoliative dermatitis, erythema multiforme, hyperpigmentation, hypertrophic scar.

Vascular: Henoch-Sehonlein purpura syndrome

8  USE IN SPECIFIC POPULATIONS 8.1  Pregnancy

Pregnancy Category C:

There are no adequate and well-controlled studies in pregnant women. ZYCLARA® Cream should be used during pregnancy only if the potential benefit justifies the potential risk to the fetus.

Note: The animal multiples of human exposure calculations were based on daily dose comparisons for the reproductive toxicology studies described in this label. The animal multiples of human exposure were based on weekly dose comparisons for the carcinogenicity studies described in this label. For the animal multiple of human exposure ratios presented in this label, the Maximum Recommended Human Dose (MRHD) was set at 2 packets (500 mg cream) per treatment of ZYCLARA® Cream (imiquimod 3.75%, 18.75 mg imiquimod).

Systemic embryofetal development studies were conducted in rats and rabbits. Oral doses of 1, 5 and 20 mg/kg/day imiquimod were administered during the period of organogenesis (gestational days 6 — 15) to pregnant female rats. In the presence of maternal toxicity, fetal effects noted at 20 mg/kg/day (190X MRHD based on AUC comparisons) included increased resorptions, decreased fetal body weights, delays in skeletal ossification, bent limb bones, and two fetuses in one litter (2 of 1567 fetuses) demonstrated exencephaly, protruding tongues and low-set ears. No treatment related effects on embryofetal toxicity or teratogenicity were noted at 5 mg/kg/day (32X MRHD based on AUC comparisons).

Intravenous doses of 0.5, 1 and 2 mg/kw/day imiquimod were administered during the period of organogenesis (gestational days 6 — 18) to pregnant female rabbits. No treatment related effects on embryofetal toxicity or teratogenicity were noted at 2 mg/kg/day (2.1X MRHD based on BSA comparisons), the highest dose evaluated in this study, or 1 mg/kg/day (134X MRHD based on AUC comparisons).

A combined fertility and peri- and post-natal development study was conducted in rats. Oral doses of 1, 1.5, 3 and 6 mg/kg/day imiquimod were administered to male rats from 70 days prior to mating through the mating period and to female rats from 14 days prior to mating through parturition and lactation. No effects on growth, fertility, reproduction or post-natal development were noted at doses up to 6 mg/kg/day (29X MRHD based on AUC comparisons), the highest dose evaluated in this study. In the absence of maternal toxicity, bent limb bones were noted in the F1 fetuses at a dose of 6 mg/kg/day (29X MRHD based on AUC comparisons). This fetal effect was also noted in the oral rat embryofetal development study conducted with imiquimod. No treatment related effects on teratogenicity were noted at 3 mg/kg/day (14X MRHD based on AUC comparisons).

8.3  Nursing Mothers

It is not known whether imiquimod is excreted in human milk following use of ZYCLARA® Cream. Because many drugs are excreted in human milk, caution should be exercised when ZYCLARA® Cream is administered to nursing women.

8.4 Pediatric Use

AK is a condition not generally seen within the pediatric population. The safety and efficacy of ZYCLARA® Cream for AK in patients less than 18 years of age has not been established.

8.5 Geriatric Use

Of the 160 subjects treated with ZYCLARA® Cream in the clinical studies, 78 subjects were 65 years or older. No overall differences in safety or effectiveness were observed between these subjects and younger subjects.

10 OVERDOSAGE

Topical overdosing of ZYCLARA® Cream could result in an increased incidence of severe local skin reactions and may increase the risk for systemic reactions.

Hypotension was reported in a clinical trial following multiple oral imiquimod doses of >200 mg (equivalent to the ingestion of imiquimod content of > 21 packets of ZYCLARA® Cream). This resolved following oral or intravenous fluid administration.

11 DESCRIPTION

ZYCLARA® Cream is intended for topical administration. Each gram contains 37.5 mg of imiquimod in a white to faintly yellow oil-in-water cream base consisting of isostearic acid, cetyl alcohol, stearyl alcohol, white petrolatum, polysorbate 60, sorbitan monostearate, glycerin, xanthan gum, purified water, benzyl alcohol, methylparaben, and propylparaben.

Chemically, imiquimod is 1-(2-methylpropyl)-1$H$-imidazo[4,5-c]quinolin-4-amine. Imiquimod has a molecular formula of C14H16N4 and a molecular weight of 240.3. Its structural formula is:

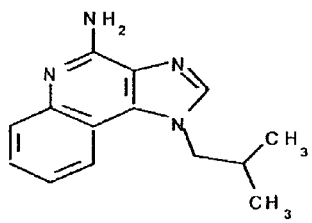

12 CLINICAL PHARMACOLOGY 12.1 Mechanism of Action

The mechanism of action of ZYCLARA® Cream in treating AK lesions is unknown.

12.2 Pharmacodynamics

The pharmacodynamics of ZYCLARA® are unknown.

Imiquimod is a Toll-like receptor 7 agonist that activates immune cells. Topical application to skin is associated with increases in markers for cytokines and immune cells.

In a study of 18 subjects with AK comparing Aldara® (imiquimod) Cream, 5% to vehicle, increases from baseline in week 2 biomarker levels were reported for CD3, CD4, CD8, CD11c, and CD68 for Aldara® (imiquimod) Cream, 5% treated subjects; however, the clinical relevance of these findings is unknown.

12.4 Pharmacokinetics

Following dosing with 2 packets once daily (18.75 mg imiquimod/day) for up to three weeks, systemic absorption of imiquimod was observed in all subjects when Zyclara® Cream was applied to the face and/or scalp in 17 subjects with at least 10 AK lesions. The mean peak serum imiquimod concentration at the end of the trial was approximately 0.323 ng/mL. The median time to maximal concentrations (Tmax) occurred at 9 hours after dosing. Based on the plasma half-life of imiquimod observed at the end of the study, 29.3±17.0 hours, steady-state concentrations can be anticipated to occur by day 7 with once daily dosing.

13 NONCLINICAL TOXICOLOGY 13.1 Carcinogenesis, Mutagenesis, Impairment of Fertility In an oral (gavage) rat carcinogenicity study, imiquimod was administered to Wistar rats on a 2X/week (up to 6 mg/kg/day) or daily (3 mg/kg/day) dosing schedule for 24 months. No treatment related tumors were noted in the oral rat carcinogenicity study up to the highest doses tested in this study of 6 mg/kg administered 2X/week in female rats (8.2X MRHD based on weekly AUC comparisons), 4 mg/kg administered 2X/week in male rats (7.1X MRHD) based on weekly AUC comparisons) or 3 mg/kg administered 7X/week to male and female rats (14X MRHD based on weekly AUC comparisons).

In a dermal mouse carcinogenicity study, imiquimod cream (up to 5 mg/kg/application imiquimod or 0.3% imiquimod cream) was applied to the backs of mice 3X/week for 24 months. A statistically significant increase in the incidence of liver adenomas and carcinomas was noted in high dose male mice compared to control male mice (24X MRHD based on weekly AUC comparisons). An increased number of skin papillomas was observed in vehicle cream control group animals at the treated site only.

In a 52-week dermal photo-carcinogenicity study, the median time to onset of skin tumor formation was decreased in hairless mice following chronic topical dosing (3X/week; 40 weeks of treatment followed by 12 weeks of observation) with concurrent exposure to UV radiation (5 days per week) with vehicle alone. No additional effect on tumor development beyond the vehicle effect was noted with the addition of the active ingredient, imiquimod, to the vehicle cream.

Imiquimod revealed no evidence of mutagenic or clastogenic potential based on the results of five in vitro genotoxicity tests (Ames assay, mouse lymphoma L5178Y assay, Chinese hamster ovary cell chromosome aberration assay, human lymphocyte chromosome aberration assay and SHE cell transformation assay) and three in vivo genotoxicity tests (rat and hamster bone marrow cytogenetics assay and a mouse dominant lethal test).

Daily oral administration of imiquimod to rats, throughout mating, gestation, parturition and lactation, demonstrated no effects on growth, fertility or reproduction, at doses up to 29X MRHD based on AUC comparisons.

14  CLINICAL STUDIES

In two double-blind, randomized, vehicle-controlled clinical studies, 319 subjects with AK were treated with ZYCLARA® Cream, or vehicle cream. Studies enrolled subjects >18 years of age with 5-20 typical visible or palpable AK lesions of the face or scalp. Study cream was applied to either the entire face (excluding ears) or balding scalp once daily for two 2-week treatment cycles separated by a 2-week no-treatment period. Subjects then continued in the study for an 8-week follow-up period during which they returned for clinical observations and safety monitoring. Study subjects ranged from 36 to 90 years of age and 54% had Fitzpatrick skin type I or II. All ZYCLARA® Cream-treated subjects were Caucasians.

On a scheduled dosing day, up to two packets of the study cream were applied to the entire treatment area prior to normal sleeping hours and left on for approximately 8 hours. Efficacy was assessed by AK lesion counts at the 8-week post-treatment visit. All AKs in the treatment area were counted, including baseline lesions as well as lesions which appeared during therapy.

Complete clearance required absence of any lesions including those that appeared during therapy in the treatment area. Complete and partial clearance rates are shown in the tables below. Partial clearance rate was defined as the percentage of subjects in whom the number of baseline AKs was reduced by 75% or more. The partial clearance rate was measured relative to the numbers of AK lesions at Baseline.

Table 3: Rate of Subjects with Complete Clearance at 8 Weeks Post Treatment

|  | ZYCLARA® Cream 3.75% | Vehicle Cream |
|---|---|---|
| Study 1 | 25.9% (21/81) | 2.5% (2/80) |
| Study 2 | 45.6% (36/79) | 10.1% (8/79) |

Table 4: Rate of Subjects with Partial Clearance (>75%) at 8 Weeks Post Treatment

|  | ZYCLARA® Cream 3.75% | Vehicle Cream |
|---|---|---|
| Study 1 | 45.7 (37/81) | 18.8 (15/80) |
| Study 2 | 73.4 (58/79) | 26.6 (21/79) |

During the course of treatment, 86% (138/160) of subjects experienced a transient increase in lesions evaluated as actinic keratoses relative to the number present at baseline within the treatment area.

16  HOW SUPPLIED/STORAGE AND HANDLING

ZYCLARA® (imiquimod) Cream, 3.75%, is supplied as follows:

Single-use packets which contain 250 mg of the cream. Available in a box of 28 packets, NDC 29336-710-28.

A pump which contains 7.5g of the cream, NDC 29336-750-75

A pump which contains 15g of the cream, NDC 29336-750-15

Store at 25°C (77°F); excursions permitted to 15° to 30°C (59° to 86°F) [see USP Controlled Room Temperature].

Avoid freezing.

*Keep out of reach of children.*

17 PATIENT COUNSELING INFORMATION

*See FDA-Approved Patient Labeling (17.7).*

17.1 Instructions for Administration

Zyclara® Cream should be used as directed by a physician *[see Dosage and Administration (2)]*. Zyclara® Cream is for external use only. Contact with the eyes, lips and nostrils should be avoided *[see Indications and Usage (1) and Dosage and Administration (2)]*. The treatment area should not be bandaged or otherwise occluded. Partially used packets or unused pumps should be discarded and not reused. Emptied pumps should be discarded. The prescriber should demonstrate the proper application technique to maximize the benefit of Zyclara® Cream therapy.

It is recommended that patients wash their hands before and after applying Zyclara® Cream.

17.2 Local Skin Reactions

Patients may experience local skin reactions during treatment with Zyclara® Cream. Potential local skin reactions include erythema, edema, erosions/ulcerations, weeping/exudate, flaking/scaling/dryness, and scabbing/crusting. These reactions can range from mild to severe in intensity and may extend beyond the application site onto the surrounding skin. Patients may also experience application site reactions such as itching, irritation or pain *[see Adverse Reactions (6)]*.

Local skin reactions may be of such an intensity that patients may require rest periods from treatment. Treatment with Zyclara® Cream can be resumed after the skin reaction has subsided, as determined by the physician. However, each treatment cycle should not be extended beyond 2 weeks due to missed doses or rest periods. Patients should contact their physician promptly if they experience any sign or symptom at the application site that restricts or prohibits their daily activity or makes continued application of the Zyclara ® Cream difficult.

Because of local skin reactions, during treatment and until healed, the treatment area is likely to appear noticeably different from normal skin. Localized hypopigmentation and hyperpigmentation have been reported following use of imiquimod cream. These skin color changes may be permanent in some patients.

17.3 Systemic Reactions

Patients may experience flu-like systemic signs and symptoms during treatment with Zyclara® Cream. Systemic signs and symptoms may include fatigue, nausea, fever, myalgia, arthralgia, and chills *[see Adverse Reactions (6)]*. An interruption of dosing or dose adjustment and an assessment of the patient should be considered.

17.4 Recommended Administration

Dosing is once daily before bedtime to the skin of the affected area (entire face or balding scalp) for two 2-week treatment cycles separated by a 2-week no-treatment period. However, the treatment period should not be extended beyond two 2-week treatment cycles due to missed doses or rest periods. Treatment should continue for the full treatment course even if all actinic keratoses appear to be gone *[see Dosage and Administration (2.1)]*.

It is recommended that patients wash their hands before and after applying Zyclara® Cream. Before applying the Zyclara® Cream, the patient should wash the treatment area with mild soap and water and allow the area to dry thoroughly.

It is recommended that the treatment area be washed with mild soap and water 8 hours following Zyclara® Cream application.

Most patients using Zyclara® Cream for the treatment of AK experience erythema, flaking/scaling/dryness and scabbing/crusting at the application site with normal dosing *[see Adverse Reactions (61)]*.

Use of sunscreen is encouraged, and patients should minimize or avoid exposure to natural or artificial sunlight (tanning beds or UVA/B treatment) while using Zyclara® Cream *[see Warnings and Precautions (5.3)]*.

Additional lesions may become apparent in the treatment area during treatment *[see Clinical Studies (14.1)]*.

FDA-Approved Patient Labeling

ZYCLARA® [zi-clar-a]

(imiquimod)

Cream

IMPORTANT: For use on the skin only (topical). Do not use ZYCLARA® Cream in or on your eyes, nostrils, mouth or vagina.

Read the Patient Information that comes with ZYCLARA® Cream before you start using it and each time you get a refill. There may be new information. This leaflet does not take the place of talking with your healthcare provider about your medical condition or treatment. If you do not understand the information, or have any questions about ZYCLARA® Cream, talk with your healthcare provider or pharmacist.

What is ZYCLARA® Cream?

ZYCLARA® Cream is a prescription medicine for use on the face or balding scalp only (a topical medicine) to treat actinic keratosis (AK).

Actinic keratosis is caused by too much sun exposure.

It is not known if ZYCLARA® Cream is safe and effective:

- in people who do not have a normal immune system.
- in the treatment of patients with xeroderma pigmentosum.
- in the treatment of superficial basal cell carcinoma.
- in the treatment of external genital warts.

It is not known if ZYCLARA® Cream is safe and effective in children younger than 18 years old.

What should I tell my healthcare provider before using ZYCLARA® Cream?

Before you use ZYCLARA® Cream, tell your healthcare provider if you:

- have problems with your immune system
- are being treated or have been treated for actinic keratosis with other medicines or surgery. You should not use ZYCLARA® Cream until you have healed from other treatments.
- have other skin problems
- have any other medical conditions
- are pregnant or planning to become pregnant. It is not known if ZYCLARA® Cream can harm your unborn baby. Talk to your healthcare provider if you are pregnant or plan to become pregnant.

- are breast-feeding or plan to breast-feed. It is not known if ZYCLARA® Cream passes into your breast milk and if it can harm your baby. Talk to your healthcare provider about the best way to feed your baby if you use ZYCLARA® Cream.

Tell your healthcare provider about all the medicines you take, including prescription and non-prescription medicines, vitamins and herbal supplements.

Especially tell your healthcare provider if you have had other treatments for actinic keratosis.

How should I use ZYCLARA® Cream?

- Do not get ZYCLARA® Cream in or near your eyes
- Do not get ZYCLARA® Cream in or on your nostrils, lips, or vagina.
- Use ZYCLARA® Cream exactly as your healthcare provider tells you to use it. Your healthcare provider will tell you where to apply ZYCLARA® Cream and how often and for how long to apply it for your condition. Do not apply ZYCLARA® Cream to other areas.
- Using too much ZYCLARA® Cream, or using it too often, or for too long can increase your chances for having a severe skin reaction or other side effects.
- Talk to your healthcare provider if you think ZYCLARA® Cream is not working for you.

How do I use ZYCLARA® Cream packets:

ZYCLARA® Cream should be applied just before your bedtime.

- Wash the area where the ZYCLARA® Cream will be applied with mild soap and water.
- Allow the area to dry.
- Wash your hands.
- Open a packet of ZYCLARA® Cream just before use.
- Apply a thin layer of ZYCLARA® Cream only to the affected area or areas to be treated. Do not use more ZYCLARA® Cream than is needed to cover the treatment area. Do not use more than two packets for each application.
- Rub the ZYCLARA® Cream in all the way to the affected area or areas.
    o Do not get ZYCLARA® Cream in or around your eyes.

- Safely throw away the open packet of ZYCLARA® Cream so that children and pets cannot get it. The open packet should be thrown away even if all the ZYCLARA® Cream was not completely used.
- After you apply ZYCLARA® Cream, wash your hands well.
- Leave the ZYCLARA® Cream on the affected area or areas for the time prescribed by your healthcare provider. Do not bathe or get the treated area wet before the right time has passed.

Do not leave ZYCLARA® Cream on your skin longer than prescribed.
- After about 8 hours, wash the treated area or areas with mild soap and water.
- If you forget to apply ZYCLARA® Cream, continue on your regular schedule and do not make up the missed dose(s).

If you get ZYCLARA® Cream in your mouth or in your eyes rinse well with water right away.

Figure 13:
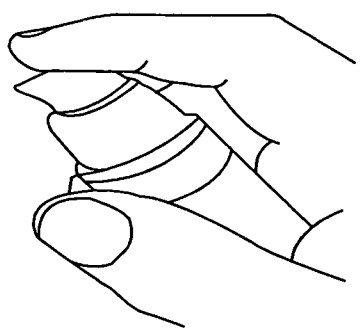
FIG. 13 is a perspective view of a proper methodology for utilizing the pump in accordance with the invention.

How do I use ZYCLARA® Cream pump:

ZYCLARA® Cream should be applied just before your bedtime.
- Wash the area where the ZYCLARA® Cream will be applied with mild soap and water.
- Allow the area to dry.
- Wash your hands
- Slightly tilt the pump as shown when dispensing ZYCLARA® Cream, as shown in FIG. 13.

- Before using the pump for the first time only, remove the cap and prime the pump by firmly pressing the top of the pump all the way down (up to five times as needed) until the ZYCLARA® Cream appears. The primed ZYCLARA® Cream should be dispensed into a tissue and then discarded. The pump is now ready to use.
- To apply the ZYCLARA® Cream, firmly press the top of the pump all of the way down to dispense the ZYCLARA® Cream into your hand.
- Apply a thin layer of ZYCLARA® Cream only to the areas to be treated as directed by your healthcare provider. Do not use more ZYCLARA® Cream than is needed to cover the treatment area.

- Do not use more than two full pump depressions for each daily application.
- Rub the ZYCLARA® Cream in all the way to the affected area or areas.
  - Do not get ZYCLARA® Cream in or around your eyes.
- After you apply ZYCLARA® Cream, wash your hands well.
- Leave the ZYCLARA® Cream on the affected area or areas for the time prescribed by your healthcare provider. Do not bathe or get the treated area wet before the right time has passed. Do not leave ZYCLARA® Cream on your skin longer than prescribed.
- After about 8 hours, wash the treated area or areas with mild soap and water.
- If you forget to apply ZYCLARA® Cream, continue on your regular schedule and do not make up the missed dose(s).
- If you get Zyclara® Cream in your mouth or in your eyes rinse well with water right away.
- When you have completed all of your doses as instructed, safely throw the pump away so that children and pets cannot get it.

What should I avoid while using ZYCLARA® Cream?

- Do not cover the treated area with bandages or other closed dressings.
- Do not use sunlamps or tanning beds, and avoid sunlight as much as possible during treatment with ZYCLARA® Cream. Use sunscreen and wear protective clothing if you go outside during daylight.

What are the possible side effects of ZYCLARA® Cream?

ZYCLARA® Cream may cause serious side effects, including:

- Local Skin Reactions: skin redness, scabbing or crusting, flaking, scaling or dryness, swelling, sores or blisters, draining (weeping)
- Flu-like symptoms: tiredness, nausea, vomiting, fever, chills, muscle pain, joint pain The most common side effects of ZYCLARA® Cream include:
- headache
- itching at application site
- tiredness
- nausea
- skin irritation

- pain at the treatment area
- fever
- loss of appetite
- dizziness
- cold sores
- pain
- chest pain
- diarrhea
- swelling of lymph nodes Tell your healthcare provider if you have any side effect that bothers you or that does not go away.

These are not all the possible side effects of ZYCLARA® Cream. For more information, ask your healthcare provider or pharmacist.

Call your doctor for medical advice about side effects. You may report side effects to FDA at 1-800-FDA-1088 or to Graceway Pharmaceuticals, LLC at 1-800-328-0255.

How do I store ZYCLARA® Cream?
- Store ZYCLARA® Cream at 59° F to 86° F (15° C to 30° C).
- Do not freeze.

Keep ZYCLARA® Cream and all medicines out of the reach of children.

General Information about ZYCLARA® Cream

Medicines are sometimes prescribed for purposes other than those listed in the patient information. Do not use ZYCLARA® Cream for a condition for which it was not prescribed. Do not give ZYCLARA® Cream to other people, even if they have the same symptoms you have. It may harm them.

This patient information leaflet summarizes the most important information about ZYCLARA® Cream. If you would like more information, talk with your healthcare provider. You can ask your pharmacist or healthcare provider for information about ZYCLARA® Cream that is written for the health professionals.

What are the ingredients in ZYCLARA® Cream?

Active Ingredient: imiquimod

Inactive ingredients: isostearic acid, cetyl alcohol, stearyl alcohol, white petrolatum, polysorbate 60, sorbitan monostearate, glycerin, xanthan gum, purified water, benzyl alcohol, methylparaben, and propylparaben.

Manufactured by
3M Health Care Limited
Loughborough LE11 1EP England
Distributed by
Graceway Pharmaceuticals, LLC
Bristol, TN 37620

[000325] PRODUCT MONOGRAPH

ZYCLARA®

(Pump or single-use sachets)

(imiquimod) Cream, 3.75% for Actinic Keratosis 9.4 mg per 250 mg single-dose packet two 7.5g pumps or one 15g pump for the total 2-cycle treatment course Immune response modifier Graceway Pharmaceuticals
252 Pall Mall St., Suite 302
London, Ontario
Canada
N6A 5P6

Date of Preparation:
July 8, 2010

Submission Control No:

TABLE OF CONTENTS

IN THE UNITED STATES PATENT AND TRADEMARK OFFICE ................................... 1

APPLICATION FOR U.S. LETTERS PATENT ................................................................. 1

Title: ......................................................................................................................................... 1

Inventors: .................................................................................................................................. 1

PART I: HEALTH PROFESSIONAL INFORMATION FOR ACTINIC KERATOSIS .......... 229
    SUMMARY PRODUCT INFORMATION ........................................................... 229
    INDICATIONS AND CLINICAL USE ................................................................. 229
    CONTRAINDICATIONS ....................................................................................... 229
    WARNINGS AND PRECAUTIONS ..................................................................... 229
    ADVERSE REACTIONS ....................................................................................... 232
    DRUG INTERACTIONS ....................................................................................... 234
    DOSAGE AND ADMINISTRATION ................................................................... 235
    OVERDOSAGE ...................................................................................................... 236
    ACTION AND CLINICAL PHARMACOLOGY ................................................. 236
    STORAGE AND STABILITY ............................................................................... 237
    DOSAGE FORMS, COMPOSITION AND PACKAGING .................................. 237

PART II: SCIENTIFIC INFORMATION ................................................................................. 239
    PHARMACEUTICAL INFORMATION ............................................................... 239
    CLINICAL TRIALS ............................................................................................... 240
    DETAILED PHARMACOLOGY .......................................................................... 241
    TOXICOLOGY ...................................................................................................... 243
    REFERENCES ....................................................................................................... 245

PART III: CONSUMER INFORMATION ............................................................................... 248
    SUMMARY PRODUCTION INFORMATION ................................................... 308

PART II: SCIENTIFIC INFORMATION ............................................................................. 318
    CLINICAL TRIALS ............................................................................................... 319

PART III: CONSUMER INFORMATION ........................................................................... 327

ZYCLARA®

(imiquimod) Cream, 3.75%

PART I: HEALTH PROFESSIONAL INFORMATION

SUMMARY PRODUCT INFORMATION

| Route of Administration | Dosage Form / Strength | Clinically Relevant Nonmedicinal Ingredients |
|---|---|---|
| Topical | Cream / 9.4 mg imiquimod per 250 mg single-dose packet (3.75 % w/w) | *For a complete listing see Dosage Forms, Composition and Packaging section.* |

Geriatrics (<65 years of age)

No overall differences in safety or effectiveness were observed in clinical studies between the geriatric population and younger subjects (see WARNINGS AND PRECAUTIONS, Geriatrics).

Pediatrics

Safety and efficacy in patients below the age of 18 years have not been established (see WARNINGS AND PRECAUTIONS, Pediatrics).

Immunosuppressed

The safety and efficacy of ZYCLARA® Cream in immunosuppressed patients have not been established (See WARNINGS AND PRECAUTIONS, Immune).

CONTRAINDICATIONS

ZYCLARA® Cream is contraindicated in individuals with a history of sensitivity reactions to imiquimod or to any of the components in the formulation. It should be discontinued if hypersensitivity to any of its ingredients is noted (See WARNINGS AND PRECAUTIONS, Sensitivity).

WARNINGS AND PRECAUTIONS

General

The efficacy of ZYCLARA® Cream in the prevention of squamous cell carcinoma (SCC) associated with AK has not been established.

The safety and efficacy of ZYCLARA® Cream topically applied to an area larger than the face or balding scalp (approximately 200 cm2) has not been established. Therefore, topical application of ZYCLARA® Cream to larger areas is not recommended.

Systemic Reactions

Flu-like signs and symptoms may accompany, or even precede, local skin reactions and may include fatigue, nausea, fever, myalgias, arthralgias, and chills. An interruption of dosing or dose adjustment and an assessment of the patient should be considered (See ADVERSE REACTIONS)

Carcinogenesis and Mutagenesis

In a hairless mouse photocarcinogenicity study with solar ultraviolet light irradiation, imiquimod cream enhanced UVR-induced skin tumour development, but not beyond that of the vehicle cream. Vehicle cream alone enhanced ultraviolet induced skin tumour development (See TOXICOLOGY, Carcinogenicity). It is recommended that patients minimize or avoid natural or artificial sunlight exposure during treatment with ZYCLARA® Cream.

Immune

The safety and efficacy of ZYCLARA® Cream in immunosuppressed patients have not been established.

ZYCLARA® Topical Cream should be used with caution in patients with pre-existing autoimmune conditions (including thyroiditis, multiple sclerosis, spondyloarthropathy, psoriasis, ulcerative colitis) (See ADVERSE REACTIONS, Post-Market Adverse Drug Reactions).

Sensitivity

Hypersensitivity reactions (urticaria) and erythema multiforme have been reported in patients receiving imiquimod cream, however causality has not been established. ZYCLARA® Cream should be discontinued immediately if these events occur.

Skin

Local skin reactions such as erythema, scabbing/crusting, flaking/scaling/dryness, and edema are common.

Intense local skin reactions including erythema, scabbing/crusting and erosion/ulceration can occur after a few applications of ZYCLARA® Cream and may require an interruption of dosing (See ADVERSE REACTIONS and DOSAGE AND ADMINISTRATION)

ZYCLARA® Cream has the potential to exacerbate inflammatory conditions of the skin, including chronic graft versus host disease.

Should a severe local skin reaction occur, the ZYCLARA® Cream should be removed by washing the treatment area with mild soap and water and drying the area thoroughly. Treatment with ZYCLARA® Cream can be resumed after consultation with the treating physician, and once the skin reaction has subsided.

Exposure to sunlight (including sunlamps) should be avoided or minimized during use of ZYCLARA® Cream because of concern for heightened sunburn susceptibility. Patients should be warned to use protective clothing (e.g. hat) when using ZYCLARA® Cream. Patients with sunburn should be advised not to use ZYCLARA® Cream until fully recovered. Patients who may have considerable sun exposure, e.g., due to their occupation, and those patients with inherent sensitivity to sunlight should exercise caution when using ZYCLARA® Cream. Phototoxicity has not been adequately assessed for ZYCLARA® Cream. The enhancement of ultraviolet carcinogenicity is not necessarily dependent on phototoxic mechanisms. Imiquimod cream shortened the time to skin tumour formation in an animal photoco-carcinogenicity study (See TOXICOLOGY, Carcinogenicity). Therefore, it is prudent for patients to minimize or avoid natural or artificial sunlight exposure.

Special Populations

Pregnant Women: Imiquimod was not teratogenic in rat or rabbit teratology studies. In rats at a high maternally toxic dose (28 times human dose on a mg/m2 basis), reduced pup weights and delayed ossification were observed. However, there are no adequate and well-controlled studies in pregnant women. Because animal reproduction studies are not always predictive of human response, this drug should be used during pregnancy only if the potential benefit justifies the potential risk to the fetus.

Nursing Women: It is not known whether topically applied imiquimod is excreted in human milk. Because many drugs are excreted in human milk, caution should be exercised when ZYCLARA® Cream is administered to nursing women.

Pediatrics (< 18 years of age): Safety and efficacy in patients below the age of 18 years have not been established.

Geriatrics (> 65 years of age): Of the 160 subjects treated with ZYCLARA® Cream in the clinical studies, 78 subjects were 65 years or older. No overall differences in safety or effectiveness were observed between these subject and younger subjects. No other clinical experience has identified differences in responses between the elderly and younger subjects, but greater sensitivity of some older individuals cannot be ruled out.

ADVERSE REACTIONS

Adverse Drug Reaction Overview

Clinical Trial Adverse Drug Reactions

The data described below reflect exposure to ZYCLARA® Cream or placebo in 319 subjects enrolled in two double-blind, placebo-controlled studies. Subjects applied ZYCLARA® Cream or placebo daily to the skin of the affected area (either the entire face or balding scalp) for two 2-week treatment cycles separated by a 2-week no treatment period.

Table 1: Adverse Reactions Occurring in > 1% of ZYCLARA®-Treated Subjects and at a Greater Frequency than with Placebo in the Combined Studies

| Preferred Term | ZYCLARA® Cream, 3.75% (N-160) | Placebo (N=159) |
|---|---|---|
| Headache | 10 (6.3%) | 5 (3.1%) |
| Application site pruritus | 7 (4.4%) | 1 (0.6%) |
| Fatigue | 7 (4.4%) | 0 (0%) |
| Nausea | 6 (3.8%) | 2 (1.3%) |
| Application site irritation | 5 (3.1%) | 0 (0%) |
| Application site pain | 5 (3.1%) | 0 (0%) |
| Pyrexia | 5 (3.1%) | 0 (0%) |
| Anorexia | 4 (2.5%) | 0 (0%) |
| Dizziness | 4 (2.5%) | 0 (0%) |
| Herpes simplex | 4 (2.5%) | 1 (0.6%) |
| Pain | 4 (2.5%) | 0 (0%) |
| Chest pain | 3 (1.9%) | 0 (0%) |
| Diarrhea | 3 (1.9%) | 0 (0%) |
| Lymphadenopathy | 3 (1.9%) | 0 (0%) |
| Application Site Swelling | 2 (1.3%) | 0 (0%) |
| Arthralgia | 2 (1.3%) | 0 (0%) |
| Blood glucose increased | 2 (1.3%) | 0 (0%) |
| Dermatitis | 2 (1.3%) | 0 (0%) |
| Food poisoning | 2 (1.3%) | 0 (0%) |
| Insomnia | 2 (1.3%) | 0 (0%) |
| Seborrhoeic keratosis | 2 (1.3%) | 0 (0%) |
| Squamous cell carcinoma | 2 (1.3%) | 1 (0.6%) |
| Vomiting | 2 (1.3%) | 1 (0.6%) |

Table 2: Application Site Reactions in ZYCLARA®-Treated Subjects as Assessed by the Investigator

| Included Term | ZYCLARA® Cream, 3.75%* (N=160) | Placebo* (N=159) |
|---|---|---|
| Any application site reaction | 17 (10.6%) | 2 (1.3%) |
| Application site pruritus | 7 (4.4%) | 1 (0.6%) |
| Application site irritation | 5 (3.1%) | 0(0%) |
| Application site pain | 5 (3.1%) | 0(0%) |
| Application site swelling | 2 (1.3%) | 0(0%) |
| Application site paraesthesia | 1 (0.6%) | 1 (0.6%) |
| Application site scar | 1 (0.6%) | 0(0%) |

* up to 2 packets daily

Local skin reactions were collected independently of the adverse event "application site reaction" in an effort to provide a better picture of the specific types of local reactions that might be seen. The most frequently reported local skin reactions were erythema, flaking/scaling/dryness, and scabbing/crusting. The prevalence and severity of local skin reactions that occurred during controlled studies are shown in the following table.

Table 3: Local Skin Reactions in the Treatment Area in ZYCLARA®-Treated Subjects as Assessed by the Investigator

|  | ZYCLARA® Cream, 3.75% (N=160) | | Placebo (N=159) | |
| --- | --- | --- | --- | --- |
|  | All Grades | Severe | All Grades | Severe |
| Erythema | 154 (96.3%) | 40 (25.2%) | 124 (78.0%) | 0 (0.0%) |
| Edema | 120 (75.0%) | 9 (5.7%) | 31 (19.5%) | 0 (0.0%) |
| Weeping/Exudate | 81 (50.6%) | 9 (5.7%) | 6 (3.8%) | 0 (0.0%) |
| Flaking/Scaling/Dryness | 147 (91.9%) | 13 (8.2%) | 123 (77.4%) | 2 (1.3%) |
| Scabbing/Crusting | 149 (93.1%) | 22 (13.8%) | 72 (45.3%) | 0 (0.0%) |
| Erosion/Ulceration | 99 (61.9%) | 17 (10.7%) | 14 (8.8%) | 0 (0.0%) |

Other adverse events observed in subjects treated with ZYCLARA® Cream in treatment regimens other than two 2-week treatment cycles include: application site bleeding, cheilitis, chills, herpes zoster, influenza-like illness, lethargy, myalgia, pancytopenia and pruritus.

Post-Market Adverse Drug Reactions

Rare reports have been received of either the onset or exacerbation of autoimmune conditions (including thyroiditis, multiple sclerosis, spondyloarthropathy, psoriasis, ulcerative colitis) in association with imiquimod 5% cream therapy.

DRUG INTERACTIONS

Overview

Interactions between ZYCLARA® Cream with other drugs have not been established.

DOSAGE AND ADMINISTRATION

Recommended Dose and Dosage Adjustment

ZYCLARA® Cream (up to 2 packets or 2 full actuations of the pump) should be applied once daily before bedtime to the skin of the affected treatment field (area) for two treatment cycles of 2 weeks each separated by a 2-week no-treatment period or as directed by physician.

Patients should be prescribed no more than 56 packets, two 7.5g pumps or one 15g pump for the total 2-cycle treatment course.

Missed Dose

Each treatment cycle should not be extended beyond 2 weeks due to missed doses or rest periods.

Administration

Before applying the ZYCLARA® Cream, the patient should wash the treatment area with mild soap and water and allow the area to dry thoroughly. ZYCLARA® Cream should be applied as a thin film to the entire treatment area and rubbed in until the ZYCLARA® Cream is no longer visible. Up to 2 packets or 2 full actuations of the pump of ZYCLARA® Cream may be applied to the treatment area (face or scalp, but not both) at each daily application. Partially-used packets should be discarded and not reused. When the treatment course is complete, any remaining packets or pumps should be discarded. ZYCLARA® Cream should be left on the skin for approximately 8 hours, after which time the ZYCLARA® Cream should be removed by washing the area and the hands with mild soap and water. The prescriber should demonstrate the proper application technique to maximize the benefit of ZYCLARA® Cream therapy.

Use of the ZYCLARA® Cream in or near the eyes, lips and nostrils should be avoided.

The application site is not to be occluded.

Local skin reactions in the treatment area are common (See ADVERSE REACTIONS).

A rest period of several days and interruption of dosing may be considered if required by the patient's discomfort or severity of the local skin reaction. However, each treatment cycle should not be extended beyond 2 weeks due to missed doses or rest periods. Response to treatment cannot be adequately assessed until resolution of local skin reactions. Lesions that do not respond to treatment should be carefully re-evaluated and management reconsidered.

A transient increase in AK lesion counts may be observed during treatment due to the likely effect of imiquimod on subclinical lesions. The patient should continue dosing as prescribed.

OVERDOSAGE

Overdosage of ZYCLARA® Cream in humans is unlikely due to minimal percutaneous absorption. Animal studies reveal a rabbit dermal lethal imiquimod dose of greater than 5000 mg/kg. Persistent topical overdosing of ZYCLARA® Cream could result in an increased incidence of severe local skin reactions and may increase the risk for systemic reactions.

The most clinically serious adverse event reported following multiple oral imiquimod doses of 200 mg was hypotension which resolved following oral or intravenous fluid administration.

ACTION AND CLINICAL PHARMACOLOGY

Mechanism of Action

In vitro studies have demonstrated that imiquimod induces the release of interferon alpha (IFN-$a$) and other cytokines from human monocytes/macrophages and keratinocytes. The panel of cytokines induced varied with the cell's tissue origin. Topical in vivo application of imiquimod cream on mouse skin resulted in increased concentrations of IFN and tumour necrosis factor (TNF) compared with skin of untreated mice.

Pharmacodynamics

The mechanism of action of imiquimod in treating actinic keratosis (AK) lesions is unknown. While the following have been observed, the clinical significance of these observations in AK is not known. In a study of 58 patients with AK treated with imiquimod 3 times per week, the response of biomarkers sensitive to imiquimod after 16 weeks of dosing increased compared to the response after the first dose. For interleukin-1 antagonist, the median concentration observed following multiple dosing was <2-fold higher than that after single dose administration, for interferon-$\alpha$ was 3-fold, and for 2'5'-oligoadenylate synthetase was approximately 3-fold.

Pharmacokinetics

Percutaneous absorption of imiquimod has been studied through intact healthy skin, the skin of genital warts, and lesions of sun damaged skin. Percutaneous absorption of [14C]imiquimod was minimal in a study involving six healthy subjects treated with a single topical application (5 mg) of [14C]imiquimod in cream formulation. No radioactivity [14C] was detected in the serum (lower limit of quantitation is 1 ng/mL) and < 0.9% of the radiolabelled dose was excreted in the urine and feces following topical application.

ZYCLARA® Cream exhibited low systemic exposure to imiquimod and its metabolites when it was applied daily for 3 weeks (18.75 mg, 2 packets once daily) to the entire face and/or balding scalp (approximately 200 cm2) of patients with AK (N=17). A mean (median) peak serum drug concentration at the end of week 3 was approximately 0.323 ng/mL. Steady-state levels were achieved in 2 weeks and Tmax ranged between 6 and 9 hours.

The apparent half-life following topical dosing of 3.75% imiquimod cream was calculated as 29 hours after daily administration of 2 packets (18.75 mg) for 3 weeks.

Special Populations and Conditions

Age: No formal pharmacokinetic study was conducted to examine age related differences in the pharmacokinetic profile of ZYCLARA® Cream.

Gender: During 3 weeks of treatment, the Cmax and AUC0-24 on Day 21 appeared to be similar in female and male subjects and lower in male subjects who applied ZYCLARA® Cream, to the balding scalp rather than the face.

STORAGE AND STABILITY

Store between 15°C and 25°C. Avoid freezing.

DOSAGE FORMS, COMPOSITION AND PACKAGING

ZYCLARA® Cream is supplied as follows:

Single-use packets which contain 250 mg of the cream. Available as a box of 28 packets.

A pump which contains 7.5g of the cream.

A pump which contains 15g of the cream.

Each gram of ZYCLARA® Cream contains 37.5 mg of imiquimod in an off-white to faintly yellow oil-in-water vanishing cream base consisting of isostearic acid, cetyl alcohol, stearyl alcohol, white petrolatum, polysorbate 60, sorbitan monostearate, glycerin, xanthan gum, purified water, benzyl alcohol, methylparaben, and propylparaben.

PART II: SCIENTIFIC INFORMATION

PHARMACEUTICAL INFORMATION

Drug Substance

Common name     Imiquimod (USAN, INN)

Chemical name: 1-(2-methylpropyl)-1*H*-imidazo[4,5-*c*]quinolin-4-amine

Molecular formula and molecular mass: $C_{14}H_{16}N_4$; MW = 240.3

Structural formula:

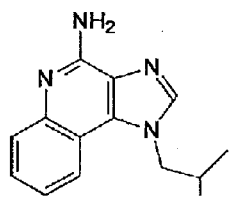

Physicochemical properties:

<u>Physical Form:</u>   Crystalline solid that varies in colour from white to off-white or buff. The compound has no odour.

| Solubility: | Practically insoluble in most common organic solvents and in aqueous systems except at extremely low pH conditions. It can be made soluble to the extent of at least 100 mg/mL in methanol (as a salt) upon the addition of a few drops of hydrochloric or acetic acid. Soluble in fatty acids such as oleic acid and isostearic acid. |
| pKa Value: | The ionization constant for imiquimod was determined by ultraviolet (UV) spectroscopy and pH-solubility to be about 7.5. |
| Melting point: | 297-299°C with sublimation. |

CLINICAL TRIALS

In two double-blind, randomized, placebo-controlled clinical studies, 319 subjects with AK were treated with 3.75% imiquimod cream, or a matching placebo cream. Studies enrolled subjects >18 years of age with 5-20 typical visible or palpable AK lesions of the face or scalp in an area that exceeded 25cm2. Study cream was applied to full face or balding scalp once daily for two 2-week treatment cycles separated by a 2-week no-treatment period. Subjects then continued in the study for an 8-week follow-up period during which they returned for clinical observations and safety monitoring. Study subjects ranged from 36 to 90 years of age and 54% had Fitzpatrick skin type I or II. All ZYCLARA® Cream-treated subjects were Caucasians.

On a scheduled dosing day, the study cream was applied to the entire treatment area prior to normal sleeping hours and left on for approximately 8 hours. Efficacy was assessed by AK lesion counts at the 8-week post-treatment visit. All AKs in the treatment area were counted, including baseline lesions as well as new or sub-clinical AK lesions which appeared during therapy.

Complete clearance required clearance of all lesions. The partial clearance rate and percent reductions of AKs were measured relative to the numbers of AK lesions at baseline. Partial clearance rate was defined as the proportion of subjects in whom the number of baseline AKs was reduced by 75% or more. Complete and partial clearance rates, and percent reductions in AK counts from baseline are shown in the efficacy endpoints Table 4 below.

Table 4: Efficacy Endpoints[a]

|  | ZYCLARA® Cream, 3.75% | Placebo cream | p-value |
|---|---|---|---|
| Complete Clearance Rate | 35.6% (57/160) | 6.3% (10/159) | <0.001 |
| Partial Clearance Rate | 59.4% (95/160) | 22.6% (36/159) | <0.001 |
| Percent Reduction of AKs (median) | 81.8% | 25.0% | <0.001 |

[a] Studies GW01-0702 and GW01-0704

Sub-clinical AK lesions may become apparent in the treatment area during treatment with ZYCLARA® Cream. During the course of treatment, >85% (138/160) of subjects experienced an increase in AK lesions relative to the number present at baseline within the treatment area. Subjects with an increase in AK lesions had a similar response to those with no increase in AK lesions.

DETAILED PHARMACOLOGY

Pharmacodynamics: Imiquimod is an immune response modifier that is not a nucleoside analogue. Saturable binding studies suggest a membrane receptor for imiquimod exists on responding cells. In vitro studies have demonstrated that imiquimod induces the production of IFN and other cytokines from a variety of human and animal cells. In addition, cytokines were produced following dermal application and oral administration in various laboratory animals and in human studies following oral administration of imiquimod. In animal models imiquimod is an effective antiviral and antitumour agent whose activity is principally due to induction of alpha interferon but other cytokines are also involved In vitro studies using isolated guinea pig myocardium, showed stimulation with tachyphylaxis development after multiple doses. Moderate to marked inhibition of agonist-induced contractions was observed in isolated guinea pig tracheal strips. Intravenous administration of a bolus dose of imiquimod caused CNS and cardiac stimulation in dogs. Little activity was found in inflammatory rat models. Some local anaesthetic activity, slight effect on locomotor, and slight effect on hexobarbital induced sleep time were observed in the mouse.

Pharmacokinetics and Metabolism: Animal and human dermal pharmacokinetic results indicate that minimal, if any, systemic absorption occurs following dermal application of imiquimod cream. Imiquimod was not quantifiable in the serum of rats dosed topically three times per week at 5 mg/kg for 4 weeks; low levels of metabolite were quantifiable after the last, but not after the first dose. In guinea pigs, after a single large (21 mg/kg) topical dose of [14C] imiquimod as a 5% cream, only low concentrations of imiquimod were quantifiable in plasma.

Oral ADME (absorption, distribution, metabolism, elimination) studies in laboratory animals, revealed extensive biotransformation followed by both urinary and biliary excretion of metabolites. Tissue distribution is rapid with clearance after 2 to 3 days with the exception of pigmented tissues - skin and uveal tract of the eye. No evidence of ocular toxicity was found in six month oral rat and monkey imiquimod toxicity studies conducted at high daily doses.

Percutaneous absorption of 5% imiquimod cream following topical application for 8 12 hours was observed across the intact skin of healthy subjects and the affected skin of subjects with either genital warts or AK. In subjects with AK, urinary recovery less than 0.6% of the applied dose was seen. Because of this low percutaneous absorption, serum levels of imiquimod and metabolites were low or undetectable in these subjects.

TOXICOLOGY

Acute Toxicity: Acute dermal toxicity studies in rabbits with unformulated imiquimod under occlusion did not reveal any toxic effects at very high dose levels - 5000 mg/kg. When administered orally, intraperitoneally, subcutaneously or intravenously, single dose studies revealed that imiquimod produced central nervous system (CNS) stimulation and convulsions at lethal doses. However, signs of CNS toxicity did not occur when animals were given lower repeat doses (100 mg/kg or lower).

Table 5

| Species | Route | $LD_{50}$ (mg/kg) |
|---|---|---|
| Mouse | oral | 403 |
| | intraperitoneal | 879 |
| Rat | oral | 1665 |
| | intraperitoneal | 763 |
| | subcutaneous | ≈ 20 |
| Rabbit | dermal | > 5000 |
| Monkey | oral | > 200 |
| | intravenous infusion | ≈ 8 |
| | intravenous bolus | > 6 |

Irritation/Sensitization Studies: Skin irritation studies in rabbits showed that imiquimod was non-irritating when dosed unformulated at 500 mg or formulated up to 250 mg per site. Unformulated imiquimod produced mild or no eye irritation in rabbits when applied unformulated at 100 mg/eye or formulated up to 5 mg/eye. Formulated imiquimod was not irritating to rat or rabbit vaginal tract when applied every other day for 10 days at 10 and 50 mg/dose respectively. Dermal sensitization studies in guinea pigs showed that the imiquimod cream was not a dermal sensitizer. Comparison of the dermal reaction to imiquimod cream in animal species (rat, mouse, rabbit) with clinical study results, reveals that mouse and rabbit results are comparable to humans. The more severe dermal irritation seen in the rat is not predictive of human response.

Long-Term Toxicity: Two repeat dose dermal toxicity studies in rats showed a compound related but non-dose related dermal irritation. A dose-related decrease in body weight of male rats was also observed. No systemic toxicity was found at doses up to 5 mg/kg three days per week for 4 weeks or at doses up to 2.5 mg/kg three days per week for 16 weeks.

The adverse effects observed for the high doses (10-30 mg/kg) in repeat dose oral toxicity studies in rats and monkeys could be related to exaggerated pharmacological effects of excessive cytokines induction and lymphoid stimulation: reduced body weight gains, anaemia, serum protein changes and death. High repeat daily doses of imiquimod did not produce necrosis in any organ; the compound is not cytotoxic. Recovery animals demonstrated that the adverse effects were readily reversible. An oral no adverse effect level of 3 mg/kg/day was determined in both rats and monkeys dosed daily for 6 months.

Carcinogenicity: Two-year bioassays in Wistar rats (up to 3 mg/kg orally per day) and CD-1 mice (up to 4.5 mg/kg applied topically 3 times per week) showed no evidence of a carcinogenic effect in male and female rats and female mice. Liver tumours were increased in male mice exposed to the highest dose concentration, compared to the unexposed controls. However, the number of tumours was within the range seen historically for male CD-1 mice. It is generally accepted that an increase in liver tumours in male mice, in the absence of other neoplastic responses in mice or rats, is not indicative of a carcinogenic risk for humans.

In a photocarcinogenicity study in hairless mice, animals received imiquimod cream 3 times per week at concentrations of 0.03%, 0.1% and 0.3% and were irradiated with solar ultraviolet light for 5 days each week for 40 weeks and observed an additional 12 weeks. Vehicle cream enhanced UVR-induced skin tumour development. Imiquimod cream had no additional effect on tumour development beyond the vehicle effect (i.e., the addition of the active ingredient, imiquimod, to the vehicle cream did not result in an additional effect beyond the vehicle effect on tumour development).

Mutagenicity: Imiquimod was without effect in a series of eight mutagenicity assays including Ames, mouse lymphoma, CHO chromosome aberration, human lymphocyte chromosome aberration, SHE cell transformation, rat and hamster bone marrow cytogenetics, and mouse dominant lethal test.

Reproduction and Teratology: Teratology studies in rats and rabbits dosed at 1-20 mg/kg orally and at 0.5-2.0 mg/kg intravenously, did not reveal any teratogenic effects. The high doses in both studies produced some adverse effects in the dams related to maternal toxicity. The maternal toxicity was reflected in the high dose pups: reduced pup weights and delayed ossification in the rat. A radiolabel intravenous study in pregnant rabbits dosed at 1 mg/kg between day 6 to 18 of gestation for a total of 13 doses, showed radiolabel in the uteri, placenta, amniotic fluid and fetuses with no preferential concentration in the conceptus.

In a rat general reproduction study which utilized daily oral doses of 1.5-6.0 mg/kg, drug-related toxicity was observed at the high dose in the F0 generation with no adverse reproductive effects. Reversible ossification defects were observed in pups at the high dose. No effects were observed in growth, development, behaviour, learning/memory or reproduction of second generation. Daily oral administration of imiquimod to rats, at doses up to 8 times recommended human dose on a mg/m2 basis throughout mating, gestation, parturition and lactation, demonstrated no impairment of reproduction.

REFERENCES

25. Arany I, Tyring S, Stanley MA, Tomai MA, Miller RL, Smith MH et al. Enhancement of the innate and cellular immune response in patients with genital warts treated with topical imiquimod cream 5%. Antiviral Res 1999;43:55-63.

26. Berman B, Bienstock L, Kuritzky L, Mayeaux EJ, Jr., Tyring SK. Actinic keratoses: sequelae and treatments. Recommendations from a consensus panel. J Fam Pract. May 2006;55(5)(suppl):1-8.

27. Bernstein DI, Harrison CJ. Effects of the Immunomodulating Agent R 837 on Acute and Latent Herpes Simplex Virus Type 2 Infections. Antimicro Agents and Chemotherapy 1989; 33(9):1511 1515.

28. Bernstein DI, Miller RL, Harrison CJ. Effects of Therapy with an Immunomodulator (Imiquimod, R 837) Alone and with Acyclovir on Genital HSV 2 Infection in Guinea Pigs When Begun After Lesion Development. Antiviral Res 1993; 20:45 55.

29. Dahl MV. Imiquimod: An immune response modifier. J Am Acad Dermatol 2000;43(1):S1-5.

30. Edwards L. Imiquimod in clinical practice. J Am Acad Dermatol 2000;43(1):S12-17.

31. Edwards L, Ferenczy A, Eron L, Baker D, Owens ML, Fox TL et al. Self-administered topical 5% imiquimod cream for external anogenital warts. Arch Dermatol 1998;134:25-30.

32. Einspahr JG, Xu MJ, Warneke J, et al. Reproducibility and expression of skin biomarkers in sun-damaged skin and actinic keratoses. Cancer Epidemiol Biomarkers Prev. Oct 2006;15(10):1841-1848.

33. Gaspari AA, Sauder DN. Immunotherapy of basal cell carcinoma: evolving approaches. Dermatol Surg 2003;29(10):1027-1034.

34. Gollnick H, Barasso R, Jappe U, Ward K, Eul A, Carey-Yard M et al. Safety and efficacy of imiquimod 5% cream in the treatment of penile genital warts in uncircumcised men when applied three times weekly or once per day. Int J STD & AIDS 2001;12:22-28.

35. Harrison CJ, Miller RL, Bernstein DI. Posttherapy Suppression of Genital Herpes Simplex Virus (HSV) Recurrences and Enhancement of HSV Specific T Cell Memory by Imiquimod in Guinea Pigs. Antimicro Agents and Chemo 1994; 38(9):2059 2064.

36. Kende M, Lupton HW, Canonico PG. Treatment of Experimental Viral Infections with Immuno modulators. Adv Biosci 1988; 68:51 63.

37. Miller RL, Birmachu W, Gerster JF et al. Imiquimod Cytokine Induction and Antiviral Activity. Intl Antiviral News 1995; 3(7):111 113.

38. Miller RL, Gerster JF, Owens ML, Slade HB, Tomai MA. Imiquimod applied topically: a novel immune response modifier and new class of drug. Int J Immunopharm 1999;21:1-14.

39. Quatresooz P, Pierard-Franchimont C, Paquet P, et al. Crossroads between actinic keratosis and squamous cell carcinoma, and novel pharmacological issues. Eur J Dermatol. Jan-Feb 2008;18(1):6-10.

40. Sauder DN. Immunomodulatory and pharmacologic properties of imiquimod. J Am Acad Dermatol 2000;43(1): S6-11.

41. Stockfleth E, Kerl H. Guidelines for the management of actinic keratoses. Eur J. Dermatol. Nov-Dec 2006;16(6):599-606.

42. Testerman TL, Gerster JF, Imbertson LM et al. Cytokine Induction by the Immunomodulators Imiquimod and S 27609. J Leuk Biol 1995; 58:365 372.

43. Torres A, Storey L, Anders M, et al. Microarray analysis of aberrant gene expression in actinic keratosis: effect of the Toll-like receptor-7 agonist imiquimod. Br J Dermatol. Dec 2007;157(6):1132-47. Epub Oct 28 2007.

44. Tyring SK. Immune-response modifiers: A new paradigm in the treatment of human papillomavirus. Curr Ther Res 2000;60(9):584-596.

45. Tyring SK, Arany I, Stanley MA, Tomai MA, Miller RL, Smith MH et al. A randomized, controlled, molecular study of condylomata acuminata clearance during treatment with imiquimod. J Infect Dis 1998;178(August):551-555.

46. Vatve M, Ortonne JP, Birch-Machin MA, Gupta G. Management of field change in actinic keratosis. Br J Dermatol. Dec 2007;157(s2):21-24.

47. Weeks CE, Gibson SJ. Induction of Interferon and Other Cytokines by Imiquimod and its Hydroxylated Metabolite R 842 in Human Blood Cells In Vitro. J Interferon Res 1994; 14:81 85.

48. Lebwohl M, Dinehart S, Whiting D, Lee PK, Tawfik N, Jorizzo J, Lee JH, Fox TL et al. Imiquimod 5% cream for the treatment of actinic keratosis: Results from two phase III, randomized, double-blind, parallel group, vehicle-controlled trials. J Am Acad Dermatol May 2004;50(5):714-21.

PART III: CONSUMER INFORMATION

ZYCLARA®
(imiquimod) Cream, 3.75%

This leaflet is part III of a three-part "Product Monograph" published when ZYCLARA® Cream was approved for sale in Canada and is designed specifically for Consumers. This leaflet is a summary and will not tell you everything about ZYCLARA® Cream. Contact your doctor or pharmacist if you have any questions about the drug.

ABOUT THIS MEDICATION

What the medication is used for:
ZYCLARA® is the brand name for imiquimod cream, 3.75%. It is used to treat actinic keratosis (AK) of the face or balding scalp in adults with normal immune systems.

What it does:
ZYCLARA® Cream is an immune response modifier. ZYCLARA® Cream is a medicine that works by stimulating your body's own immune response.

When it should not be used:

Do not use ZYCLARA® Cream if you are allergic to imiquimod, or other medications that contain imiquimod (e.g. Aldara® Cream), or any of the other ingredients in ZYCLARA® Cream.

What the medicinal ingredient is:

Imiquimod.

What the important nonmedicinal ingredients are:

Isostearic acid, cetyl alcohol, stearyl alcohol, white petrolatum, polysorbate 60, sorbitan monostearate, glycerin, xanthan gum, purified water, benzyl alcohol, methylparaben, and propylparaben.

What dosage forms it comes in:

ZYCLARA® Cream contains 37.5 mg imiquimod per gram (3.75%) and is supplied in single-use packets which contain 250 mg of the cream and in pumps which contain 7.5g or 15g of the cream. The single-use packets are available as boxes of 28 packets.

| WARNINGS AND PRECAUTIONS |

- ZYCLARA® Cream should not be used in patients under 18 years of age
- Avoid exposure to sunlight, sunlamp or tanning-bed during the treatment with ZYCLARA® Cream. Wear protective clothing and hat if you go outside during daylight
- ZYCLARA® Cream may cause severe skin reactions
- ZYCLARA® Cream may also cause flu-like symptoms before or during local skin reactions

BEFORE you use ZYCLARA® Creamtalk to your doctor or pharmacist if:
- you have or had other skin cancers or other growths on your body
- you are immunocompromised (have weak immune system)

- you have or have had any other treatment for your actinic keratosis, such as freezing or surgery
- you are pregnant or planning to become pregnant
- you are breastfeeding or planning to breastfeed ZYCLARA® Cream treatment is not recommended on areas larger than either the face or balding scalp.

INTERACTIONS WITH THIS MEDICATION

Tell your doctor or pharmacist about all the medicines you take or have taken, including prescription and non-prescription medicines, vitamins and herbal supplements. It is not known if ZYCLARA® Cream and other medicines can affect each other.

PROPER USE OF THIS MEDICATION

Use ZYCLARA® Cream exactly as prescribed by your doctor. Do not use ZYCLARA® Cream until your doctor has shown you the right way to use it.

Usual adult dose:
Apply ZYCLARA® Cream to the affected area(s) once a day just before bedtime.

Maximum daily dose is 500 mg (2 packets of 250 mg each or 2 full actuations of the pump).

ZYCLARA® Cream should not be applied to areas larger than either the face or balding scalp.

The treatment consists of two 2-week treatment cycles, each cycle is separated by two weeks without treatment.

How to apply ZYCLARA® Cream packets:
- Wash the area to be treated with mild soap and water. Allow the area to dry
- Wash your hands
- Open a new packet(s) of ZYCLARA® Cream just before use
- Apply a thin layer of ZYCLARA® Cream ONLY to the affected area(s) to be treated. Do not use more than two packets for each application
- Rub the ZYCLARA® Cream in all the way to the affected area(s). Avoid the ZYCLARA® Cream in or around your eyes, lips and nostrils. If ZYCLARA® Cream accidentally gets in your mouth, your eyes, and nostrils rinse well with water right away
- Do not cover the treated area(s)
- Safely throw away the open packet of ZYCLARA® Cream, including any unused packet, so that children and pets cannot get it
- After applying ZYCLARA® Cream, wash your hands well with soap and water
- Leave the ZYCLARA® Cream on the affected area(s) for about 8 hours or as instructed by your doctor. Do not bathe or get the treated area(s) wet during the treatment period
- After the treatment period, wash the treated area(s) with mild soap and water How to apply ZYCLARA® Cream pumps:
- Wash the area to be treated with mild soap and water. Allow the area to dry
- Wash your hands
- Before using the pump for the first time only, remove the cap and prime the pump by pressing the top of the pump all the way down (one or more times as needed) until the product appears. Discard this portion of the product
- Apply a thin layer of ZYCLARA® Cream ONLY to the affected area(s) to be treated. Do not use more than two full pump depressions for each daily application
- Rub the ZYCLARA® Cream in all the way to the affected area(s). Avoid the ZYCLARA® Cream in or around your eyes, lips and nostrils. If ZYCLARA® Cream accidentally gets in your mouth, your-eyes, and nostrils rinse well with water right away
- Do not cover the treated area(s)
- After applying ZYCLARA® Cream, wash your hands well with soap and water

- Leave the ZYCLARA® Cream on the affected area(s) for about 8 hours or as instructed by your doctor. Do not bathe or get the treated area(s) wet during the treatment period
- After the treatment period, wash the treated area(s) with mild soap and water
- When you have completed all of your doses as instructed, safely throw the pump away so that children and pets cannot get it.

Avoid exposure to sunlight, sunlamp or tanning-bed during the treatment with ZYCLARA® Cream.

Overdose:

If you have used more ZYCLARA® Cream than you should, contact your doctor, or poison control centre.

Missed Dose:

If you miss a dose of ZYCLARA® Cream, wait until the next night to apply it. Do not make up the missed dose.

SIDE EFFECTS AND WHAT TO DO ABOUT THEM

Possible side effects in the treatment area observed in studies of Zyclara® Cream include:

Very common: redness, scabbing or crusting, flaking or dry skin, swelling, small open sores, drainage; Common: itching, irritation, pain; Uncommon: abnormal sensation, scarring; Very rare: bleeding.

During treatment and until the skin has healed, your skin in the treatment area is likely to appear noticeably different from normal skin. Side effects at the site where ZYCLARA® Cream is applied are common. Sometimes the side effects go outside of the area where ZYCLARA® Cream was applied. Actinic keratoses that were not seen before may appear during treatment and may later go away. You have a higher chance for severe skin reactions if you use too much ZYCLARA® Cream or use it the wrong way. If your skin breaks down, if sores develop during the first week of treatment, or if you get any skin reactions that affect your daily activities or do not go away, stop ZYCLARA® Cream right away and call your healthcare provider. Sometimes, ZYCLARA® Cream must be stopped for a while to allow your skin to heal. Talk to your healthcare provider if you have questions about your treatment or skin reactions.

Other possible side effects observed in studies of Zyclara® Cream include:

Common: headache, tiredness, nausea, fever, loss of appetite, dizziness, herpes outbreak, pain, diarrhea, swollen lymph nodes, joint aches, skin irritation, difficulty sleeping; Uncommon: chills, influenza-like symptoms, muscle aches, lack of energy, and itching; Very rare: lip cracking, low blood counts.

| SERIOUS SIDE EFFECTS, HOW OFTEN THEY HAPPEN AND WHAT TO DO ABOUT THEM | | | |
|---|---|---|---|
| Symptom/effect | Talk with your Doctor or Pharmacist | | Stop taking drug and call your Doctor or Pharmacist |
| | Only if severe | In all cases | |
| *Uncommon* | | | |
| Serious diarrhea | | X | X |
| *Very rare* | | | |
| Serious low blood counts (pancytopenia) | | X | X |

These are not all the side effects of ZYCLARA® Cream. For more information, ask your healthcare provider or pharmacist.

| HOW TO STORE IT |
|---|

Store ZYCLARA® Cream between 15-25° C. Do not freeze.

Safely throw away ZYCLARA® Cream that is out of date or that you do not need.

Keep ZYCLARA® Cream and all medicines out of the reach of children. REPORTING SUSPECTED SIDE EFFECTS To monitor drug safety, Health Canada through the Canada Vigilance Program collects information on serious and unexpected effects of drugs. If you suspect you have had a serious or unexpected reaction to this drug you may notify Canada Vigilance:

You can report any suspected adverse reaction associated with the use of health products in the Canada Vigilance Program by one of the following 3 ways:

Report online at www.healthcanada.gc.ca/medeffect

Call toll-free at 1-866-234-2345

Complete a Canada Vigilance Reporting Form and:
- ☐ Fax toll-free to 1-866-678-6789, or
- ☐ Mail to: Canada Vigilance Program
  Health Canada
  Postal Locator 0701C
  Ottawa, ON K1A0K9

Postage paid labels, Canada Vigilance Reproting Form and the adverse reaction reporting guidelines are available on the MedEffect™ Canada Web site at www.healthcanada.gc.ca/medeffect.

*Note: Should you require information related to the management of side effects, contact your health professional. The Canada Vigilance Program does not provide medical advice.*

| MORE INFORMATION |

This document plus the full product monograph, prepared for health professionals can be found at:

http://www.gracewaypharma.ca or by contacting the sponsor, Graceway Pharmaceuticals, at: 1-800-328-0255

This leaflet was prepared by Graceway Pharmaceuticals, 252 Pall Mall St., Suite 302, London, Ontario, N6A 5P6

Last revised: July 8, 2010

Attachment XV
(Draft FDA Label)

[000326] HIGHLIGHTS OF PRESCRIBING INFORMATION

These highlights do not include all the information needed to use ZYCLARA® safely and effectively. See full prescribing information for ZYCLARA® Cream.

ZYCLARA® (imiquimod) Cream, 2.5%
For topical use only
Initial U.S. Approval: 1997

---------- INDICATIONS AND USAGE ----------

ZYCLARA® Cream is indicated for the topical treatment of clinically typical, visible or palpable actinic keratoses (AK) of the full face or balding scalp in immunocompetent adults.(1.1)

---------- DOSAGE AND ADMINISTRATION ----------

ZYCLARA® Cream is not for oral, ophthalmic, or intravaginal use.(2)

Once daily to the skin of the affected area (either the entire face or balding scalp) for two 2-week treatment cycles separated by a 2-week no-treatment period. (2.1)

---------- DOSAGE FORMS AND STRENGTHS ----------

Cream, 2.5%, white to faintly yellow Cream. (3)

---------- CONTRAINDICATIONS ----------

- None (4)

---------- WARNINGS AND PRECAUTIONS ----------

- Intense local inflammatory reactions can occur (e.g., skin weeping, erosion). Dosing interruption may be required (2, 5.1, 6)

- Flu-like systemic signs and symptoms including fatigue, nausea, fever, myalgias, arthralgias, and chills. Dosing interruption may be required (2, 5.2, 6)
  - Avoid exposure to sunlight and sunlamps (5.3). Wear sunscreen daily (17.4).
  - Avoid concomitant use of Zyclara® Cream 2.5% and any other imiquimod cream.

---------------------------------------ADVERSE REACTIONS ---------------------------------------

Most common Adverse Reactions (incidence >50%) are local skin reactions erythema, edema, weeping/exudate, flaking/scaling/dryness, scabbing/crusting and erosion/ulceration (6.2). Other reported reactions (occurring in >2% of ZYCLARA®-Treated Subjects) include headache, fatigue, nausea and fever (see 6.1).

To report SUSPECTED ADVERSE REACTIONS, contact Graceway

Pharmaceuticals, LLC at 1-800-328-0255 or FDA at 1-800-FDA-1088 or www.fda.gov/medwatch.

See 17 for PATIENT COUNSELING INFORMATION and FDA-approved patient labeling.

Issued: MM YYYY

FULL PRESCRIBING INFORMATION: CONTENTS\*

1  INDICATIONS AND USAGE
   1.1 Actinic Keratosis
   1.2 Unevaluated Populations

2  DOSAGE AND ADMINISTRATION
   2.1 Actinic Keratosis

3  DOSAGE FORMS AND STRENGTHS

| | |
|---|---|
| 4 | CONTRAINDICATIONS |
| 5 | WARNINGS AND PRECAUTIONS |
| | 5.1 Local Skin Reactions |
| | 5.2 Systemic Reactions |
| | 5.3 Ultraviolet Light Exposure |
| | 5.4 Unevaluated Uses: Actinic Keratosis |
| 6 | ADVERSE REACTIONS |
| | 6.1 Clinical Trials Experience |
| | 6.2 Postmarketing Experience |
| 8 | USE IN SPECIFIC POPULATIONS |
| | 8.1 Pregnancy |
| | 8.3 Nursing Mothers |
| | 8.4 Pediatric Use |
| | 8.5 Geriatric Use |
| 10 | OVERDOSAGE |
| 11 | DESCRIPTION |
| 12 | CLINICAL PHARMACOLOGY |
| | 12.1 Mechanism of Action |
| | 12.2 Pharmacodynamics |
| | 12.3 Pharmacokinetics |
| 13 | NONCLINICAL TOXICOLOGY |
| | 13.1 Carcinogenesis, Mutagenesis, Impairment of Fertility |
| 14 | CLINICAL STUDIES |

16 HOW SUPPLIED/STORAGE AND HANDLING

17 PATIENT COUNSELING INFORMATION 17.1 Instructions for Administration:

17.2 Local Skin Reactions:

17.3 Systemic Reactions:

17.4 Recommended Administration

FULL PRESCRIBING INFORMATION

1 INDICATIONS AND USAGE

1.1 Actinic Keratosis

ZYCLARA® Cream 2.5% is indicated for the topical treatment of clinically typical visible or palpable, actinic keratoses (AK), of the full face or balding scalp in immunocompetent adults.

1.2 Unevaluated Populations

Safety and efficacy have not been established for ZYCLARA® Cream 2.5% in the treatment of actinic keratosis, with more than one 2-cycle treatment course in the same area.

The safety and efficacy of ZYCLARA® Cream 2.5% in immunosuppressed patients have not been established.

The safety and efficacy have not been established for ZYCLARA® Cream 2.5% in the treatment of patients with xeroderma pigmentosum.

The safety and efficacy have not been established for ZYCLARA® Cream 2.5% in the treatment of superficial basal cell carcinoma.

The safety and efficacy have not been established for ZYCLARA® Cream 2.5% in the treatment of external genital warts.

ZYCLARA® Cream 2.5% should be used with caution in patients with pre-existing autoimmune conditions.

2 DOSAGE AND ADMINISTRATION

ZYCLARA® Cream 2.5% is not for oral, ophthalmic, or intravaginal use.

2.1 Actinic Keratosis

ZYCLARA® Cream 2.5% should be applied once daily before bedtime to the skin of the affected area (either entire face or balding scalp) for two 2-week treatment cycles separated by a 2-week no-treatment period. ZYCLARA® Cream 2.5% should be applied as a thin film to the entire treatment area and rubbed in until the cream is no longer visible. Up to 2 packets or 2 full actuations of the pump of ZYCLARA® Cream 2.5% may be applied to the treatment area at each application. ZYCLARA® Cream 2.5% should be left on the skin for approximately 8 hours, after which time the cream should be removed by washing the area with mild soap and water. The prescriber should demonstrate the proper application technique to maximize the benefit of ZYCLARA® Cream 2.5% therapy.

Patients should wash their hands before and after applying ZYCLARA® Cream 2.5%.

Avoid use in or on the lips and nostrils. Do not use in or near the eyes.

Local skin reactions in the treatment area are common *[see Adverse Reactions (6.1, 6.2)]*. A rest period of several days may be taken if required by the patient's discomfort or severity of the local skin reaction. However, neither 2-week treatment cycle should be extended due to missed doses or rest periods. A transient increase in AK lesion counts may be observed during treatment. Response to treatment cannot be adequately assessed until resolution of local skin reactions. The patient should continue dosing as prescribed. Treatment should continue for the full treatment course even if all actinic keratoses appear to be gone. Lesions that do not respond to treatment should be carefully re-evaluated and management reconsidered.

ZYCLARA® Cream 2.5% is packaged in single-use packets, with 28 packets (250mg/packet) supplied per box, a 7.5g pump and a 15g pump. Each ZYCLARA® Cream 2.5% pump actuation delivers a similar amount of cream as one packet. Patients should be prescribed no more than 56 packets, two 7.5g pumps or one 15g pump for the total 2-cycle treatment course. Partially used packets should be discarded and not reused. When the treatment course is complete, any remaining packets or pumps should be discarded.

3 DOSAGE FORMS AND STRENGTHS

Cream, 2.5%, white to faintly yellow cream.

4 CONTRAINDICATIONS

None.

5 WARNINGS AND PRECAUTIONS

5.1 Local Skin Reactions

Intense local skin reactions including skin weeping or erosion can occur after a few applications of ZYCLARA® Cream 2.5% and may require an interruption of dosing *[see Dosage and Administration (2) and Adverse Reactions (6)]*. ZYCLARA® Cream 2.5% has the potential to exacerbate inflammatory conditions of the skin, including chronic graft versus host disease.

Administration of ZYCLARA® Cream 2.5% is not recommended until the skin is healed from any previous drug or surgical treatment.

Concomitant use of ZYCLARA® Cream 2.5% and any other imiquimod creams, in the same treatment area, should be avoided since they contain the same active ingredient (imiquimod) and may increase the risk for and severity of local skin reactions.

5.2 Systemic Reactions

Flu-like signs and symptoms may accompany, or even precede, local skin reactions and may include fatigue, nausea, fever, myalgias, arthralgias, and chills. An interruption of dosing and an assessment of the patient should be considered *[see Adverse Reactions (6)]*.

Lymphadenopathy occurred in 4 (2.5%) of subjects treated with ZYCLARA® Cream 2.5% *[see Adverse Reactions (6)]*. This reaction resolved in all subjects by 4 weeks after completion of treatment.

The safety of concomitant use of ZYCLARA® Cream 2.5% and any other imiquimod creams has not been established and should be avoided since they contain the same active ingredient (imiquimod) and may increase the risk for and severity of systemic reactions.

5.3 Ultraviolet Light Exposure

Exposure to sunlight (including sunlamps) should be avoided or minimized during use of ZYCLARA® Cream 2.5% because of concern for heightened sunburn susceptibility. Patients should be warned to use protective clothing (e.g., a hat) when using ZYCLARA® Cream 2.5%. Patients with sunburn should be advised not to use ZYCLARA® Cream 2.5% until fully recovered. Patients who may have considerable sun exposure, e.g. due to their occupation, and those patients with inherent sensitivity to sunlight should exercise caution when using ZYCLARA® Cream 2.5%.

In an animal photo-carcinogenicity study, imiquimod cream shortened the time to skin tumor formation *[see Nonclinical Toxicology (13.1)]*. The enhancement of ultraviolet carcinogenicity is not necessarily dependent on phototoxic mechanisms. Therefore, patients should minimize or avoid natural or artificial sunlight exposure.

6 ADVERSE REACTIONS

Because clinical trials are conducted under widely varying conditions, adverse reaction rates observed in the clinical trials of a drug cannot be directly compared to rates in the clinical trials of another drug and may not reflect the rates observed in practice.

6.1 Clinical Trials Experience:

The data described below reflect exposure to ZYCLARA® Cream 2.5% or vehicle in 319 subjects enrolled in two double-blind, vehicle-controlled trials. Subjects applied up to two packets of ZYCLARA® Cream 2.5% or vehicle daily to the skin of the affected area (either entire face or balding scalp) for two 2-week treatment cycles separated by a 2-week no treatment period.

Table 1: Selected Adverse Reactions Occurring in ≥ 2% of ZYCLARA® Cream 2.5% Treated Subjects and at a Greater Frequency than with Vehicle in The Combined Studies

| Preferred Term | ZYCLARA® Cream 2.5% (N=160) | Vehicle (N=159) |
|---|---|---|
| Application site pruritus | 6 (4%) | 1 (<1%) |
| Influenza like illness | 6 (4%) | 0 (0%) |
| Application site irritation | 4 (3%) | 0 (0%) |
| Arthralgia | 4 (3%) | 0 (0%) |
| Lymphadenopathy | 4 (3%) | 0 (0%) |
| Oral herpes | 4 (3%) | 0 (0%) |

Table 2: Local Skin Reactions in the Treatment Area in ZYCLARA®-Treated Subjects as Assessed by the Investigator

|  | ZYCLARA® Cream 2.5% (N=160) | | Vehicle (N=159) | |
|---|---|---|---|---|
|  | All Grades* | Severe | All Grades* | Severe |
| Erythema | 154 (96%) | 23 (14%) | 124 (78%) | 0 (0%) |
| Flaking/Scaling/Dryness | 141 (88%) | 7 (4%) | 123 (77%) | 2 (1%) |
| Scabbing/Crusting | 135 (84%) | 15 (9%) | 72 (45%) | 0 (0%) |
| Edema | 101 (63%) | 6 (4%) | 31 (19%) | 0 (0%) |
| Erosion/Ulceration | 84 (52%) | 15 (9%) | 14 (9%) | 0 (0%) |
| Weeping/Exudate | 63 (39%) | 2 (1%) | 6 (4%) | 0 (0%) |

* All Grades: mild, moderate or severe

Local skin reactions may extend beyond treatment area.

Overall, in the clinical trials, 7% (11/160) of subjects on ZYCLARA® Cream 2.5% and 0% on vehicle cream required rest periods due to adverse reactions.

Other adverse reactions observed-in subjects treated with ZYCLARA® Cream 2.5% include: application site bleeding, application site swelling, arthralgia, cheilitis, chills, dermatitis, herpes zoster, influenza-like illness, insomnia, lethargy, myalgia, pancytopenia, pruritus, squamous cell carcinoma, and vomiting.

6.2 Postmarketing Experience

There are currently no post-marketing adverse reactions reported for Zyclara® Cream 2.5%.

The following adverse reactions have been identified during post-approval use of Aldara (imiquimod) Cream, 5% and Zyclara® Cream 3.75%. Because these reactions are reported voluntarily from a population of uncertain size, it is not always possible to reliably estimate their frequency or establish a causal relationship to drug exposure.

Body as a Whole: angioedema.

Cardiovascular: capillary leak syndrome, cardiac failure, cardiomyopathy, pulmonary edema, arrhythmias (tachycardia, supraventricular tachycardia, atrial fibrillation, palpitations), chest pain, ischemia, myocardial infarction, syncope.

Endocrine: thyroiditis.

Gastro-Intestinal System Disorders: abdominal pain.

Hematological: decreases in red cell, white cell and platelet counts (including idiopathic thrombocytopenic purpura), lymphoma Hepatic: abnormal liver function Infections and Infestations: herpes simplex.

Neuropsychiatric: agitation, cerebrovascular accident, convulsions (including febrile convulsions), depression, insomnia, multiple sclerosis aggravation, paresis, suicide.

Respiratory: dyspnea.

Urinary System Disorders: proteinuria, urinary retention, dysuria.

Skin and Appendages: exfoliative dermatitis, erythema multifollne, hyperpigmentation, hypertrophic scar.

Vascular: Henoch-Schonlein purpura syndrome

8 USE IN SPECIFIC POPULATIONS

8.1 Pregnancy

Pregnancy Category C:

There are no adequate and well-controlled studies in pregnant women. ZYCLARA® Cream 2.5% should be used during pregnancy only if the potential benefit justifies the potential risk to the fetus.

Note: The animal multiples of human exposure calculations were based on daily dose comparisons for the reproductive toxicology studies described in this label. The animal multiples of human exposure were based on weekly dose comparisons for the carcinogenicity studies described in this label. For the animal multiple of human exposure ratios presented in this label, the Maximum Recommended Human Dose (MRHD) was set at 2 packets (500 mg cream) per treatment of ZYCLARA® Cream (imiquimod 3.75%, 18.75 mg imiquimod).

Systemic embryofetal development studies were conducted in rats and rabbits. Oral doses of 1, 5 and 20 mg/kg/day imiquimod were administered during the period of organogenesis (gestational days 6 - 15) to pregnant female rats. In the presence of maternal toxicity, fetal effects noted at 20 mg/kg/day (190X MRHD based on AUC comparisons) included increased resorptions, decreased fetal body weights, delays in skeletal ossification, bent limb bones, and two fetuses in one litter (2 of 1567 fetuses) demonstrated exencephaly, protruding tongues and low-set ears. No treatment related effects on embryofetal toxicity or teratogenicity were noted at 5 mg/kg/day (32X MRHD based on AUC comparisons).

Intravenous doses of 0.5, 1 and 2 mg/kg/day imiquimod were administered during the period of organogenesis (gestational days 6 - 18) to pregnant female rabbits. No treatment related effects on embryofetal toxicity or teratogenicity were noted at 2 mg/kg/day (2.1X MRHD based on BSA comparisons), the highest dose evaluated in this study, or 1 mg/kg/day (134X MRHD based on AUC comparisons).

A combined fertility and pefi- and post-natal development study was conducted in rats. Oral doses of 1, 1.5, 3 and 6 mg/kg/day imiquimod were administered to male rats from 70 days prior to mating through the mating period and to female rats from 14 days prior to mating through parturition and lactation. No effects on growth, fertility, reproduction or post-natal development were noted at doses up to 6 mg/kg/day (29X MRHD based on AtiC comparisons), the highest dose evaluated in this study. In the absence of maternal toxicity, bent limb bones were noted in the F1 fetuses at a dose of 6 mg/kg/day (29X MRHD based on AUC comparisons). This fetal effect was also noted in the oral rat embryofetal development study conducted with imiquimod. No treatment related effects on teratogenicity were noted at 3 mg/kg/day (14X MRHD based on AUC comparisons).

8.3 Nursing Mothers

It is not known whether imiquimod is excreted in human milk following use of ZYCLARA® Cream 2.5%. Because many drugs are excreted in human milk, caution should be exercised when ZYCLARA® Cream 2.5% is administered to nursing women.

8.4 Pediatric Use

AK is a condition not generally seen within the pediatric population. The safety and efficacy of ZYCLARA® Cream 2.5% for AK in patients less than 18 years of age has not been established.

8.5 Geriatric Use

Of the 160 subjects treated with ZYCLARA® Cream 2.5% in the clinical studies, 72 subjects were 65 years or older. No overall differences in safety or effectiveness were observed between these subjects and younger subjects.

10 OVERDOSAGE

Topical overdosing of ZYCLARA® Cream 2.5% could result in an increased incidence of severe local skin reactions and may increase the risk for systemic reactions.

Hypotension was reported in a clinical trial following multiple oral imiquimod doses of >200 mg (equivalent to the ingestion of imiquimod content of > 32 packets of ZYCLARA® Cream 2.5%). This resolved following oral or intravenous fluid administration.

11 DESCRIPTION

ZYCLARA® Cream 2.5% is intended for topical administration. Each gram contains 25 mg of imiquimod in a white to faintly yellow oil-in-water Cream base consisting of isostearic acid, cetyl alcohol, stearyl alcohol, white petrolatum, polysorbate 60, sorbitan monostearate, glycerin, xanthan gum, purified water, benzyl alcohol, methylparaben, and propylparaben.

Chemically, imiquimod is 1-(2-methylpropyl)-1$H$-imidazo[4,5-c]quinolin-4-amine. Imiquimod has a molecular formula of $C_{14}H_{16}N_4$ and a molecular weight of 240.3. Its structural formula is:

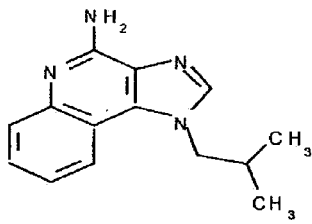

12 CLINICAL PHARMACOLOGY

12.1 Mechanism of Action

The mechanism of action of ZYCLARA® Cream 2.5% in treating AK lesions is unknown.

12.2 Pharmacodynamics

The pharmacodynamics of ZYCLARA® Cream 2.5% are unknown.

Imiquimod is a Toll-like receptor 7 agonist that activates immune cells. Topical application to skin is associated with increases in markers for cytokines and immune cells.

In a study of 18 subjects with AK comparing Aldara (imiquimod) Cream, 5% to vehicle, increases from baseline in week 2 biomarker levels were reported for CD3, CD4, CD8, CD11c, and CD68 for Aldara (imiquimod) Cream, 5% treated subjects; however, the clinical relevance of these findings is unknown.

12.3 Pharmacokinetics

Following dosing with 2 packets once daily (18.75 mg imiquimod/day) for up to three weeks, systemic absorption of imiquimod was observed in all subjects when Zyclara® Cream 3.75% was applied to the face and/or scalp in 17 subjects with at least 10 AK lesions. The mean peak serum imiquimod concentration at the end of the trial was approximately 0.323 ng/mL. The median time to maximal concentrations ($T_{max}$) occurred at 9 hours after dosing. Based on the plasma half-life of imiquimod observed at the end of the study, 29.3±17.0 hours, steady-state concentrations can be anticipated to occur by day 7 with once daily dosing.

13 NONCLINICAL TOXICOLOGY

13.1 Carcinogenesis, Mutagenesis, Impairment of Fertility

In an oral (gavage) rat carcinogenicity study, imiquimod was administered to Wistar rats on a 2X/week (up to 6 mg/kg/day) or daily (3 mg/kg/day) dosing schedule for 24 months. No treatment related tumors were noted in the oral rat carcinogenicity study up to the highest doses tested in this study of 6 mg/kg administered 2X/week in female rats (8.2X MRHD based on weekly AUC comparisons), 4 mg/kg administered 2X/week in male rats (7.1X MRHD) based on weekly AUC comparisons) or 3 mg/kg administered 7X/week to male and female rats (14X MRHD based on weekly AUC comparisons).

In a dermal mouse carcinogenicity study, imiquimod cream (up to 5 mg/kg/application imiquimod or 0.3% imiquimod cream) was applied to the backs of mice 3X/week for 24 months. A statistically significant increase in the incidence of liver adenomas and carcinomas was noted in high dose male mice compared to control male mice (24X MRHD based on weekly AUC comparisons). An increased number of skin papillomas was observed in vehicle cream control group animals at the treated site only.

In a 52-week dermal photo-carcinogenicity study, the median time to onset of skin tumor formation was decreased in hairless mice following chronic topical dosing (3X/week; 40 weeks of treatment followed by 12 weeks of observation) with concurrent exposure to UV radiation (5 days per week) with vehicle alone. No additional effect on tumor development beyond the vehicle effect was noted with the addition of the active ingredient, imiquimod, to the vehicle cream.

Imiquimod revealed no evidence of mutagenic or clastogenic potential based on the results of five in vitro genotoxicity tests (Ames assay, mouse lymphoma L5178Y assay, Chinese hamster ovary cell chromosome aberration assay, human lymphocyte chromosome aberration assay and SHE cell transformation assay) and three in vivo genotoxicity tests (rat and hamster bone marrow cytogenetics assay and a mouse dominant lethal test).

Daily oral administration of imiquimod to rats, throughout mating, gestation, parturition and lactation, demonstrated no effects on growth, fertility or reproduction, at doses up to 29X MRHD based on AUC comparisons.

14 CLINICAL STUDIES

In two double-blind, randomized, vehicle-controlled clinical studies, 319 subjects with AK were treated with ZYCLARA® Cream 2.5%, or vehicle cream. Studies enrolled subjects >18 years of age with 5-20 typical visible or palpable AK lesions of the face or scalp. Study cream was applied to either the entire face (excluding ears) or balding scalp once daily for two 2-week treatment cycles separated by a 2-week no-treatment period. Subjects then continued in the study for an 8-week follow-up period during which they returned for clinical observations and safety monitoring. Study subjects ranged from 40 to 90 years of age and 53% had Fitzpatrick skin type I or II. All ZYCLARA® Cream 2.5%-treated subjects were Caucasians.

On a scheduled dosing day, up to two packets of the study cream were applied to the entire treatment area prior to normal sleeping hours and left on for approximately 8 hours. Efficacy was assessed by AK lesion counts at the 8-week post-treatment visit. All AKs in the treatment area were counted, including baseline lesions as well as lesions which appeared during therapy.

Complete clearance required absence of any lesions including those that appeared during therapy in the treatment area. Complete and partial clearance rates are shown in the tables below. Partial clearance rate was defined as the percentage of subjects in whom the number of baseline AKs was reduced by 75% or more. The partial clearance rate was measured relative to the numbers of AK lesions at Baseline.

Table 3: Rate of Subjects with Complete Clearance at 8 Weeks Post Treatment

|  | ZYCLARA® Cream 2.5% | Vehicle Cream |
|---|---|---|
| Study 1 | 23.5% (19/81) | 2.5% (2/80) |
| Study 2 | 38.0% (30/79) | 10.1% (8/79) |

Table 4: Rate of Subjects with Partial Clearance (≥75%) at 8 Weeks Post Treatment

|  | ZYCLARA® Cream 2.5% | Vehicle Cream |
|---|---|---|
| Study 1 | 42.0% (34/81) | 18.8% (15/80) |
| Study 2 | 54.4% (43/79) | 26.6% (21/79) |

During the course of treatment, 84% (135/160) of subjects experienced a transient increase in lesions evaluated as actinic keratoses relative to the number present at baseline within the treatment area.

Subjects achieving complete clearance of all AKs at End-of-Study in the studies described above, were eligible to enroll in an open-label, 12 month observational study. Thirty-nine eligible subjects treated with Zyclara® Cream 2.5% were followed for up to 12 months to determine the proportion of subjects who sustained clearance of all AKs (new or old) in the previous treatment area.

Table X Estimated Sustained Complete Clearance Rates of Full Treatment Area

| Follow-up Visit after 8-week Posttreatment Assessment (N=39 complete clearance) | No. of Subjects who Remained Clinically Clear | No. of Subjects with AK Recurrence | No of Subjects who Discontinued at the Visit with no AKs[1] | Estimated Rate of Subjects who Clinically Cleared and Remained Clear |
|---|---|---|---|---|
| Month 6 | 21 | 17 | 1 | 54% |
| Month 12 | 13 | 26 | 0 | 33% |

[1] Reasons for discontinuation included *lost to follow-up*.

16 HOW SUPPLIED/STORAGE AND HANDLING

ZYCLARA® (imiquimod) Cream, 2.5% is supplied as follows:

Single-use packets which contain 250 mg of the cream. Available in a box of 28 packets NDC 29336-710-28.

A pump which contains 7.5g of the cream, NDC XXXXX-XXX-XX

A pump which contains 15g of the cream, NDC XXXXX-XXX-XX

Store at 25°C (77°F); excursions permitted to 15°C to 30°C (59° to 86°F) [see USP Controlled Room Temperature].

Avoid freezing.

*Keep out of reach of children.*

17 PATIENT COUNSELING INFORMATION

*See FDA Approved Patient Labeling (17.7)*

17.1 Instructions for Administration

Zyclara® Cream 2.5% Should be used as directed by a physician *[see Dosage and Administration (2)]*. Zyclara® Cream 2.5% is for external use only. Contact with the eyes, lips and nostrils should be avoided *[see Indications and Usage (1) and Dosage and Administration (2)]*.

The treatment area should not be bandaged or otherwise occluded. Partially used packets or unused pumps should be discarded and not reused. Emptied pumps should be discarded. The prescriber should demonstrate the proper application technique to maximize the benefit of Zyclara® Cream 2.5% therapy.

It is recommended that patients wash their hands before and after applying Zyclara® Cream 2.5%.

17.2 Local Skin Reactions

Patients may experience local skin reactions during treatment with Zyclara® Cream 2.5%. Potential local skin reactions include erythema, edema, erosions/ulcerations, weeping/exudate, flaking/scaling/dryness, and scabbing/crusting. These reactions can range from mild to severe in intensity and may extend beyond the application site onto the surrounding skin. Patients may also experience application site reactions such as itching, irritation or pain *[see Adverse Reactions (6)]*.

Local skin reactions may be of such an intensity that patients may require rest periods from treatment. Treatment with Zyclara® Cream 2.5% can be resumed after the skin reaction has subsided, as deteitnined by the physician. However, each treatment cycle should not be extended beyond 2 weeks due to missed doses or rest periods. Patients should contact their physician promptly if they experience any sign or symptom at the application site that restricts or prohibits their daily activity or makes continued application of the cream difficult.

Because of local skin reactions, during treatment and until healed, the treatment area is likely to appear noticeably different from normal skin. Localized hypopigmentation and hyperpigmentation have been reported following use of imiquimod cream. These skin color changes may be permanent in some patients.

17.3 Systemic Reactions

Patients may experience flu-like systemic signs and symptoms during treatment with Zyclara® Cream 2.5%. Systemic signs and symptoms may include fatigue, nausea, fever, myalgia, arthralgia, and chills *[see Adverse Reactions (6)]*. An interruption of dosing or dose adjustment and an assessment of the patient should be considered.

17.4 Recommended Administration

Dosing is once daily before bedtime to the skin of the affected area (entire face or balding scalp) for two 2-week treatment cycles separated by a 2-week no-treatment period. However, the treatment period should not be extended beyond two 2-week treatment cycles due to missed doses or rest periods. Treatment should continue for the full treatment course even if all actinic keratoses appear to be gone *[see Dosage and Administration (2.1)]*.

It is recommended that patients wash their hands before and after applying Zyclara® Cream 2.5%. Before applying the cream, the patient should wash the treatment area with mild soap and water and allow the area to dry thoroughly.

It is recommended that the treatment area be washed with mild soap and water 8 hours following Zyclara® Cream 2.5% application.

Most patients using Zyclara® Cream 2.5% for the treatment of AK experience erythema, flaking/scaling/dryness and scabbing/crusting at the application site with normal dosing *[see Adverse Reactions (6.1)]*.

Use of sunscreen is encouraged, and patients should minimize or avoid exposure to natural or artificial sunlight (tanning beds or UVA/B treatment) while using Zyclara® Cream *[see Warnings and Precautions (5.3)]*.

Additional lesions may become apparent in the treatment area during treatment *[see Clinical Studies (14.1)]*.

FDA-Approved Patient Labeling
ZYCLARA® [zi-clar-a]
(imiquimod)
Cream 2.5%

---
IMPORTANT: For use on the skin only (topical). Do not use ZYCLARA® Cream 2.5% in or on your eyes, nostrils, mouth or vagina.

---

Read the Patient Information that comes with ZYCLARA® Cream 2.5% before you start using it and each time you get a refill. There may be new information. This leaflet does not take the place of talking with your healthcare provider about your medical condition or treatment. If you do not understand the information, or have any questions about ZYCLARA® Cream, talk with your healthcare provider or pharmacist.

What is ZYCLARA® Cream 2.5%?

ZYCLARA® Cream 2.5% is a prescription medicine for use on the face or balding scalp only (a topical medicine) to treat actinic keratosis (AK).

Actinic keratosis is caused by too much sun exposure.

It is not known if ZYCLARA® Cream 2.5% is safe and effective:

- in people who do not have a normal immune system.

- in the treatment of patients with xeroderma pigmentosum.

- in the treatment of superficial basal cell carcinoma.

- in the treatment of external genital warts.

It is not known if ZYCLARA® Cream 2.5% is safe and effective in children younger than 18 years old.

What should I tell my healthcare provider before using ZYCLARA® Cream 2.5%?

Before you use ZYCLARA® Cream 2.5%, tell your healthcare provider if you:

- have problems with your immune system

- being treated or have been treated for actinic keratosis with other medicines or surgery. You should not use ZYCLARA® Cream 2.5% until you have healed from other treatments

- have other skin problems

- have any other medical conditions

- are pregnant or planning to become pregnant. It is not known if ZYCLARA® Cream 2.5% can harm your unborn baby. Talk to your healthcare provider if you are pregnant or plan to become pregnant.

- are breast-feeding or plan to breast-feed. It is not known if ZYCLARA® Cream 2.5% passes into your breast milk and if it can harm your baby. Talk to your healthcare provider about the best way to feed your baby if you use ZYCLARA® Cream 2.5%.

Tell your healthcare provider about all the medicines you take, including prescription and non-prescription medicines, vitamins and herbal supplements.

Especially tell your healthcare provider if you have had other treatments for actinic keratosis.

How should I use ZYCLARA® Cream 2.5%?

- Do not get ZYCLARA® Cream 2.5% in or near your eyes

- Do not get ZYCLARA® Cream 2.5% in or on your nostrils, lips, or vagina.

- Use ZYCLARA® Cream 2.5% exactly as your healthcare provider tells you to use it. Your healthcare provider will tell you where to apply ZYCLARA® Cream 2.5% and how often and for how long to apply it for your condition. Do not apply ZYCLARA® Cream 2.5% to other areas.

- Using too much ZYCLARA® Cream 2.5%, or using it too often, or for too long can increase your chances for having a severe skin reaction or other side effects.

- Talk to your healthcare provider if you think ZYCLARA® Cream 2.5% is not working for you.

How do I use ZYCLARA® Cream 2.5% packets?

ZYCLARA® Cream 2.5% should be applied just before your bedtime.

- Wash the area where the cream will be applied with mild soap and water.

- Allow the area to dry.

- Wash your hands.

- Open a packet of ZYCLARA® Cream 2.5% just before use.

- Apply a thin layer of Zyclara® Cream 2.5% only to the affected area or areas to be treated. Do no use more ZYCLARA® Cream 2.5% than is needed to cover the treatment area. Do no use more than two packets for each application.

- Rub the cream in all the way to the affected area or areas.

- Safely throw away the open packet of ZYCLARA® Cream 2.5% so that children and pets cannot get it. The open package should be thrown away even if all the ZYCLARA® Cream was not completely used.

- After you apply ZYCLARA® Cream 2.5%, wash your hands well

- Leave the Cream on the affected area or areas for the time prescribed by your healthcare provider. Do not bathe or get the treated area wet before the right time has passed.

- Do not leave ZYCLARA® Cream 2.5% on your skin longer than prescribed.

- After about 8 hours, wash the treated area or areas with mild soap and water.

- If you forget to apply ZYCLARA® Cream 2.5%, continue on your regular schedule and do not make up the missed doses(s).

- If you get ZYCLARA® Cream 2.5% in your mouth or in your eyes rinse well with water right away.

How do I use ZYCLARA® Cream 2.5% pump?

ZYCLARA® Cream 2.5% should be applied just before your bedtime.
- Wash the area where the cream will be applied with mild soap and water.

- Allow the area to dry.
- Wash your hands.
- Slightly tilt the pump as shown when dispensing cream, as shown in FIG. 13.
- Before using the pump for the first time only, remove the cap and prime the pump by firmly pressing the top of the pump all the way down (up to five times as needed) until the cream appears. The primed cream should be dispensed into a tissue and then discarded. The pump is now ready to use.
- To apply the cream, firmly press the top of the pump all of the way down to dispense the cream into your hand.
- Apply a thin layer of ZYCLARA® Cream 2.5% only to the areas to be treated as directed by your healthcare provider. Do not use more ZYCLARA® Cream 2.5% than is needed to cover the treatment area.
- Do not use more than two full pump depressions for each daily application.
- Rub the cream in all the way to the affected area or areas.
    - Do not get ZYCLARA® Cream 2.5% in or around your eyes.
- After you apply ZYCLARA® Cream 2.5%, wash your hands well.
- Leave the cream on the affected area or areas for the time prescribed by your healthcare provider. Do not bathe or get the treated area wet before the right time has passed. Do not leave ZYCLARA® Cream 2.5% on your skin longer than prescribed.
- After about 8 hours, wash the treated area or areas with mild soap and water.
- If you forget to apply ZYCLARA® Cream 2.5%, continue on your regular schedule and do not make up the missed dose(s).
- If you get ZYCLARA® Cream 2.5% in your mouth or in your eyes rinse well with water right away.
- When you have completed all of your doses as instructed, safely throw the pump away so that children and pets cannot get it.

What should I avoid while using ZYCLARA® Cream 2.5%?

- Do not cover the treated area with bandages or other closed dressings.

- Do not use sunlamps or tanning beds, and avoid sunlight as much as possible during treatment with ZYCLARA® Cream 2.5%. Use sunscreen and wear protective clothing if you go outside during daylight.

What are the possible side effects of ZYCLARA® Cream 2.5%?

ZYCLARA® Cream 2.5% may cause serious side effects, including:

- Local Skin Reactions: skin redness, scabbing or crusting, flaking, scaling or dryness, swelling, sores or blisters, draining (weeping)

- Flu-like symptoms: tiredness, nausea, vomiting, fever, chills, muscle pain, joint pain The most common side effects of ZYCLARA® Cream 2.5% include:

- headache
- itching at application site
- tiredness
- nausea
- skin irritation
- pain at the treatment area
- fever
- loss of appetite
- dizziness
- cold sores
- pain
- chest pain
- diarrhea
- swelling of lymph nodes Tell your healthcare provider if you have any side effect that bothers you or that does not go away.

These are not all the possible side effects of ZYCLARA® Cream 2.5%. For more information, ask your healthcare provider or pharmacist.

Call your doctor for medical advice about side effects. You may report side effects to the FDA at 1-800-FDA-1088 or to Graceway Pharmaceuticals, LLC at 1-800-328-0255.

How do I store ZYCLARA® Cream?
- Store ZYCLARA® Cream 2.5% at 59° F to 86° F (15° C to 30° C).
- Do not freeze.

Keep ZYCLARA® Cream 2.5% and all medicines out of the reach of children.

General Information about ZYCLARA® Cream 2.5%

Medicines are sometimes prescribed for purposes other than those listed in the patient information. Do not use ZYCLARA® Cream 2.5% for a condition for which it was not prescribed. Do not give ZYCLARA® Cream 2.5% to other people, even if they have the same symptoms you have. It may harm them.

This patient information leaflet summarizes the most important information about ZYCLARA® Cream 2.5%. If you would like more information, talk with your healthcare provider. You can ask your pharmacist or healthcare provider for information about ZYCLARA® Cream 2.5% that is written for the health professionals.

What are the ingredients in ZYCLARA® Cream?

Active Ingredient: imiquimod

Inactive ingredients: isostearic acid, cetyl alcohol, stearyl alcohol, white petrolatum, polysorbate 60, sorbitan monostearate, glycerin, xanthan gum, purified water, benzyl alcohol, methylparaben, and propylparaben.

Manufactured by
    3M Health Care Limited
    Loughborough LE11 1EP England

Distributed by
    Graceway Pharmaceuticals, LLC
    Bristol, TN 37620

Issued: XXX XXXX

The complete disclosures of the patents, patent documents, labels and publications cited herein, including U.S. Pat. No. 6,991,139 and Attachments 1-XV, are incorporated herein by reference in their entireties as if each were individually reproduced and incorporated. In case of conflict, the present specification, including definitions, shall control. Various modifications and alterations to this invention will become apparent to those skilled in the art without departing from the scope and spirit of this invention. Illustrative embodiments and examples are provided as examples only and are not intended to limit the scope of the present invention. The scope of the invention is limited only by the claims set forth as follows.

Having described our invention, we claim:

1. A method of treating a patient having a dermal and/or mucosal-associated condition with a topical semi-solid imiquimod pharmaceutical formulation, said method comprising:
    actuating a dispensing device, the dispensing device comprising a dispensing package that includes a hollow main body portion and a manually-operated airless pumping device mounted on the main body portion, the main body portion defining a fluid storage chamber and the airless pumping device defining a dispensing duct which terminates in a self-closing discharge orifice, the fluid storage chamber being pre-filled with the imiquimod pharmaceutical formulation, wherein manual operation of the airless pumping device causes a portion of the imiquimod cream to be withdrawn from within the fluid storage chamber into the dispensing duct thereby opening the self-closing discharge orifice dispensing the imiquimod formulation from the dispensing package through the self-closing discharge orifice so as to dispense therefrom an effective unit-dose amount of the topical semi-solid imiquimod pharmaceutical formulation for treating the dermal and/or mucosal-associated condition; and
    applying the effective unit-dose amount to a treatment area diagnosed with the dermal and/or mucosal-associated condition in accordance with an effective treatment regimen to treat the dermal and/or mucosal-associated condition.
2. A method as recited in claim 1, wherein the topical semi-solid imiquimod pharmaceutical formulation is a topical imiquimod pharmaceutical cream.
3. A method as recited in claim 2, wherein the topical imiquimod pharmaceutical cream contains imiquimod in an amount by weight of about 1% to about 10% w/w.
4. A method as recited in claim 2, wherein the topical imiquimod pharmaceutical cream contains imiquimod in an amount by weight of about 1% to about 5% w/w.
5. A method as recited in claim 2, wherein the topical imiquimod pharmaceutical cream contains imiquimod in an amount by weight of about 2.5% w/w.
6. A method as recited in claim 2, wherein the topical imiquimod pharmaceutical cream contains imiquimod in an amount by weight of about 3.75% w/w.
7. A method as recited in claim 2, wherein the topical imiquimod pharmaceutical cream contains imiquimod in an amount by weight of about 5% w/w.
8. A method as recited in claim 1, wherein the topical dermal and/or mucosal-associated condition is external genital warts.
9. A method as recited in claim 1, wherein the topical dermal and/or mucosal-associated condition is perianal warts.
10. A method as recited in claim 1, wherein the topical dermal and/or mucosal-associated condition is actinic keratosis.
11. A method as recited in claim 1, wherein the topical dermal and/or mucosal-associated condition is superficial basal cell carcinoma.
12. A method as recited in claim 8, wherein the unit-dose amount is applied to the treatment area diagnosed with external genital warts once daily for up to 8 weeks.
13. A method as recited in claim 9, wherein the unit-dose amount is applied to the treatment area diagnosed with perianal genital warts once daily for up to 8 weeks.
14. A method as recited in claim 8, wherein the unit-dose amount is applied to the treatment area diagnosed with external genital warts once daily three times each week for up to 16 weeks.
15. A method as recited in claim 9, wherein the unit-dose amount is applied to the treatment area diagnosed with perianal genital warts once daily three times each week for up to 16 weeks.
16. A method as recited in claim 10, wherein the unit-dose amount is applied to the treatment area diagnosed with actinic keratosis once daily in accordance with a 2×2 ×2 week or 3×3×3 week treatment regimen.
17. A method as recited in claim 10, wherein the unit-dose amount is applied to the treatment area diagnosed with actinic keratosis once daily in accordance with a 3×3×3 week treatment regimen, wherein the first 3 week cycle is a daily treatment cycle, the second 3 week cycle is a rest cycle and the third 3 week cycle is another daily treatment cycle.
18. A method as recited in claim 10, wherein the unit-dose amount is applied to the treatment area diagnosed with actinic keratosis once daily two times each week for up to 16 weeks.
19. A method as recited in claim 11, wherein the unit-dose amount is applied to the treatment area diagnosed with superficial basal cell carcinoma warts once daily for five consecutive days each week for up to 6 weeks.
20. A method as recited in claim 12, wherein the unit-dose amount is a topical imiquimod pharmaceutical cream that contains imiquimod in an amount by weight of about 3.75% w/w.
21. A method as recited in claim 12, wherein the unit-dose amount is a topical imiquimod pharmaceutical cream that contains imiquimod in an amount by weight of about 2.5% w/w.
22. A method as recited in claim 14, wherein the unit-dose amount is a topical imiquimod pharmaceutical cream that contains imiquimod in an amount by weight of about 5% w/w.
23. A method as recited in claim 16, wherein the unit-dose amount is a topical imiquimod pharmaceutical cream that contains imiquimod in an amount by weight of about 3.75% w/w.
24. A method as recited in claim 16, wherein the unit-dose amount is a topical imiquimod pharmaceutical cream that contains imiquimod in an amount by weight of about 2.5% w/w.
25. A method as recited in claim 18, wherein the unit-dose amount is a topical imiquimod pharmaceutical cream that contains imiquimod in an amount by weight of about 5% w/w.
26. A method as recited in claim 19, wherein the unit-dose amount is a topical imiquimod pharmaceutical cream that contains imiquimod in an amount by weight of about 5% w/w.
27. A method of instructing a patient to practice as recited in claim 1, including the step of providing instruction to the patient on how to practice said methods.

28. A method of instructing a prescriber to prescribe as recited in claim 1, including the step of providing instruction to the prescriber on how to prescribe said methods.

29. A method as recited in claim 27, wherein said providing instruction includes the step of providing the instruction on a label or package insert.

30. A method for treating a patient diagnosed with a dermal and/or mucosal condition by use of a topical semi-solid imiquimod pharmaceutical formulation, said method comprising:
  priming a pump pre-filled with the topical semi-solid imiquimod pharmaceutical formulation in an amount sufficient to deliver a predefined number of single unit-dose amounts effective to treat the dermal and/or mucosal condition in accordance with a treatment regimen, to prepare the pump to dispense a first single unit dose amount of the predefined number of single unit-dose amounts for treatment; and
  pumping the primed pump to dispense an effective single unit dose amount for application onto a treatment area diagnosed with the dermal and/or mucosal-associated condition in accordance with the treatment regimen,
  wherein each effective single unit dose amount dispensed from the pump is rubbed onto the treatment area until the topical semi-solid imiquimod pharmaceutical formulation is no longer visible, and
  wherein the rubbed-in single unit dosage amount is left on the treatment area for a pre-defined treatment period in accordance with the treatment regimen to treat the dermal and/or mucosal condition.

31. A method as recited in claim 30, wherein said method includes the further steps of:
  washing the treatment area following the treatment period with soap and water to remove the topical semi-solid imiquimod pharmaceutical formulation from the treatment area; and
  drying the treatment area prior to said pumping.

32. A method as recited in claim 30, wherein said method includes the further steps of:
  washing the patient's hands with soap and water before and after dispensing the single-unit dose amount onto the treatment area;
  washing the treatment area with soap and water; and
  allowing the treatment area to dry before said pumping.

33. A method as recited in claim 30, wherein said method includes the further step of avoiding contact of the topical semi-solid imiquimod pharmaceutical formulation with the patient's eyes, lips, nostrils and/or vagina.

34. A method as recited in claim 30, wherein the treatment regimen is a 16 week treatment regimen, and wherein said pumping step includes: pumping the primed pump twice each week during the 16 week treatment regimen to dispense the single-unit dose amount onto the treatment area two separate times a week for each of the 16 weeks.

35. A method as recited in claim 30, wherein the treatment regimen is a 16 week treatment regimen, and wherein said pumping step includes: pumping the primed pump three times each week during the 16 week treatment regimen to dispense the single-unit dose amount onto the treatment area three separate times a week for each of the 16 weeks.

36. A method as recited in claim 30, wherein the treatment regimen is up to about 8 weeks, and wherein said pumping step includes:
  pumping the primed pump daily each week during the 8 week treatment regimen to dispense the single-unit dose amount onto the treatment each day for each of the 8 weeks.

37. A method as recited in claim 30, wherein the treatment regimen is a 6 week treatment regimen, and wherein said pumping step includes:
  pumping the primed pump five consecutive days each week during the 6 week treatment regimen to dispense the single-unit dose amount onto the treatment area five consecutive days for each of the 6 weeks.

38. A method as recited in claim 30, wherein the treatment regimen is a 6 week treatment regimen consisting of 3 two-week treatment cycles, and wherein said pumping step includes:
  pumping the primed pump daily during the first two-week treatment cycle to dispense daily the single dose amounts onto the treatment area during the first two-week treatment cycle;
  not pumping the primed pump during the second two-week treatment cycle; and
  pumping the primed pump daily, without conducting said priming, during the third two-week treatment cycle to dispense daily the single dose amounts onto the treatment area during the third two-week treatment cycle.

39. A method as recited in claim 30, wherein the treatment regimen is a 9 week treatment regimen consisting of 3 three-week treatment cycles, and wherein said pumping step includes:
  pumping the primed pump daily during the first three-week treatment cycle to dispense daily the single dose amounts onto the treatment area during the first three-week treatment cycle;
  refraining from pumping the primed pump during the second three-week treatment cycle; and
  pumping the primed pump daily, without conducting said priming step, during the third three-week treatment cycle to dispense daily the single dose amounts onto the treatment area during the third three-week treatment cycle.

40. A method as recited in claim 34, wherein said pumping step includes the further steps of:
  resting for a period of time of up to about two weeks, wherein said resting period involves refraining from pumping the primed pump between said scheduled pumping in accordance with the treatment regimen; and
  resuming said pumping of the primed pump in accordance with the treatment regimen without conducting said priming step.

41. A method as recited in claim 30, wherein the delinal and/or mucosal condition is external warts.

42. A method as recited in claim 30, wherein the dermal and/or mucosal condition is perianal warts.

43. A method as recited in claim 30, wherein the dermal and/or mucosal condition is actinic keratosis.

44. A method as recited in claim 30, wherein the dermal and/or mucosal condition is superficial basal cell carcinoma.

45. A method as recited in claim 34, wherein the dermal and/or mucosal condition is actinic keratosis.

46. A method as recited in claim 35, wherein the dermal and/or mucosal condition is external warts.

47. A method as recited in claim 35, wherein the dermal and/or mucosal condition is perianal warts.

48. A method as recited in claim 36, wherein the dermal and/or mucosal condition is external warts.

49. A method as recited in claim 36, wherein the dermal and/or mucosal condition is perianal warts.

50. A method as recited in claim 37, wherein the dermal and/or mucosal condition is superficial basal cell carcinoma.

51. A method as recited in claim 38, wherein the dermal and/or mucosal condition is actinic keratosis.

52. A method as recited in claim 39, wherein the dermal and/or mucosal condition is actinic keratosis.

53. A method as recited in claim 30, wherein the pump is prefilled with about 7.5 grams of the topical semi-solid imiquimod pharmaceutical formulation.

54. A method as recited in claim 30, wherein the prefilled pump is prefilled with about 15 grams of the topical semi-solid imiquimod pharmaceutical formulation.

55. A method as recited in claim 30, wherein the topical semi-solid imiquimod pharmaceutical formulation is an imiquimod pharmaceutical cream.

56. A method as recited in claim 34, wherein the imiquimod pharmaceutical cream is 5% imiquimod pharmaceutical cream.

57. A method as recited in claim 36, wherein the imiquimod pharmaceutical cream is a 3.75% imiquimod pharmaceutical cream.

58. A method as recited in claim 36, wherein the imiquimod pharmaceutical cream is a 2.5% imiquimod pharmaceutical cream.

59. A method as recited in claim 30, wherein the single unit dose amount dispensed during each said pumping step is about 240 mg.

60. A method as recited in claim 30, wherein said pumping step dispenses at least about 85% of the single unit dose amount during each said pumping step during treatment.

61. A method as recited in claim 30, wherein said pumping step dispenses at least about 95% of the single unit dose amount during each said pumping step.

62. A method as recited in claim 30, wherein said pumping step dispenses at least about 96% of the single unit dose amount during each said pumping step.

63. A method as recited in claim 30, wherein said pumping step dispenses at least about 97% of the single unit dose amount during each said pumping step.

64. A method of instructing a patient to practice as recited in claim 30, including the step of providing instruction to the patient on how to practice said methods.

65. A method of instructing a prescriber to prescribe as recited in claim 30, including the step of providing instruction to the prescriber on how to prescribe said methods.

66. A method as recited in claim 64, wherein said providing instruction includes the step of providing the instruction on a label or package insert.

67. The method of claim 1, wherein the dispensing device is adapted to dispense a single product stored therein, the single product comprising the imiquimod formulation.

68. The method of claim 1, wherein the dispensing device is adapted to protect a remaining imiquimod formulation remaining within the dispensing device after each actuation from air contact, oxidation, degradation and contamination such that subsequent actuations of the dispensing device each dispense a subsequent effective unit-dose amount.

69. The method of claim 68 wherein repeated actuations consistently and repeatedly dispense the effective unit-dose amount upon each actuation during treatment.

70. The method of claim 69, wherein the dispensing device is pre-filled with a pre-fill amount corresponding to the treatment regimen such that repeated actuations of the dispensing device deliver a predefined number of single unit-dose amounts effective to treat the dermal and/or mucosal condition in accordance with the effective treatment regimen.

71. The method of claim 1, further comprising:
sealingly closing the self-closing discharge orifice with leak-tight contact upon completion of each actuation thereby avoiding air contact with a remaining amount of the imiquimod formulation remaining within the dispensing duct such that a subsequent effective unit-dose comprises the remaining amount of imiquimod formulation.

72. The method of claim 1, wherein a substantial portion of the imiquimod formulation drawn into the dispensing duct upon each actuation remains within the dispensing duct after actuation so that a uniform and consistent amount unit-dose of the imiquimod formulation is dispensed per each subsequent actuation.

73. The method of claim 1, wherein about 85% or more of the imiquimod formulation drawn into the dispensing duct upon each actuation remains within the dispensing duct after actuation so that a uniform and consistent amount unit-dose of the imiquimod formulation is dispensed per each subsequent actuation.

74. The method of claim 1, wherein actuating the dispensing device comprises actuating the dispensing device up to two full actuations.

75. The method of claim 1, wherein an amount of the imiquimod formulation dispensed per one actuation is the same upon each subsequent actuation when actuating the dispensing device during treatment.

76. The method of claim 1, wherein the dispensing device is adapted so as to not be readily disassemblable by the patient so that a remaining amount of imiquimod formulation remaining with the dispensing duct after each actuation remains effective and to avoid exposing the patient to excess imiquimod formulation.

\* \* \* \* \*